United States Patent
Sourdive et al.

(10) Patent No.: US 12,144,825 B2
(45) Date of Patent: Nov. 19, 2024

(54) CELLULAR IMMUNOTHERAPY FOR REPETITIVE ADMINISTRATION

(71) Applicant: CELLECTIS, Paris (FR)

(72) Inventors: David Sourdive, Levallois-Perret (FR); Aymeric Duclert, St Maur des Fosses (FR); Mathieu Simon, Paris (FR); Philippe Duchateau, Draveil (FR); Alan Marc Williams, New York, NY (US); Laurent Poirot, Paris (FR)

(73) Assignee: CELLECTIS, Paris (FR)

( * ) Notice: Subject to any disclaimer, the term of this patent is extended or adjusted under 35 U.S.C. 154(b) by 978 days.

(21) Appl. No.: 16/625,678

(22) PCT Filed: Jul. 2, 2018

(86) PCT No.: PCT/EP2018/067857
§ 371 (c)(1),
(2) Date: Dec. 21, 2019

(87) PCT Pub. No.: WO2019/002633
PCT Pub. Date: Jan. 3, 2019

(65) Prior Publication Data
US 2022/0233588 A1   Jul. 28, 2022

(30) Foreign Application Priority Data

Jun. 30, 2017 (DK) ............................ PA201770542
Oct. 19, 2017 (WO) ................. PCT/EP2017/076798
Feb. 9, 2018 (WO) ................. PCT/EP2018/053343

(51) Int. Cl.
*A61K 35/17* (2015.01)
*A61K 39/00* (2006.01)
*C12Q 1/6881* (2018.01)

(52) U.S. Cl.
CPC .......... *A61K 35/17* (2013.01); *A61K 39/4611* (2023.05); *A61K 39/4631* (2023.05); *C12Q 1/6881* (2013.01)

(58) Field of Classification Search
CPC ................ A61K 35/17; A61K 39/4611; A61K 39/4631; C12Q 1/6881
See application file for complete search history.

(56) References Cited

U.S. PATENT DOCUMENTS

2016/0206656 A1* 7/2016 Gilbert .................. A61K 45/06
2017/0304418 A1 10/2017 Ichim et al.

FOREIGN PATENT DOCUMENTS

| WO | 2013/074916 A1 | 5/2013 |
| WO | 2013166051 A1 | 11/2013 |
| WO | 2015/164740 A1 | 4/2015 |
| WO | 2015/075175 A1 | 5/2015 |

OTHER PUBLICATIONS

Ruella et al. Catch me if you can: Leukemia Escape after CD19-Directed T Cell Immunotherapies. Computational and Structural Biotechnology Journal. 14:357-362 (Year: 2016).*
Torikai et al. A foundation for universal T-cell based immunotherapy: T cells engineered to express a CD19-specific chimeric-antigen-receptor and eliminate expression of endogenous TCR. Blood. 2012;119(24):5697-5705 (Year: 2012).*
Tiercy. How to select the best available related or unrelated donor of hematopoietic stem cells? Haematologica vol. 101(6):680-687. (Year: 2016).*
European Patent Office, International Search Report of PCT Application No. PCT/EP2018/067857, Sep. 4, 2018 (3 pages).
Qasim et al., Molecular remission of infant B-ALL after infusion of universal TALEN gene-edited CAR T cells, Sci. Transl. Med. 9, eaaj2013 (2017) Jan. 25, 2017, 1-8.
Sadelain et al., The basic principles of chimeric antigen receptor (CAR) design, Cancer Discov. Apr. 2013 ; 3(4):388-398.
Brudno et al. Allogeneic T Cells That Express an Anti-CD19 Chimeric Antigen Receptor Induce Remissions of B-Cell Malignancies That Progress After Allogeneic Hematopoietic Stem-Cell Transplantation Without Causing Graft-Versus-Host Disease. Journal of Clinical Oncology. 2016, 34(10), 1112-1121.
Hampe. B Cells in Autoimmune Diseases. Scientifica, 2012, 215308, 1-18.
Kochenderfer et al. Donor-Derived Anti-CD19 Chimeric-Antigen-Receptor-Expressing T Cells Cause Regression Of Malignancy Persisting After Allogeneic Hematopoietic Stem Cell Transplantation. Blood, 2013, 122 (21), 151, 1-3.

* cited by examiner

*Primary Examiner* — Taeyoon Kim
(74) *Attorney, Agent, or Firm* — Arrigo, Lee, Guttman & Mouta-Bellum LLP

(57) ABSTRACT

The present invention provides composition kits and methods for treating cancer in a human by immunotherapy using successive doses of CAR-T cells with no or reduced anamnestic immune reaction in one individual (P).

20 Claims, 6 Drawing Sheets

CELLULAR IMMUNOTHERAPY FOR REPETITIVE ADMINISTRATION

CROSS REFERENCE TO RELATED APPLICATIONS

This application is a U.S. National Stage Application of PCT Application No. PCT/EP2018/067857 under 37 C.F.R. § 371, with an international filing date of Jul. 2, 2018, which claims priority to Danish Patent Application No. PA201770542 filed Jun. 30, 2017, PCT Application No. PCT/EP2017/076798 filed Oct. 19, 2017, and PCT Application No. PCT/EP2018/053343 filed Feb. 9, 2018, all of which are herein incorporated by reference in their entirety.

FIELD OF THE INVENTION

The present invention relates to a set of n pharmaceutical unit doses comprising engineered cells and a pharmaceutically acceptable vehicle, suitable for cellular immunotherapy, inducing no or reduced anamnestic response.

BACKGROUND OF THE INVENTION

Adoptive immunotherapy is one of the promising strategies to treat diseases such as viral infections or cancer. The cells used for adoptive immunotherapy can be generated either by differentiation of immune cell progenitors, expansion of antigen-specific T-cells or redirection of T-cells or of differentiated immune cell progenitors through genetic engineering (Park, Rosenberg et al. 2011).

For directing cells towards specific pathological cells, transgenic T-cell receptors (TCR) or chimeric antigen receptors (CARs) can be successfully expressed at the cell surface, even in the absence of endogenous TCR. These synthetic receptors comprise a targeting moiety that is associated with one or more signaling domains in a single fusion molecule or consists in several non-covalently linked transmembrane domains as described in (WO2014039523A1).

In numerous studies, the binding moiety of a CAR can redirect the activity of the immune cells expressing it, towards a specific molecule, preferably expressed on a tumor or pathological cell. Thus, single-chain antibody (scFv), comprising the light and heavy variable fragments of a monoclonal antibody joined by a flexible linker can be very efficient. Binding moieties based on receptor or ligand domains have also been used successfully. Such extracellular domains are linked to signaling domains initially derived from the cytoplasmic region of the CD28, CD3zeta, 4-1BB or from the Fc receptor gamma chains in CAR of first, second and third generations. Binding of CAR to pathological cells results in signaling and triggers a cascade of events including degranulation, release of cytokines, and eventually leading to the destruction of target cells.

Thus, CARs allow cytotoxic T-cells to be re-directed against specific antigens expressed at the surface of tumor cells including lymphomas (Jena, Dotti et al. 2010) and destruction of these target cells.

The current protocol for the treatment of patients using adoptive immunotherapy is based on autologous cell transfer. Under this approach, T lymphocytes recovered from a given patient, are genetically modified or selected ex vivo, cultivated in vitro in order to amplify the number of cells and finally re-infused into the patient.

Autologous transfer of engineered immune cells was reported to induce undesired immune reaction including cytokine storm, GVHD (that may be an autoimmune disease), or immune reaction against the edited molecules that sometimes comprised mouse antibody fragments (Villa N Y, Rahman M M, McFadden G, Cogle C R. Therapeutics for Graft-versus-Host Disease: From Conventional Therapies to Novel Virotherapeutic Strategies. Lamfers M L M, Chiocca E A, eds. Viruses. 2016; 8(3):85. doi:10.3390/v8030085).

In addition, autologous therapies face substantial technical and logistic hurdles to practical application; their generation requires expensive dedicated facilities and expert personnel, they must be generated in a short time following a patient's diagnosis, and in many cases, pretreatment of the patient has resulted in degraded immune function, such that the patient's lymphocytes may be present in low numbers, may be poorly functional or even dysfunctional. Because of these hurdles, each patient's autologous cell preparation is effectively a new product, resulting in substantial variations in efficacy and safety.

To answer the need of providing engineered cells that could be used in all patients with limited undesired immune reaction against the host, cells from healthy individuals engineered to destroy cancer cells may be used. However, T cells from one individual when transferred to another individual can be detrimental to the host resulting in graft versus host disease (GvHD) and leading to potentially serious tissue damage and death. The molecular mechanisms responsible for acute or chronic GVHD have been at least partially identified. Recognition of MHC disparities between the donor and recipient through specific TCR(s) that can lead to T cells proliferation and to the development of GvHD in recipients of allogeneic cells. To overcome this problem, new techniques of gene editing have been used to reduce the expression of TCR genes encoding the various subunits of the endogenous TCR (Domain-swapped T cell receptors improve the safety of TCR gene therapy. (Bethune M T, Gee M H, Bunse M, et al. Domain-swapped T cell receptors improve the safety of TCR gene therapy. Rath S, ed. eLife. 2016; 5:e19095. doi:10.7554/eLife.19095).

Thus, so called "Allogeneic TCR KO therapeutic cells" or "off the shelve—ready to use—CART cells" have been engineered to be redirected against pathological cells, cancerous, or infected and to induce no or reduced GVHD. Infusion of such TCR-KO cells into patients significantly reduced GVHD or significantly reduces the risk of GVHD and increased survival in patients suffering refractory AML in at least two pediatric patients (Gray N, 2016. http://www.biopharmadive.com/news/cellectis-t-cell-therapy-clears-leukemia-in-second-baby/418862/).

One problem met with allogeneic cell therapy or organ transplant, or even with autologous cell therapies or grafts expressing ectopic antigens, lies in a possible immunological reaction and rejection of grafted cells, tissues or organs (the "Graft") when an individual has been previously exposed to one or more antigen(s) present on the Graft (born by cells) and not tolerated by the immune system. In case of re exposure to said antigen, an "Anamnestic Response" is likely to reject efficiently and/or rapidly the Graft.

Such situations are known to happen especially when the graft bears macromolecular features (e.g. proteins, sugars, lipids or combinations thereof) that are not present in the grafted individual (or not tolerated by its immune system).

The case is observed when the grafts bear molecules, such as HLA alleles products, that are different from those of the individual if the individual has been exposed to, in the past.

Graft rejection due to an anamnestic response that involves different compartments of the immune system.

Thus, the rejected antigen(s) are recognized by antibodies and/or by specific receptors of T lymphocytes (TCRs).

Yet it may be desirable to perform two or more consecutive Grafts and to minimize anamnestic Responses (any immune response due to repeated exposure), especially for treating solid cancer.

Thus, when using adoptive engineered T-cell immunotherapy to target antigens born by cancer cells, it may be useful to make repeated and consecutive treatments targeting the same or different antigen of the same cancer marker. It may be also useful to make successive treatments targeting a different antigen in case of new, or relapse or even refractory cancer. In all cases, an anamnestic response should be avoided and side effects minimized.

There is therefore a strong need in identifying solutions to these problems, for reducing the side effects of successive immunotherapy whether using "allogenic" or "autologous" immunotherapy and improving the efficiency and safety of such treatments.

The proposed technical solutions in the present invention pertain to minimize Anamnestic Responses, and also to achieve Anamnestic Responses minimization or inhibition in absence of major side effects related to immunotherapy such as graft-versus-host diseases host versus graft reaction when grafting one or consecutive doses of T-cells, with a real and substantive decrease and control in tumor mass during immunotherapy, in particular during allogenic or autologous immunotherapy using CAR-expressing cells.

SUMMARY OF THE INVENTION

The following methods are provided:

1. The present invention generally provides a method for preparing a set or a kit of n pharmaceutical unit doses comprising engineered cells and a pharmaceutically acceptable vehicle, comprising the step of:
   i) genotyping and/or phenotyping the HLA molecules and/or HLA alleles of a patient P,
   ii) selecting and/or providing at least 5 samples of cells from human donor(s) by choosing:
      a) samples of cells fully matching the HLA molecules and/or HLA alleles born by cells of P, or
      a') samples of cells bearing a number of mismatching as low as possible, as compared to P, optionally said cells being further genetically modified to match the HLA molecules and/or HLA alleles born by cells of P or being further genetically modified so that said cells do no express any potentially anamnestogenic molecule,
   iii) modifying cells by introducing at least one chimeric antigen receptor (CAR) or one T-cell receptor (TCR) and/or inactivating at least one component of the TCR gene.
2. The method according to 1, wherein the HLA molecules are selected from HLA-A, HLA-B, HLA-C, HLA-DR, and a combination thereof is provided and preferred.
3. The method according to 1 or 2, wherein the HLA of samples of a') match more than 80% of the HLA of P is also provided.
4. The method according to any one of 1 to 3, wherein the step of choosing samples of cells comprises selecting a triple homozygote on HLA-A, HLA-B and HLA-DR genes is provided.
5. The method according to any one of 1 to 3, wherein the step of choosing samples of cells comprises selecting a double homozygote on 2 of HLA-A, HLA-B and HLA-DR genes is provided.
6. The method according to any one of 1 to 5, wherein a donor is selected based on i) the frequency of his or her HLA typing in a database, ii) on his or her HLA typing as compared to the other donors, and optionally iii) the level of matching with P, using a computer software or program analyzing and selecting at least 6/6 and preferably 10/10 HLA alleles matching is provided.
7. As another general aspect, the present invention provides a method for preparing a set of successive injection doses for use of performing a sequential (N=graft number) treatment in a patient of allogeneic peripheral blood cells coming from different donors aiming at reducing risk of anamnestic response and graft-versus-host disease, comprising the step of:
   (a) randomly sampling several groups of 5 donors comprised in a bank of donors;
   (b) comparing the genotypes of the 5 donors within said groups with respect to their HLA-A, HLA-B and HLA-DR alleles;
   (c) selecting the groups of five donors which present no HLA-A, HLA-B and HLA-DR allele in common;
   (d) selecting in the groups obtained from step (c) those displaying at least 50% match of HLA-A, HLA-B and HLA-DR alleles with the genotype of at least 80% (fmin), preferably more than 90% and even more preferentially more than 95% of the ethnic population of said patient;
   (e) engineering the allogeneic peripheral blood cells from each of the donors selected from step (d) to reduce or impair expression of the TCR in said peripheral blood cells;
   (f) optionally, expanding the engineered peripheral blood cells from the blood sample; and
   (g) conditioning the engineered peripheral blood cells from the different donors separately.
8. The method according to 7, wherein the peripheral blood cells are immune cells, preferably T-cells is provided.
9. As another general aspect, the invention provides a set or a kit of n pharmaceutical unit doses obtainable by a method according to any one of the above 1 to 6.
10. A set or kit of n pharmaceutical unit doses as any one of those described in Table 1 is part of the invention.
11. As another general aspect, the invention provides a kit of successive doses obtainable by the method of 7 or 8.
12. As another general aspect, the invention provides a kit comprising at least 2, preferably at least 3, more preferably at least 4, and even more preferably at least 5 compositions comprising different allogeneic peripheral blood cells for sequential injection into a patient with reduced risk of anamnestic response and graft-versus host disease, wherein said allogeneic peripheral blood cells are respectively selected from donors being homozygous with respect to their HLA-A, HLA-B and HLA-DR alleles and said donors share no HLA-A, HLA-B and HLA-DR allele in common.
13. As another aspect, the invention provides the kit according to 12, wherein said peripheral blood cells are T-cells.
14. As another aspect, the invention provides the kit according to 12 or 13, wherein said peripheral blood cells are genetically engineered to inactivate the T-cell receptor.

15. The kit according to any one of 12 to 14 is provided, wherein said peripheral blood cells are endowed with a chimeric antigen receptor.
16. As another general aspect, the invention provides a method for preparing a set or a kit of n pharmaceutical unit doses comprising engineered cells and a pharmaceutically acceptable vehicle, comprising the step of:
   a) selecting at least 5 samples of immune cells with the no common HLA allele with each other, or
   a) selecting at least 5 samples of immune cells with no common HLA allele with each other and with those against which P was previously immunized, or
   a) selecting at least 5 samples of immune cells with no common HLA-A, HLA-B, HLA-C and HLA-DR allele with each other and with those against which P was previously immunized, or
   a) selecting at least 5 samples of immune cells with no common HLA-A, HLA-B, HLA-C and HLA-DR allele with each other and with those against which P was previously immunized and the frequency with which they these alleles are represented in the general population is more than 0.6% and not less than 0.1%, or
   a) selecting at least 5 samples of immune cells with no common HLA-A, HLA-B, HLA-C and HLA-DR allele with each other and with those against which P was previously immunized and the frequency with which they these alleles are represented in the general population is more than 5e−5.

As another aspect, the invention provides a method for preparing a set or a kit of n pharmaceutical unit doses for immunotherapy of a patient P comprising said the step of:

Providing target cells (T) from at least two donor cells samples from a bank, preferably from 5 donors selected according to the present invention n=5, T1, T2, T3, T4, T5 and/or from P him or herself, or Providing target cells (T) from at least two donor cells samples from a bank, preferably from 5 donors n=5, T1, T2, T3, T4, T5 and/or from P him or herself, Irradiating T, or T1, T2, T3, T4, T5, Contacting at least one time (T) or T1, T2, T3, T4, T5, with immune cells of the patient P intended to be treated (E), before and/or after P was exposed to any immune cells (such as during pregnancy, transfused platelets or engineered immune cells of a donor cells sample),
   measuring the cytolytic activity of E towards irradiated donor cells sample(s) T (T may be cells of P as a control or for measuring anti-CART cells activity) by calculating a number of live target cells in contact with effectors for 1 day, 2 days, 3 days, 4 days or 5 days, divided by the number of live target cells in the absence of effectors grown for the same length of time, at different E:T ratios: from 1:10 000 to 10 000:1, preferably from 100:1 to 1:100, even more preferably from 20:1, 10:1, 5:1, 1:1, 1:5, 1:15, 1:30, even more preferably 5:1,
   comparing the cytolytic activity E towards T to those of an individual X towards its own irradiated immunes cells (autologous system—FIG. 5) and towards irradiated immune cells (T) from another individual Y—the cells of X may be haploidentical, matching or mismatching cells of Y, X may or may not have been immunized with cells of Y wherein cells of X are exposed 3 times to the cells of Y before measuring the CTL activity of X vis-à-vis Y.

The method is provided wherein E are activated using CD3/CD28 antibodies, and/or E are contacted once, two, or three times with irradiated T, at different ratios E:T from 1:10 000 to 10 000:1, preferably from 100:1 to 1:100, even more preferably from 20:1, 10:1, 5:1, 1:1, 1:5, 1:15, 1:30 before measuring the cytolytic activity.

Viable target cells are determined (normalized) over the viability of target cells without E, The method comprises a further step of engineering the original cells of the donor cells sample T for immunotherapy, if E when activated 3 times with said target cells has a cytolytic activity above 0.2 and between 0.2 and 1, preferably 0.5, even more preferably 1 or 0.9 as determined by measuring the number of live target cells in contact with effectors for 1 day, 2 days, 3 days, 4 days or at 5 days, divided by the number of live target cells in the absence of effectors grown for the same length of time, at a ratio E:T 1:1.

The invention provides a method further comprising a step of:
   contacting E (immune cells of P) with irradiated T2, T3, T4, T5 wherein E comprises cells from P after treatment with engineered T1, to detect a potential CTL activity against the UCART intended to be injected after engineered T1, as a second, third etc treatment,
   if a cytolytic activity of E is detected against irradiated T2 (number of viable cells in the E:T2 1:1 mixture over number of viable cells T2 without E) and is less than 1, or less than 0.5 as compared to control, then T2 may set aside and not used for treating P.

The present invention generally provides a set or kit of n pharmaceutical unit doses comprising engineered cells and a pharmaceutically acceptable vehicle, inducing no or reduced anamnestic immune reaction in one individual (P), as compared to an anamnestic reaction in said individual P if previously exposed to an immunogenic antigen born by cells, against which P has acquired immunity (preferably a T cell dependent antigen) and then subsequently grafted with a unit dose of engineered cells comprising said immunogenic antigen born by cells against which P has acquired immunity.

The present invention provides the set or kit of n pharmaceutical unit doses comprising engineered cells and a pharmaceutically acceptable vehicle, according to the above comprising pharmaceutical unit doses obtained from P.

The set or kit of n pharmaceutical unit doses comprising engineered cells and a pharmaceutically acceptable vehicle, according to the above comprising pharmaceutical unit doses obtained from a donor different from P.

The set or kit of n pharmaceutical compositions according to any one of the above wherein n is at least 5.

The present invention generally provides the set or kit of n pharmaceutical unit doses, according to the above wherein cells in each pharmaceutical unit doses comprise at least one CAR or a TCR and said CAR or TCR is the same and/or is different, in the n successive doses.

The present invention generally provides the set or kit of n pharmaceutical unit doses, according to any one of the above wherein the immunogenic antigens born by cell in a pharmaceutical unit dose comprise at least a product encoded by at least one of the HLA alleles as described in http://hla.alleles.org/nomenclature/updates/201606.html.

The present invention provides the set of n pharmaceutical unit doses, according to any one of the above wherein the pharmaceutical unit doses are used sequentially by order of preference such that the pharmaceutical unit doses wherein immunogenic antigens born by engineered cells match those of the patient are used first, then the pharmaceutical unit doses wherein the immunogenic antigens born by the unengineered or engineered cells of the donors mismatch those of the donor P.

The present invention provides the set or kit of n pharmaceutical unit doses according to any one of the above for use as a medicament in immunotherapy for the prevention or treatment of a cancer.

The set or kit of n pharmaceutical unit doses for use according the above wherein said cancer is a relapse refractory cancer or a cancer complication such as metastasis is also provided.

In one aspect, the present invention provides a set or kit of n pharmaceutical unit doses comprising engineered cells and a pharmaceutically acceptable vehicle, for use according to the above wherein each pharmaceutical unit dose is in combination with at least one immunosuppressive drug.

The present invention provides a set or kit of n pharmaceutical unit doses comprising engineered cells and a pharmaceutically acceptable vehicle, for use according to the above wherein each pharmaceutical unit dose is in combination with a at least one of the following treatments selected from X-rays, gamma rays, charged particles, corticosteroid, biologic, antibody, inosine monophosphate dehydrogenase (IMDH) inhibitor, mtor inhibitor and a combination thereof.

The present invention provides the set or kit of n pharmaceutical unit doses comprising engineered cells and a pharmaceutically acceptable vehicle, for use according to the above wherein each pharmaceutical unit dose is in combination with fludarabine and cyclophosphamide.

The set or kit of n pharmaceutical unit doses comprising engineered cells and a pharmaceutically acceptable vehicle, for use according to the above, wherein each pharmaceutical unit dose is administered every 45 days and the day after fludarabine and cyclophosphamide that were administered for 3 to 5 days.

The present invention provides a set or kit of n pharmaceutical unit doses comprising engineered cells and a pharmaceutically acceptable vehicle, for use according to the above for use in a sequential treatment of a patient suffering a CLL, ALL, MM.

The present invention provides a bank of at least 230 donors for the preparation of a set or kit of n pharmaceutical unit doses according to any one of 1 to 14.

The present invention provides a bank of at least 230 donors for the preparation of a set or kit of n pharmaceutical unit doses according to any one of the above.

The present invention provides a set or kit of n pharmaceutical unit doses as any one of those described in Table 1.

In this embodiment, cell samples described in Table 1 were engineered so that the TCR was inactivated, a gene encoding a chimeric antigen receptor was introduced into each sample.

The present invention provides a method for preparing a set or a kit of n pharmaceutical unit doses comprising engineered cells and a pharmaceutically acceptable vehicle, comprising the step of:
  (a) genotyping and/or phenotyping the HLA molecules and/or HLA alleles of a patient P,
  (b) measuring and quantifying the existing antibodies and/or CTL responses of said patient P,
  (c) selecting and/or providing at least 5 samples of cells from a bank of donor(s) by choosing:
    (i) donors (donor cell samples) fully matching the immunogenic antigen born by cells of P,
    (ii) donors (donor cell samples) bearing a number of mismatching as low as possible, as compared to P, preferably selecting samples with no common antigen(s) between paired donors, and optionally modifying cells to match P,
  (d) modifying cells by introducing at least one CAR or TCR and/or inactivating at least one component of the TCR gene.

The present invention provides a method for preparing a set or a kit of n pharmaceutical unit doses comprising engineered cells and a pharmaceutically acceptable vehicle, comprising the step of:
  (a) genotyping and/or phenotyping the HLA molecules and/or HLA alleles of a patient P,
  (b) optionally measuring and quantifying the existing antibodies and/or CTL responses of said patient P,
  (c) selecting and/or providing at least 5 samples of cells from a bank of donor(s) by choosing:
    (iii) donors (donor cell samples) fully matching the immunogenic antigen born by cells of P, and/or
    (iv) donors (donor cell samples) bearing a number of mismatching as low as possible, as compared to P, preferably selecting samples with no common antigen(s) between paired donors,
    (v) optionally modifying cells to match P,
  (d) modifying cells by introducing at least one CAR or TCR and/or inactivating at least one component of the TCR gene.

In one aspect, the present invention provides a method for preparing a set or a kit of n pharmaceutical unit doses comprising engineered cells and a pharmaceutically acceptable vehicle, comprising the step of:
  selecting and/or providing cells from a bank of donor(s) by choosing using a computer software:
  donors (donor cell samples) with no common antigen(s) between paired donors, preferably said antigens are MHC molecules class I and/or class II, more preferably HLA-A, HLA-B, HLA-C, HLA DR, even more preferably HLA-A, HLA-B, HLA-C, HLA-DP, HLA-DQ, HLA-DR, HLA-DM, HLA-DOA, HLA-DOB,
  or donors (donor cell samples) with no common antigen(s) between paired donors, preferably said antigens are MHC molecules class I and/or class II, more preferably HLA-A, HLA-B, HLA-C, HLA DR, even more preferably HLA-A, HLA-B, HLA-C, HLA-DP, HLA-DQ, HLA-DR, HLA-DM, HLA-DOA, HLA-DOB,
  and the frequency of with which said alleles of said MHC molecule is detected is observed in the general population is comprised between 0.1% modifying cells by introducing at least one CAR or TCR and/or inactivating at least one component of the TCR gene, The present invention provides a method for preparing a set or a kit of n pharmaceutical unit doses comprising engineered cells and a pharmaceutically acceptable vehicle, comprising the step of:
  (e) optionally genotyping and/or phenotyping the HLA molecules and/or HLA alleles of a patient P,
  (f) optionally measuring and quantifying the existing antibodies and/or CTL responses of said patient P,
  (g) selecting and/or providing at least 5 samples of cells from a bank of donor(s) by choosing:
    (vi) donors (donor cell samples) bearing a number of mismatching as low as possible, as compared to P, preferably selecting samples with no common antigen(s) between paired donors,
    (vii) modifying cells to match P,
  (e) modifying cells by introducing at least one CAR or TCR and/or inactivating at least one component of the TCR gene.

The present invention generally provides a set or kit of n pharmaceutical unit doses comprising engineered cells and a pharmaceutically acceptable vehicle, for use as a sequential therapy, inducing no or reduced anamnestic immune reaction in one individual (P), as compared to an anamnestic reaction in said individual P if previously exposed to an immunogenic antigen born by cells, against which P has acquired immunity (preferably a T cell dependent antigen) and then subsequently grafted with a unit dose of engineered cells comprising said immunogenic antigen born by cells against which P has acquired immunity.

The present invention also provides a set or kit of n pharmaceutical unit doses comprising engineered cells and a pharmaceutically acceptable vehicle, for use either alone or in combination with at least one immunosuppressive drug.

In another aspect, the present invention also provides a set or kit of n pharmaceutical unit doses comprising engineered cells and a pharmaceutically acceptable vehicle, for use in combination with at least one immunosuppressive drug, as above wherein successive doses of the same sample of cells or of the same engineered cells are used as a sequential therapy or for redosing.

In another aspect, the present invention also provides a set or kit of n pharmaceutical unit doses comprising engineered cells and a pharmaceutically acceptable vehicle, according to any one of the above, in combination with a at least one of the following treatments selected from X-rays, gamma rays, charged particles, corticosteroid, biologics, antibody, inosine monophosphate dehydrogenase (IMDH) inhibitor, mtor inhibitor and a combination thereof.

In another aspect, the present invention also provides a set or kit of n pharmaceutical unit doses comprising engineered cells and a pharmaceutically acceptable vehicle, according to any one of the above, in combination with a at least one of the following treatments selected from corticosteroid, biologics, antibody, inosine monophosphate dehydrogenase (IMDH) inhibitor, mtor inhibitor and a combination thereof.

In another aspect, the present invention also provides a set or kit of n pharmaceutical unit doses comprising engineered cells and a pharmaceutically acceptable vehicle, according to the above comprising engineered cells and a pharmaceutically acceptable vehicle, for use combined with a at least two immunosuppressant drugs.

In another aspect, the present invention also provides the set or kit of n pharmaceutical unit doses comprising engineered cells and a pharmaceutically acceptable vehicle, according to the above for use in combination with or combined to fludarabine and cyclophosphamide.

In still another aspect, the present invention also provides a set or kit of n pharmaceutical unit doses comprising engineered cells and a pharmaceutically acceptable vehicle, according to any one of the above, for use in combination with fludarabine and cyclophosphamide, wherein said unit dose is administered and every 45 days and the day after fludarabine and cyclophosphamide that were administered for 3 to 5 days.

In another aspect, the present invention also provides a set or kit of n pharmaceutical unit doses comprising engineered cells and a pharmaceutically acceptable vehicle, according to the above for use in a patient suffering CLL.

In another aspect, the present invention also provides a set or kit of n pharmaceutical unit doses comprising engineered cells and a pharmaceutically acceptable vehicle, according to the above wherein each of the n doses is obtained from P.

In one aspect, the present invention also provides a set or kit of n pharmaceutical unit doses, according to as above wherein each of the n doses is obtained from a donor.

In one aspect, the present invention also provides a set or kit of n pharmaceutical unit doses, according to as above wherein each of the n doses is obtained from a different donor and different from P.

In one aspect, the present invention also provides a set or kit of n pharmaceutical compositions as above wherein n is at least 5.

In one aspect, the present invention also provides a set or kit of n pharmaceutical unit doses, according to any one of the above wherein cells in each pharmaceutical unit doses comprise at least one CAR or a TCR and said CAR or TCR is the same and/or is different, in the n successive doses.

In one aspect, the present invention also provides a set or kit of n pharmaceutical unit doses, according to any one of the above wherein the immunogenic antigens born by cell comprise at least a product encoded by at least one of the HLA alleles as described in http://hla.alleles.org/nomenclature/updates/201606.html as published in Nomenclature|How an allele is named|Nomenclature Reports|Nomenclature Updates|Nomencl ature Committee|HLA WorkshopsNomenclature for Factors of the HLA System-June 2016 with a date of identification and date of modification if modified.

Compiled by Steven G. E. Marsh for the WHO Nomenclature Committee for Factors of the HLA System.

Published In: HLA (2016) 88:142-51. Human Immunology (2016) 77:1309-17. International Journal of Immunogenetics (2016) 43:320-9.

The date at which these alleles were first identified is indicated in the database.

In addition, Annex I herewith enclosed reproduces alleles identified in http://hla.alleles.org/nomenclature/updates/201606.html as Jun. 29 2018.

The present invention includes the finished number of alleles as described in http://hla.alleles.org/nomenclature/updates/201606.html also reported in Annex I and dated before and on Jun. 30, 2017.

Immunogenic antigens born by the engineered cells comprise molecules of the MHC and others molecules, including a chimeric antigen receptor.

In one aspect, the present invention also provides a set or kit of n pharmaceutical unit doses, according to any one of the above wherein the set or kit of n doses is, for use as a sequential therapy.

Each dose of a set or kit of n pharmaceutical unit doses, according to the present invention is administered to a Patient P in a need thereof, one after the other with a time interval between two administrations ranging from 1 hours to 20 years.

In one aspect, the present invention also provides a set or kit of n pharmaceutical unit doses, according to any one of the above wherein the set or kit of n doses is provided, for use as a sequential therapy said sequential therapy comprising administering first, doses comprising immunogenic antigens born by the engineered cells fully matching those of the patient P and then cells matching those of P either originally from matching donors and engineered or from cells that were engineered not only to target a cancer, but also to match as much as possible the immunogenic antigens born by the cells of P.

In the case of cells fully matching with P, (immunogenic antigens born by the engineered cells fully match immunogenic antigens born by cells of P), cells are most preferably originally from P, preferably obtained when P was healthy.

Matching according to the present invention means the most preferably at least 10 HLA markers (alleles) out of 10 (10/10) matching with P: two A markers, two B markers, two C markers, two DRB1 markers and two DQ, to match, when cells are not from P.

Less matching may be permitted with the limit of mismatching being set as 2 mismatching out of 10, and some mismatching to be avoided to be defined as below.

For example, an adult donor should match at least 6 of the 8 HLA markers (two A markers, two B markers, two C markers, two DRB1 markers), Preferably, at least a 7 of 8 match.

If using cord blood cells as original material, a cord blood unit should match at least 4 of 6 (4/6) again no more than 2 mismatches) markers at HLA-A, -B, and -DRB1

In the case of matching donors, cells may be from matching twins, siblings, donors with from most preferred to less preferred 10/10, 9/9, 8/8, 7/7, 6/6 HLA matching or any of such cells engineered to match P.A third category of engineered cells may be present in a set of or kit of n pharmaceutical unit doses, according to the present invention, comprising cells with 2 HLA mismatches. In that later case, cells in a set or a kit should never bear the same mismatches as any other cell samples in the set or kit so that P will never be exposed two times to the same antigen born by cell.

If P already benefited from a transplant, cells tissue or organ, cells in a set or a kit should never bear the same mismatches as any other cell samples in the set or kit and as those in previous grafts if any.

The present invention contemplates a set of or kit of n pharmaceutical unit doses, consisting of cells having no more than two mismatches with P and said two mismatches are different in all the n pharmaceutical unit doses, optionally with mismatches expressed from previous grafts, P was engrafted with, unless P had a bone marrow transplant. In that later case, the set of or kit of n pharmaceutical unit doses, should consist of cells having no more than two mismatches between them in the n pharmaceutical unit doses and with the HLA of the transplant.

In all cases, immunogenic antigens born by the engineered cells must avoid expressing or bearing any immunogenic antigen against which the individual is already immunized against. This is achieved by identifying the preexisting immune response in P.

The level of detection of HLA (or HLA typing) is at least by serology, by analyzing the Ab present in P using for example microlymphocytotoxicity test, and at best by a molecular method known in the art.

P may receive as a successive treatment, first, doses comprising immunogenic antigens born by the engineered cells, fully matching those of the patient P, and then doses comprising immunogenic antigens born by the engineered cells of the donors of n doses that do not match those of the patient.

In other words, the CAR-T cells fully matching P (in terms of HLA molecules) are preferably and at first administered to P (autologous transfer, graft with cells from matching individuals, twins, siblings, haploidentical cells, allogenic cells engineered to have no MHC molecules, or to match P), then if not available, allogenic cells having no common antigen by pair—to avoid exposing P twice to the same antigen; moreover, particular mismatching are avoided and particular detrimental sequential injections are avoided. (see below for particular combination of successive doses to be avoided.

In one aspect, the present invention also provides a set or kit of n pharmaceutical unit doses according to any one of the above for use as a medicament in immunotherapy for the prevention or treatment of cancer.

In one aspect, the present invention also provides a set or kit of n pharmaceutical unit doses according to the above for the treatment of a relapse refractory cancer or of cancer complications such as metastasis.

In one aspect, the present invention also provides a set or kit of n pharmaceutical unit doses as any one of those described in Table 1.

In one aspect, the present invention also provides a bank of at least 230 donors for the preparation of a set or kit of n pharmaceutical unit doses according to any one of the above.

In one aspect, the present invention also provides a method for preparing a set or a kit of n pharmaceutical unit doses comprising engineered cells and a pharmaceutically acceptable vehicle, comprising the step of:
  i) genotyping and/or phenotyping the HLA molecules and/or HLA alleles of a patient P (optional),
  ii) measuring and quantifying the existing antibodies and/or CTL responses of said patient P (optional),
  iii) selecting and/or providing at least 5 samples of cells from human donor(s) by choosing:
    a) samples of cells fully matching the immunogenic antigen born by cells of P, or
    a') choosing samples of cells bearing a number of mismatching as low as possible, as compared to P, modifying cells for cells to match P or
      modifying cells for cells to express no antigen born by cells potentially inducing an anamnestic response, or
    a") selecting samples with the less possible of common antigen(s) with each other and with those to which P was previously immunized against,
  iv) modifying cells by introducing at least one CAR or one TCR and/or inactivating at least one component of the TCR gene.

In one aspect, the present invention provides a method for preparing a set or a kit of n pharmaceutical unit doses comprising engineered cells and a pharmaceutically acceptable vehicle, comprising the step of:
  genotyping and/or phenotyping the HLA molecules and/or HLA alleles of a patient P (optional),
  measuring and quantifying the existing antibodies and/or CTL responses of said patient P (optional),
  selecting and/or providing at least 5 samples of cells from human donor(s) by choosing
    samples of cells fully matching the immunogenic antigen born by cells of P, or
    samples of cells bearing a number of mismatching as low as possible, as compared to P,
  or
    modifying cells for cells to match the HLA allele of P, or
    modifying cells for cells to express no antigen born by cells potentially inducing an anamnestic response, or
    selecting samples with no common antigen(s) with each other and with those to which P was previously immunized against,
  v) modifying cells by introducing at least one CAR or one TCR and/or inactivating at least one component of the TCR gene.

In one aspect, the present invention provides a method for preparing a set or a kit of n pharmaceutical unit doses comprising engineered cells and a pharmaceutically acceptable vehicle, comprising the step of:

selecting and/or providing at least 5 samples of cells from human donor(s) by choosing:
samples with no common antigen(s) with each other and with those to which P was previously immunized against,
vi) modifying cells by introducing at least one CAR or one TCR and/or inactivating at least one component of the TCR gene.

The set or kit of n pharmaceutical unit doses comprising engineered cells and a pharmaceutically acceptable vehicle of the invention wherein each of the n doses is obtained from P.

The set or kit of n pharmaceutical unit doses, according to the above wherein each of the n doses is obtained from a donor, and at least one of the donors is P.

The set or kit of n pharmaceutical unit doses, according to the above wherein each of the n doses is obtained from a different donor and different from P.

The set or kit of n pharmaceutical compositions according to the above wherein n is at least 5.

The set or kit of n pharmaceutical unit doses, according to the above wherein cells in each pharmaceutical unit doses comprise at least one CAR or one TCR and said CAR or TCR is the same and/or is different, in the n successive doses.

The set or kit of n pharmaceutical unit doses, according to the above wherein the immunogenic antigens born by cell comprise at least a product encoded by at least one of the HLA alleles as described in http://hla.alleles.org/nomenclature/updates/201606.html.

The set or kit of n pharmaceutical unit doses, according to the above wherein the immunogenic antigens born by cell are variant alleles of the products encoded by the following loci: HLA-A, HLA-B, HLA-C, HLA-DP, HLA-DQ and HLA-DR, or a combination thereof.

The set or kit of n pharmaceutical unit doses according to the above, wherein matching engineered cells to cells of P corresponds to an HLA typing preferably (to a molecular HLA typing), more preferably to a high resolution molecular typing] with a score of 7/7, preferably 8/8 and more preferably 9/9, and ideally 10/10, with the HLA typing of cells of P.

The set or kit of n pharmaceutical unit doses according to any one of the above characterized in that the HLA typing of at least one of the n doses and preferably of all n doses is 10/10 high resolution match at HLA-A, -B, -C, DRB1 and DQB11 loci.

The set or kit of n pharmaceutical doses according to the above, characterized in that the HLA typing of at least one of the n doses, matches (with a score of 6/6 or 7/7, preferably 8/8 and more preferably 9/9 or 10/10) the HLA typing of the patient P and comprises at most one mismatch at a locus selected from HLA-A,-B, -C, -DRB1 or DQB11 locus, preferably a single mismatch at a locus selected from HLA-A,-B, -DRB1 or DQB11 locus more preferably at HLA-DQ and less preferably at HLA-C.

The set or kit of n pharmaceutical unit doses, according to any one of the above wherein the doses are used as a sequential therapy by order of preference such that:
The immunogenic antigens born by the un engineered or engineered cells of the donors of the n doses match those of the patient,
The immunogenic antigens born by the un engineered or engineered cells matching those of P are first used then if mismatching, the mismatching immunogenic antigens born by the un engineered or engineered cells should be different in each of the unit dose used (after the other one) so that P is never exposed twice to the same antigen. Even if an immune response is developed in P, P will not be reexposed to the antigen against which P developed an immune response.

Thus, the immunogenic antigens born by the un engineered or engineered cells of the donors of n-m (with n≥m≥2) of the n doses all match those of the patient, and if Mk is the set of immunogenic antigen(s) unmatched with P present in the k-th of the m consecutive not matched doses, then the k-th of these m administered doses (with k 2) should not to bear the immunogenic antigens present in the union of M1, M2, . . . , M(k−1). In addition, M1 may avoid any immunogenic antigen against which the individual is already immunized against.

The set or kit of n pharmaceutical unit doses, according to the above in which
the doses including engineered cells bearing immunogenic antigens all fully matching those of the patient are administered before the other doses, which are administered after, in the increasing level of mismatch.

The set or kit of n pharmaceutical unit doses, according to the above in which the doses of engineered cells bearing immunogenic antigens not fully matched with the immunogenic antigens of the patient are administered in the increasing order of mismatch with the patient and, when bearing the same number of said mismatch, in the preferred order as follows:
(If already exposed to a mismatch for A) then use (mismatched for B) before (mismatched for DQB1),
(If already exposed to a mismatch for A) then use (mismatched for C) before (mismatched for DQB1),
(If already exposed to a mismatch for C) then use (mismatched for A) before (mismatched for B),
(If already exposed to a mismatch for C) then use (mismatched for A) before (mismatched for DRB1),
(If already exposed to a mismatch for C) then use (mismatched for DQB1) before (mismatched for DRB1),
(If already exposed to a mismatch for DPB1) then use (mismatched for DQB1) before (mismatched for DRB1),
(If already exposed to a mismatch for DQB1) then use (mismatched for A) before (mismatched for B),
(If already exposed to a mismatch for DQB1) then use (mismatched for A),
(If already exposed to a mismatch for DQB1) then use (mismatched for C) before (mismatched for A),
(If already exposed to a mismatch for DPB1) then use (mismatched for DRB3,4,5) before (mismatched for C),
(If already exposed to a mismatch for DQB1) then use (mismatched for A) before (mismatched for DRB3,4,5),
(If already exposed to a mismatch for DPB1, DRB3,4,5) then use (mismatched for DQB1) before (mismatched for C),
(If already exposed to a mismatch for C, DRB3,4,5, DQB1, DPB1) then use (mismatched for A) before (mismatched for B, DRB1).

The set or kit of n pharmaceutical doses according to any one of the above characterized in that the following matches are recommended for a dose of engineered cells per kilogram body weight:
at least 6/6 HLA match for a dose comprising >3×10$^7$ engineered cells per kilogram body weight or above,
at least 5/6 HLA match for a dose comprising >4×10$^7$ engineered cells per kilogram body weight or above, at least 4/6 HLA match for a dose comprising >5×10⁷ engineered cells per kilogram body weight or above.

The set or kit of n pharmaceutical unit doses according to any one of the above, characterized in that each of their HLA allele unmatched with P has a frequency in the human population of less than 6% but more than 0.1%.

The set or kit of n pharmaceutical unit doses according to any one of the above, characterized in that sequential administration of engineered cells bearing HLA alleles mismatched with P in haplotypes A/DRB1 followed by mismatched with P in haplotypes B/C followed by mismatched with P in haplotypes DQ should be avoided.

The set or kit of n pharmaceutical unit doses according to any one of the above characterized in that said engineered primary cells are HLA haploidentical to P.

The set or kit of n pharmaceutical unit doses according to any one of the above wherein said engineered cells in each dose express at least one CAR and/or a TCR targeting a molecule constitutively or temporarily over expressed on pathological cells as compared to healthy cells or expressed only on pathological cells.

The set or kit of n pharmaceutical unit doses according to any one of the above wherein said at least one CAR or TCR is specific for a molecule selected from a group consisting of: DR4, CD19, CD123, CD20, CD22, CD38, CD30, CS-1, CLL-1, HSP70, BCMA, VEGF, DR4, GD2, the cancer testis (CT) antigens, MUC1, GD2, o acetyl GD2, HM1.24 (CD317), CYP1B1, SP17, PRAME, Wilms' Tumour 1 (WT1), heat shock protein gp96, thyroid stimulating hormone receptor (TSHR); CD171; CS-1 (CD2 subset 1, CRACC, SLAMF7, CD319, and 19A24); C-type lectin-like molecule-1 (CLL-1); ganglioside GD3 (aNeu5Ac(2-8) aNeu5Ac(2-3)bDGalp(I-4)bDGlcp (I-I)Cer); Tn antigen (Tn Ag); Fms-Like Tyrosine Kinase 3 (FLT3); CD38; CD44v6; B7H3 (CD276); KIT (CD117); Interleukin-13 receptor subunit alpha-2 (IL-13Ra2); Interleukin 11 receptor alpha (IL-IIRa); prostate stem cell antigen (PSCA); Protease Serine 21 (PRSS21); vascular endothelial growth factor receptor 2 (VEGFR2); Lewis (Y) antigen; CD24; Platelet-derived growth factor receptor beta (PDGFR-beta); stage-specific embryonic antigen-4 (SSEA-4); Mucin 1, cell surface associated (MUC1); epidermal growth factor receptor (EGFR); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Fucosyl GM1; sialyl Lewis adhesion molecule (sLe); ganglioside GM3 (aNeu5Ac(2-3)bDGalp(I-4)bDGlcp(I-I)Cer; TGS5; high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Cytochrome P450 1B 1 (CYP1B 1); CCCTC-Binding Factor (Zinc Finger Protein)-Like (BORIS); Squamous Cell Carcinoma Antigen Recognized By T Cells 3 (SART3); Paired box protein Pax-5 (PAX5); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLECi2A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1) and a combination thereof, preferably chosen from DR4, CD19, CD123, CD20, CD22, CD38, CD30, CS-1, CLL-1, HSP70, BCMA, VEGF, DR4, GD2, O-acethyl GD2, the cancer testis (CT) antigens, MUC1, MUC16, HM1.24 (CD317), CYP1B1, SP17, PRAME, Wilms' tumour 1 (WT1), heat shock protein gp96, claudine18.2, and a combination thereof.

The set or kit of n pharmaceutical unit doses according to any one of the above for use as a medicament in immunotherapy.

The set or kit of n pharmaceutical unit doses according to any one of the above for use as a medicament in immunotherapy for the prevention or treatment of cancer.

The set or kit of n pharmaceutical unit doses according to any one of above for use as a medicament in immunotherapy for the prevention or treatment of infectious disease, for the clearance of chronical viral infection.

The set or kit of n pharmaceutical unit doses according to any one of the above for the treatment of a relapse refractory cancer or of cancer complications such as metastasis.

The set or kit of n pharmaceutical unit doses according to any one of the above as described in Table 1.

The set or kit of n pharmaceutical unit doses according to any one of the above for the treatment of hematological cancers, of solid cancers or of hematological and solid cancers.

The set or kit of n pharmaceutical unit doses according to any one of the above for the treatment of successive cancers, of successive hematological cancers, of successive solid cancers or of successive hematological and solid cancers.

A hematological cancer or hematological malignancies means cancers that affect the blood and lymph system. The cancer may begin in blood-forming tissue (e.g., bone marrow), or in the cells of the immune system. Some types of hematologic malignancies include: LeukemiaNon-Hodgkin lymphoma, Hodgkin lymphoma, Multiple myeloma. Are included in hematological cancers any cells in the blood of lymph node that began in a tissue and circulates in the blood.

The set or kit of n pharmaceutical unit doses according to any one of the above wherein each dose is used in combination with another drug, in combination with another anti-cancer drug, anti-GVHD drug and engineered cells in said dose are engineered to be resistant to said drug.

The set or kit of n pharmaceutical unit doses according to any one of the above wherein engineered cells comprise at least one inactivated gene coding for a TCR alpha subunit, wherein engineered cells comprise at least one inactivated gene coding for a TCR alpha subunit allele.

The set or kit of n pharmaceutical unit doses according to any one of the above wherein engineered cells comprise an inactivated beta2 microglobulin gene, an inactivated CTIIA gene or genes modification for MHC molecules matching those of P.

The set or kit of n pharmaceutical unit doses comprising engineered cells and a pharmaceutically acceptable vehicle, according to the above wherein engineered cells comprise at least one inactivated gene coding for a TCR subunit and an inactivated beta2 microglobulin gene.

The set or kit of n pharmaceutical unit doses comprising engineered cells and a pharmaceutically acceptable vehicle, according to the above wherein engineered cells comprise at least one inactivated gene coding for a TCR alpha subunit and an inactivated CTIIA gene.

The set or kit of n pharmaceutical unit doses comprising engineered cells and a pharmaceutically acceptable vehicle, according to the above wherein engineered cells comprise at least one inactivated gene coding for a TCR alpha subunit and genes modification for MHC molecules matching those of P.

The set or kit of n pharmaceutical unit doses comprising engineered cells and a pharmaceutically acceptable vehicle, according to the above wherein at least one inactivated gene coding for a TCR alpha subunit and an inactivated CTIIA gene and genes modification for MHC molecules matching those of P.

The set or kit of n pharmaceutical unit doses according to any one of the above wherein engineered cells in at least one dose comprise a deletion, an insertion or a mutation conferring resistance to an anti-cancer drug.

The set or kit of n pharmaceutical unit doses according to any one of the above wherein engineered cells in at least one dose comprise a deletion, an insertion or a mutation conferring resistance to an anti-cancer drug affecting the activity of CAR-T cells.

The set or kit of n pharmaceutical unit doses according to any one of the above wherein engineered cells in at least one dose comprise a deletion, an insertion or a mutation conferring resistance to an anti-cancer drug wherein said anti-cancer drug at a dose having an anticancer activity alters the efficiency of CART-T cells, and/or the survival of T cells.

The set or kit of n pharmaceutical unit doses according to any one of the above wherein engineered cells in at least one dose comprise a deletion, an insertion or a mutation conferring resistance to PNA.

PNA means purine nucleoside analogs.

The set or kit of n pharmaceutical unit doses according to any one of the above wherein engineered cells in at least one dose comprise an inactivated gene encoding one of the following molecules, CD52, Deoxycytidine kinase (dCK), glucocorticoid receptor (GR) and a combination thereof.

Deoxycytidine kinase (dCK) is an enzyme which is encoded by the DCK gene in humans.

The set or kit of n pharmaceutical unit doses according to any one of the above wherein cells in at least one dose are engineered to be resistant to tumor-induced hypoxia, to tumor-induced adenosine, to tumor-induced inhibition of anti-cancer cells activity by cytokines and/or chemokines.

The set or kit of n pharmaceutical unit doses according to any one of the above wherein n is at least 2, wherein n is at least 3, or 3, at least 4, or 4, at least 5, or 5, at least 6, or 6, at least 7, or 7, at least 8, or 8, at least 9, or 9 at least 10 or 10, preferably 5.

A bank of at least 230 donors for the preparation of a set of n pharmaceutical unit doses according to any one of the above.

The bank according to the above, for the preparation of a set of n pharmaceutical unit doses, with n is at least 5, or 5 comprising engineered cells.

The bank according to the above, for use to prepare a set of n pharmaceutical unit doses according to any one of claim 1 to 33 as a medicament for immunotherapy in one individual patient P in a need thereof.

The bank according to the above, for use to prepare a set of n pharmaceutical unit doses according to any one of the above as a medicament for immunotherapy in one individual patient P in a need thereof.

The bank according to the above, for use to prepare a set of n pharmaceutical unit doses according to any one the above as a medicament for immunotherapy in one individual patient P in a need thereof.

The bank according to the above, wherein the donors used for preparing the set of n pharmaceutical unit doses of engineered cells, exclude previous donors of cells, organ or tissues in P, unless said donor is P.

The bank according to the above, wherein are excluded previous donors of cells, organ or tissues in P, unless said donor is P.

The bank according to any one of the above, wherein the donors have no common allele between paired two donors unless the common allele matches those of P.

The bank according to any one of the above, wherein the donors have no common allele between paired two donors, and said non common allele between paired two donors comprises at least 1 locus involved in anamnestic response, or said non common allele between paired two donors comprising one of the following loci HLA-A, HLA-B, HLA-C, HLA-DP, HLA-DQ and HLA-DR, preferably HLA-C, more preferably HLA-C, HLA-DP, HLA-DQ and HLA-DR, or said non common allele between paired two donors comprising at least 1 locus involved in anamnestic response, and said non common allele between paired two donors comprising the following loci HLA-A, HLA-B, HLA-C, HLA-DP, HLA-DQ and HLA-DR, preferably HLA-C, more preferably HLA-C, HLA-DP, HLA-DQ and HLA-DR.

The present invention provides a bank according to any one of the above, wherein the donors have no common allele between paired two donors, and said non common allele between paired two donors comprises at least 1 locus involved in anamnestic response, and/or said non common allele between paired two donors comprise one of the following loci HLA-A, HLA-B, HLA-C, HLA-DP, HLA-DQ and HLA-DR, or said non common allele between paired two donors comprise at least 1 locus involved in anamnestic response, and said non common allele between paired two donors comprising the following loci HLA-A, HLA-B, HLA-C and HLA-DR.

The bank according to any one of the above, wherein engineered cells are beta2 microglobulin deficient and/or CTIIA deficient and said non common allele between paired two donors comprises the following molecules, HLA-DP, HLA-DQ, and HLA-DR.

The bank according to any one of the above, wherein engineered cells are beta2 microglobulin deficient and/or CTIIA deficient and said non common allele between paired two donors comprises a molecules of the MHC which expression is not regulated by beta2 microglobulin or CTIIA.

The present invention also provides a set or kit of n pharmaceutical unit doses comprising engineered cells and a pharmaceutically acceptable vehicle, inducing no or reduced anamnestic immune reaction in one individual (P), as compared to an anamnestic reaction in said individual P if previously exposed to an immunogenic antigen born by cells, against which P has acquired immunity (preferably a T cell dependent antigen) and then subsequently grafted with a unit dose of engineered cells comprising said immunogenic antigen born by cells against which P has acquired immunity wherein engineered cells exhibit at least two HLA mismatches with cells of P and are administered in combination with a treatment that allows said cells to be tolerated by the host and have an anti-cancer activity for at least 45 days, and (administered) every 45 days for 45 days, 90 days, 135 days, 180 days, 225 days, or 270, 315 days.

The bank according to any one of the above wherein each pharmacological unit dose of cells is administered to one individual P in a time interval between two administrations ranging from an half day, one day, two days, three days four days, five days, six days, seven days, eight days, nine days, ten days, eleven days, twelve days, thirteen days, fourteen days, fifteen days, sixteen days, seventeen days, eighteen days, nineteen days, twenty days, 30 days, 40 days, 45 days, 50 days, 60 days, 90 days, 120 days, 180 days, 225, 270, 315, 8 months, 12 months a year, 2 years, 3 years, 4, 5, 6, 7, 8, 9, 10 years, 11, 12, 13, 14, 15, 16, 17, 18, 19, 20, 30, 40, 50, 60, 70, years to 90 years, preferably 6 months or any time between an half day and 80 years.

The bank according to any one of the above comprising at most 230 different donors for preparing a set of 5 successive pharmaceutical unit doses of chimeric antigen receptor (CAR) or TCR expressing engineered primary cells.

The bank according to any one of the above comprising at least 230 different donors for preparing a set of n successive pharmaceutical unit doses of chimeric antigen receptor (CAR) or TCR expressing engineered primary cells, n>5.

The bank according to any one of the above wherein the HLA of at least one donor match those of the previous graft (bone marrow) and may not fully match those of P, to prevent a Host versus graft rejections. (match between the treatment and a previous graft).

The set of 5 doses of engineered primary cells according to the above wherein said engineered primary cells comprise at least one inactivated TCR gene allele.

The set of 5 doses of engineered primary cells as in Table 1 endowed with at least one CAR or a with a T cell receptor (TCR).

A set or kit of 5 doses of engineered primary cells as above comprising one of the following haplotype (A-B-DRB1):
29-58-0807
68-75-0413
32-42-0302
2-70-1322
69-35-1305

A set or kit of 5 doses of engineered primary cells as above wherein cells comprises one of the following haplotype (A-B-DRB1)
29-58-0807
68-75-0413
32-42-0302
2-70-1322
69-35-1305

A method for preparing a set of n pharmaceutical unit doses comprising engineered cells and a pharmaceutically acceptable vehicle, comprising the step of:
genotyping and/or phenotyping the HLA molecules or HLA alleles of a patient P, as performed in WO0161043 (A2), or WO0161043 (A3), or WO0161043 (A9),
measuring and quantifying the existing antibodies and/or CTL responses of said patient,
selecting and/or providing at least 5 samples of cells (grafts) from 5 different human donors by choosing by order of preference:
samples of cells fully matching the immunogenic antigen born by cells of P, comprising no immunogenic antigen P was already immunized against, or
samples of cells bearing a number of mismatching immunogenic antigens born by cells as low as possible, as compared to those of P (including immunogenic antigen P was already immunized against) and
modifying cells for altering the expression of said immunogenic antigens born by cells P was already immunized against if any and either modifying cells for matching said immunogenic antigens born by cells to the immunogenic antigens born by cells of P or
modifying cells so that they do not express any potentially anamnestogenic molecule (inducing an anamnestogenic response), or
selecting samples with the less possible of common antigen with each other and with those to which P was previously immunized against unless they match those of P,
selecting samples with no common antigen with each other and with those P was previously immunized against, unless they match those of P,
modifying cells by introducing at least one CAR or TCR different in each sample and/or inactivating at least one component of the TCR gene.

A method for preparing a set of n pharmaceutical unit doses comprising engineered cells and a pharmaceutically acceptable vehicle, comprising the step of:
genotyping and/or phenotyping the HLA molecules or HLA alleles of a patient P, as performed in WO0161043 (A2), or WO0161043 (A3), or WO0161043 (A9),
measuring and quantifying the existing antibodies and/or CTL responses of said patient,
selecting and/or providing at least 5 samples of cells (grafts) from 5 different human donors by choosing by order of preference:
samples of cells fully matching the immunogenic antigen born by cells of P, comprising no immunogenic antigen P was already immunized against and modifying cells by introducing at least one CAR or TCR different in each sample and/or inactivating at least one component of the TCR gene.
or
samples of cells bearing a number of mismatching immunogenic antigens born by cells as low as possible, as compared to those of P (including immunogenic antigen P was already immunized against) and
modifying cells for altering the expression of said immunogenic antigens born by cells P was already immunized against if any and either modifying cells for matching said immunogenic antigens born by cells to the immunogenic antigens born by cells of P and modifying cells by introducing at least one CAR or TCR different in each sample and/or inactivating at least one component of the TCR gene.

or modifying cells so that they do not express any potentially anamnestogenic molecule (inducing an anamnestogenic response), and modifying cells by introducing at least one CAR or TCR different in each sample and/or inactivating at least one component of the TCR gene.

or selecting samples with no common antigen with each other (preferably no common antigen) and with those P was previously immunized against, unless they match those of P, and modifying cells by introducing at least one CAR or TCR different in each sample and/or inactivating at least one component of the TCR gene. In a particular embodiment, a method is provided for preparing a set of n pharmaceutical unit doses comprising engineered cells and a pharmaceutically acceptable vehicle, comprising the step of:

a) genotyping the HLA molecules of P,
b) measuring and quantifying the existing antibodies and/or CTL responses of said patient,
c) selecting and/or providing samples of cells by choosing samples of cells matching the immunogenic antigen born by cells of P,
d) modifying cells by introducing at least one CAR or TCR different in each sample and/or inactivating at least one component of the TCR gene.

In step c) cells in the n pharmaceutical unit doses are either naturally matching cells of P or are engineered for matching with cells of P.

In particular embodiments, in the method of the invention provided, the immunogenic antigens born by the engineered cells of the donors of n-m (with n≥m≥2) of the n doses obtained at the end of the selection and engineering all match those of the patient, and if Mk is the set of immunogenic antigen(s) unmatched with P present in the k-th of the m consecutive not matched doses, then the k-th of these m administered doses (with k 2) should not to bear the immunogenic antigens present in the union of M1, M2, . . . , M(k-1). In addition, M1 may avoid any immunogenic antigen against which the individual is already immunized against.

The method for preparing a set of n pharmaceutical unit doses comprising engineered cells and a pharmaceutically acceptable vehicle, according to the above, wherein the step of modifying cells comprises:

introducing at the same time into said cells:
at least one nucleic acid comprising an exogenous nucleotide or polynucleotide sequence, and
at least one sequence-specific reagent that specifically targets a selected endogenous locus in the genome, preferably said endogenous locus is an endogenous locus encoding a TCR gene A or B.

"At the same time" means simultaneously or just one after the other (within an interval of hours).

A method for engineering cells is described in PCT/EP2017/076798 incorporated herein by reference in its entirety. In one embodiment introducing at the same time into said cells:
at least one nucleic acid comprising an exogenous nucleotide or polynucleotide sequence, and
at least one sequence-specific reagent that specifically targets a selected endogenous locus in the genome, preferably said endogenous locus is an endogenous locus encoding a TCR gene A or B, is performed using adeno associated virus particles.

The method according to the above, wherein the immunogenic antigens born by cell comprises one of the HLA molecules selected from any one of those described in http://hla.alleles.org/nomenclature/updates/201606.html.

Indeed, it now well established that MHC molecules are involved in immune response against foreign antigen.

It is admitted that HLA class II (HLA-II) molecules or proteins present on the cell surface peptide antigens from extracellular proteins including proteins of an extracellular pathogen, while HLA class I proteins present peptides from intracellular proteins or pathogens. Sugars may be also presented. Loaded HLA class II proteins on the cell surface interact with CD4+ helper T cells. The interaction leads to recruitment of leukocytes, inflammation, and/or B cells-mediated humoral responses. Several HLA class II gene loci have been identified to date, including HLA-DM (HLA-DMA and HLA-DMB that encode HLA-DM a chain and HLA-DM 3 chain, respectively), HLA-DO (HLA-DOA and HLA-DOB that encode HLA-DO α chain and HLA-DO β chain, respectively), HLA-DP (HLA-DPA and HLA-DPB that encode HLA-DP α chain and HLA-DP β chain, respectively), HLA-DQ (HLA-DQA and HLA-DQB that encode HLA-DQ α chain and HLA-DQ β chain, respectively), and HLA-DR (HLA-DRA and HLA-DRB that encode HLA-DR α chain and HLA-DR β chain, respectively).

The method according to any one of the above, wherein the immunogenic antigens born by cell comprises at least one of the HLA molecules selected from HLA-A, HLA-B, HLA-C, HLA-DR, and a combination thereof.

The method according to any one of the above, wherein HLA of samples match more than 80% to the HLA of P.

The method according to any one of the above, comprising a step of genetically engineering cells to inactivate at least one immune check point.

A method according to any one the above, comprising a step of genetically engineering cells conferring resistance to a drug.

The method according to any one of the above, comprising a step of genetically engineering cells for matching immunogenic antigens born by cells to those of P.

The method according to any one of the above, comprising a step of genetically engineering cells for matching immunogenic antigens born by cells to those of previous graft in P.

The method according to any one the above, wherein the step of genetically engineering cells is performed by the use of specific rare-cutting endonuclease.

The method according to any one of the above, wherein said rare-cutting endonuclease is a TALE-nuclease or a CRISPR/Cas nuclease.

The method according to any one the above, wherein the step of genetically engineering cells is performed by the use of specific rare-cutting endonuclease using technic as in WO2016183345 (A1).

The method according to any one of the above, wherein the step of genetically engineering cells is performed by homologous recombination mediated gene targeting.as in PCT/EP2017/076798 or In WO2014153470A2 with Zn finger endonucleases or WO2014204729A1.

The method according to any one of the above, wherein the step of choosing samples of cells comprises selecting a triple homozygote on HLA-A, HLA-B and HLA-DR genes.

The method according to any one of the above, wherein the step of choosing samples of cells comprises selecting a double homozygote on 2 of HLA-A, HLA-B and HLA-DR genes.

The method according to any one of the above, wherein the step of choosing samples of cells comprises selecting a donor available in database.

The method according to any one of the above, wherein the step of choosing samples of cells comprises selecting a donor available in database whose genotype of his HLA alleles has a frequency in the human population of less than 6% but more than 0.1%.

The method according to any one of the above, wherein the step of choosing samples of cells comprises selecting a donor available in database whose genotype of his HLA A, B, C and DR alleles has a frequency in the human population of less than 6% but more than 0.1%.

The method according to any one of the above, wherein a donor is defined as belonging to subpopulation selected from Caucasian, African, Asian.

The method according to any one claim of the above wherein a donor is defined according to at least one genetic marker according to The Human Genome Project1, the SNP Consortium2 and/or the International HapMap Project3 comprising ~10 million common DNA variants.

In still another aspect, the present inventors provide a kit of n pharmaceutical unit doses comprising engineered cells and a pharmaceutically acceptable vehicle, wherein each unit dose is combined to a at least two immunosuppressant drugs.

In still another aspect, the present inventors provide a kit of n pharmaceutical unit doses comprising engineered cells and a pharmaceutically acceptable vehicle, wherein each unit dose is combined to fludarabine and cyclophosphamide.

In still another aspect, the present inventors provide a kit of n pharmaceutical unit doses comprising engineered cells and a pharmaceutically acceptable vehicle, as above wherein said kit or set is combined to fludarabine and cyclophosphamide and administered periodically, said period being every 45 days, or every 20 day to every 50 days.

In still another aspect, the present inventors provide a kit of n pharmaceutical unit doses comprising engineered cells and a pharmaceutically acceptable vehicle, for use just after fludarabine and cyclophosphamide administered for 3 to 5 days every 45 days.

In still another aspect, the present inventors provide a kit of n pharmaceutical unit doses comprising engineered cells and a pharmaceutically acceptable vehicle, for use just after fludarabine and cyclophosphamide administered for 3 to 5 days every 45 days for use in a patient suffering CLL.

In still another aspect, the present inventors provide a kit of n pharmaceutical unit doses comprising engineered cells expressing a CAR specific for CD123 and a pharmaceutically acceptable vehicle, for use just after fludarabine and cyclophosphamide administered for 3 to 5 days every 45 days for use in a patient suffering AML.

In still another aspect, the present inventors provide a kit of n pharmaceutical unit doses comprising engineered cells expressing a CAR specific for CD22 and/or CD19 and a pharmaceutically acceptable vehicle, for use just after fludarabine and cyclophosphamide administered for 3 to 5 days every 14 days, 30 days, 45 days, or for use in a patient.

The method for preparing a kit of n pharmaceutical unit doses of the invention is provided and in particular embodiments comprises a step of introducing into cells:

i) at least one nucleic acid comprising an exogenous polynucleotide sequence to be integrated at a selected endogenous locus to encode at least one NK cell inhibitor;

ii) at least one sequence-specific reagent that specifically targets said selected endogenous locus, wherein said exogenous polynucleotide sequence is inserted by targeted gene integration into said endogenous locus.

In the Method provided just below said sequence specific reagent comprises a nuclease, preferably a specific endonuclease reagent, and more preferably a TAL-nuclease, said specific endonuclease reagent may be selected from a RNA or DNA-guided endonuclease, such as Cas9 or Cpf1, a RNA or DNA guide, a TAL-endonuclease, a zing finger nuclease, a homing endonuclease or any combination thereof.

In the Method provided, said targeted gene integration is operated by homologous recombination or NHEJ into said immune cells.

In the Method provided, the exogenous polynucleotide sequence may be integrated under transcriptional control of an endogenous promoter present at said locus.

The Method provided may be a method, wherein said endogenous locus at which the exogenous polynucleotide sequence may be integrated is a locus expressing a MHC I component, such as B2m.

The Method provided may be a method, wherein insertion of one of the exogenous sequence(s) inactivates gene expression, preferably cell surface expression of protein encoded by said gene.

The Method provided may be a method, wherein said endogenous promoter is selected to be active during immune cell activation.

Method, wherein said endogenous promoter at said endogenous locus is responsive to T-cell activation, such as one selected from Table 6.

In a preferred embodiment, the method comprises integrating an exogenous sequence into a gene selected from TCR, PD1 CD25, B2M wherein said exogenous sequence encodes a NK inhibitor, preferably said exogenous sequence encoding a NK inhibitor comprise sequences encoding non polymorphic class I molecules, such as HLA-F, HLA-G or HLA-E or fragment(s) thereof comprising an heavy chain epitope thereof, more preferably said exogenous sequence when integrated at β2m endogenous locus, results into the expression of a fusion of a HLA-E or HLA-G or fragment thereof with β2m. Even more preferably said fusion of a HLA-E or HLA-G of fragment thereof with β2m fragments results into the expression of dimers or trimers of HLA-E or of HLA-G.

In particular embodiments, said exogenous sequence encoding a NK inhibitor comprise a sequence encoding viral a evasin or fragment(s) comprising an epitope thereof, such as from UL16 (also called ULBP1—Uniprot ref.: #Q9BZM6).

An engineered T-cell obtainable by the method just below is provided and part of the kit or set of engineered cells of the invention. In preferred embodiments, the engineered T-cell comprises at least one chimeric antigen receptor. In more preferred embodiments, the engineered T-cell comprises a genotype with two inactivated genes as [TCR]neg [β2m]neg A therapeutically effective population of engineered immune cells for each of the pharmaceutical doses in a set or kit comprising at least 30%, preferably 50%, more preferably 80% of engineered T-cells is provided.

The method for preparing said cells is provided here and is as described in PCT/EP2018/055957 which is incorporated herewith by reference in its entirety.

A kit is intended to treat one pathology, preferably a cancer requiring several treatments or a sustained treatment. (several successive doses of the same treatment.

A set may be used in P to treat successive pathologies preferably cancers.

A set may be used in P to treat successive pathologies preferably a cancer.

Figure 1:
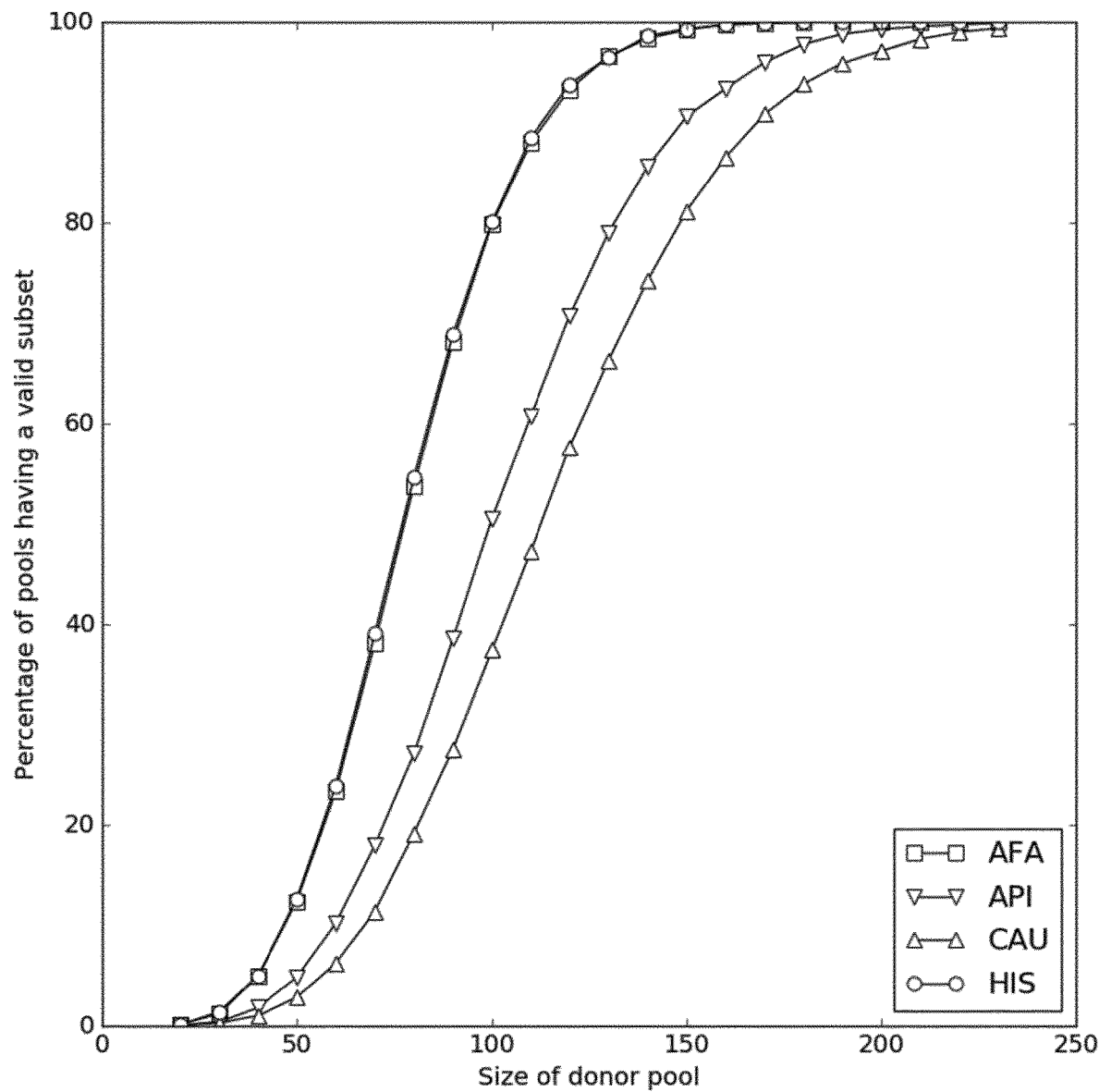
FIG. 1: Sample size comprising a kit or a set of pharmaceutical dose units according to the present invention in four different populations

Table 2: Patient coverage (1=100%) of 4 runs performed for (m) number of mismatches ranging from 12 to 15.

Table 3: Frequency of coverage (1=100%) for each group of 5 donors and for individual run (total of 30 runs) for 2 values of mismatch (m=20 and m=22)

Table 4: best set of haplotypes

Table 5: example of sets of 5 donors (homozygous) with a maximized graft potential using HLAA-B and DRB1

Table 6: Preferred human endogenous gene loci responsive to T-cell activation

DETAILED DESCRIPTION OF THE INVENTION

Unless specifically defined herein, all technical and scientific terms used herein have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

The present invention is drawn to a set or a kit of engineered cells for immunotherapy inducing no or reduced anamnestic immune reaction in one individual (P).

Nomenclature for Factors of the HLA System
Nomenclature of HLA Alleles

Each HLA allele name has a unique number corresponding to up to four sets of digits separated by colons. The length of the allele designation is dependent on the sequence of the allele and that of its nearest relative. All alleles receive at least a four digit name, which corresponds to the first two sets of digits, longer names are only assigned when necessary.

The digits before the first colon describe the type, which often corresponds to the serological antigen carried by an allotype. The next set of digits are used to list the subtypes, numbers being assigned in the order in which DNA sequences have been determined. Alleles whose numbers differ in the two sets of digits must differ in one or more nucleotide substitutions that change the amino acid sequence of the encoded protein. Alleles that differ only by synonymous nucleotide substitutions (also called silent or non-coding substitutions) within the coding sequence are distinguished by the use of the third set of digits. Alleles that only differ by sequence polymorphisms in the introns, or in the 5' or 3' untranslated regions that flank the exons and introns, are distinguished by the use of the fourth set of digits.

In addition to the unique allele number, there are additional optional suffixes that may be added to an allele to indicate its expression status. Alleles that have been shown not to be expressed—'Null' alleles—have been given the suffix 'N'. Alleles that have been shown to be alternatively expressed may have the suffix 'L', 'S', 'C', 'A' or 'Q'.

The suffix 'L' is used to indicate an allele which has been shown to have 'Low' cell surface expression when compared to normal levels. The 'S' suffix is used to denote an allele specifying a protein which is expressed as a soluble, 'Secreted' molecule but is not present on the cell surface. The 'C' suffix is assigned to alleles that produce proteins that are present in the 'Cytoplasm' and not on the cell surface. An 'A' suffix indicates an 'Aberrant' expression where there is some doubt as to whether a protein is actually expressed. A 'Q' suffix is used when the expression of an allele is 'Questionable', given that the mutation seen in the allele has been shown to affect normal expression levels in other alleles.

As of June 2016, no alleles have been named with the 'C' or 'A' suffixes.

An allele is a variant form of a gene. Explained in greater detail, each gene resides at a specific locus (location on a chromosome) in two copies, one copy of the gene inherited from each parent. The copies, however, are not necessarily the same. When the copies of a gene differ from each other, they are known as alleles. A given gene may have multiple different alleles, though only two alleles are present at the gene's locus in any individual.

According to some aspects, a set or a kit of engineered cells for immunotherapy is used with a combination of immunosuppressive drugs inducing no or reduced anamnestic immune reaction in one individual (P).

The present invention provides a set or kit of n pharmaceutical unit doses comprising engineered cells and a pharmaceutically acceptable vehicle, for use as a sequential therapy inducing no or reduced anamnestic immune reaction in one individual (P) as compared to an anamnestic reaction in said individual P if previously exposed to an immunogenic antigen born by cells, optionally engineered, or to a unit dose comprising engineered cells and expressing an anamnestogenic molecule for said P or an antigen against which P has acquired immunity (preferably a T cell dependent antigen) and then subsequently grafted with a unit dose of engineered cells or tissue comprising said anamnestogenic molecule or antigen against which P has acquired immunity.

According to the present invention, no or reduced anamnestic immune reaction in one individual (P) means no or reduced anamnestic immune reaction as compared to an anamnestic immune reaction in P re-exposed to an immunogenic antigen born by cells, and/or an immunogenic antigen born by engineered cells, an anamnestogenic molecule, against which P has acquired immunity.

Sequential means sequential administration (one after the other)—of at least two, preferably at least 3, more preferably at least 4, and even more preferably at least 5 consecutive doses.

This implied that n pharmaceutical unit doses comprising engineered cells and a pharmaceutically acceptable vehicle, each, individually or together is used as a medicament.

An anamnestic reaction may be a renewed rapid production of an antibody on the second (or subsequent) encounter with the same antigen anamnestic response is an immune reaction, immune response, immunologic response—a bodily defense reaction that recognizes an antigen: such as a viral antigen or fungus antigen or bacteria antigen or an antigen in a transplanted organ or cell) and produces antibodies specific against that antigen.

The set or kit of n pharmaceutical unit doses or of n pharmaceutical compositions provided is for the treatment of one unique individual P, and depends on previous graft in P, for example previous autologous graft or previous allogenic grafts in P, including bone marrow transplant or adoptive transfer of a blood product such as immune engineered cells.

A donor according to the present invention is a donor cell, a sample or cells from one donor.

In general, donor, ie donor cells may be or may not be from different donor cells and cells may be engineered not to express an antigen that may be responsible for an anamnestic response in P for the purpose of the invention.

The invention comprises to provide successive doses of engineered cells as successive treatment(s) or as a treatment and to prevent and anamnestic immune reaction, taking into account potential previous grafts administered to the patient P.

In particular embodiments, the invention comprises a set of n pharmaceutical unit doses or of n pharmaceutical compositions inducing no or reduce anamnestic response when re exposing P to an antigen involved in an anamnestic immune reaction. This is achieved, by controlling the time between two injections and/or administering a drug or a combination of drugs (before, at the same time/after administration of engineered immune cells, to alter, inhibit or prevent said anamnestic immune reaction.

This may be performed for example, by destroying temporarily (the time to destroy cancer cells and/or metastasis) any immune cells involved in such immune reaction, by administering of a compound with anti-adjuvant effect.

Thus, in one embodiment any injection of engineered immune cell is preceded by an administration of a drug or a treatment (debulking, rays) that may temporarily or definitively affects the activity of the immune system, (immuno suppression) such as a lymphodepleting drug, a drug depleting T and/or B lymphocytes, a drug reducing the activity of specific subsets of immune cells.

Immunosupressives Drugs

Any one of the following drugs or a combination thereof may be used before and/or during immunotherapy using a unit dose of the set of the invention ultimately inducing no or reduced anamnestic response:

Corticosteroids
    prednisone (Deltasone, Orasone)
    budesonide (Entocort EC)
    prednisolone (Millipred)
    Calcineurin inhibitors
    cyclosporine (Neoral, Sandimmune, SangCya)
    tacrolimus (Astagraf XL, Envarsus XR, Prograf)
    mTOR inhibitors
    sirolimus (Rapamune)
    everolimus (Afinitor, Zortress)
    IMDH inhibitors
    azathioprine (Azasan, Imuran)
    leflunomide (Arava)
    mycophenolate (CellCept, Myfortic)
Biologics
    abatacept (Orencia)
    adalimumab (Humira)
    anakinra (Kineret)
    certolizumab (Cimzia)
    etanercept (Enbrel)

golimumab (Simponi)
infliximab (Remicade)
ixekizumab (Taltz)
natalizumab (Tysabri)
rituximab (Rituxan)
secukinumab (Cosentyx)
tocilizumab (Actemra)
ustekinumab (Stelara)
vedolizumab (Entyvio)
QBEN10
Antibodies
basiliximab (Simulect)
daclizumab (Zinbryta)
muromonab (Orthoclone OKT3)
alemtuzumab
Rituximab
QBEN10

Effective doses of any of these immunosuppressant drugs used alternately with immunotherapy are either those usually given in patients benefiting from bi or tri therapy such as bi-therapy cyclophosphamide, fludarabine, or tri-therapy such as cyclophosphamide, fludarabine rituximab or cyclophamide, fludarabine or mitoxantrone.

Accordingly, the present invention also provides a set of n pharmaceutical unit doses combined to a at least one, preferably 2 of the following treatments selected from debulking, ray, X-rays, gamma rays, charged particles, corticosteroid, biologics, antibody, imdh inhibitor, mtor inhibitor and a combination thereof.

Accordingly, the present invention also provides a set of n pharmaceutical unit doses combined to a at least one, preferably 4 of the following treatments selected from debulking, ray, X-rays, gamma rays, charged particles, corticosteroid, biologics, antibody, imdh inhibitor, mtor inhibitor and a combination thereof, inducing no anamnestic response in the treated patient.

The present invention provides a set of n pharmaceutical unit doses comprising allogenic cells, preferably allogenic engineered cells, more preferably allogenic engineered cells from 1 donor different from P combined to a at least one of the following treatments selected from debulking, corticosteroid, biologics, antibody, imdh inhibitor, mtor inhibitor and a combination thereof.

mTOR inhibitors are a class of drugs that inhibit the mechanistic target of rapamycin (mTOR), which is a serine/threonine-specific protein kinase that belongs to the family of phosphatidylinositol-3 kinase (PI3K) related kinases (PIKKs). mTOR regulates cellular metabolism, growth, and proliferation by forming and signaling through two protein complexes, mTORC1 and mTORC2. Preferably mTOR inhibitors are rapalogs (rapamycin and its analogs), selected from sirolimus, Temsirolimus, Everolimus, or Ridaforolimus.

The present invention provides a set of n pharmaceutical unit doses comprising allogenic cells, preferably allogenic engineered cells, more preferably allogenic engineered cells from 1 donor different from P combined to a at least one of the following treatments selected from debulking ray, X-rays, gamma rays, charged particles and a combination thereof.

The present invention also encompasses successive doses of the same sample of cells or of the same engineered cells for a successive immunotherapy in P, or redosing, combined to a at least one of the following treatments selected from debulking, ray, X-rays, gamma rays, charged particles, corticosteroid, biologics, antibody, imdh inhibitor, mtor inhibitor and a combination thereof.

The present invention also encompasses successive doses of the same sample of cells or of the same engineered cells for a successive immunotherapy in P, or redosing, combined to a at least one of the following treatments selected from debulking, ray, X-rays, gamma rays, charged particles, corticosteroid, biologics, antibody, imdh inhibitor, mtor inhibitor and a combination thereof, for their use according to the following schedule:

The same antigens (different samples of cells from the same batch of cells such as UCART123 cells), each combined to a treatment inhibiting or suppressing or attenuating an immune reaction (such as fludarabine/cyclophosphamide), in particular inhibiting or suppressing an amnestic immune reaction (by inhibiting immune cells), are injected several times (at least 2, preferably at least 3 times) in one individual (who optionally got a debulking treatment, preferably a 7+3 treatment), at a constant time interval such as, every 45 days.

In particular embodiments, P is first treated (debulking) with a regimen intended to affect the immune system, such as "7+3 regimen" before the first immunotherapy injection, then again with a lymphodepleting treatment and successive injection of a second dose of engineered immune cells, preferably 45 days after the first one, etc. until cancer cells are exhausted.

"7+3" in the context of chemotherapy is an acronym for a chemotherapy regimen that is most often used today (as of 2014) as first-line induction therapy (to induce remission) in acute myelogenous leukemia, excluding the acute promyelocytic leukemia form, which is better treated with ATRA and/or arsenic trioxide and requires less chemotherapy (if requires it at all, which is not always the case).

The name "7+3" comes from the duration of chemotherapy course, which consists of 7 days of standard-dose cytarabine, and 3 days of an anthracycline antibiotic or an anthracenedione, most often daunorubicin (can be substituted for doxorubicin or idarubicin or mitoxantrone).

Dosing Regimen

| Drug | Dose | Mode | Days |
| --- | --- | --- | --- |
| Standard-dose cytarabine plus daunorubicin (DA or DAC chemotherapy) | | | |
| Cytarabine | 100-200 mg/m$^2$ | IV continuous infusion over 24 hours | Days 1-7 |
| Daunorubicin | (45) 60-90 mg/m$^2$ | IV bolus | Days 1-3 |
| Standard-dose cytarabine plus Idarubicin (IA or IAC chemotherapy) | | | |
| Cytarabine | 100-200 mg/m$^2$ | IV continuous infusion over 24 hours | Days 1-7 |
| Idarubicin | 12 mg/m$^2$ | IV bolus | Days 1-3 |
| Standard-dose cytarabine plus mitoxantrone (MA or MAC chemotherapy) | | | |
| Cytarabine | 100-200 mg/m$^2$ | IV continuous infusion over 24 hours | Days 1-7 |
| Mitoxantrone | 7 mg/m$^2$ | IV infusion | Days 1, 3 and 5 |

Intensified Versions intensifed the "7+3" regimen to improve its efficacy achieved by prolonging the course (cytarabine for 10 days instead of 7, or daunorubicin/idarubicin for 4-5 days instead of 3).

According to the present invention vinca alkaloids (vincristine or vinblastine) or are glucocorticoids (like prednisolone) or methotrexatenot associated to the "7+3" regimen, when used to treat AML.

For the purpose of the present invention, each dose of engineered cells is administered to a patient at repeated or different times interval, said time interval in comprised between from 1 day to 70 years.

The samples to prepare the successive doses may be selected based on their "content" in molecules of the major histocompatibility complex so that they will be matching at best the MHC of the patient and if not matching P, the content in MHC should be different from any other MHC alleles of the other sample doses to be administered or already administered or both.

In a general aspect, the present inventors provide a set of n pharmaceutical unit doses comprising engineered cells and a pharmaceutically acceptable vehicle, for use either alone or in combination with at least one immunosuppressive drug, as a sequential therapy inducing no or reduced anamnestic immune reaction in one individual (P) as compared to an anamnestic reaction in said individual P if previously exposed to an immunogenic antigen born by cells, against which P has acquired immunity (preferably a T cell dependent antigen) and then subsequently re-exposed to said immunogenic antigen born by cells, against which P has acquired immunity.

The present inventors identified, a set of n pharmaceutical unit doses comprising engineered cells and a pharmaceutically acceptable vehicle, used either alone or in combination with at least one immunosuppressive drug, for use as a sequential therapy inducing no or reduced anamnestic immune reaction in one individual (P) as compared to an anamnestic reaction in said individual P if previously exposed to an immunogenic antigen born by cells, optionally engineered, or to a unit dose comprising engineered cells and expressing an anamnestogenic molecule for said P or an antigen against which P has acquired immunity (preferably a T cell dependent antigen) and then subsequently grafted with a unit dose of engineered cells or tissue comprising said anamnestogenic molecule or antigen against which P has acquired immunity.

In particular embodiments, a set of n pharmaceutical unit doses according to the invention is provided, wherein each of the n doses is obtained from P.

In particular embodiments, a set of n pharmaceutical unit doses is provided, wherein each of the n doses is obtained from P and either from the same batch (carring the exact same antigens) or targeting the same antigen but engineered differently. In that case, the time between two uses is determined so that no anamnestic response is mounted, optionally an immune suppressive drug is administered.

In particular embodiments, the present invention provides a set of n pharmaceutical unit doses wherein each of the n doses preferably from P, and may be from a donor other than P matching the antigen born by cells of P.

In particular embodiments, the present invention provides a set of n pharmaceutical unit doses, wherein each of the n doses is obtained from a different donor and different from P.

In particular embodiments, the present invention provides a set of n pharmaceutical unit doses wherein n is at least 5.

In particular embodiments, the present invention provides a set of n pharmaceutical unit doses, wherein cells in each pharmaceutical unit doses comprise at least one CAR or a TCR and said CAR or TCR is the same, has the same antigen specificity or is different, has a different antigen specificity in the n successive doses.

Cells according to the present invention are suitable for immunotherapy. Cells may be for example, primary cells, primary T cells, primary CD4 T cells, primary CD4 T regulatory cells, primary CD8 T cells, primary NKT cells, In some embodiments, the cells are T cells. In some embodiments, the cells are T cells precursors.

In particular embodiments, cells according to the present invention are suitable for immunotherapy and may be stem cells, cells engineered and programmed to differentiated into cytotoxic cells.

According, to the present invention cells may be primary cells, for example, primary immune cells, or primary stem cells, primary T cells, primary IPS derived from primary T cells, primary CD4 T cells, primary CD4 T reg cells, primary CD8 T cells, primary NKT cells.

The present invention provides a set of n pharmaceutical unit doses wherein the immunogenic antigens born by cell comprise at least a product encoded by at least one of the HLA alleles as described in http://hla.alleles.org/nomenclature/updates/201606.html. An initial list was Published In:HLA (2016) 88:142-51. Human Immunology (2016) 77:1309-17. International Journal of Immunogenetics (2016) 43:320-9. The HLA alleles in http://hla.alleles.org/nomenclature/updates/201606.html all dated before June 30th 2017 are part of the present invention.

The present invention provides a set of n pharmaceutical unit doses wherein the immunogenic antigens born by cell all match those of P or do not induce any immune reaction once administered into P and/or when administered twice in P.

In other embodiments, the set of n pharmaceutical unit doses, according to the above is a set wherein the immunogenic antigens born by cells comprise at least a product encoded by at least one of the HLA alleles selected from HLA-A, HLA-B, HLA-C, HLA-DP, HLA-DQ and HLA-DR, or a combination thereof.

In particular embodiments, the immunogenic antigens born by cell comprise variant alleles of the products encoded by the following loci: HLA-A, HLA-B, HLA-C, HLA-DP, HLA-DQ and HLA-DR, or a combination thereof, preferably the immunogenic antigens born by cell are variant alleles of the products encoded HLA-DP, HLA-DQ and HLA-DR and cells have an inactivated beta2 microglobulin, (no more MHC class I) more preferably cells comprises in addition, no or limited HLA-DP, HLA-DQ and HLA-DR alleles due to inactivation of a CTIIA gene.

HLA System

The HLA gene family provides instructions for making a group of related proteins known as the human leukocyte antigen (HLA) complex. The HLA complex helps the immune system distinguish the body's own proteins from proteins made by foreign invaders such as viruses, bacteria or allogeneic in case of tissue or organ graft. In humans, the MHC complex consists of more than 200 genes located close together on chromosome 6. There are six main MHC class II genes in humans: HLA-DPA1, HLA-DPB1, HLA-DQA1, HLA-DQB1, HLA-DRA, and HLA-DRB1. MHC class II genes provide instructions for making proteins that are present almost exclusively on the surface of certain immune system cells. Like MHC class I proteins, these proteins display peptides to the immune system. HLA genes have many possible variations, allowing each person's immune system to react to a wide range of foreign invaders. Some HLA genes have hundreds of identified versions (alleles), each of which is given a particular number (such as HLA-B27). Closely related alleles are categorized together; for example, at least 40 very similar alleles are subtypes of HLA-B27. These subtypes are designated as HLA-B*2701 to HLA-B*2743.

Resolution of HLA

According to the Guidelinesfor reporting HLA typings ss defined at HLA-NET meeting on March 17th-18th 2011 in Athens, the allelic resolution is a DNA-based typing result consistent with a single allele as defined in a given version of the WHO HLA Nomenclature Report.

High resolution is defined as a set of alleles that specify and encode the same protein sequence for the peptide binding region of an HLA molecule and that excludes alleles that are not expressed as cell-surface proteins. It identifies HLA alleles at the resolution level of the 2nd field (formerly 4-digit) or more, at least resolving all ambiguities resulting from polymorphisms located within exons 2 and 3 for class I loci, and exon 2 for class II loci.

Intermediate resolution is defined as a DNA-based typing result that includes a subset of alleles sharing the digits in the first field of their allele name and that excludes some alleles sharing this field.

Low resolution is a DNA-based typing result at the level of the first field (formerly 2-digit) in the DNA based nomenclature. If none of the above resolutions can be achieved, DNA-based low resolution typings are accepted.

The set or kit of n pharmaceutical unit doses according to the invention in particular embodiments the immunogenic antigens born by cell matching those of P. Matching corresponds to an HLA typing preferably (to a molecular HLA typing), more preferably to a high resolution molecular typing] score of 7/7, preferably 8/8 and more preferably 9/9, and ideally 10/10, with the HLA typing of cells of P.

In one embodiment cells in one or several of the unit doses may be haploidentical to those of P.

Preferably, donors are selected so that donors and recipient P have closely matched cell types. Type is determined by human leukocyte antigens (HLA), proteins on the surface of the body's cells. They allow the immune system to determine whether cells belong to the host and can be left alone or are foreign or diseased and should be eliminated. To reduce the risk that the transplant will result in an attack on normal, healthy tissue, donors whose HLA type is as close as possible to the recipient's are selected, preferably.

The present invention encompasses haploidentical grafts, in which a healthy first-degree relative—a parent, sibling, or child—serve as a donor. Instead of a near-total HLA match, donors for a haploidentical transplant need be only a 50 percent match to the recipient.

In that later case, several days after the transplant, P will receive a very high dose of the chemotherapy drug Cytoxan (cyclophosphamide). This causes a sharp decline in active T cells, key contributors to graft-versus-host disease (GVHD), a potential side effect of transplantation in which donated immune system cells mount an attack on the body.

Standard doses of cyclophosphamide range from 100 h 200 mg/m$^2$/day (2.5 to 5 mg/kg/day) for 1 to 14 days, repeated every 2 to 4 weeks. Standard (450-1000 mg/m2), High doses are considered as 500 to 1000 mg/m$^2$ or 500-1000 mg/m$^2$ IV monthly for 6 doses or >1000 mg/m$^2$.

In a particular embodiment, the set of n pharmaceutical unit doses according to the invention is characterized in that the HLA typing of at least one of the n doses and preferably of all n doses is 10/10 high resolution match at HLA-A, -B, -C, DRB1 and DQB11 loci, with P.

In particular embodiments, the set of n pharmaceutical unit doses according to the invention is characterized in that the HLA typing of at least one of the n doses, matches (6/6, 7/7, preferably 8/8 and more preferably 9/9, 10/10) the HLA typing of the patient P and comprises at most one mismatch at a locus selected from HLA-A, -B, -C, -DRB1 or DQB11 locus, preferably a single mismatch at a locus selected from HLA-A,-B, -DRB1 or DQB11 locus more preferably at HLA-DQ and less preferably at HLA-C.

According to the present invention in the set of n pharmaceutical unit doses, cells may present 1 mismatch with P and said mismatch being different in each unit dose.

According to the present invention, the dose(s) in the set of n pharmaceutical unit doses used first in a sequential therapy by order of preference are comprised between 102 to 1010 cells 10$^2$, 10$^3$, 10$^4$, 10$^5$, 10$^6$, 10$^7$, 10$^8$, 10$^9$, 10$^{10}$, cells preferably of CAR-expressing cells, or essential purified (less than 3% TCR positive engineered TCR-negative cells. in a preferred embodiments doses of cells ranges between 10$^4$ and 10$^8$ cells per dose/kg more preferably between 10$^5$, 10$^6$, 10$^7$ per dose/kg, even more preferably 1.25×105 cells/kg to 5.05×106 cells/kg.

In general cells in all samples of the invention are TCR-negative T cells, inducing no GVHD in P.

According to the present invention, the dose(s) in the set of n pharmaceutical unit doses used first in a sequential therapy by order of preference are:
  those wherein immunogenic antigens born by the unengineered or engineered cells fully match those of the patient, (for example successive autologous transfers of at least 3 consecutive doses),
  those wherein immunogenic antigens born by the unengineered or engineered cells match
  those of the patient, whether cells were selected base on their HLA (twins) or engineered to match those of the patients or to have no major immunogenic antigens born by cells, (haploidentical donors or universal donors as in WO2016183041A3 incorporated herein by reference) with no armful HLA.

Cells may be obtained according to the methods and invention described in WO 2017081288 A1 incorporated herein by reference or in PCT/US2014/024660 or in WO/2014/165177 incorporated herein by reference,
  then those having the less mismatch with P and said mismatch being different in each unit dose, the following case are therefore contemplated and part of the present invention:

The immunogenic antigens born by the unengineered or engineered cells of the donors of the n doses match those of the patient,
  the immunogenic antigens born by the unengineered or engineered cells of the donors of n−1 of the n doses all match those of the patient,
  the immunogenic antigens born by the unengineered or engineered cells of the donors of n-m (with n≥m≥2) of the n doses all match those of the patient, and if Mk is the set of immunogenic antigen(s) unmatched with P present in the k-th of the m consecutive not matched doses, then the k-th of these m administered doses (with k 2) should not to bear the immunogenic antigens present in the union of M1, M2, . . . , M(k−1). In addition, M1 may avoid any immunogenic antigen against which the individual is already immunized against.

According to particular embodiments, the set of n pharmaceutical unit doses according to the invention is characterized in that: immunogenic antigens not fully matching with the immunogenic antigens of the patient, are administered in the increasing order of mismatch with the patient and, in one of the following order selected from (If already exposed to a mismatch for A) then use (mismatched for B) before (mismatched for DQB1),
(If already exposed to a mismatch for A) then use (mismatched for C) before (mismatched for DQB1),
(If already exposed to a mismatch for C) then use (mismatched for A) before (mismatched for B),
(If already exposed to a mismatch for C) then use (mismatched for A) before (mismatched for DRB1),
(If already exposed to a mismatch for C) then use (mismatched for DQB1) before (mismatched for DRB1),
(If already exposed to a mismatch for DPB1) then use (mismatched for DQB1) before (mismatched for DRB1),
(If already exposed to a mismatch for DQB1) then use (mismatched for A) before (mismatched for B),
(If already exposed to a mismatch for DQB1) then use (mismatched for A),
(If already exposed to a mismatch for DQB1) then use (mismatched for C) before (mismatched for A),
(If already exposed to a mismatch for DPB1) then use (mismatched for DRB3,4,5) before (mismatched for C),
(If already exposed to a mismatch for DQB1) then use (mismatched for A) before (mismatched for DRB3,4,5),
(If already exposed to a mismatch for DPB1, DRB3,4,5) then use (mismatched for DQB1) before (mismatched for C),
(If already exposed to a mismatch for C, DRB3,4,5, DQB1, DPB1) then use (mismatched for A) before (mismatched for B, DRB1).

The present invention further provides a set of n pharmaceutical doses characterized in that the following matches are recommended for a dose of engineered cells per kilogram body weight: at least 6/6 HLA match for a dose comprising >3×10⁷ engineered cells per kilogram body weight or above; at least 5/6 HLA match for a dose comprising >4×10⁷ engineered cells per kilogram body weight or above; or at least 4/6 HLA match for a dose comprising >5×10⁷ engineered cells per kilogram body weight or above.

The present invention further provides a set of n pharmaceutical unit doses characterized in that each of their HLA allele unmatched with P has a frequency in the human population of less than 6% but more than 0.1%.

The present invention further provides a set of n pharmaceutical unit doses characterized in that sequential administration of engineered cells bearing HLA alleles mismatched with P in haplotypes A/DRB1 followed by mismatched with P in haplotypes B/C followed by mismatched with P in haplotypes DQ should be avoided.

The present invention further provides a set of n pharmaceutical unit doses characterized in that said engineered primary cells are HLA haploidentical to P.

The present invention further provides a set of n pharmaceutical unit doses characterized in that said engineered cells in each dose express at least one CAR and/or a TCR targeting a molecule constitutively or temporarily expressed on pathological cells as compared to healthy cells or expressed only on pathological cells.

The present invention further provides a set or kit of n pharmaceutical unit doses characterized in that: said at least one CAR is specific for a molecule selected from a group consisting of: DR4, CD19, CD123, CD20, CD22, CD38, CD30, CS-1, CLL-1, HSP70, BCMA, VEGF, DR4, GD2, the cancer testis (CT) antigens, MUC1, GD2, o acetyl GD2, HM1.24 (CD317), CYP1B1, SP17, PRAME, Wilms' Tumour 1 (WT1), heat shock protein gp96, thyroid stimulating hormone receptor (TSHR); CD171; CS-1 (CD2 subset 1, CRACC, SLAMF7, CD319, and 19A24); C-type lectin-like molecule-1 (CLL-1); ganglioside GD3 (aNeu5Ac(2-8) aNeu5Ac(2-3)bDGalp(I-4)bDGlcp(I-I)Cer); Tn antigen (Tn Ag); Fms-Like Tyrosine Kinase 3 (FLT3); CD38; CD44v6; B7H3 (CD276); KIT (CD117); Interleukin-13 receptor subunit alpha-2 (IL-13Ra2); Interleukin 11 receptor alpha (IL-IIRa); prostate stem cell antigen (PSCA); Protease Serine 21 (PRSS21); vascular endothelial growth factor receptor 2 (VEGFR2); Lewis (Y) antigen; CD24; Platelet-derived growth factor receptor beta (PDGFR-beta); stage-specific embryonic antigen-4 (SSEA-4); Mucin 1, cell surface associated (MUC1); epidermal growth factor receptor (EGFR); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Fucosyl GM1; sialyl Lewis adhesion molecule (sLe); ganglioside GM3 (aNeu5Ac(2-3)bDGalp(I-4)bDGlcp(I-I)Cer; TGS5; high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Cytochrome P450 1B 1 (CYP1B 1); CCCTC-Binding Factor (Zinc Finger Protein)-Like (BORIS); Squamous Cell Carcinoma Antigen Recognized By T Cells 3 (SART3); Paired box protein Pax-5 (PAX5); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLECi2A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1) and a combination thereof.

The CAR may preferably be chosen from DR4, CD19, CD123, CD20, CD22, CD38, CD30, CS-1, CLL-1, HSP70, BCMA, VEGF, DR4, GD2, O-acethyl GD2, the cancer testis (CT) antigens, MUC1, MUC16, HM1.24 (CD317), CYP1B1, SP17, PRAME, Wilms' tumour 1 (WT1), heat shock protein gp96, claudine18.2, and a combination thereof.

In a preferred embodiment, the CAR is directed against one of the following targets: mesothelin FRα, L1-CAM, CAIX, GD2, O-acethyl GD2, FAP, Lewis Y, EGFRvIII, HER2, CD20, PSMA, kLC, CD30, CEA.

In another preferred embodiment, the CAR is directed against one of the following target: α-folate receptor (FRα); L1-cell adhesion molecule (L1-CAM); carboxy-anhydrase-IX (CAIX), Fibroblast activation protein (FAP), human epidermal growth factor receptor 2 (HER2); carcinoembryonic antigen (CEA); Prostate Specific Membrane Antigen (PSMA); CD79a or CD79b, CD20 or CD268, C type lectin domain family 14 member A; also EGFR5 (CLEC14a), Epithelial cell adhesion molecule (EPCAM), Liv-1, or Zinc transporter LIV-1 (SLC39A6), Cholinergic Receptor Nicotinic Alpha 2 Subunit (CHRNA2), A Disintegrin and metalloproteinase domain-containing protein 10, (ADAM10) or CDw156 or CD156cADAM10, Delta-like 3 (DLL3), C type lectin domain family 14 member A; also EGFR5, (CLEC14a).

CLEC14a is a 51 kDa (predicted) member of the C type lectin domain family of proteins. It is a type transmembrane protein, apparently expressed in brain and about which little is known. Mature human CLEC14A is 469 amino acids in length.

The CAR molecule comprises an antigen binding domain, a transmembrane domain, and an intracellular domain comprising a costimulatory domain and/or a primary signaling domain, wherein said antigen binding domain binds to the tumor antigen associated with a disease, and said tumor antigen is selected from a group consisting of: CD19 molecule (CD19); membrane spanning 4-domains A1 (MS4A1 also known as CD20); CD22 molecule (CD22); CD24 molecule (CD24); CD248 molecule (CD248); CD276 molecule (CD276 or B7H3); CD33 molecule (CD33); CD38 molecule (CD38); CD44v6; CD70 molecule (CD70); CD72; CD79a; CD79b; interleukin 3 receptor subunit alpha (IL3RA also known as CD123); TNF receptor superfamily member 8 (TNFRSF8 also known as CD30); KIT proto-oncogene receptor tyrosine kinase (CD117); V-set pre-B cell surrogate light chain 1 (VPREB1 or CD179a); adhesion G protein-coupled receptor E5 (ADGRE5 or CD97); TNF receptor superfamily member 17 (TNFRSF17 also known as BCMA); SLAM family member 7 (SLAMF7 also known as CS1); L1 cell adhesion molecule (L1CAM); C-type lectin domain family 12 member A (CLEC12A also known as CLL-1); tumor-specific variant of the epidermal growth factor receptor (EGFRvIII); thyroid stimulating hormone receptor (TSHR); Fms related tyrosine kinase 3 (FLT3); ganglioside GD3 (GD3); Tn antigen (Tn Ag); lymphocyte antigen 6 family member G6D (LY6G6D); Delta like canonical Notch ligand 3 (DLL3); Interleukin-13 receptor subunit alpha-2 (IL-13RA2); Interleukin 11 receptor subunit alpha (I11RA); mesothelin (MSLN); Receptor tyrosine kinase like orphan receptor 1 (ROR1); Prostate stem cell antigen (PSCA); erb-b2 receptor tyrosine kinase 2 (ERBB2 or Her2/neu); Protease Serine 21 (PRSS21); Kinase insert domain receptor (KDR also known as VEGFR2); Lewis y antigen (LewisY); Solute carrier family 39 member 6 (SLC39A6); Fibroblast activation protein alpha (FAP); Hsp70 family chaperone (HSP70); Platelet-derived growth factor receptor beta (PDGFR-beta); Cholinergic receptor nicotinic alpha 2 subunit (CHRNA2); Stage-Specific Embryonic Antigen-4 (SSEA-4); Mucin 1, cell surface associated (MUC1); mucin 16, cell surface associated (MUC16); claudin 18 (CLDN18); claudin 6 (CLDN6); Epidermal Growth Factor Receptor (EGFR); Preferentially expressed antigen in melanoma (PRAME); Neural Cell Adhesion Molecule (NCAM); ADAM metallopeptidase domain 10 (ADAM10); Folate receptor 1 (FOLR1); Folate receptor beta (FOLR2); Carbonic Anhydrase IX (CA9); Proteasome subunit beta 9 (PSMB9 or LMP2); Ephrin receptor A2 (EphA2); Tetraspanin 10 (TSPAN10); Fucosyl GM1 (Fuc-GM1); sialyl Lewis adhesion molecule (sLe); TGS5; high molecular weight-melanoma-associated antigen (HMW-MAA); o-acetyl-GD2 ganglioside (OAcGD2); tumor endothelial marker 7-related (TEM7R); G protein-coupled receptor class C group 5, member D (GPRC5D); chromosome X open reading frame 61 (CXORF61); ALK receptor tyrosine kinase (ALK); Polysialic acid; Placenta-specific 1 (PLAC1); hexasaccharide portion of globoH glycoceramide (GloboH); NY-BR-1 antigen; uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 family member K (LY6K); olfactory receptor family 51 subfamily E member 2 (OR51E2); TCR Gamma Alternate Reading Frame Protein (TARP); Wilms tumor protein (WT1); ETV6-AML1 fusion protein due to 12; 21 chromosomal translocation (ETV6-AML1); sperm autoantigenic protein 17 (SPA17); X Antigen Family, Member 1E (XAGE1E); TEK receptor tyrosine kinase (Tie2); melanoma cancer testis antigen-1 (MAD-CT-1); melanoma cancer testis antigen-2 (MAD-CT-2); Fos-related antigen 1; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Cytochrome P450 1B 1 (CYP1B 1); CCCTC-Binding Factor (Zinc Finger Protein)-Like (BORIS); Squamous Cell Carcinoma Antigen Recognized By T Cells 3 (SART3); Paired box protein Pax-5 (PAX5); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); immunoglobulin lambda-like polypeptide 1 (IGLL1), and Heat shock protein 70 (HSP70).

The TCR molecule comprises an antigen binding domain, wherein said antigen binding domain binds to the tumor antigen associated with a disease, and said tumor antigen is selected from a group consisting of PCTA-I/Galectin 8, CD171, TAG72, CEA, EPCAM, PSCA, PRSS21, PDGFR-beta, Prostase, PAP, ELF2M, Ephrin B2, IGF-I receptor, CAIX, gp100, bcr-abl, tyrosinase, GM3, NY-ESO-1, LAGE-la, MAGE-A1, legumain, HPV E6, E7, MAGE A1, prostein, survivin and telomerase, PCTA-I/Galectin 8, MelanA/MARTI, Ras mutant, TRP-2, RAGE-1, RU1, RU2, and intestinal carboxyl esterase.

Any one of these set of n pharmaceutical unit doses is provided for use as a medicament in immunotherapy.

Any one of these set of n pharmaceutical unit doses is provided for use as a medicament in successive immunotherapy.

Any one of these set of n pharmaceutical unit doses is provided for use as a medicament against particular tumors against which a successive and constant targeting is required. High rate growing tumors are concerned here.

Any one of these set of n pharmaceutical unit doses is provided for use as a medicament in immunotherapy for the prevention or treatment of cancer.

Any one of these set of n pharmaceutical unit doses is provided for use as a medicament in immunotherapy for the prevention or treatment of an infectious disease, for the clearance of chronical viral infection.

Any one of these set of n pharmaceutical unit doses is provided for the treatment of a relapse refractory cancer or of cancer complications such as metastasis.

Any one of these set of n pharmaceutical unit doses is provided for the treatment of hematological cancers, of solid cancers or of hematological and solid cancers.

Any one of these set of n pharmaceutical unit doses is provided for the treatment of successive cancers, of successive hematological cancers, of successive solid cancers or of successive hematological and solid cancers.

Any one of these set of n pharmaceutical unit doses is provided wherein each dose is used in combination with another drug, in combination with another anti-cancer drug, anti-GVHD drug.

Accordingly, said drug can be given at the same time before or after the unit dose and engineered cells in said dose are engineered to be resistant to said drug if necessary.

Thus, the present invention provides a set of n pharmaceutical unit doses wherein each dose is used after a treatment inhibiting and/or affecting the survival or the effect of the preceding unit dose already injected.

The present invention provides a set of n pharmaceutical unit doses as above wherein engineered cells comprise at least one inactivated gene coding for a TCR alpha subunit.

In all samples constituting the n pharmaceutical unit doses, cells are endowed with a CAR or a TCR which cell surface expression may be activated, constitutive, conditional.

Preferably, the present invention provides a set of n pharmaceutical unit doses as above wherein engineered cells comprise at least one inactivated gene coding for a TCR alpha subunit.

Preferably, the present invention provides a set of n pharmaceutical unit doses as above wherein engineered cells comprise at least one inactivated gene coding for a TCR alpha subunit allele.

The present invention provides a set of n pharmaceutical unit doses as above wherein engineered cells comprise at least one of the following: an inactivated beta2 microglobulin gene, an inactivated CTIIA gene, genes modifications for MHC molecules matching those of P.

The present invention provides a set of n pharmaceutical unit doses as above wherein engineered cells comprise an inactivated beta2 microglobulin gene, and an inactivated CTIIA gene.

The present invention provides a set of n pharmaceutical unit doses as above wherein engineered cells comprise genes modification(s) altering (down-regulating MHC molecules expression and/or matching MHC molecules to those of P.

The present invention provides a set of n pharmaceutical unit doses as above wherein engineered cells comprise at least one inactivated gene coding for a TCR subunit and an inactivated beta2 microglobulin gene.

The present invention provides a set of n pharmaceutical unit doses as above wherein engineered cells comprise at least one inactivated gene coding for a TCR alpha subunit and an inactivated CTIIA gene.

The present invention provides a set of n pharmaceutical unit doses as above wherein engineered cells comprise at least one inactivated gene coding for a TCR alpha subunit and genes modification for MHC molecules matching those of P.

The present invention provides a set of n pharmaceutical unit doses as above wherein engineered cells comprise at least one inactivated gene coding for a TCR alpha subunit and an inactivated CTIIA gene and genes modification for MHC molecules matching those of P.

The present invention provides a set of n pharmaceutical unit doses as above wherein engineered cells in at least one dose comprise a deletion, an insertion or a mutation conferring resistance to a drug preferably to an anti-cancer drug.

Preferably said anticancer drug affects the survival and/or the activity of CAR-T cells without any deletion, insertion or mutation conferring resistance to a drug.

The present inventors identified a set of n pharmaceutical unit doses as above wherein TCR-negative CAR-expressing engineered cells can be used as a treatment without any deletion, insertion or mutation conferring resistance to a drug, preferably an immunosuppressive drug, or several immunosuppressive drugs more preferably an immunosuppressive drug or several immunosuppressive drugs used for 2 to 5 days before one pharmaceutical unit doses.

The present invention provides a set of n pharmaceutical unit doses as above wherein engineered cells are used with an anti-cancer drug at a dose efficient for an anticancer activity.

The successive doses at 10 to 50 days interval for 3 to 4 cycles is one essential features of particular embodiments of the present invention for the treatment of relapse refractory cancers The present invention provides a set of n pharmaceutical unit doses wherein engineered cells in at least one dose comprise a deletion, an insertion or a mutation conferring resistance to PNA.

The present invention provides a set of n pharmaceutical unit doses as above wherein engineered cells in at least one dose comprise an inactivated gene encoding one of the following molecules, CD52, dCK, GR and a combination thereof, preferably said inactivated gene encoding one of the following molecules, CD52, dCK, GR comprises an insertion of a CAR or a TCR as listed above.

In addition, cells may be engineered as described in WO2015155341 incorporated herein by reference, for resistance to arginine or tryptophane, or in WO2015075195 or in PCT/EP2017/058922 or in PCT/EP2017/058923 all incorporated herein by reference.

Immune Check Points

The present invention provides allogeneic T-cells (less or no alloreactive) expressing a CAR or a TCR, in particular any of the CAR described above, wherein at least one gene expressing one or more component of T-cell receptor (TCR) is inactivated and/or one gene selected from the genes CTLA4, PPP2CA, PPP2CB, PTPN6, PTPN22, PDCD1, LAG 3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, CSK, PAG1, SIT1, FOXP3, PRDM1, BATF, GUCY1A2, GUCY1A3, GUCY1B2, GUCY1B3, is inactivated as referred to in WO2014/184741 incorporated herein by reference.

Cells may carry out additional gene inactivation(s) leading to product expression inhibition as described in WO2015121454 A1.

The present invention provides a set or kit of n pharmaceutical unit doses as above wherein engineered cells in at least one dose comprise an inactivated gene encoding one of the following molecules, CD52, dCK, GR and a combination thereof, preferably said inactivated gene encoding one of the following molecules, CD52, dCK, GR comprises an insertion of a CAR specific for any one of the following antigen:

BCMA, CD33, EGFRVIII, Flt3, WT1, CD70, MUC1, PRAME, TSPAN10, CLAUDIN18.2, DLL3, LY6G6D, CD 38, HSP70, CD30, CD123, CS1, CD22, CLL-1, MUC1, GD2, CD19, CD123, CD20, CD22, CD38, CD30, CS-1, CLL-1, HSP70, BCMA, VEGF, DR4, GD2, the cancer testis (CT) antigens, MUC1, GD2, o acetyl GD2, HM1.24 (CD317), CYP1B1, SP17, PRAME, Wilms' Tumour 1 (WT1), heat shock protein gp96, thyroid stimulating hormone receptor (TSHR); CD171; CS-1 (CD2 subset 1, CRACC, SLAMF7, CD319, and 19A24); C-type lectin-like molecule-1 (CLL-1); ganglioside GD3 (aNeu5Ac(2-8) aNeu5Ac(2-3)bDGalp(I-4)bDGlcp(I-I)Cer); Tn antigen (Tn Ag); Fms-Like Tyrosine Kinase 3 (FLT3); CD38; CD44v6; B7H3 (CD276); KIT (CD117); Interleukin-13 receptor subunit alpha-2 (IL-13Ra2); Interleukin 11 receptor alpha (IL-IIRa); prostate stem cell antigen (PSCA); Protease Serine 21 (PRSS21); vascular endothelial growth factor receptor 2 (VEGFR2); Lewis (Y) antigen; CD24; Platelet-derived growth factor receptor beta (PDGFR-beta); stage-specific embryonic antigen-4 (SSEA-4); Mucin 1, cell surface associated (MUC1); epidermal growth factor receptor (EGFR); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Fucosyl GM1; sialyl Lewis adhesion molecule (sLe); ganglioside GM3 (aNeu5Ac(2-3)bDGalp(I-4)bDGlcp(I-I)Cer; TGS5; high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Cytochrome P450 1B 1 (CYP1B 1); CCCTC-Binding Factor (Zinc Finger Protein)-Like (BORIS); Squamous Cell Carcinoma Antigen Recognized By T Cells 3 (SART3); Paired box protein Pax-5 (PAX5); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLECi2A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1) and a combination thereof, preferably chosen from DR4, CD19, CD123, CD20, CD22, CD38, CD30, CS-1, CLL-1, HSP70, BCMA, VEGF, DR4, GD2, O-acethyl GD2, the cancer testis (CT) antigens, MUC1, MUC16, HM1.24 (CD317), CYP1B1, SP17, PRAME, Wilms' tumour 1 (WT1), heat shock protein gp96, claudine18.2, and a combination thereof.

In a preferred embodiment, the CAR is directed against one of the following target mesothelin, FRα, L1-CAM, CAIX, GD2, O-acethyl GD2, FAP, Lewis Y, EGFRvIII, HER2, CD20, PSMA, kLC, CD30, CEA, FRα, α-folate receptor; L1-CAM, L1-cell adhesion molecule; CAIX, carboxy-anhydrase-IX; FAP, Fibroblast activation protein; HER2, human epidermal growth factor receptor 2; CEA, carcinoembryonic antigen; PSMA, Prostate Specific Membrane Antigen; CEA, Carcino Embryonic Antigen, FAP, HER2, CD79a or CD79b, CD20 or CD268, CLEC14a, (EPCAM), Liv-1, or Zinc transporter LIV-1 (SLC39A6), Cholinergic Receptor Nicotinic Alpha 2 Subunit (CHRNA2), A Disintegrin and metalloproteinase domain-containing protein 10, (ADAM10) or CDw156 or CD156cADAM10, Delta-like 3 (DLL3).

More preferably, said CAR is selected from a CAR specific for one of the following targets: CD123, CD38, CS1, CD19, HSP70 CLL-1, CD22, CD30, Oacethyl-GD2, BCMA, FLT3, MUC-16, MUC-1, DLL3, EGFRV-III, FAP, HER2, CD79a CD79b, Liv-1, CHRNA2, ADAM10.

Any of the CAR expressed may carry additional epitope(s) or mimetope(s) allowing purification and/or selective in vivo deletion as described in PCT/EP2016/051467 incorporated herein by reference.

The present invention provides a set of n pharmaceutical unit doses wherein cells in at least one dose are engineered to be resistant to tumor-induced hypoxia, to tumor-induced adenosine secretion, to tumor-induced inhibition of anti-cancer cells activity by cytokines and/or chemokines.

The present invention provides a set of n pharmaceutical unit doses wherein n is at least 2, wherein n is at least 3, or 3, at least 4, or 4, at least 5, or 5, at least 6, or 6, at least 7, or 7, at least 8, or 8, at least 9, or 9 at least 10 or 10, preferably 5.

The present invention provides a set of n pharmaceutical unit doses for use as a sequential therapy against cancer inducing no or reduced anamnestic immune reaction in one individual (P), as compared to an anamnestic reaction in said individual P if previously exposed to an immunogenic antigen born by cells or to a unit dose comprising engineered cells, and expressing an anamnestogenic molecule for said P or an antigen against which P has acquired immunity (preferably a T cell dependent antigen) and then subsequently grafted with a unit dose of engineered cells or tissue comprising said anamnestogenic molecule or antigen against which P has acquired immunity.

The present invention provides a set of n pharmaceutical unit doses as above for use as a sequential therapy against a hematological cancer.

The present invention provides a set of n pharmaceutical unit doses as above for use as a sequential therapy against a hematological cancer selected from the group consisting of a myeloproliferative cancer, Blastic plasmacytoid dendritic cell neoplasm (BPDCN), acute Myelogenous Leukemia (AML), Chronic Myelogenous Leukemia (CML), Non hogdkin lymphoma (NHL), multiple myeloma (MM), Acute Lymphocytic Leukemia (ALL), and Chronic Lymphocytic Leukemia (CLL).

The present invention provides a set of n pharmaceutical unit doses as above for use as a sequential therapy against a relapse and/or refractory for of hematological cancer selected from the group consisting of a myeloproliferative cancer, Blastic plasmacytoid dendritic cell neoplasm (BPDCN), acute Myelogenous Leukemia (AML), Chronic Myelogenous Leukemia (CML), Non hogdkin lymphoma (NHL), multiple myeloma (MM), Acute Lymphocytic Leukemia (ALL), Chronic Lymphocytic Leukemia (CLL).

The present invention provides a set of n pharmaceutical unit doses as above for use as a sequential therapy against a solid cancer, a sarcoma, a carcinoma, a blastoma, or a germ cell tumor.

The present invention provides a set of n pharmaceutical unit doses as above for use as a sequential therapy against a solid cancer, affecting nervous tissue, intestinal tissue, liver, stomach, esophagus, head and neck, a soft tissue, pancreas, intestine, colon, breast, eye, bladder, gall bladder, prostate, ovary, uterus, lung, or testicle.

The present invention provides a set of n pharmaceutical unit doses as above for use as a sequential therapy against a solid cancer affecting bones.

In one embodiment, the present invention provides a set of n pharmaceutical unit doses as above wherein a unit dose can be used every 45 days in debulked patient in combination (preferably just after) with an immunosuppressive drug or a combination of immunosuppressive drugs according to the invention, that is to say without inducing an undesired immune anamnestic reaction. Thus, the present inventors provided a set of n pharmaceutical unit doses comprising either autologous or allogenic engineered immune cells that could be administered or used according to a protocol designed to obtain no anamnestic response in P.

Thus, the present inventors provided a set of n pharmaceutical unit doses comprising engineered immune cells that could be administered regardless of their MHC background when used according to a protocol designed to obtain no anamnestic response in P. Preferably cell are TCR-negative cells.

A set or a kit of n pharmaceutical unit doses comprising engineered immune cells wherein unit doses are used one after the other, at a at least 7 days interval, at least 20 days interval, at least 45 days interval, preferably at least 45 days interval and preceded by a treatment with an immunosuppressive drug or a combination of immunosuppressive drugs.

mTOR inhibitors are a class of drugs that inhibit the mechanistic target of rapamycin (mTOR), which is a serine/threonine-specific protein kinase that belongs to the family of phosphatidylinositol-3 kinase (PI3K) related kinases (PIKKs). mTOR regulates cellular metabolism, growth, and proliferation by forming and signaling through two protein complexes, mTORC1 and mTORC2. Preferably mTOR inhibitors are rapalogs (rapamycin and its analogs), selected from sirolimus, Temsirolimus, Everolimus, or Ridaforolimus.

According to the present invention the object provided is a kit comprising a set of n pharmaceutical unit doses of engineered immune cells and an immunosuppressive drug or a combination of immunosuppressive drugs for their successive use (ie a suppressive drug or a combination of successive drugs and then a unit dose of engineered immune cells) in a patient, preferably a lymphodepleted patient, every 30 to 60 days, preferably every 45 days.

According to the invention, a patient is first conditioned, then treated with immunosuppressive drug(s), for 2 to 5 days (preferably 3 to 4 days) and then immediately after, receive a unit dose, then 40 to 45 days later the patient is treated again with said immunosuppressive drug(s), and then with another unit dose (another cycle) and so on for at least 2, 3, 4, 5, 6, 7, 8, 9, 10 cycles, preferably for more than 2 cycles.

Under these conditions and according to the definition of the present invention, no anamnestic response is measured in treated Patients.

Preferably cells comprise an inactivated TCR alpha gene, beta2 microglobulin gene, and a CAR as described above.

The present invention presents the advantage of leaving the possibility to the initial immune system of the patient to self-renew and to be cleared of cancer cells; the treatment because of its repetition end up clearing cancer cells.

According to the present invention, the CAR-expressing engineered immune cells from the same batch can be used for successive cycles of injection every cycles, preferably every 45 days without anamnestic reaction when combined (preceded by an immunosuppressive drug).

A cycle may be an administered every 10, 20, 30, 40, 50, or 60, preferably 45 days.

A cycle is a 2 to 5 days treatment with at least two immunosuppressive drugs as described above followed by an injection of from 10 to 109 engineered cells.

In a preferred embodiment, the rate of cancer cell duplication is calculated and the time between two cycles is decreased or increased, to prevent relapse refractory cells and/or attenuate side effects in P; a cycle may be a 3-4 days Fludarabine/cyclophosphamide, then a unit dose of engineered cells.

In a preferred embodiment, a patient P first received a 7+3 debulking treatment then, a 3 to 4 days treatment with a combination of fludarabine and cyclophosphamide followed by an injection with $6.2510^6$ CAR-expressing engineered cells/kg, preferably a CD123 CAR T (recognizing a CD123 antigen on cancer cells).

In one embodiment, the present invention provides a set of n pharmaceutical unit doses as above wherein a unit dose is used every 45 days in a conditioned patient just after a 4 to 5 days treatment with fludarabine and cyclophosphamide. The first CAR is a specific for CD19—expressing cells, the second is specific for CD22 or C79a, or CD79b.

In particular embodiments, according to the present invention, a 3 to 4 or 4 to 5 days treatment with fludarabine and cyclophosphamide, and optionally rituximab is followed by an injection of the same CAR-expressing T cells according to the present invention and no anamnestic response is measured in these Patients.

In particular embodiments, according to the present invention, a 3 to 4 or 4 to 5 days treatment with fludarabine and cyclophosphamide, and optionally rituximab is followed by an injection of the same TCR-negative CAR-expressing T cells according to the present invention and no anamnestic response is measured in these Patients.

In one embodiment, the present invention provides a set of n pharmaceutical unit doses as above wherein a unit dose is used every 45 days just after a 3 to 4 days treatment with fludarabine and cyclophosphamide.

In one embodiment, the present invention provides a set of n pharmaceutical unit doses of allogenic CART cells used after a treatment with immunosuppressive drugs such as Fludarabine, cyclophosphamide, and rituximab in a patient suffering CLL.

In one embodiment, the present invention provides a set of n pharmaceutical unit doses of allogenic CART cells used after a treatment with immunosuppressive drugs such as Fludarabine, cyclophosphamide, and rituximab in a patient suffering ALL.

In one embodiment, the present invention provides a set of n pharmaceutical unit doses of allogenic CART cells used after a treatment with immunosuppressive drugs such as Fludarabine, cyclophosphamide, and rituximab in a patient suffering AML.

In one embodiment, the present invention provides a set of n pharmaceutical unit doses of allogenic CART cells used after a treatment with immunosuppressive drugs such as Fludarabine, cyclophosphamide, and rituximab in a patient suffering NHL.

In one embodiment, the present invention provides a set of n pharmaceutical unit doses of allogenic CART cells used after a treatment with immunosuppressive drugs such as Fludarabine, cyclophosphamide, and rituximab in a patient suffering MM.

In one embodiment, the present invention provides a set of n pharmaceutical unit doses of allogenic CART cells used after a treatment with immunosuppressive drugs such as Fludarabine, cyclophosphamide, and rituximab in a patient suffering BPDCN.

In one embodiment, the present invention provides a set of n pharmaceutical unit doses of allogenic CART cells used after a treatment with immunosuppressive drugs in a patient suffering a solid cancer.

In one embodiment, the present invention provides a set of n pharmaceutical unit doses of allogenic CART cells used after a treatment with anti-cancer drugs in a patient suffering a solid cancer.

An anticancer drug may be any one of the following: appropriately administered according to the prescription and doses by a medical doctor as function of pathology treated:

Abiraterone Acetate
Abitrexate (Methotrexate)
Abraxane (Paclitaxel Albumin-stabilized Nanoparticle Formulation)
ABVD
ABVE
ABVE-PC
AC
AC-T
Adcetris (Brentuximab Vedotin)
ADE
Ado-Trastuzumab Emtansine
Adriamycin (Doxorubicin Hydrochloride)
Afatinib Dimaleate
Afinitor (Everolimus)
Akynzeo (Netupitant and Palonosetron Hydrochloride)
Aldara (Imiquimod)
Aldesleukin
Alecensa (Alectinib)
Alectinib
Alemtuzumab
Alkeran for Injection (Melphalan Hydrochloride)
Alkeran Tablets (Melphalan)
Alimta (Pemetrexed Disodium)
Aloxi (Palonosetron Hydrochloride)
Alunbrig (Brigatinib)
Ambochlorin (Chlorambucil)
Amboclorin (Chlorambucil)
Amifostine
Aminolevulinic Acid
Anastrozole
Aprepitant
Aredia (Pamidronate Disodium)
Arimidex (Anastrozole)
Aromasin (Exemestane)
Arranon (Nelarabine)
Arsenic Trioxide
Arzerra (Ofatumumab)
Asparaginase *Erwinia chrysanthemi*
Atezolizumab
Avastin (Bevacizumab)
Avelumab
Axitinib
Azacitidine
B
Bavencio (Avelumab)
BEACOPP
Becenum (Carmustine)
Beleodaq (Belinostat)
Belinostat
Bendamustine Hydrochloride
BEP
Bevacizumab
Bexarotene
Bexxar (Tositumomab and Iodine I 131 Tositumomab)
Bicalutamide
BiCNU (Carmustine)
Bleomycin
Blinatumomab
Blincyto (Blinatumomab)
Bortezomib
Bosulif (Bosutinib)
Bosutinib
Brentuximab Vedotin
Brigatinib
BuMel
Busulfan
Busulfex (Busulfan)
C
Cabazitaxel
Cabometyx (Cabozantinib-S-Malate)
Cabozantinib-S-Malate
CAF
Campath (Alemtuzumab)
Camptosar (Irinotecan Hydrochloride)
Capecitabine
CAPOX
Carac (Fluorouracil—Topical)
Carboplatin
CARBOPLATIN-TAXOL
Carfilzomib
Carmubris (Carmustine)
Carmustine
Carmustine Implant
Casodex (Bicalutamide)
CEM Ceritinib
Cerubidine (Daunorubicin Hydrochloride)
Cervarix (Recombinant HPV Bivalent Vaccine)
Cetuximab
CEV
Chlorambucil
CHLORAMBUCIL-PREDNISONE
CHOP
Cisplatin
Cladribine
Clafen (Cyclophosphamide)
Clofarabine
Clofarex (Clofarabine)
Clolar (Clofarabine)
CMF
Cobimetinib
Cometriq (Cabozantinib-S-Malate)
COPDAC
COPP
COPP-ABV
Cosmegen (Dactinomycin)
Cotellic (Cobimetinib)
Crizotinib
CVP
Cyclophosphamide
Cyfos (Ifosfamide)
Cyramza (Ramucirumab)
Cytarabine
Cytarabine Liposome
Cytosar-U (Cytarabine)
Cytoxan (Cyclophosphamide)
D
Dabrafenib
Dacarbazine
Dacogen (Decitabine)
Dactinomycin
Daratumumab
Darzalex (Daratumumab)
Dasatinib
Daunorubicin Hydrochloride
Decitabine
Defibrotide Sodium
Defitelio (Defibrotide Sodium)
Degarelix
Denileukin Diftitox
Denosumab
DepoCyt (Cytarabine Liposome)
Dexamethasone
Dexrazoxane Hydrochloride
Dinutuximab
Docetaxel
Doxil (Doxorubicin Hydrochloride Liposome)
Doxorubicin Hydrochloride
Doxorubicin Hydrochloride Liposome
Dox-SL (Doxorubicin Hydrochloride Liposome)
DTIC-Dome (Dacarbazine)
Durvalumab
E
Efudex (Fluorouracil—Topical)
Elitek (Rasburicase)
Ellence (Epirubicin Hydrochloride)
Elotuzumab
Eloxatin (Oxaliplatin)
Eltrombopag Olamine
Emend (Aprepitant)
Empliciti (Elotuzumab)
Enzalutamide
Epirubicin Hydrochloride
EPOCH
Erbitux (Cetuximab)
Eribulin Mesylate
Erivedge (Vismodegib)
Erlotinib Hydrochloride
Erwinaze (Asparaginase *Erwinia chrysanthemi*)
Ethyol (Amifostine)
Etopophos (Etoposide Phosphate)
Etoposide
Etoposide Phosphate
Evacet (Doxorubicin Hydrochloride Liposome)
Everolimus
Evista (Raloxifene Hydrochloride)
Evomela (Melphalan Hydrochloride)
Exemestane
F
5-FU (Fluorouracil Injection)
5-FU (Fluorouracil—Topical)
Fareston (Toremifene)
Farydak (Panobinostat)
Faslodex (Fulvestrant)
FEC
Femara (Letrozole)
Filgrastim
Fludara (Fludarabine Phosphate)
Fludarabine Phosphate
Fluoroplex (Fluorouracil—Topical)
Fluorouracil Injection
Fluorouracil—Topical
Flutamide
Folex (Methotrexate)
Folex PFS (Methotrexate)
FOLFIRI
FOLFIRI-BEVACIZUMAB
FOLFIRI-CETUXIMAB
FOLFIRINOX
FOLFOX
Folotyn (Pralatrexate)
FU-LV
Fulvestrant
G
Gardasil (Recombinant HPV Quadrivalent Vaccine)
Gardasil 9 (Recombinant HPV Nonavalent Vaccine)
Gazyva (Obinutuzumab)
Gefitinib
Gemcitabine Hydrochloride
GEMCITABINE-CISPLATIN
GEMCITABINE-OXALIPLATIN
Gemtuzumab Ozogamicin
Gemzar (Gemcitabine Hydrochloride)
Gilotrif (Afatinib Dimaleate)
Gleevec (Imatinib Mesylate)
Gliadel (Carmustine Implant)
Gliadel wafer (Carmustine Implant)
Glucarpidase
Goserelin Acetate
H
Halaven (Eribulin Mesylate)
Hemangeol (Propranolol Hydrochloride)
Herceptin (Trastuzumab)
HPV Bivalent Vaccine, Recombinant
HPV Nonavalent Vaccine, Recombinant
HPV Quadrivalent Vaccine, Recombinant
Hycamtin (Topotecan Hydrochloride)
Hydrea (Hydroxyurea)
Hydroxyurea Hyper-CVAD
I
Ibrance (Palbociclib)
Ibritumomab Tiuxetan
Ibrutinib
ICE
Iclusig (Ponatinib Hydrochloride)
Idamycin (Idarubicin Hydrochloride)
Idarubicin Hydrochloride
Idelalisib
Ifex (Ifosfamide)
Ifosfamide
Ifosfamidum (Ifosfamide)
IL-2 (Aldesleukin)
Imatinib Mesylate
Imbruvica (Ibrutinib)
Imfinzi (Durvalumab)
Imiquimod
Imlygic (Talimogene Laherparepvec)
Inlyta (Axitinib)
Interferon Alfa-2b, Recombinant
Interleukin-2 (Aldesleukin)
Intron A (Recombinant Interferon Alfa-2b)
Iodine I 131 Tositumomab and Tositumomab
Ipilimumab
Iressa (Gefitinib)
Irinotecan Hydrochloride
Irinotecan Hydrochloride Liposome
Istodax (Romidepsin)
Ixabepilone
Ixazomib Citrate
Ixempra (Ixabepilone)
J
Jakafi (Ruxolitinib Phosphate)
JEB
Jevtana (Cabazitaxel)
K
Kadcyla (Ado-Trastuzumab Emtansine)
Keoxifene (Raloxifene Hydrochloride)
Kepivance (Palifermin)
Keytruda (Pembrolizumab)
Kisqali (Ribociclib)
Kyprolis (Carfilzomib)
L
Lanreotide Acetate
Lapatinib Ditosylate
Lartruvo (Olaratumab)
Lenalidomide
Lenvatinib Mesylate
Lenvima (Lenvatinib Mesylate)
Letrozole
Leucovorin Calcium
Leukeran (Chlorambucil)
Leuprolide Acetate
Leustatin (Cladribine)
Levulan (Aminolevulinic Acid)
Linfolizin (Chlorambucil)
LipoDox (Doxorubicin Hydrochloride Liposome)
Lomustine
Lonsurf (Trifluridine and Tipiracil Hydrochloride)
Lupron (Leuprolide Acetate)
Lupron Depot (Leuprolide Acetate)
Lupron Depot-Ped (Leuprolide Acetate)
Lynparza (Olaparib)
M
Marqibo (Vincristine Sulfate Liposome)
Matulane (Procarbazine Hydrochloride)
Mechlorethamine Hydrochloride
Megestrol Acetate
Mekinist (Trametinib)
Melphalan
Melphalan Hydrochloride
Mercaptopurine
Mesna
Mesnex (Mesna)
Methazolastone (Temozolomide)
Methotrexate
Methotrexate LPF (Methotrexate)
Methylnaltrexone Bromide
Mexate (Methotrexate)
Mexate-AQ (Methotrexate)
Midostaurin
Mitomycin C
Mitoxantrone Hydrochloride
Mitozytrex (Mitomycin C)
MOPP
Mozobil (Plerixafor)
Mustargen (Mechlorethamine Hydrochloride)
Mutamycin (Mitomycin C)
Myleran (Busulfan)
Mylosar (Azacitidine)
Mylotarg (Gemtuzumab Ozogamicin)
N
Nanoparticle Paclitaxel (Paclitaxel Albumin-stabilized Nanoparticle Formulation)
Navelbine (Vinorelbine Tartrate)
Necitumumab
Nelarabine
Neosar (Cyclophosphamide)
Netupitant and Palonosetron Hydrochloride
Neulasta (Pegfilgrastim)
Neupogen (Filgrastim)
Nexavar (Sorafenib Tosylate)
Nilandron (Nilutamide)
Nilotinib
Nilutamide
Ninlaro (Ixazomib Citrate)
Niraparib Tosylate Monohydrate
Nivolumab
Nolvadex (Tamoxifen Citrate)
Nplate (Romiplostim)
O
Obinutuzumab
Odomzo (Sonidegib)
OEPA
Ofatumumab
OFF
Olaparib
Olaratumab
Omacetaxine Mepesuccinate
Oncaspar (Pegaspargase)
Ondansetron Hydrochloride
Onivyde (Irinotecan Hydrochloride Liposome)
Ontak (Denileukin Diftitox)
Opdivo (Nivolumab)
OPPA
Osimertinib
Oxaliplatin
P
Paclitaxel
Paclitaxel Albumin-stabilized Nanoparticle Formulation
PAD
Palbociclib
Palifermin Palonosetron Hydrochloride
Palonosetron Hydrochloride and Netupitant
Pamidronate Disodium
Panitumumab
Panobinostat
Paraplat (Carboplatin)
Paraplatin (Carboplatin)
Pazopanib Hydrochloride
PCV
PEB
Pegaspargase
Pegfilgrastim
Peginterferon Alfa-2b
PEG-Intron (Peginterferon Alfa-2b)
Pembrolizumab
Pemetrexed Disodium
Perjeta (Pertuzumab)
Pertuzumab
Platinol (Cisplatin)
Platinol-AQ (Cisplatin)
Plerixafor
Pomalidomide
Pomalyst (Pomalidomide)
Ponatinib Hydrochloride
Portrazza (Necitumumab)
Pralatrexate
Prednisone
Procarbazine Hydrochloride
Proleukin (Aldesleukin)
Prolia (Denosumab)
Promacta (Eltrombopag Olamine)
Propranolol Hydrochloride
Provenge (Sipuleucel-T)
Purinethol (Mercaptopurine)
Purixan (Mercaptopurine)
Q
R
Radium 223 Dichloride
Raloxifene Hydrochloride
Ramucirumab
Rasburicase
R-CHOP
R-CVP
Recombinant Human Papillomavirus (HPV) Bivalent Vaccine
Recombinant Human Papillomavirus (HPV) Nonavalent Vaccine
Recombinant Human Papillomavirus (HPV) Quadrivalent Vaccine
Recombinant Interferon Alfa-2b
Regorafenib
Relistor (Methylnaltrexone Bromide)
R-EPOCH
Revlimid (Lenalidomide)
Rheumatrex (Methotrexate)
Ribociclib
R-ICE
Rituxan (Rituximab)
Rituximab
Rolapitant Hydrochloride
Romidepsin
Romiplostim
Rubidomycin (Daunorubicin Hydrochloride)
Rubraca (Rucaparib Camsylate)
Rucaparib Camsylate
Ruxolitinib Phosphate
Rydapt (Midostaurin)
S
Sclerosol Intrapleural Aerosol (Talc)
Siltuximab
Sipuleucel-T
Somatuline Depot (Lanreotide Acetate)
Sonidegib
Sorafenib Tosylate
Sprycel (Dasatinib)
STANFORD V
Sterile Talc Powder (Talc)
Steritalc (Talc)
Stivarga (Regorafenib)
Sunitinib Malate
Sutent (Sunitinib Malate)
Sylatron (Peginterferon Alfa-2b)
Sylvant (Siltuximab)
Synribo (Omacetaxine Mepesuccinate)
T
Tabloid (Thioguanine)
TAC
Tafinlar (Dabrafenib)
Tagrisso (Osimertinib)
Talc
Talimogene Laherparepvec
Tamoxifen Citrate
Tarabine PFS (Cytarabine)
Tarceva (Erlotinib Hydrochloride)
Targretin (Bexarotene)
Tasigna (Nilotinib)
Taxol (Paclitaxel)
Taxotere (Docetaxel)
Tecentriq (Atezolizumab)
Temodar (Temozolomide)
Temozolomide
Temsirolimus
Thalidomide
Thalomid (Thalidomide)
Thioguanine
Thiotepa
Tolak (Fluorouracil—Topical)
Topotecan Hydrochloride
Toremifene
Torisel (Temsirolimus)
Tositumomab and Iodine I 131 Tositumomab
Totect (Dexrazoxane Hydrochloride)
TPF
Trabectedin
Trametinib
Trastuzumab
Treanda (Bendamustine Hydrochloride)
Trifluridine and Tipiracil Hydrochloride
Trisenox (Arsenic Trioxide)
Tykerb (Lapatinib Ditosylate)
U
Unituxin (Dinutuximab)
Uridine Triacetate
V
VAC
Vandetanib
VAMP
Varubi (Rolapitant Hydrochloride)
Vectibix (Panitumumab)
VeIP
Velban (Vinblastine Sulfate)
Velcade (Bortezomib)
Velsar (Vinblastine Sulfate)
Vemurafenib Venclexta (Venetoclax)
Venetoclax
Viadur (Leuprolide Acetate)
Vidaza (Azacitidine)
Vinblastine Sulfate
Vincasar PFS (Vincristine Sulfate)
Vincristine Sulfate
Vincristine Sulfate Liposome
Vinorelbine Tartrate
VIP
Vismodegib
Vistogard (Uridine Triacetate)
Voraxaze (Glucarpidase)
Vorinostat
Votrient (Pazopanib Hydrochloride)
W
Wellcovorin (Leucovorin Calcium)
X
Xalkori (Crizotinib)
Xeloda (Capecitabine)
XELIRI
XELOX
Xgeva (Denosumab)
Xofigo (Radium 223 Dichloride)
Xtandi (Enzalutamide)
Y
Yervoy (Ipilimumab)
Yondelis (Trabectedin)
Z
Zaltrap (Ziv-Aflibercept)
Zarxio (Filgrastim)
Zejula (Niraparib Tosylate Monohydrate)
Zelboraf (Vemurafenib)
Zevalin (Ibritumomab Tiuxetan)
Zinecard (Dexrazoxane Hydrochloride)
Ziv-Aflibercept
Zofran (Ondansetron Hydrochloride)
Zoladex (Goserelin Acetate)
Zoledronic Acid
Zolinza (Vorinostat)
Zometa (Zoledronic Acid)
Zydelig (Idelalisib)
Zykadia (Ceritinib)
Zytiga (Abiraterone Acetate)
Bank In another general aspect, the present invention provides a bank of at least 230 donors for the preparation of a set a kit of n pharmaceutical unit doses according to any one of the above.

The present invention provides a bank as above, for the preparation of a set of n pharmaceutical unit doses, with n is at least 5.

The present invention provides a bank as above, for the preparation of a set of n pharmaceutical unit doses, with n is 5.

The present invention provides a bank as above, for the preparation of a set of n pharmaceutical unit doses, for use as a medicament for immunotherapy in one individual patient P in a need thereof.

The bank as above, for the preparation of a set of 5 pharmaceutical unit doses, for use as a medicament for immunotherapy in one individual patient P in a need thereof.

The bank, as above, wherein the donors used for preparing the set of n pharmaceutical unit doses of engineered cells, excludes previous donors of cells, organ or tissues in P, unless said donor is P.

The bank according to any one of the above wherein the donors have no common allele between paired two donors unless the common allele matches those of P.

The bank according to any one of the above, wherein the donors have no common allele between paired two donors, and
  said non common allele(s) between paired two donors code at least 1 locus involved in anamnestic response, or
  said non common allele(s) between paired two donors comprise one of the following loci HLA-A, HLA-B, HLA-C, HLA-DP, HLA-DQ and HLA-DR, preferably HLA-C, more preferably HLA-C, HLA-DP, HLA-DQ and HLA-DR, or
  said non common allele(s) between paired two donors comprise at least 1 locus involved in anamnestic response, and said non common allele(s) between paired two donors comprise one of the following loci HLA-A, HLA-B, HLA-C, HLA-DP, HLA-DQ and HLA-DR, and a combination thereof preferably HLA-C, more preferably HLA-C, HLA-DP, HLA-DQ and HLA-DR.

The present invention provides a bank as above wherein engineered cells are beta2 microglobulin deficient and/or CTIIA deficient and said non common allele(s) between paired two donors comprises the following molecules, HLA-DP, HLA-DQ, and HLA-DR.

The present invention provides a bank as above wherein each pharmacological unit dose of cells is administered to one individual P in a time interval between two administrations ranging from an half day, one day, two days, three days four days, five days, six days, seven days, eight days, nine days, ten days, eleven days, twelve days, thirteen days, fourteen days, fifteen days, sixteen days, seventeen days, eighteen days, nineteen days, twenty days, 30 days, 40 days, 45 days, 50 days, 60 days, 90 days, 120 days, 180 days, 8 months, 12 months a year, 2 years, 3 years, 4, 5, 6, 7, 8, 9, 10 years, 11, 12, 13, 14, 15, 16, 17, 18, 19, 20, 30, 40, 50, 60, 70, years to 90 years, preferably 6 months or any time between an half day and 80 years.

The present invention provides a bank as above comprising at most 230 different donors for preparing a set of 5 successive pharmaceutical unit doses of chimeric antigen receptor (CAR) or of TCR expressing engineered primary cells.

The present invention provides a bank as above wherein the HLA of at least one donor match those of the previous graft (bone marrow) and may not fully match those of P, to prevent a Host versus Graft rejection.

The present invention provides a bank as any one of the above wherein said engineered primary cells comprise at least one inactivated TCR gene allele.

The present invention provides a bank as any one of the above endowed with at least one CAR or a with a T cell receptor (TCR).

A set of 5 doses of engineered primary cells according to those above each with the following haplotype (A-B-DRB1) haplotype: 29-58-0807, 68-75-0413, 32-42-0302, 2-70-1322, 69-35-1305. Other examples are in table 1.

The present invention is also directed to a method for preparing a set of n pharmaceutical unit doses comprising engineered cells and a pharmaceutically acceptable vehicle, comprising the step of:
  i) genotyping and/or phenotyping the HLA molecules or HLA alleles of a patient P,
  ii) measuring and quantifying the existing antibodies and/or CTL responses of said patient, iii) selecting and/or providing among 230 donors, at least 5 samples of cells (grafts) by choosing by order of preference:
   a) donors or samples of cells fully matching the immunogenic antigen born by cells of P,
   a') donors or samples of cells comprising no immunogenic antigen P was already immunized against or
   a") choosing donors or samples of cells, bearing a number of mismatching immunogenic antigens born by cells as low as possible, as compared to P (including immunogenic antigen P was already immunized against) and
iv) modifying cells for altering the expression of said immunogenic antigens born by cells P was already immunized against if any and either modifying cells for matching said immunogenic antigens born by cells to the immunogenic antigens born by cells of P.
the first two steps may be performed by a method as described in incorporated herein by reference.

The present invention provides a method for preparing a set of n pharmaceutical unit doses comprising:
   selecting donor or samples of cell with the less possible of common antigen with each other and with those to which P was previously immunized against unless they match those of P,
   modifying cells by introducing at least one CAR or TCR different in each sample and/or inactivating at least one component of the TCR gene.

The present invention provides a method for preparing a set of n pharmaceutical unit doses comprising engineered cells and a pharmaceutically acceptable vehicle, according to the above wherein the step of modifying cells comprises:
   introducing at the same time into said cells:
   At least one nucleic acid comprising an exogenous nucleotide or exogenous polynucleotide sequence, and
      at least one sequence-specific reagent that specifically targets a selected endogenous locus in the genome, preferably said endogenous locus is an endogenous locus encoding a TCR gene A or B.

In preferred embodiments, said exogenous polynucleotide encodes a CAR.

In preferred embodiments, said sequence-specific reagent is rare cutting endonuclease selected from a TALEN, a crispr, a Zn Finger, a megaTAL, . . . .

The present invention provides a method according to the above, wherein the immunogenic antigens born by cell comprises one of the HLA molecules selected from any one of those described in http://hla.alleles.org/nomenclature/updates/201606.html.

The present invention provides a method according to the above, wherein the immunogenic antigens born by cell comprises at least one of the HLA molecules selected from HLA-A, HLA-B, HLA-C, HLA-DR, and a combination thereof.

The present invention provides a method according to the above, wherein HLA of samples match more than 80% to the HLA of P.

The present invention provides a method according to the above, comprising a step of genetically engineering cells to inactivate at least one immune check point.

The present invention provides a method according to the above, a method as above comprising a step of genetically engineering cells conferring resistance to a drug.

The present invention provides a method according to the above, comprising a step of genetically engineering cells for matching immunogenic antigens born by cells to those of P.

The present invention provides a method according to the above, comprising a step of genetically engineering cells for matching immunogenic antigens born by cells to those of previous graft in P.

The present invention provides a method according to the above, wherein the step of genetically engineering cells comprises using a specific rare-cutting endonuclease.

The present invention provides a method according to the above, wherein said rare-cutting endonuclease is a TALE-nuclease or a CRISPR/Cas nuclease.

The present invention provides a method according to the above, wherein the step of genetically engineering cells is performed by homologous recombination mediated gene targeting.

The present invention provides a method according to the above, wherein the step of choosing samples of cells comprises selecting a triple homozygote on HLA-A, HLA-B and HLA-DR genes.

The present invention provides a method according to the above, wherein the step of choosing samples of cells comprises selecting a double homozygote on 2 of HLA-A, HLA-B and HLA-DR genes.

The present invention provides a method according to the above, wherein the step of choosing samples of cells comprises selecting a donor available in a database.

A data base according to the present invention may be any one of the database already existing for potential donors, in particular for organ or cell transplants.

The present invention provides a method according to the above, wherein a donor is defined as belonging to subpopulation selected from Caucasian, African, Asian.

The present invention provides a method according to the above, wherein a donor is defined according to at least one genetic marker according to The Human Genome Project1, the SNP Consortium2 and/or the International HapMap Project3 comprising ~10 million common DNA variants.

The present invention provides a method according to the above, wherein a donor is selected based on i) the frequency of his or her HLAtyping in a database ii) on his or her HLAtyping as compared to the other donors of the set (the cells of whom will be used in the n−1 unit doses of the set according to the present invention). Optionally a donor will be selected based on iii) the level of matching with P using a computer software or program analyzing and selecting at least 6/6 and preferably 10/10 HLA alleles matching.

The present inventors found that surprisingly the solution to the present technical problem of providing cell for immunotherapy also minimizes particular side effects due to immunotherapy.

The invention is especially useful to avoid other side effects due to immunotherapy such as cytokine storm.

In one embodiment, the invention provides a set of n pharmaceutical unit doses comprising engineered cells and a pharmaceutically acceptable vehicle, wherein administering immuno-modulating or immuno-suppressing medical regimen(s) before administering engineered immune cells allows reducing and/or delaying a rejection and give time for the Graft to operate its intended purpose (e.g., destroy cancer cells in immunotherapy against cancer).

In a particular embodiment, the invention provides a set of n pharmaceutical unit doses comprising engineered cells and a pharmaceutically acceptable vehicle, wherein administering immuno-modulating or immuno-suppressing medical regimen(s) before administering engineered immune cells allows re-exposure to the same antigen without inducing any subsequent anamnestic response.

Such regimen has various impacts on the various compartments of the immune system that were characterized here in patients and may be responsible for the higher efficacy on some of them over others.

For example, lymphodepletion (e.g. through treatment with cyclophosphamide and fludarabine) may have more impact on the activities of T-cells than on the action of circulating antibodies.

A T-independent B cell response may occur and participate to the immune reaction in the skin (GVHD) and/or the gut). Particular immunosuppressant drug inhibiting tissue specific immune cells or mucosal immune cells in the intestine may therefore prevent related GVHD (skin bs gut).

The rejection of Graft, especially in individuals already immunized against one or more antigen(s) present in said Graft, can thus be difficult to control through medical regimen(s) alone.

The present invention provides therefore a method for selecting donors or cells for preparing successive units or doses of immune cells for immunotherapy expressing no or reduced TCR and inducing no or reduced anamnestic response based on one or several of the following criteria:
- the cell surface expression of anamnestic molecules shared and not shared with the host intended to be treated,
- the expression of anamnestic molecules unshared with the host intended to be treated, shared by pair donors,
- the expression of anamnestic molecules unshared with the host intended to be treated, shared by pair donors and the selection, among said molecules of those inducing the less anamnestic responses.

The present invention provides a method for selecting donors for preparing successive antigen expressing cells comprising a step of modifying genes involved in graft versus host diseases, and/or in anamnestic responses, to match the graft to P or to the previous graft administered to P (analysis of the antibodies in P), in case of previous allogenic stem cells transplantation and/or bone marrow transplantation.

The present invention provides a method for selecting donors for preparing successive antigen expressing cells by expressing molecule(s) inhibiting said anamnestic response in said engineered cells.

The present invention encompasses sets of engineered T-cells that carry surface proteins such as MHC molecules that are not present in the receiving individual, in addition to the antigen recognizing receptor (e.g. a chimeric antigen receptor).

Optionally, cells in a unit dose of the set of n pharmaceutical unit doses may be further be engineered to match MHC molecules and not being inhibited by cancer cells, said cells may be used in a treatment with immunosuppressant drugs.

The present invention provides a set or kit of n pharmaceutical unit doses of engineered cells, wherein each individual dose comprises immunogenic antigens born by cells that are identical or match to those of P, and immunogenic antigens born by engineered cells that have no common epitope with those of engineered cells in each of the n−1 other doses.

This allows the immune system of P not to be exposed twice to allogenic antigens and avoid mounting an anamnestic reaction.

The present invention provides a set of unit doses wherein cells may have common antigen. The present invention provides a set of unit doses wherein cells may have common MHC molecules.

According to the present invention, in particular embodiments, the second dose used in P (and none of the following ones administered to P) should bear the same immunogenic antigens carried by, for example the CAR. Thus, said CAR should be different in each unit dose even if binding to the same antigen.

In particular embodiments, the second dose used in P (and all of the following ones administered to P) may bear the same immunogenic antigens carried by, for example the CAR. Thus, said CAR can be identical in each unit dose when each dose is used for a successive administration just after at least one immunosuppressive drug, preferably a combination of fludarabine, cyclophosphamide, optionally rituximab.

According to the present invention, in particular embodiments, the second dose administered in P (and the following ones) should not bear the immunogenic antigens carried by the first one or by previous grafts (unless these antigens do not generate any immune response).

As an illustration:
First injection: anti-CD123 CAR T cells prepared with T cells isolated from P, engineered and then reinjected to P
Second injection: anti-CD123 CAR made with another anti-CD123 antigen binding domain using T cells isolated from P, to be reinjected to P.

According to the present invention, in particular embodiments, the set or kit of n pharmaceutical unit doses of engineered cells, for use as a sequential therapy inducing no or reduced anamnestic immune reaction in one individual (P) should be administered by order of preference such as:

At first, those having identical immunogenic antigens born by cells to those expressed by constituting immune cells of P, preferably, autologous, HLA identical to P,
then, doses wherein cells are engineered so that MHC class I and class II match those of P,
then, those wherein the immunogenic antigens born by cells match (scores 6/6 7/7, 8/8, 9/9, 10/10) those of the P
(cells are from an identical twin (syngeneic, HLA identical), from a sibling, relative, (allogeneic, which can be HLA identical, haploidentical, or mismatched),
then, doses wherein the immunogenic antigens born by the engineered cells do not fully match those of the patient in the increasing level of mismatch and if M is the set of immunogenic antigen(s) unmatched with P present in the k-th of the m consecutive not fully matched doses, then the k-th of these m administered doses (with k≥2) should not to bear the immunogenic antigens present in the union of M1, M2, . . . , M(k−1). In addition, M may avoid any immunogenic antigen against which the individual is already immunized against.

In one embodiment, engineered CAR-expressing cells may be administered according to the method described in PCT/US2013/032129 as inducing a reduced the risk of sustained engraftment and graft-versus-host disease.

In general, within the set of n pharmaceutical unit doses of engineered cells, for use as a sequential therapy inducing no or reduced anamnestic immune reaction in one individual (P) the dose selected to be administered first is selected by order of preference, so that immunogenic antigens of engineered cells match the most possible those of P (for sequential therapy using autologous transfer, cells of P are engineered with different CAR of TCR), or engineered cells are modified so that the MHC class I and class II molecules fully match those of P (score of 6:6, preferably 8:8, more preferably 10:10), or are compatible with P (engineered cells with no class I and no class II molecules by deleting the beta 2 microglobuline and CTIIA genes, engineering cells), or with specific combination of MHC molecules compatible with P (that will induce no or reduced anamnestic immune reaction), Cells must present a degree of mismatch the lowest possible with immunogenic antigens expressed on hematopoietic cells of P (no more than 5/8 mismatches, preferably no more than one mismatch).

Cells used here may be immune cells engineered according to any of previous methods described, for example, in WO2014/184143 or in WO2014191128 or in WO2016160620A3, all incorporated by reference, in particular for methods.

Successive treatments, with cells of the invention induce no or very moderate Anamnestic Responses against allogeneic T-cells as a graft and at least open a window of time sufficient for said grafted T-cells to attack the individual's pathological tissues in the absence of graft-versus-host and host versus graft reaction.

Another aspect of the present invention is a method for preparing a set of n pharmaceutical unit doses of engineered cells, for use as a sequential therapy inducing no or reduced anamnestic immune reaction in one individual (P) comprising the following steps:
  v) fixing n to a given value, such as n=5,
  vi) choosing randomly n donors from a given population of at least 230 donors, vii) selecting n anamnestic compatible donors;
  viii) endowing cells from each donor with a CAR, or with a multifunctional CAR, of with a part of a CAR that is linkable (covalently or non-covalently) to an appropriate scfv or binding domain when needed, preferably by inserting said CAR into the TCR locus using a TALEN® rare cutting endonuclease.
  ix) optionally, engineering separately each sample of cells by inactivating a TCRA gene (TCR alpha gene), a beta2miccroglobulin gene and CTIIA gene,
  x) freezing said samples.

Cells in a sample or in a pharmaceutical unit dose may be a population of cells, (such as peripheral blood monocytes (PBMC), a population of T cells, a population of essentially purified T cells.

Another aspect of the present invention is a method for treating a patient using a kit or a set of n pharmaceutical unit doses of engineered cells, as a sequential therapy inducing no or reduced anamnestic immune reaction in one individual (P).

Embodiments of such methods can be derived from any of the kit or set of n pharmaceutical unit doses of engineered cells, for use as a sequential therapy inducing no or reduced anamnestic immune reaction in one individual (P).
General Method To favor the absence of anamnestic Response against a Graft, one can minimize the number of Immunogenic Antigens in the previous Graft(s).

This can be achieved by:
  choosing or engineering a Graft closely related to the receiving individual (e.g. autologous, haplotype—matched, etc.), or
  choosing or engineering a Graft that bears a limited number of Immunogenic antigens, through homozygosity or presence of only one functional allele, for variable genes which alleles are involved in immunization.

If said Immunogenic Antigens are HLA molecules, HLA-A, -B, C and/or DR homozygocity leading to the presence of 3 (for triple homozygocity, i.e. on all three HLA-A, -B, and DR genes), 4 (for double homozygocity, i.e. on two of HLA-A, -B, or DR genes) or 5 (for single homozygocity, i.e. on one of HLA-A, -B, or DR genes) different HLA antigens known to be variable instead of 6 on the surface of the Graft, reduces the Immunogenic Antigens against which the individual will be immunized when receiving said Graft.

Likewise, absence of HLA-A, or —B or C or -DR, either natural or engineered, on the surface of the Graft, reduces the Immunogenic Antigens against which the individual can potentially be immunized when receiving said Graft. A method step to achieve such reduced number of HLA expressed genes can be gene disruption (e.g. using nuclease-based gene editing, or homologous recombination mediated gene targeting), or ectopic expression of antisense or interfering molecules such as RNA that block said expression. Preferably a method as described in PA 2016 70840 is implemented.

Alternatively, replacement of one or more alleles of one or more HLA molecules by an allele present in the grafted individual, reduces the Immunogenic antigens against which the individual can potentially be immunized when receiving said Graft.

The present invention provides a method to achieve such replacement of HLA coding genes by homologous recombination mediated targeted DNA sequence substitution in the genome of the grafted cells.

Alternatively, it can be achieved by a combination of ectopic expression of the HLA allele that is present in the grafted individual, with gene disruption (e.g. using nuclease-based gene editing, or homologous recombination mediated gene targeting) of the Immunogenic HLA ectopic expression of antisense or interfering molecules such as RNA that block said expression (provided its action is specific on the HLA which expression is to be alleviated).

If said Immunogenic Antigens are blood type antigens it is part of the present invention to determine the red blood cells' type of an individual: AB, O, Rhesus, KEL, Duffy, etc.) as a preliminary step of preparing a set according to the invention.

Other strategies may be pursued in order to limit the presence of Immunogenic Antigens at the surface of the grafted cells or their progeny.

The present invention encompasses a method comprising selecting donors with homozygosis on one or more said immunogenic red blood cells type Antigen(s); engineering nucleated red blood cells, or cell precursor's genome in order to limit the number of said Immunogenic red blood cells type Antigen(s) that will be expressed on red blood cells; or substitute antigens (by targeted homologous recombination or by a combination of ectopic expression of an allele present in the grafted individual with the inactivation or the blocking of the expression of the gene encoding the undesirable allele(s)).

If the treatment is intended for a particular population in which the representation of immunogenic variant alleles have biased frequencies (i.e. some variant alleles are more frequent than others) then, the order in which the consecutive Grafts are made can also be optimized. It is part of the present invention to design a sequence of consecutive chosen sets of Immunogenic Antigens known to be varying in the population.

If the patients are likely to have been exposed to foreign cells or tissue (e.g. having received transfusion, platelets or having been grafted, due to its condition) then the probability that they have been exposed to a given Immunogenic Antigen is linked to the abundance of said Immunogenic Antigen. Therefore, the cells or tissues bearing the smallest set or the set of least frequent Immunogenic Antigens should be used first. Subsequently, one could graft cells or tissues bearing sets of more frequent Immunogenic Antigens that are different from those to which the patient was exposed to previously, and so forth for consecutive grafts. For the first graft, the absence of preexisting immunity against the first set of Immunogenic Antigens can be tested for each patient in order to avoid inducing an anamnestic reaction.

3) Method for CAR T Cell Adoptive Immunotherapies

In the case of adoptive CAR T cell adoptive immunotherapies it may be desirable to re-administer the product to a patient through repeat dosing through time. Such an approach may lead to Anamnestic Responses if the CAR molecule or any other ectopically expressed antigen, is, itself, an Immunogenic Antigen, and/or if the product is allogeneic and carries other Immunogenic Antigens, such as variant alleles of surface protein encoding genes for MHC molecules, example (e.g. HLA-C).

In the first case, changing the immunogenic epitopes of the CAR molecule, while still targeting the tumor with consecutive dosing can be an approach. However, this requires a different product for each re-treatment.

In the second case, using allogeneic cells from different donors, so that each Graft does not bear Immunogenic Antigens present in any preceding Grafts can be done to avoid Anamnestic Responses. However, since the Graft is itself including T-cells, then absence of rapid rejection may open a window of time sufficient for said grafted T-cells to attack the individual's tissues through graft-versus-host disease.

A means to achieve repeat allogeneic T-cell based treatment with both absence of Anamnestic Response that could lead to rapid rejection and absence of graft-versus-host disease at each repeated dosing is to eliminate the presence of T-cell receptor at the T-cell surface in the graft (e.g. through the disruption of the gene coding for one functional TCR chain), or render TCR-mediated activation inefficient in these T-cells, and choosing sequentially grafted cells pursuant to one of the methods described hereabove.

Using twice or more times cells from one donor to be administered to another with no or reduced anamnestic response is achieved according to the present invention according to the following general principle:

To minimize the generation of a potential Anamnestic Responses:

if Mn is the set of antigen(s) in the n-th consecutive Graft leading to immunization of the individual (the "Immunogenic Antigens"), then Graft number i (with i≥2) should be designed not to bear Immunogenic Antigens present in the union of M1, M2, . . . , M(i-1)—no exposure two times to the same antigen.

In addition, the first graft may avoid bearing any antigen(s) against which the individual is already immunized from start.

To achieve this, the following technical means are herewith provided:

Bank of Donors: any bank available over the world may be used.

Set of 5 donors cells (Table 1)

TABLE 1

Examples of sets of n pharmaceutical unit doses according to the invention

| A_all1 | C_all1 | B_all1 | DRB1_all1 | freq_all1 | A_all2 | C_all2 | B_all2 | DRB1_all2 | freq_all2 |
|---|---|---|---|---|---|---|---|---|---|
| A*23 | C*07 | B*07 | DRB1*11 | 0.003157 | A*68 | C*12 | B*39 | DRB1*15 | 2.721e-05 |
| A*24 | C*03 | B*40 | DRB1*04 | 0.0005642 | A*34 | C*08 | B*81 | DRB1*14 | 7.517e-05 |
| A*11 | C*04 | B*35 | DRB1*01 | 0.001565 | A*03 | C*16 | B*15 | DRB1*07 | 2.13e-05 |
| A*02 | C*15 | B*27 | DRB1*08 | 5.655e-05 | A*17 | C*12 | B*42 | DRB1*08 | 0.0005784 |
| A*36 | C*06 | B*58 | DRB1*13 | 0.000129 | A*30 | C*05 | B*18 | DRB1*03 | 0.001305 |
| A*02 | C*16 | B*45 | DRB1*07 | 0.001197 | A*02 | C*04 | B*53 | DRB1*07 | 0.001852 |
| A*11 | C*03 | B*55 | DRB1*01 | 0.0001235 | A*01 | C*07 | B*08 | DRB1*13 | 0.0007583 |
| A*29 | C*15 | B*07 | DRB1*03 | 0.0002103 | A*29 | C*06 | B*13 | DRB1*15 | 8.188e-05 |
| A*03 | C*14 | B*51 | DRB1*04 | 8.269e-06 | A*30 | C*18 | B*57 | DRB1*11 | 0.0005077 |
| A*23 | C*02 | B*15 | DRB1*10 | 0.0003071 | A*33 | C*08 | B*14 | DRB1*08 | 0.0001075 |
| A*30 | C*17 | B*42 | DRB1*09 | 0.0004067 | A*30 | C*18 | B*81 | DRB1*15 | 3.863e-05 |
| A*24 | C*04 | B*35 | DRB1*08 | 0.0001959 | A*23 | C*04 | B*44 | DRB1*11 | 0.0006464 |
| A*33 | C*16 | B*51 | DRB1*03 | 0.0001037 | A*15 | C*51 | B*51 | DRB1*04 | 0.000111 |
| A*03 | C*05 | B*18 | DRB1*13 | 0.000123 | A*34 | C*06 | B*58 | DRB1*12 | 0.0002954 |
| A*02 | C*07 | B*07 | DRB1*01 | 0.0008568 | A*02 | C*02 | B*15 | DRBl*10 | 0.000545 |
| A*34 | C*18 | B*13 | DRB1*15 | 9.92e-05 | A*32 | C*05 | B*18 | DRB1*03 | 0.0001231 |
| A*02 | C*07 | B*49 | DRB1*04 | 0.0007124 | A*30 | C*07 | B*58 | DRB1*08 | 8.375e-05 |
| A*03 | C*03 | B*44 | DRB1*12 | 3.261e-05 | A*33 | C*14 | B*15 | DRB1*12 | 8.459e-05 |
| A*68 | C*04 | B*53 | DRB1*13 | 0.004694 | A*36 | C*04 | B*53 | DRB1*13 | 0.001966 |
| A*23 | C*17 | B*42 | DRB1*01 | 8.755e-05 | A*23 | C*17 | B*41 | DRB1*07 | 0.0002013 |
| A*02 | C*08 | B*14 | DRB1*13 | 0.0003797 | A*02 | C*16 | B*45 | DRB1*15 | 0.001481 |
| A*74 | C*17 | B*42 | DRB1*03 | 0.00101 | A*03 | C*07 | B*07 | DRB1*14 | 0.0004314 |
| A*26 | C*18 | B*57 | DRB1*16 | 0.0001605 | A*36 | C*12 | B*39 | DRB1*10 | 2.082e-05 |
| A*30 | C*04 | B*53 | DRB1*01 | 0.0006437 | A*01 | C*05 | B*44 | DRB1*04 | 0.0002385 |
| A*68 | C*03 | B*15 | DRB1*11 | 0.001143 | A*23 | C*03 | B*82 | DRB1*07 | 3.009e-05 |
| A*30 | C*02 | B*18 | DRB1*07 | 0.0006125 | A*29 | C*06 | B*13 | DRB1*01 | 0.0006964 |
| A*68 | C*03 | B*15 | DRB1*10 | 0.0004289 | A*74 | C*03 | B*15 | DRB1*13 | 0.0002079 |
| A*23 | C*18 | B*57 | DRB1*16 | 0.0001774 | A*01 | C*07 | B*49 | DRB1*04 | 0.0002911 |
| A*34 | C*04 | B*44 | DRB1*15 | 0.0061 | A*11 | C*12 | B*52 | DRB1*15 | 0.0002136 |
| A*33 | C*16 | B*78 | DRB1*11 | 0.0006852 | A*33 | C*17 | B*42 | DRB1*03 | 0.002083 |
| A*30 | C*07 | B*49 | DRB1*08 | 0.000272 | A*33 | C*03 | B*82 | DRB1*13 | 5.023e-06 |
| A*24 | C*12 | B*52 | DRB1*12 | 5.285e-05 | A*03 | C*16 | B*45 | DRB1*01 | 0.0007718 |
| A*66 | C*02 | B*35 | DRB1*15 | 1.509e-05 | A*11 | C*15 | B*40 | DRB1*04 | 2.8e-05 |
| A*02 | C*05 | B*18 | DRB1*03 | 0.0007658 | A*14 | B*15 | | DRB1*10 | 3.536e-05 |
| A*68 | C*08 | B*53 | DRB1*07 | 4.376e-06 | A*68 | C*04 | B*44 | DRB1*07 | 0.0001224 |
| A*36 | C*04 | B*53 | DRB1*09 | 0.0004325 | A*30 | C*17 | B*42 | DRB1*03 | 0.01787 |
| A*34 | C*07 | B*49 | DRB1*15 | 0.0005125 | A*66 | C*07 | B*58 | DRB1*15 | 0.003966 |
| A*68 | C*18 | B*57 | DRB1*07 | 0.0002172 | A*01 | C*06 | B*57 | DRB1*07 | 0.002167 |
| A*03 | C*08 | B*14 | DRB1*13 | 0.0009844 | A*32 | C*02 | B*40 | DRB1*13 | 0.0003019 |

TABLE 1-continued

Examples of sets of n pharmaceutical unit doses according to the invention

| A_all1 | C_all1 | B_all1 | DRB1_all1 | freq_all1 | A_all2 | C_all2 | B_all2 | DRB1_all2 | freq_all2 |
|---|---|---|---|---|---|---|---|---|---|
| A*02 | C*16 | B*51 | DRB1*04 | 0.0003065 | A*24 | C*05 | B*44 | DRB1*01 | 0.0001754 |
| A*31 | C*07 | B*57 | DRB1*15 | 0.0009013 | A*30 | C*08 | B*14 | DRB1*11 | 0.0003484 |
| A*68 | C*06 | B*58 | DRB1*12 | 0.007993 | A*01 | C*06 | B*37 | DRB1*10 | 0.0003316 |
| A*36 | C*04 | B*53 | DRB1*07 | 0.0008137 | A*02 | C*16 | B*35 | DRB1*16 | 4.711e−05 |
| A*33 | C*14 | B*15 | DRB1*01 | 0.002405 | A*23 | C*03 | B*15 | DRB1*03 | 0.0007087 |
| A*74 | C*17 | B*42 | DRB1*08 | 0.000252 | A*24 | C*15 | B*40 | DRB1*04 | 0.0002546 |
| A*29 | C*16 | B*44 | DRB1*07 | 0.00365 | A*03 | C*17 | B*42 | DRB1*03 | 0.001267 |
| A*66 | C*18 | B*57 | DRB1*13 | 0.0001513 | A*68 | C*06 | B*58 | DRB1*12 | 0.007993 |
| A*26 | C*15 | B*07 | DRB1*09 | 5.164e−06 | A*11 | C*03 | B*55 | DRB1*04 | 0.0003062 |
| A*36 | C*04 | B*53 | DRB1*11 | 0.007603 | A*23 | C*07 | B*08 | DRB1*11 | 0.000506 |
| A*02 | C*02 | B*15 | DRB1*10 | 0.000545 | A*02 | C*08 | B*14 | DRB1*01 | 0.0003176 |
| A*26 | C*08 | B*14 | DRB1*15 | 2.872e−05 | A*30 | C*17 | B*42 | DRB1*03 | 0.01787 |
| A*02 | C*07 | B*49 | DRB1*09 | 0.0009877 | A*11 | C*07 | B*49 | DRB1*04 | 4.847e−05 |
| A*34 | C*04 | B*53 | DRB1*11 | 0.0003874 | A*68 | C*06 | B*58 | DRB1*12 | 0.007993 |
| A*03 | C*15 | B*07 | DRB1*08 | 3.053e−05 | A*74 | C*02 | B*15 | DRB1*13 | 0.004945 |
| A*29 | C*16 | B*44 | DRB1*07 | 0.00365 | A*23 | C*16 | B*45 | DRB1*07 | 0.0002827 |
| A*23 | C*04 | B*53 | DRB1*11 | 0.0009138 | A*03 | C*03 | B*40 | DRB1*04 | 0.0002916 |
| A*66 | C*07 | B*58 | DRB1*15 | 0.003966 | A*34 | C*08 | B*81 | DRB1*07 | 9.025e−05 |
| A*01 | C*06 | B*37 | DRB1*10 | 0.0003316 | A*29 | C*18 | B*57 | DRB1*16 | 3.826e−05 |
| A*02 | C*17 | B*42 | DRB1*03 | 0.002911 | A*02 | C*05 | B*44 | DRB1*13 | 0.001305 |
| A*11 | C*01 | B*15 | DRB1*01 | 3.069e−05 | A*30 | C*15 | B*07 | DRB1*08 | 0.0001173 |
| A*11 | C*07 | B*40 | DRB1*08 | 0.002916 | A*11 | C*07 | B*08 | DRB1*03 | 0.0007981 |
| A*24 | C*03 | B*35 | DRB1*12 | 0.0002231 | A*24 | C*08 | B*39 | DRB1*12 | 0.0002281 |
| A*33 | C*14 | B*44 | DRB1*13 | 0.008246 | A*03 | C*05 | B*44 | DRB1*13 | 0.001207 |
| A*29 | C*15 | B*07 | DRB1*14 | 0.0002312 | A*04 | C*04 | B*13 | DRB1*15 | 0.0003808 |
| A*01 | C*06 | B*57 | DRB1*07 | 0.01502 | A*01 | C*12 | B*52 | DRB1*04 | 0.0005686 |
| A*02 | C*03 | B*15 | DRB1*04 | 0.00176 | A*33 | C*03 | B*58 | DRB1*03 | 0.02193 |
| A*24 | C*01 | B*46 | DRB1*09 | 0.001994 | A*68 | C*12 | B*52 | DRB1*15 | 0.0008358 |
| A*31 | C*14 | B*51 | DRB1*12 | 0.0003705 | A*11 | C*15 | B*40 | DRB1*14 | 0.0009395 |
| A*29 | C*16 | B*44 | DRB1*07 | 0.0002388 | A*01 | C*06 | B*57 | DRB1*07 | 0.01502 |
| A*26 | C*07 | B*07 | DRB1*01 | 0.0002666 | A*03 | C*07 | B*07 | DRB1*10 | 0.0006538 |
| A*24 | C*15 | B*40 | DRB1*15 | 0.003183 | A*74 | C*14 | B*51 | DRB1*14 | 0.0002743 |
| A*29 | C*03 | B*58 | DRB1*08 | 0.0001012 | A*03 | C*07 | B*07 | DRB1*03 | 0.0005034 |
| A*01 | C*06 | B*57 | DRB1*04 | 0.0006848 | A*01 | C*06 | B*57 | DRB1*07 | 0.01502 |
| A*02 | C*08 | B*15 | DRB1*12 | 0.005328 | A*11 | C*08 | B*15 | DRB1*13 | 0.0005381 |
| A*31 | C*04 | B*35 | DRB1*11 | 0.0003107 | A*30 | C*04 | B*53 | DRB1*11 | 2.271e−05 |
| A*24 | C*15 | B*40 | DRB1*14 | 0.002038 | A*26 | C*07 | B*08 | DRB1*03 | 0.005979 |
| A*01 | C*05 | B*44 | DRB1*04 | 4.014e−05 | A*31 | C*14 | B*51 | DRB1*04 | 0.0008849 |
| A*11 | C*06 | B*13 | DRB1*07 | 0.0005233 | A*11 | C*06 | B*57 | DRB1*07 | 0.001795 |
| A*33 | C*03 | B*58 | DRB1*13 | 0.01294 | A*33 | C*08 | B*48 | DRB1*11 | 0.0001055 |
| A*02 | C*01 | B*46 | DRB1*09 | 0.01723 | A*34 | C*01 | B*56 | DRB1*08 | 7.898e−05 |
| A*02 | C*08 | B*15 | DRB1*12 | 0.005328 | A*02 | C*14 | B*51 | DRB1*04 | 0.001701 |
| A*31 | C*03 | B*40 | DRB1*08 | 0.0005602 | A*30 | C*06 | B*13 | DRB1*07 | 0.01237 |
| A*11 | C*01 | B*55 | DRB1*09 | 0.0003733 | A*29 | C*15 | B*07 | DRB1*10 | 0.007929 |
| A*24 | C*07 | B*39 | DRB1*11 | 0.0001551 | A*01 | C*05 | B*44 | DRB1*15 | 6.035e−05 |
| A*33 | C*04 | B*35 | DRB1*14 | 0.0001962 | A*04 | C*04 | B*35 | DRB1*13 | 0.0004817 |
| A*03 | C*07 | B*39 | DRB1*01 | 1.329e−05 | A*32 | C*02 | B*40 | DRB1*11 | 2.87e−05 |
| A*34 | C*01 | B*56 | DRB1*15 | 0.000108 | A*02 | C*01 | B*46 | DRB1*14 | 0.003246 |
| A*24 | C*04 | B*35 | DRB1*12 | 0.008261 | A*11 | C*12 | B*52 | DRB1*04 | 0.001365 |
| A*01 | C*06 | B*37 | DRB1*10 | 0.008149 | A*01 | C*15 | B*51 | DRB1*10 | 2.451e−05 |
| A*33 | C*14 | B*44 | DRB1*13 | 0.008246 | A*33 | C*03 | B*58 | DRB1*13 | 0.01294 |
| A*33 | C*03 | B*58 | DRB1*03 | 0.02193 | A*29 | C*15 | B*07 | DRB1*10 | 0.007929 |
| A*02 | C*01 | B*46 | DRB1*09 | 0.01723 | A*02 | C*01 | B*59 | DRB1*11 | 6.179e−05 |
| A*24 | C*08 | B*15 | DRB1*15 | 0.002794 | A*24 | C*04 | B*40 | DRB1*12 | 0.0003139 |
| A*11 | C*14 | B*51 | DRB1*14 | 0.001141 | A*68 | C*12 | B*52 | DRB1*04 | 0.0005001 |
| A*32 | C*07 | B*49 | DRB1*13 | 0.0007053 | A*30 | C*06 | B*13 | DRB1*07 | 0.01237 |
| A*01 | C*15 | B*40 | DRB1*15 | 0.002227 | A*24 | C*12 | B*35 | DRB1*14 | 0.0007384 |
| A*33 | C*03 | B*58 | DRB1*03 | 0.02193 | A*33 | C*03 | B*58 | DRB1*11 | 0.000773 |
| A*02 | C*01 | B*46 | DRB1*04 | 0.003169 | A*02 | C*01 | B*46 | DRB1*09 | 0.01723 |
| A*26 | C*06 | B*50 | DRB1*07 | 0.0001232 | A*26 | C*14 | B*51 | DRB1*13 | 0.0001299 |
| A*11 | C*08 | B*15 | DRB1*12 | 0.0137 | A*11 | C*08 | B*15 | DRB1*12 | 0.0137 |
| A*24 | C*04 | B*35 | DRB1*12 | 0.008261 | A*34 | C*04 | B*15 | DRB1*15 | 0.002322 |
| A*29 | C*15 | B*07 | DRB1*09 | 0.0004643 | A*02 | C*01 | B*46 | DRB1*09 | 0.01723 |
| A*01 | C*06 | B*57 | DRB1*07 | 0.01502 | A*30 | C*08 | B*14 | DRB1*08 | 0.0003167 |
| A*33 | C*03 | B*58 | DRB1*03 | 0.02193 | A*11 | C*07 | B*18 | DRB1*14 | 0.000175 |
| A*32 | C*12 | B*52 | DRB1*04 | 0.0001125 | A*32 | C*14 | B*51 | DRB1*01 | 0.0001429 |
| A*24 | C*01 | B*46 | DRB1*08 | 0.00131 | A*02 | C*01 | B*46 | DRB1*09 | 0.01723 |
| A*11 | C*04 | B*35 | DRB1*13 | 0.001629 | A*11 | C*15 | B*40 | DRB1*03 | 0.0002661 |
| A*01 | C*06 | B*57 | DRB1*07 | 0.01502 | A*01 | C*06 | B*37 | DRB1*07 | 0.0004736 |
| A*34 | C*03 | B*15 | DRB1*15 | 4.472e−05 | A*32 | C*12 | B*52 | DRB1*15 | 0.001089 |
| A*33 | C*07 | B*44 | DRB1*14 | 0.0004577 | A*03 | C*07 | B*07 | DRB1*12 | 0.0001265 |
| A*32 | C*07 | B*44 | DRB1*07 | 0.0003241 | A*33 | C*03 | B*58 | DRB1*03 | 0.02193 |
| A*31 | C*14 | B*51 | DRB1*13 | 0.0009911 | A*29 | C*15 | B*07 | DRB1*10 | 0.007929 |
| A*02 | C*01 | B*46 | DRB1*14 | 0.003246 | A*02 | C*01 | B*55 | DRB1*14 | 0.0004371 |
| A*24 | C*04 | B*15 | DRB1*12 | 0.001001 | A*24 | C*04 | B*35 | DRB1*11 | 0.003399 |
| A*11 | C*12 | B*52 | DRB1*15 | 0.004114 | A*11 | C*12 | B*52 | DRB1*15 | 0.004114 |

TABLE 1-continued

Examples of sets of n pharmaceutical unit doses according to the invention

| A_all1 | C_all1 | B_all1 | DRB1_all1 | freq_all1 | A_all2 | C_all2 | B_all2 | DRB1_all2 | freq_all2 |
|---|---|---|---|---|---|---|---|---|---|
| A*33 | C*03 | B*58 | DRB1*03 | 0.02193 | A*11 | C*08 | B*15 | DRB1*15 | 0.003506 |
| A*01 | C*12 | B*52 | DRB1*10 | 5.91e−05 | A*23 | C*07 | B*49 | DRB1*11 | 7.531e−05 |
| A*24 | C*04 | B*35 | DRB1*12 | 0.008261 | A*24 | C*15 | B*40 | DRB1*14 | 0.002038 |
| A*02 | C*01 | B*46 | DRB1*09 | 0.01723 | A*01 | C*46 | B*46 | DRB1*04 | 0.003169 |
| A*30 | C*06 | B*13 | DRB1*07 | 0.01237 | A*03 | C*05 | B*44 | DRB1*13 | 0.001207 |
| A*32 | C*01 | B*55 | DRB1*03 | 2.443e−05 | A*29 | C*15 | B*07 | DRB1*10 | 0.0006019 |
| A*01 | C*02 | B*27 | DRB1*04 | 0.0002964 | A*11 | C*04 | B*35 | DRB1*01 | 0.007259 |
| A*30 | C*06 | B*13 | DRB1*07 | 0.007169 | A*03 | C*08 | B*14 | DRB1*07 | 0.0008185 |
| A*33 | C*12 | B*18 | DRB1*11 | 0.0001174 | A*33 | C*07 | B*49 | DRB1*11 | 9.849e−05 |
| A*02 | C*05 | B*44 | DRB1*13 | 0.005356 | A*24 | C*03 | B*15 | DRB1*13 | 0.002524 |
| A*26 | C*06 | B*57 | DRB1*07 | 0.0004316 | A*24 | C*17 | B*41 | DRB1*13 | 0.0003503 |
| A*01 | C*07 | B*08 | DRB1*03 | 0.06069 | A*01 | C*07 | B*08 | DRB1*03 | 0.06069 |
| A*23 | C*05 | B*44 | DRB1*11 | 4.872e−05 | A*11 | C*04 | B*51 | DRB1*04 | 0.0003029 |
| A*02 | C*01 | B*56 | DRB1*08 | 0.0001613 | A*02 | C*03 | B*40 | DRB1*15 | 0.001866 |
| A*32 | C*02 | B*27 | DRB1*14 | 6.508e−05 | A*32 | C*12 | B*39 | DRB1*01 | 1.763e−05 |
| A*31 | C*03 | B*15 | DRB1*08 | 1.543e−05 | A*68 | C*03 | B*15 | DRB1*04 | 0.0006084 |
| A*01 | C*07 | B*08 | DRB1*01 | 0.002432 | A*03 | C*07 | B*08 | DRB1*03 | 0.003262 |
| A*02 | C*02 | B*27 | DRB1*13 | 0.0005833 | A*26 | C*06 | B*13 | DRB1*07 | 0.000306 |
| A*24 | C*04 | B*35 | DRB1*11 | 0.005438 | A*11 | C*04 | B*35 | DRB1*14 | 0.001555 |
| A*32 | C*05 | B*44 | DRB1*12 | 0.001237 | A*30 | C*12 | B*39 | DRB1*16 | 1.842e−05 |
| A*02 | C*15 | B*51 | DRB1*04 | 0.001614 | A*02 | C*12 | B*39 | DRB1*01 | 0.0002136 |
| A*31 | C*05 | B*18 | DRB1*03 | 0.0001124 | A*11 | C*03 | B*55 | DRB1*03 | 7.01e−05 |
| A*01 | C*04 | B*35 | DRB1*11 | 0.002479 | A*66 | C*17 | B*41 | DRB1*11 | 0.0003676 |
| A*03 | C*07 | B*07 | DRB1*13 | 0.003443 | A*03 | C*07 | B*07 | DRB1*15 | 0.03074 |
| A*24 | C*02 | B*27 | DRB1*08 | 9.369e−05 | A*29 | C*16 | B*44 | DRB1*07 | 0.01451 |
| A*30 | C*06 | B*13 | DRB1*07 | 0.007169 | A*31 | C*02 | B*27 | DRB1*04 | 0.0008165 |
| A*25 | C*12 | B*18 | DRB1*03 | 0.0002444 | A*01 | C*07 | B*08 | DRB1*03 | 0.06069 |
| A*02 | C*16 | B*51 | DRB1*13 | 0.0003818 | A*24 | C*03 | B*55 | DRB1*14 | 0.0005714 |
| A*03 | C*04 | B*35 | DRB1*01 | 0.01249 | A*03 | C*04 | B*35 | DRB1*15 | 0.001563 |
| A*32 | C*01 | B*56 | DRB1*11 | 1.917e−05 | A*32 | C*05 | B*44 | DRB1*08 | 9.857e−05 |
| A*03 | C*15 | B*51 | DRB1*03 | 0.0001099 | A*02 | C*06 | B*57 | DRB1*03 | 0.0003007 |
| A*01 | C*07 | B*08 | DRB1*15 | 0.00396 | A*01 | C*07 | B*08 | DRB1*15 | 0.00396 |
| A*32 | C*02 | B*40 | DRB1*11 | 0.001106 | A*24 | C*02 | B*27 | DRB1*13 | 0.0003746 |
| A*26 | C*01 | B*55 | DRB1*16 | 5.849e−05 | A*23 | C*04 | B*44 | DRB1*07 | 0.006499 |
| A*33 | C*08 | B*14 | DRB1*01 | 0.005181 | A*25 | C*12 | B*18 | DRB1*04 | 0.001295 |
| A*11 | C*02 | B*27 | DRB1*04 | 0.0005281 | A*03 | C*01 | B*56 | DRB1*01 | 0.0003074 |
| A*66 | C*17 | B*41 | DRB1*13 | 0.001591 | A*24 | C*03 | B*55 | DRB1*14 | 0.0005714 |
| A*02 | C*07 | B*07 | DRB1*15 | 0.01917 | A*02 | C*07 | B*08 | DRB1*03 | 0.007894 |
| A*29 | C*16 | B*44 | DRB1*07 | 0.01451 | A*01 | C*06 | B*57 | DRB1*07 | 0.01053 |
| A*26 | C*12 | B*38 | DRB1*11 | 0.001022 | A*26 | C*04 | B*35 | DRB1*11 | 0.0003807 |
| A*02 | C*02 | B*27 | DRB1*11 | 0.00116 | A*31 | C*06 | B*13 | DRB1*11 | 1.6e−05 |
| A*24 | C*12 | B*52 | DRB1*15 | 0.0003649 | A*33 | C*08 | B*14 | DRB1*01 | 0.005181 |
| A*26 | C*15 | B*51 | DRB1*14 | 1.099e−05 | A*25 | C*14 | B*51 | DRB1*04 | 3.607e−05 |
| A*01 | C*07 | B*08 | DRB1*03 | 0.06069 | A*01 | C*07 | B*08 | DRB1*03 | 0.06069 |
| A*03 | C*03 | B*40 | DRB1*13 | 0.001099 | A*29 | C*16 | B*44 | DRB1*07 | 0.01451 |
| A*29 | C*07 | B*08 | DRB1*08 | 0.0004027 | A*01 | C*07 | B*08 | DRB1*15 | 0.00396 |
| A*31 | C*02 | B*27 | DRB1*16 | 2.356e−05 | A*68 | C*08 | B*14 | DRB1*04 | 0.0002478 |
| A*66 | C*17 | B*41 | DRB1*13 | 0.001591 | A*03 | C*04 | B*35 | DRB1*13 | 0.001499 |
| A*24 | C*06 | B*13 | DRB1*07 | 0.001954 | A*24 | C*03 | B*55 | DRB1*14 | 0.0005714 |
| A*02 | C*05 | B*44 | DRB1*11 | 0.003592 | A*02 | C*15 | B*40 | DRB1*11 | 1.618e−05 |
| A*68 | C*02 | B*15 | DRB1*01 | 1.801e−05 | A*01 | C*03 | B*40 | DRB1*13 | 0.0005959 |
| A*11 | C*04 | B*35 | DRB1*07 | 0.0007907 | A*31 | C*12 | B*39 | DRB1*12 | 0.0002944 |
| A*02 | C*05 | B*18 | DRB1*03 | 0.001402 | A*02 | C*17 | B*41 | DRB1*11 | 0.0002487 |
| A*03 | C*06 | B*50 | DRB1*04 | 0.0001175 | A*32 | C*01 | B*51 | DRB1*16 | 8.043e−06 |
| A*24 | C*07 | B*07 | DRB1*15 | 0.007112 | A*24 | C*07 | B*07 | DRB1*15 | 0.007112 |
| A*24 | C*02 | B*27 | DRB1*08 | 9.369e−05 | A*02 | C*03 | B*40 | DRB1*13 | 0.009252 |
| A*26 | C*04 | B*35 | DRB1*10 | 1.56e−05 | A*30 | C*07 | B*07 | DRB1*11 | 2.721e−05 |
| A*23 | C*06 | B*50 | DRB1*03 | 0.0004085 | A*23 | C*06 | B*50 | DRB1*03 | 0.0004085 |
| A*11 | C*05 | B*44 | DRB1*04 | 0.0008435 | A*68 | C*05 | B*44 | DRB1*04 | 0.0005429 |
| A*29 | C*08 | B*14 | DRB1*07 | 0.0007233 | A*01 | C*12 | B*52 | DRB1*15 | 0.002165 |
| A*01 | C*12 | B*52 | DRB1*15 | 0.002165 | A*23 | C*06 | B*50 | DRB1*11 | 7.347e−05 |
| A*31 | C*04 | B*35 | DRB1*16 | 7.623e−05 | A*33 | C*08 | B*14 | DRB1*03 | 0.0009013 |
| A*02 | C*07 | B*07 | DRB1*04 | 0.00323 | A*03 | C*03 | B*15 | DRB1*04 | 0.01345 |
| A*32 | C*05 | B*44 | DRB1*12 | 0.001237 | A*03 | C*16 | B*44 | DRB1*07 | 0.0009758 |
| A*26 | C*01 | B*27 | DRB1*01 | 0.001064 | A*30 | C*17 | B*41 | DRB1*13 | 7.82e−05 |
| A*29 | C*06 | B*57 | DRB1*04 | 3.386e−05 | A*29 | C*16 | B*44 | DRB1*15 | 0.001493 |
| A*33 | C*08 | B*14 | DRB1*01 | 0.008527 | A*01 | C*07 | B*08 | DRB1*13 | 0.00139 |
| A*30 | C*02 | B*15 | DRB1*08 | 0.0004999 | A*02 | C*03 | B*55 | DRB1*03 | 1.49e−05 |
| A*23 | C*18 | B*81 | DRB1*11 | 0.0001724 | A*11 | C*04 | B*53 | DRB1*12 | 0.0001142 |
| A*24 | C*12 | B*18 | DRB1*16 | 6.415e−05 | A*24 | C*12 | B*35 | DRB1*14 | 0.0003592 |
| A*03 | C*15 | B*51 | DRB1*04 | 0.0004235 | A*24 | C*08 | B*14 | DRB1*04 | 0.0006364 |
| A*69 | C*01 | B*55 | DRB1*11 | 0.001084 | A*68 | C*07 | B*58 | DRB1*13 | 0.0002623 |
| A*26 | C*12 | B*38 | DRB1*16 | 6.468e−05 | A*31 | C*04 | B*35 | DRB1*01 | 0.0003212 |
| A*11 | C*16 | B*44 | DRB1*07 | 0.0008302 | A*32 | C*02 | B*40 | DRB1*07 | 7.065e−05 |
| A*02 | C*14 | B*51 | DRB1*08 | 0.001072 | A*23 | C*05 | B*18 | DRB1*08 | 1.144e−05 |
| A*02 | C*03 | B*55 | DRB1*14 | 0.0002772 | A*24 | C*04 | B*35 | DRB1*11 | 0.006232 |

TABLE 1-continued

Examples of sets of n pharmaceutical unit doses according to the invention

| A_all1 | C_all1 | B_all1 | DRB1_all1 | freq_all1 | A_all2 | C_all2 | B_all2 | DRB1_all2 | freq_all2 |
|---|---|---|---|---|---|---|---|---|---|
| A*33 | C*08 | B*14 | DRB1*01 | 0.008527 | A*30 | C*05 | B*18 | DRB1*03 | 0.007131 |
| A*29 | C*16 | B*44 | DRB1*07 | 0.01859 | A*29 | C*06 | B*45 | DRB1*10 | 3.654e−05 |
| A*26 | C*14 | B*51 | DRB1*13 | 7.124e−05 | A*11 | C*01 | B*27 | DRB1*13 | 0.000135 |
| A*68 | C*07 | B*39 | DRB1*04 | 0.01084 | A*03 | C*07 | B*07 | DRB1*15 | 0.01243 |
| A*36 | C*04 | B*53 | DRB1*11 | 0.0005302 | A*68 | C*03 | B*40 | DRB1*08 | 0.001516 |
| A*03 | C*16 | B*51 | DRB1*07 | 0.002625 | A*03 | C*08 | B*14 | DRB1*03 | 0.0003327 |
| A*32 | C*07 | B*41 | DRB1*13 | 0.0001315 | A*33 | C*14 | B*15 | DRB1*01 | 8.384e−05 |
| A*01 | C*12 | B*52 | DRB1*15 | 0.002952 | A*30 | C*17 | B*42 | DRB1*12 | 0.0002373 |
| A*02 | C*02 | B*27 | DRB1*14 | 0.0004907 | A*02 | C*02 | B*27 | DRB1*16 | 0.000199 |
| A*68 | C*07 | B*39 | DRB1*08 | 0.001856 | A*24 | C*04 | B*35 | DRB1*14 | 0.003123 |
| A*02 | C*02 | B*51 | DRB1*11 | 0.0005321 | A*02 | C*12 | B*38 | DRB1*13 | 0.001337 |
| A*26 | C*06 | B*45 | DRB1*15 | 0.0001306 | A*01 | C*16 | B*44 | DRB1*07 | 0.001227 |
| A*31 | C*03 | B*40 | DRB1*04 | 0.004814 | A*03 | C*03 | B*40 | DRB1*03 | 0.0001478 |
| A*23 | C*08 | B*14 | DRB1*10 | 0.0001535 | A*11 | C*01 | B*27 | DRB1*01 | 0.002777 |
| A*01 | C*12 | B*52 | DRB1*15 | 0.002952 | A*74 | C*02 | B*15 | DRB1*13 | 0.000418 |
| A*11 | C*04 | B*35 | DRB1*14 | 0.001842 | A*11 | C*01 | B*27 | DRB1*01 | 0.002777 |
| A*29 | C*16 | B*44 | DRB1*07 | 0.01859 | A*24 | C*07 | B*39 | DRB1*04 | 0.005418 |
| A*30 | C*05 | B*18 | DRB1*03 | 0.007131 | A*30 | C*05 | B*18 | DRB1*03 | 0.007131 |
| A*03 | C*06 | B*58 | DRB1*11 | 0.0001786 | A*68 | C*03 | B*40 | DRB1*08 | 0.001516 |
| A*31 | C*04 | B*35 | DRB1*08 | 0.004621 | A*24 | C*04 | B*35 | DRB1*11 | 0.006232 |
| A*03 | C*14 | B*51 | DRB1*13 | 6.458e−05 | A*74 | C*02 | B*15 | DRB1*03 | 0.0005566 |
| A*30 | C*17 | B*42 | DRB1*07 | 9.229e−05 | A*26 | C*06 | B*50 | DRB1*07 | 3.272e−05 |
| A*11 | C*16 | B*44 | DRB1*04 | 3.486e−05 | A*02 | C*03 | B*40 | DRB1*04 | 0.009908 |
| A*29 | C*07 | B*07 | DRB1*15 | 0.0007765 | A*68 | C*07 | B*49 | DRB1*10 | 0.001377 |
| A*26 | C*06 | B*37 | DRB1*10 | 0.0005673 | A*11 | C*04 | B*35 | DRB1*14 | 0.001842 |
| A*01 | C*07 | B*08 | DRB1*03 | 0.01862 | A*33 | C*08 | B*14 | DRB1*03 | 0.002193 |
| A*02 | C*01 | B*56 | DRB1*01 | 0.0008082 | A*31 | C*02 | B*27 | DRB1*08 | 0.0005152 |
| A*32 | C*05 | B*18 | DRB1*11 | 0.0001083 | A*03 | C*16 | B*51 | DRB1*07 | 0.002625 |
| A*24 | C*15 | B*07 | DRB1*13 | 4.209e−05 | A*24 | C*03 | B*15 | DRB1*13 | 0.001007 |
| A*02 | C*06 | B*57 | DRB1*07 | 0.002188 | A*36 | C*16 | B*45 | DRB1*01 | 1.066e−05 |
| A*24 | C*05 | B*44 | DRB1*13 | 0.0006041 | A*24 | C*04 | B*35 | DRB1*08 | 0.003573 |
| A*74 | C*02 | B*15 | DRB1*11 | 0.0005171 | A*32 | C*03 | B*15 | DRB1*15 | 0.000523 |
| A*33 | C*08 | B*14 | DRB1*03 | 0.002193 | A*01 | C*08 | B*08 | DRB1*03 | 0.01862 |
| A*26 | C*12 | B*38 | DRB1*04 | 0.002758 | A*23 | C*15 | B*51 | DRB1*14 | 1.148e−05 |
| A*03 | C*02 | B*27 | DRB1*07 | 5.808e−05 | A*02 | C*15 | B*51 | DRB1*08 | 0.001543 |
| A*30 | C*03 | B*15 | DRB1*12 | 6.318e−05 | A*26 | C*01 | B*55 | DRB1*11 | 2.915e−05 |
| A*23 | C*04 | B*44 | DRB1*03 | 0.0003317 | A*68 | C*04 | B*53 | DRB1*13 | 0.001859 |
| A*33 | C*08 | B*14 | DRB1*04 | 0.0005816 | A*33 | C*08 | B*14 | DRB1*01 | 0.008527 |
| A*11 | C*12 | B*52 | DRB1*15 | 0.002151 | A*24 | C*07 | B*39 | DRB1*14 | 0.007802 |
| A*33 | C*03 | B*15 | DRB1*10 | 0.000148 | A*01 | C*08 | B*14 | DRB1*11 | 0.0001791 |
| A*02 | C*07 | B*39 | DRB1*08 | 0.003265 | A*11 | C*07 | B*07 | DRB1*15 | 0.001642 |
| A*30 | C*05 | B*18 | DRB1*03 | 0.007131 | A*03 | C*06 | B*58 | DRB1*03 | 5.731e−05 |
| A*68 | C*04 | B*53 | DRB1*13 | 0.001859 | A*29 | C*16 | B*44 | DRB1*07 | 0.01859 |
| A*24 | C*12 | B*38 | DRB1*14 | 0.0004747 | A*31 | C*15 | B*51 | DRB1*01 | 0.0002266 |
| A*23 | C*07 | B*07 | DRB1*14 | 8.503e−05 | A*29 | C*16 | B*44 | DRB1*07 | 0.01859 |
| A*02 | C*17 | B*42 | DRB1*03 | 0.0002518 | A*30 | C*06 | B*47 | DRB1*01 | 6.823e−06 |
| A*31 | C*04 | B*35 | DRB1*04 | 0.004404 | A*31 | C*04 | B*35 | DRB1*04 | 0.004404 |
| A*24 | C*03 | B*40 | DRB1*08 | 0.005647 | A*11 | C*14 | B*51 | DRB1*13 | 0.0002266 |
| A*32 | C*01 | B*27 | DRB1*11 | 0.0002196 | A*68 | C*08 | B*14 | DRB1*15 | 0.0001939 |
| A*23 | C*07 | B*07 | DRB1*11 | 0.003157 | A*68 | C*12 | B*39 | DRB1*15 | 2.721e−05 |
| A*24 | C*03 | B*40 | DRB1*04 | 0.0005642 | A*34 | C*08 | B*81 | DRB1*14 | 7.517e−05 |
| A*11 | C*04 | B*35 | DRB1*01 | 0.001565 | A*03 | C*16 | B*15 | DRB1*07 | 2.13e−05 |
| A*02 | C*15 | B*27 | DRB1*08 | 5.655e−05 | A*02 | C*17 | B*42 | DRB1*08 | 0.0005784 |
| A*36 | C*06 | B*58 | DRB1*13 | 0.000129 | A*30 | C*05 | B*18 | DRB1*03 | 0.001305 |
| A*02 | C*16 | B*45 | DRB1*07 | 0.001197 | A*02 | C*04 | B*53 | DRB1*07 | 0.001852 |
| A*11 | C*03 | B*55 | DRB1*01 | 0.0001235 | A*01 | C*07 | B*08 | DRB1*13 | 0.0007583 |
| A*29 | C*15 | B*07 | DRB1*03 | 0.0002103 | A*29 | C*06 | B*13 | DRB1*15 | 8.188e−05 |
| A*03 | C*14 | B*51 | DRB1*04 | 8.269e−06 | A*30 | C*18 | B*57 | DRB1*11 | 0.0005077 |
| A*23 | C*02 | B*15 | DRB1*10 | 0.0003071 | A*33 | C*08 | B*14 | DRB1*08 | 0.0001075 |
| A*30 | C*17 | B*42 | DRB1*09 | 0.0004067 | A*30 | C*18 | B*81 | DRB1*15 | 3.863e−05 |
| A*24 | C*04 | B*35 | DRB1*08 | 0.0001959 | A*23 | C*04 | B*44 | DRB1*11 | 0.0006464 |
| A*33 | C*16 | B*51 | DRB1*03 | 0.0001037 | A*01 | C*15 | B*51 | DRB1*04 | 0.000111 |
| A*03 | C*05 | B*18 | DRB1*13 | 0.000123 | A*34 | C*06 | B*58 | DRB1*12 | 0.0002954 |
| A*02 | C*07 | B*07 | DRB1*01 | 0.0008568 | A*02 | C*02 | B*15 | DRB1*10 | 0.000545 |
| A*34 | C*18 | B*13 | DRB1*15 | 9.92e−05 | A*32 | C*05 | B*18 | DRB1*03 | 0.0001231 |
| A*02 | C*07 | B*49 | DRB1*04 | 0.0007124 | A*30 | C*07 | B*58 | DRB1*08 | 8.375e−05 |
| A*03 | C*03 | B*44 | DRB1*12 | 3.261e−05 | A*33 | C*14 | B*15 | DRB1*12 | 8.459e−05 |
| A*68 | C*04 | B*53 | DRB1*13 | 0.004694 | A*36 | C*04 | B*53 | DRB1*13 | 0.001966 |
| A*23 | C*17 | B*42 | DRB1*01 | 8.755e−05 | A*23 | C*17 | B*41 | DRB1*07 | 0.0002013 |
| A*02 | C*08 | B*14 | DRB1*13 | 0.0003797 | A*02 | C*16 | B*45 | DRB1*15 | 0.001481 |
| A*74 | C*17 | B*42 | DRB1*03 | 0.00101 | A*03 | C*07 | B*07 | DRB1*14 | 0.0004314 |
| A*26 | C*18 | B*57 | DRB1*16 | 0.0001605 | A*36 | C*12 | B*39 | DRB1*10 | 2.082e−05 |
| A*30 | C*04 | B*53 | DRB1*01 | 0.0006437 | A*01 | C*05 | B*44 | DRB1*04 | 0.0002385 |
| A*68 | C*03 | B*15 | DRB1*11 | 0.001143 | A*23 | C*03 | B*82 | DRB1*07 | 3.009e−05 |
| A*30 | C*02 | B*18 | DRB1*07 | 0.0006125 | A*29 | C*06 | B*13 | DRB1*01 | 0.0006964 |
| A*68 | C*03 | B*15 | DRB1*10 | 0.0004289 | A*74 | C*03 | B*15 | DRB1*13 | 0.0002079 |

TABLE 1-continued

Examples of sets of n pharmaceutical unit doses according to the invention

| A_all1 | C_all1 | B_all1 | DRB1_all1 | freq_all1 | A_all2 | C_all2 | B_all2 | DRB1_all2 | freq_all2 |
|---|---|---|---|---|---|---|---|---|---|
| A*23 | C*18 | B*57 | DRB1*16 | 0.0001774 | A*01 | C*07 | B*49 | DRB1*04 | 0.0002911 |
| A*34 | C*04 | B*44 | DRB1*15 | 0.0061 | A*11 | C*12 | B*52 | DRB1*15 | 0.0002136 |
| A*33 | C*16 | B*78 | DRB1*11 | 0.0006852 | A*33 | C*17 | B*42 | DRB1*03 | 0.002083 |
| A*30 | C*07 | B*49 | DRB1*08 | 0.000272 | A*33 | C*03 | B*82 | DRB1*13 | 5.023e-06 |
| A*24 | C*12 | B*52 | DRB1*12 | 5.285e-05 | A*03 | C*16 | B*45 | DRB1*01 | 0.0007718 |
| A*66 | C*02 | B*35 | DRB1*15 | 1.509e-05 | A*11 | C*15 | B*40 | DRB1*04 | 2.8e-05 |
| A*02 | C*05 | B*18 | DRB1*03 | 0.0007658 | A*02 | C*14 | B*15 | DRB1*10 | 3.536e-05 |
| A*68 | C*08 | B*53 | DRB1*07 | 4.376e-06 | A*68 | C*04 | B*44 | DRB1*07 | 0.0001224 |
| A*36 | C*04 | B*53 | DRB1*09 | 0.0004325 | A*30 | C*17 | B*42 | DRB1*03 | 0.01787 |
| A*34 | C*07 | B*49 | DRB1*15 | 0.0005125 | A*66 | C*07 | B*58 | DRB1*15 | 0.003966 |
| A*68 | C*18 | B*57 | DRB1*07 | 0.0002172 | A*01 | C*06 | B*57 | DRB1*07 | 0.002167 |
| A*03 | C*08 | B*14 | DRB1*13 | 0.0009844 | A*32 | C*02 | B*40 | DRB1*13 | 0.0003019 |
| A*02 | C*16 | B*51 | DRB1*04 | 0.0003065 | A*24 | C*05 | B*44 | DRB1*01 | 0.0001754 |
| A*31 | C*07 | B*57 | DRB1*15 | 0.0009013 | A*30 | C*08 | B*14 | DRB1*11 | 0.0003484 |
| A*68 | C*06 | B*58 | DRB1*12 | 0.007993 | A*01 | C*06 | B*37 | DRB1*10 | 0.0003316 |
| A*36 | C*04 | B*53 | DRB1*07 | 0.0008137 | A*02 | C*16 | B*35 | DRB1*16 | 4.711e-05 |
| A*33 | C*14 | B*15 | DRB1*01 | 0.002405 | A*23 | C*03 | B*15 | DRB1*03 | 0.0007087 |
| A*74 | C*17 | B*42 | DRB1*08 | 0.000252 | A*24 | C*15 | B*40 | DRB1*04 | 0.0002546 |
| A*29 | C*16 | B*44 | DRB1*07 | 0.00365 | A*03 | C*17 | B*42 | DRB1*03 | 0.001267 |
| A*66 | C*18 | B*57 | DRB1*13 | 0.0001513 | A*68 | C*06 | B*58 | DRB1*12 | 0.007993 |
| A*26 | C*15 | B*07 | DRB1*09 | 5.164e-06 | A*11 | C*03 | B*55 | DRB1*04 | 0.0003062 |
| A*36 | C*04 | B*53 | DRB1*11 | 0.007603 | A*23 | C*07 | B*08 | DRB1*11 | 0.000506 |
| A*02 | C*02 | B*15 | DRB1*10 | 0.000545 | A*02 | C*08 | B*14 | DRB1*01 | 0.0003176 |
| A*26 | C*08 | B*14 | DRB1*15 | 2.872e-05 | A*30 | C*17 | B*42 | DRB1*03 | 0.01787 |
| A*02 | C*07 | B*49 | DRB1*09 | 0.0009877 | A*11 | C*07 | B*49 | DRB1*04 | 4.847e-05 |
| A*34 | C*04 | B*53 | DRB1*11 | 0.0003874 | A*68 | C*06 | B*58 | DRB1*12 | 0.007993 |
| A*03 | C*15 | B*07 | DRB1*08 | 3.053e-05 | A*74 | C*02 | B*15 | DRB1*13 | 0.004945 |
| A*29 | C*16 | B*44 | DRB1*07 | 0.00365 | A*23 | C*16 | B*45 | DRB1*07 | 0.0002827 |
| A*23 | C*04 | B*53 | DRB1*11 | 0.0009138 | A*03 | C*03 | B*40 | DRB1*04 | 0.0002916 |
| A*66 | C*07 | B*58 | DRB1*15 | 0.003966 | A*34 | C*08 | B*81 | DRB1*07 | 9.025e-05 |
| A*01 | C*06 | B*37 | DRB1*10 | 0.0003316 | A*29 | C*18 | B*57 | DRB1*16 | 3.826e-05 |
| A*02 | C*17 | B*42 | DRB1*03 | 0.002911 | A*02 | C*05 | B*44 | DRB1*13 | 0.001305 |
| A*11 | C*01 | B*15 | DRB1*01 | 3.069e-05 | A*30 | C*15 | B*07 | DRB1*08 | 0.0001173 |
| A*11 | C*07 | B*40 | DRB1*08 | 0.002916 | A*11 | C*07 | B*08 | DRB1*03 | 0.0007981 |
| A*24 | C*03 | B*35 | DRB1*12 | 0.0002231 | A*24 | C*08 | B*39 | DRB1*12 | 0.0002281 |
| A*33 | C*14 | B*44 | DRB1*13 | 0.008246 | A*03 | C*05 | B*44 | DRB1*13 | 0.001207 |
| A*29 | C*15 | B*07 | DRB1*14 | 0.0002312 | A*02 | C*04 | B*13 | DRB1*15 | 0.0003808 |
| A*01 | C*06 | B*57 | DRB1*07 | 0.01502 | A*01 | C*12 | B*52 | DRB1*04 | 0.0005686 |
| A*02 | C*03 | B*15 | DRB1*04 | 0.00176 | A*33 | C*03 | B*58 | DRB1*03 | 0.02193 |
| A*24 | C*01 | B*46 | DRB1*09 | 0.001994 | A*68 | C*12 | B*52 | DRB1*15 | 0.0008358 |
| A*31 | C*14 | B*51 | DRB1*12 | 0.0003705 | A*11 | C*15 | B*40 | DRB1*14 | 0.0009395 |
| A*29 | C*16 | B*44 | DRB1*07 | 0.0002388 | A*01 | C*06 | B*57 | DRB1*07 | 0.01502 |
| A*26 | C*07 | B*07 | DRB1*01 | 0.0002666 | A*03 | C*07 | B*07 | DRB1*10 | 0.0006538 |
| A*24 | C*15 | B*40 | DRB1*15 | 0.003183 | A*74 | C*14 | B*51 | DRB1*14 | 0.0002743 |
| A*29 | C*03 | B*58 | DRB1*08 | 0.0001012 | A*03 | C*07 | B*07 | DRB1*03 | 0.0005034 |
| A*01 | C*06 | B*57 | DRB1*04 | 0.0006848 | A*01 | C*06 | B*57 | DRB1*07 | 0.01502 |
| A*02 | C*08 | B*15 | DRB1*12 | 0.005328 | A*11 | C*08 | B*15 | DRB1*13 | 0.0005381 |
| A*31 | C*04 | B*35 | DRB1*11 | 0.0003107 | A*30 | C*04 | B*53 | DRB1*11 | 2.271e-05 |
| A*24 | C*15 | B*40 | DRB1*14 | 0.002038 | A*26 | C*07 | B*08 | DRB1*03 | 0.005979 |
| A*01 | C*05 | B*44 | DRB1*04 | 4.014e-05 | A*31 | C*14 | B*51 | DRB1*04 | 0.0008849 |
| A*11 | C*06 | B*13 | DRB1*07 | 0.0005233 | A*11 | C*06 | B*57 | DRB1*07 | 0.001795 |
| A*33 | C*03 | B*58 | DRB1*13 | 0.01294 | A*33 | C*08 | B*48 | DRB1*11 | 0.0001055 |
| A*02 | C*01 | B*46 | DRB1*09 | 0.01723 | A*34 | C*01 | B*56 | DRB1*08 | 7.898e-05 |
| A*02 | C*08 | B*15 | DRB1*12 | 0.005328 | A*02 | C*14 | B*51 | DRB1*04 | 0.001701 |
| A*31 | C*03 | B*40 | DRB1*08 | 0.0005602 | A*30 | C*06 | B*13 | DRB1*07 | 0.01237 |
| A*11 | C*01 | B*55 | DRB1*09 | 0.0003733 | A*29 | C*15 | B*07 | DRB1*10 | 0.007929 |
| A*24 | C*07 | B*39 | DRB1*11 | 0.0001551 | A*01 | C*05 | B*44 | DRB1*15 | 6.035e-05 |
| A*33 | C*04 | B*35 | DRB1*14 | 0.0001962 | A*32 | C*04 | B*35 | DRB1*13 | 0.0004817 |
| A*03 | C*07 | B*39 | DRB1*01 | 1.329e-05 | A*32 | C*02 | B*40 | DRB1*11 | 2.87e-05 |
| A*34 | C*01 | B*56 | DRB1*15 | 0.000108 | A*02 | C*01 | B*46 | DRB1*14 | 0.003246 |
| A*24 | C*04 | B*35 | DRB1*12 | 0.008261 | A*11 | C*12 | B*52 | DRB1*04 | 0.001365 |
| A*01 | C*06 | B*37 | DRB1*10 | 0.008149 | A*01 | C*15 | B*51 | DRB1*10 | 2.451e-05 |
| A*33 | C*14 | B*44 | DRB1*13 | 0.008246 | A*33 | C*03 | B*58 | DRB1*13 | 0.01294 |
| A*33 | C*03 | B*58 | DRB1*03 | 0.02193 | A*29 | C*15 | B*07 | DRB1*10 | 0.007929 |
| A*02 | C*01 | B*46 | DRB1*09 | 0.01723 | A*02 | C*01 | B*59 | DRB1*11 | 6.179e-05 |
| A*24 | C*08 | B*15 | DRB1*15 | 0.002794 | A*24 | C*04 | B*40 | DRB1*12 | 0.0003139 |
| A*11 | C*14 | B*51 | DRB1*14 | 0.001141 | A*68 | C*12 | B*52 | DRB1*04 | 0.0005001 |
| A*32 | C*07 | B*49 | DRB1*13 | 0.0007053 | A*30 | C*06 | B*13 | DRB1*07 | 0.01237 |
| A*01 | C*15 | B*40 | DRB1*15 | 0.002227 | A*24 | C*12 | B*35 | DRB1*14 | 0.0007384 |
| A*33 | C*03 | B*58 | DRB1*03 | 0.02193 | A*33 | C*03 | B*58 | DRB1*11 | 0.000773 |
| A*02 | C*01 | B*46 | DRB1*04 | 0.003169 | A*02 | C*01 | B*46 | DRB1*09 | 0.01723 |
| A*26 | C*06 | B*50 | DRB1*07 | 0.0001232 | A*26 | C*14 | B*51 | DRB1*13 | 0.0001299 |
| A*11 | C*08 | B*15 | DRB1*12 | 0.0137 | A*11 | C*08 | B*15 | DRB1*12 | 0.0137 |
| A*24 | C*04 | B*35 | DRB1*12 | 0.008261 | A*34 | C*04 | B*15 | DRB1*15 | 0.002322 |
| A*29 | C*15 | B*07 | DRB1*09 | 0.0004643 | A*02 | C*01 | B*46 | DRB1*09 | 0.01723 |
| A*01 | C*06 | B*57 | DRB1*07 | 0.01502 | A*30 | C*08 | B*14 | DRB1*08 | 0.0003167 |

TABLE 1-continued

Examples of sets of n pharmaceutical unit doses according to the invention

| A_all1 | C_all1 | B_all1 | DRB1_all1 | freq_all1 | A_all2 | C_all2 | B_all2 | DRB1_all2 | freq_all2 |
|---|---|---|---|---|---|---|---|---|---|
| A*33 | C*03 | B*58 | DRB1*03 | 0.02193 | A*11 | C*07 | B*18 | DRB1*14 | 0.000175 |
| A*32 | C*12 | B*52 | DRB1*04 | 0.0001125 | A*32 | C*14 | B*51 | DRB1*01 | 0.0001429 |
| A*24 | C*01 | B*46 | DRB1*08 | 0.00131 | A*02 | C*01 | B*46 | DRB1*09 | 0.01723 |
| A*11 | C*04 | B*35 | DRB1*13 | 0.001629 | A*11 | C*15 | B*40 | DRB1*03 | 0.0002661 |
| A*01 | C*06 | B*57 | DRB1*07 | 0.01502 | A*01 | C*06 | B*37 | DRB1*07 | 0.0004736 |
| A*34 | C*03 | B*15 | DRB1*15 | 4.472e−05 | A*32 | C*12 | B*52 | DRB1*15 | 0.001089 |
| A*33 | C*07 | B*44 | DRB1*14 | 0.0004577 | A*03 | C*07 | B*07 | DRB1*12 | 0.0001265 |
| A*32 | C*07 | B*44 | DRB1*07 | 0.0003241 | A*33 | C*03 | B*58 | DRB1*03 | 0.02193 |
| A*31 | C*14 | B*51 | DRB1*13 | 0.0009911 | A*29 | C*15 | B*07 | DRB1*10 | 0.007929 |
| A*02 | C*01 | B*46 | DRB1*14 | 0.003246 | A*02 | C*01 | B*55 | DRB1*14 | 0.0004371 |
| A*24 | C*04 | B*15 | DRB1*12 | 0.001001 | A*24 | C*04 | B*35 | DRB1*11 | 0.003399 |
| A*11 | C*12 | B*52 | DRB1*15 | 0.004114 | A*11 | C*12 | B*52 | DRB1*15 | 0.004114 |
| A*33 | C*03 | B*58 | DRB1*03 | 0.02193 | A*08 | C*03 | B*15 | DRB1*15 | 0.003506 |
| A*01 | C*12 | B*52 | DRB1*10 | 5.91e−05 | A*23 | C*07 | B*49 | DRB1*11 | 7.531e−05 |
| A*24 | C*04 | B*35 | DRB1*12 | 0.008261 | A*24 | C*15 | B*40 | DRB1*14 | 0.002038 |
| A*02 | C*01 | B*46 | DRB1*09 | 0.01723 | A*02 | C*01 | B*46 | DRB1*04 | 0.003169 |
| A*30 | C*06 | B*13 | DRB1*07 | 0.01237 | A*05 | C*05 | B*44 | DRB1*13 | 0.001207 |
| A*32 | C*01 | B*55 | DRB1*03 | 2.443e−05 | A*29 | C*15 | B*07 | DRB1*10 | 0.0006019 |
| A*01 | C*02 | B*27 | DRB1*04 | 0.0002964 | A*11 | C*04 | B*35 | DRB1*01 | 0.007259 |
| A*30 | C*06 | B*13 | DRB1*07 | 0.007169 | A*03 | C*08 | B*14 | DRB1*07 | 0.0008185 |
| A*33 | C*12 | B*18 | DRB1*11 | 0.0001174 | A*07 | C*07 | B*49 | DRB1*11 | 9.849e−05 |
| A*02 | C*05 | B*44 | DRB1*13 | 0.005356 | A*24 | C*03 | B*15 | DRB1*13 | 0.002524 |
| A*26 | C*06 | B*57 | DRB1*07 | 0.0004316 | A*24 | C*17 | B*41 | DRB1*13 | 0.0003503 |
| A*01 | C*07 | B*08 | DRB1*03 | 0.06069 | A*01 | C*07 | B*08 | DRB1*03 | 0.06069 |
| A*23 | C*05 | B*44 | DRB1*11 | 4.872e−05 | A*11 | C*04 | B*51 | DRB1*04 | 0.0003029 |
| A*02 | C*01 | B*56 | DRB1*08 | 0.0001613 | A*02 | C*03 | B*40 | DRB1*15 | 0.001866 |
| A*32 | C*02 | B*27 | DRB1*14 | 6.508e−05 | A*32 | C*12 | B*39 | DRB1*01 | 1.763e−05 |
| A*31 | C*03 | B*15 | DRB1*08 | 1.543e−05 | A*68 | C*03 | B*15 | DRB1*04 | 0.0006084 |
| A*01 | C*07 | B*08 | DRB1*01 | 0.002432 | A*03 | C*07 | B*08 | DRB1*03 | 0.003262 |
| A*02 | C*02 | B*27 | DRB1*13 | 0.0005833 | A*26 | C*06 | B*13 | DRB1*07 | 0.000306 |
| A*24 | C*04 | B*35 | DRB1*11 | 0.005438 | A*11 | C*04 | B*35 | DRB1*14 | 0.001555 |
| A*32 | C*05 | B*44 | DRB1*12 | 0.001237 | A*30 | C*12 | B*39 | DRB1*16 | 1.842e−05 |
| A*02 | C*15 | B*51 | DRB1*04 | 0.001614 | A*02 | C*12 | B*39 | DRB1*01 | 0.0002136 |
| A*31 | C*05 | B*18 | DRB1*03 | 0.0001124 | A*11 | C*03 | B*55 | DRB1*03 | 7.01e−05 |
| A*01 | C*04 | B*35 | DRB1*11 | 0.002479 | A*66 | C*17 | B*41 | DRB1*11 | 0.0003676 |
| A*03 | C*07 | B*07 | DRB1*13 | 0.003443 | A*03 | C*07 | B*07 | DRB1*15 | 0.03074 |
| A*24 | C*02 | B*27 | DRB1*08 | 9.369e−05 | A*29 | C*16 | B*44 | DRB1*07 | 0.01451 |
| A*30 | C*06 | B*13 | DRB1*07 | 0.007169 | A*02 | C*02 | B*27 | DRB1*04 | 0.0008165 |
| A*25 | C*12 | B*18 | DRB1*03 | 0.0002444 | A*01 | C*07 | B*08 | DRB1*03 | 0.06069 |
| A*02 | C*16 | B*51 | DRB1*13 | 0.0003818 | A*24 | C*03 | B*55 | DRB1*14 | 0.0005714 |
| A*03 | C*04 | B*35 | DRB1*01 | 0.01249 | A*03 | C*04 | B*35 | DRB1*15 | 0.001563 |
| A*32 | C*01 | B*56 | DRB1*11 | 1.917e−05 | A*32 | C*05 | B*44 | DRB1*08 | 9.857e−05 |
| A*03 | C*15 | B*51 | DRB1*03 | 0.0001099 | A*02 | C*06 | B*57 | DRB1*03 | 0.0003007 |
| A*01 | C*07 | B*08 | DRB1*15 | 0.00396 | A*01 | C*07 | B*08 | DRB1*15 | 0.00396 |
| A*32 | C*02 | B*40 | DRB1*11 | 0.001106 | A*24 | C*02 | B*27 | DRB1*13 | 0.0003746 |
| A*26 | C*01 | B*55 | DRB1*16 | 5.849e−05 | A*23 | C*04 | B*44 | DRB1*07 | 0.006499 |
| A*33 | C*08 | B*14 | DRB1*01 | 0.005181 | A*25 | C*12 | B*18 | DRB1*04 | 0.001295 |
| A*11 | C*02 | B*27 | DRB1*04 | 0.0005281 | A*03 | C*01 | B*56 | DRB1*01 | 0.0003074 |
| A*66 | C*17 | B*41 | DRB1*13 | 0.001591 | A*24 | C*03 | B*55 | DRB1*14 | 0.0005714 |
| A*02 | C*07 | B*07 | DRB1*15 | 0.01917 | A*02 | C*07 | B*08 | DRB1*03 | 0.007894 |
| A*29 | C*16 | B*44 | DRB1*07 | 0.01451 | A*01 | C*06 | B*57 | DRB1*07 | 0.01053 |
| A*26 | C*12 | B*38 | DRB1*11 | 0.001022 | A*26 | C*04 | B*35 | DRB1*11 | 0.0003807 |
| A*02 | C*02 | B*27 | DRB1*11 | 0.00116 | A*31 | C*06 | B*13 | DRB1*11 | 1.6e−05 |
| A*24 | C*12 | B*52 | DRB1*15 | 0.0003649 | A*33 | C*08 | B*14 | DRB1*01 | 0.005181 |
| A*26 | C*15 | B*51 | DRB1*14 | 1.099e−05 | A*25 | C*14 | B*51 | DRB1*04 | 3.607e−05 |
| A*01 | C*07 | B*08 | DRB1*03 | 0.06069 | A*01 | C*07 | B*08 | DRB1*03 | 0.06069 |
| A*03 | C*03 | B*40 | DRB1*13 | 0.001099 | A*29 | C*16 | B*44 | DRB1*07 | 0.01451 |
| A*29 | C*07 | B*58 | DRB1*08 | 0.0004027 | A*01 | C*07 | B*08 | DRB1*15 | 0.00396 |
| A*31 | C*02 | B*27 | DRB1*16 | 2.356e−05 | A*68 | C*08 | B*14 | DRB1*04 | 0.0002478 |
| A*66 | C*17 | B*41 | DRB1*13 | 0.001591 | A*03 | C*04 | B*35 | DRB1*13 | 0.001499 |
| A*24 | C*06 | B*13 | DRB1*07 | 0.001954 | A*24 | C*03 | B*55 | DRB1*14 | 0.0005714 |
| A*02 | C*05 | B*44 | DRB1*11 | 0.003592 | A*02 | C*15 | B*40 | DRB1*11 | 1.618e−05 |
| A*68 | C*02 | B*15 | DRB1*01 | 1.801e−05 | A*03 | C*03 | B*40 | DRB1*13 | 0.0005959 |
| A*11 | C*04 | B*35 | DRB1*07 | 0.0007907 | A*31 | C*12 | B*39 | DRB1*12 | 0.0002944 |
| A*02 | C*05 | B*18 | DRB1*03 | 0.001402 | A*02 | C*17 | B*41 | DRB1*11 | 0.0002487 |
| A*03 | C*06 | B*50 | DRB1*04 | 0.0001175 | A*32 | C*01 | B*51 | DRB1*16 | 8.043e−06 |
| A*24 | C*07 | B*07 | DRB1*15 | 0.007112 | A*24 | C*07 | B*07 | DRB1*15 | 0.007112 |
| A*24 | C*02 | B*27 | DRB1*08 | 9.369e−05 | A*02 | C*03 | B*40 | DRB1*13 | 0.009252 |
| A*26 | C*04 | B*35 | DRB1*10 | 1.56e−05 | A*30 | C*07 | B*07 | DRB1*11 | 2.721e−05 |
| A*23 | C*06 | B*50 | DRB1*03 | 0.0004085 | A*23 | C*06 | B*50 | DRB1*03 | 0.0004085 |
| A*11 | C*05 | B*44 | DRB1*04 | 0.0008435 | A*68 | C*05 | B*44 | DRB1*04 | 0.0005429 |
| A*29 | C*08 | B*14 | DRB1*07 | 0.0007233 | A*01 | C*12 | B*52 | DRB1*15 | 0.002165 |
| A*01 | C*12 | B*52 | DRB1*15 | 0.002165 | A*23 | C*06 | B*50 | DRB1*11 | 7.347e−05 |
| A*31 | C*04 | B*35 | DRB1*16 | 7.623e−05 | A*33 | C*08 | B*14 | DRB1*03 | 0.0009013 |
| A*02 | C*07 | B*07 | DRB1*04 | 0.00323 | A*02 | C*03 | B*15 | DRB1*04 | 0.01345 |
| A*32 | C*05 | B*44 | DRB1*12 | 0.001237 | A*03 | C*16 | B*44 | DRB1*07 | 0.0009758 |

TABLE 1-continued

Examples of sets of n pharmaceutical unit doses according to the invention

| A_all1 | C_all1 | B_all1 | DRB1_all1 | freq_all1 | A_all2 | C_all2 | B_all2 | DRB1_all2 | freq_all2 |
|---|---|---|---|---|---|---|---|---|---|
| A*26 | C*01 | B*27 | DRB1*01 | 0.001064 | A*30 | C*17 | B*41 | DRB1*13 | 7.82e−05 |
| A*29 | C*06 | B*57 | DRB1*04 | 3.386e−05 | A*29 | C*16 | B*44 | DRB1*15 | 0.001493 |
| A*33 | C*08 | B*14 | DRB1*01 | 0.008527 | A*01 | C*07 | B*08 | DRB1*13 | 0.00139 |
| A*30 | C*02 | B*15 | DRB1*08 | 0.0004999 | A*02 | C*03 | B*55 | DRB1*03 | 1.49e−05 |
| A*23 | C*18 | B*81 | DRB1*11 | 0.0001724 | A*11 | C*04 | B*53 | DRB1*12 | 0.0001142 |
| A*24 | C*12 | B*18 | DRB1*16 | 6.415e−05 | A*24 | C*12 | B*35 | DRB1*14 | 0.0003592 |
| A*03 | C*03 | B*15 | DRB1*04 | 0.0004235 | A*24 | C*08 | B*48 | DRB1*14 | 0.0006364 |
| A*69 | C*01 | B*55 | DRB1*11 | 0.001084 | A*68 | C*07 | B*58 | DRB1*13 | 0.0002623 |
| A*26 | C*12 | B*38 | DRB1*16 | 6.468e−05 | A*31 | C*04 | B*35 | DRB1*01 | 0.0003212 |
| A*11 | C*16 | B*44 | DRB1*07 | 0.0008302 | A*32 | C*02 | B*40 | DRB1*07 | 7.065e−05 |
| A*02 | C*14 | B*51 | DRB1*08 | 0.001072 | A*23 | C*05 | B*18 | DRB1*08 | 1.144e−05 |
| A*02 | C*03 | B*55 | DRB1*14 | 0.0002772 | A*24 | C*04 | B*35 | DRB1*11 | 0.006232 |
| A*33 | C*08 | B*14 | DRB1*01 | 0.008527 | A*24 | C*05 | B*18 | DRB1*03 | 0.007131 |
| A*29 | C*16 | B*44 | DRB1*07 | 0.01859 | A*29 | C*06 | B*45 | DRB1*10 | 3.654e−05 |
| A*26 | C*14 | B*51 | DRB1*13 | 7.124e−05 | A*11 | C*01 | B*27 | DRB1*13 | 0.000135 |
| A*68 | C*07 | B*39 | DRB1*04 | 0.01084 | A*03 | C*07 | B*07 | DRB1*15 | 0.01243 |
| A*36 | C*04 | B*53 | DRB1*11 | 0.0005302 | A*68 | C*03 | B*40 | DRB1*08 | 0.001516 |
| A*03 | C*16 | B*51 | DRB1*07 | 0.002625 | A*03 | C*08 | B*14 | DRB1*03 | 0.0003327 |
| A*32 | C*07 | B*41 | DRB1*13 | 0.0001315 | A*33 | C*14 | B*15 | DRB1*01 | 8.384e−05 |
| A*01 | C*12 | B*52 | DRB1*15 | 0.002952 | A*30 | C*17 | B*42 | DRB1*12 | 0.0002373 |
| A*02 | C*02 | B*27 | DRB1*14 | 0.0004907 | A*02 | C*02 | B*27 | DRB1*16 | 0.000199 |
| A*68 | C*07 | B*39 | DRB1*08 | 0.001856 | A*24 | C*04 | B*35 | DRB1*14 | 0.003123 |
| A*02 | C*02 | B*51 | DRB1*11 | 0.0005321 | A*02 | C*12 | B*38 | DRB1*13 | 0.001337 |
| A*26 | C*06 | B*45 | DRB1*15 | 0.0001306 | A*01 | C*16 | B*44 | DRB1*07 | 0.001227 |
| A*31 | C*03 | B*40 | DRB1*04 | 0.004814 | A*03 | C*03 | B*40 | DRB1*03 | 0.0001478 |
| A*23 | C*08 | B*14 | DRB1*10 | 0.0001535 | A*11 | C*01 | B*27 | DRB1*01 | 0.002777 |
| A*01 | C*12 | B*52 | DRB1*15 | 0.002952 | A*74 | C*02 | B*15 | DRB1*13 | 0.000418 |
| A*11 | C*04 | B*35 | DRB1*14 | 0.001842 | A*11 | C*01 | B*27 | DRB1*01 | 0.002777 |
| A*29 | C*16 | B*44 | DRB1*07 | 0.01859 | A*24 | C*07 | B*39 | DRB1*04 | 0.005418 |
| A*30 | C*05 | B*18 | DRB1*03 | 0.007131 | A*30 | C*05 | B*18 | DRB1*03 | 0.007131 |
| A*03 | C*06 | B*58 | DRB1*11 | 0.0001786 | A*68 | C*03 | B*40 | DRB1*08 | 0.001516 |
| A*31 | C*04 | B*35 | DRB1*08 | 0.004621 | A*24 | C*04 | B*35 | DRB1*11 | 0.006232 |
| A*03 | C*14 | B*51 | DRB1*13 | 6.458e−05 | A*74 | C*02 | B*15 | DRB1*03 | 0.0005566 |
| A*30 | C*17 | B*42 | DRB1*07 | 9.229e−05 | A*26 | C*06 | B*50 | DRB1*07 | 3.272e−05 |
| A*11 | C*16 | B*44 | DRB1*04 | 3.486e−05 | A*02 | C*03 | B*40 | DRB1*04 | 0.009908 |
| A*29 | C*07 | B*07 | DRB1*15 | 0.0007765 | A*68 | C*07 | B*49 | DRB1*10 | 0.001377 |
| A*26 | C*06 | B*37 | DRB1*10 | 0.0005673 | A*11 | C*04 | B*35 | DRB1*14 | 0.001842 |
| A*01 | C*07 | B*08 | DRB1*03 | 0.01862 | A*33 | C*08 | B*14 | DRB1*03 | 0.002193 |
| A*02 | C*01 | B*56 | DRB1*01 | 0.0008082 | A*31 | C*02 | B*27 | DRB1*08 | 0.0005152 |
| A*32 | C*05 | B*18 | DRB1*11 | 0.0001083 | A*03 | C*16 | B*51 | DRB1*07 | 0.002625 |
| A*24 | C*15 | B*07 | DRB1*13 | 4.209e−05 | A*24 | C*03 | B*15 | DRB1*13 | 0.001007 |
| A*02 | C*06 | B*57 | DRB1*07 | 0.002188 | A*36 | C*16 | B*45 | DRB1*01 | 1.066e−05 |
| A*24 | C*05 | B*44 | DRB1*13 | 0.0006041 | A*24 | C*04 | B*35 | DRB1*08 | 0.003573 |
| A*74 | C*02 | B*15 | DRB1*11 | 0.0005171 | A*32 | C*03 | B*15 | DRB1*15 | 0.000523 |
| A*33 | C*08 | B*14 | DRB1*03 | 0.002193 | A*01 | C*07 | B*08 | DRB1*03 | 0.01862 |
| A*26 | C*12 | B*38 | DRB1*04 | 0.002758 | A*23 | C*15 | B*51 | DRB1*14 | 1.148e−05 |
| A*03 | C*02 | B*27 | DRB1*07 | 5.808e−05 | A*02 | C*15 | B*51 | DRB1*08 | 0.001543 |
| A*30 | C*03 | B*15 | DRB1*12 | 6.318e−05 | A*26 | C*01 | B*55 | DRB1*11 | 2.915e−05 |
| A*23 | C*04 | B*44 | DRB1*03 | 0.0003317 | A*68 | C*04 | B*53 | DRB1*13 | 0.001859 |
| A*33 | C*08 | B*14 | DRB1*04 | 0.0005816 | A*33 | C*08 | B*14 | DRB1*01 | 0.008527 |
| A*11 | C*12 | B*52 | DRB1*15 | 0.002151 | A*24 | C*07 | B*39 | DRB1*14 | 0.007802 |
| A*33 | C*03 | B*15 | DRB1*10 | 0.000148 | A*01 | C*08 | B*14 | DRB1*11 | 0.0001791 |
| A*02 | C*07 | B*39 | DRB1*08 | 0.003265 | A*11 | C*07 | B*07 | DRB1*15 | 0.001642 |
| A*30 | C*05 | B*18 | DRB1*03 | 0.007131 | A*03 | C*06 | B*58 | DRB1*03 | 5.731e−05 |
| A*68 | C*04 | B*53 | DRB1*13 | 0.001859 | A*29 | C*16 | B*44 | DRB1*07 | 0.01859 |
| A*24 | C*12 | B*38 | DRB1*14 | 0.0004747 | A*31 | C*15 | B*51 | DRB1*01 | 0.0002266 |
| A*23 | C*07 | B*07 | DRB1*14 | 8.503e−05 | A*29 | C*16 | B*44 | DRB1*07 | 0.01859 |
| A*02 | C*17 | B*42 | DRB1*03 | 0.0002518 | A*30 | C*06 | B*47 | DRB1*01 | 6.823e−06 |
| A*31 | C*04 | B*35 | DRB1*04 | 0.004404 | A*31 | C*04 | B*35 | DRB1*04 | 0.004404 |
| A*24 | C*03 | B*40 | DRB1*08 | 0.005647 | A*11 | C*14 | B*51 | DRB1*13 | 0.0002266 |
| A*32 | C*01 | B*27 | DRB1*11 | 0.0002196 | A*68 | C*08 | B*14 | DRB1*15 | 0.0001939 | freq_all1: allele 1 frequency
freq_all2: allele 2 frequency

A method according to the present invention is provided to find the best set of 5 donors using a data base of a blood bank comprising:

Analyzing the genotype of HLA alleles of each donor

Selecting 5 donors with no common allele between two donors and the frequency of the genotypes in the human population or in samples of the population of these donors is not lower than a given threshold "fmin" (to make feasible find such donors); and the percentage of patients that can be treated with at most "m" mismatches be the highest possible; with m is 1 to 10, preferably not more than 2, ordering donors s from the lowest frequency to the highest frequency I the human population (to preserve the maximum potential of the patient to have a graft without side effects).

The present invention provides a method for preparing a kit or set of 5 doses of engineered cells for immunotherapy comprising the steps of the method to find the best set of 5 donors of the invention and further comprising:

Analyzing the preexisting immune response of a patient P against cells of said 5 donors, to predict the compatibility, Engineering cells of at least one donor, preferably of the five donors by engineering the genes, or gene regions involved in cell surface expression of the TCR and or the MHC.

Introducing coding sequences such as sequences coding for a chimeric antigen receptor, to increase the affinity and chemotactic activity of cancer cells for engineered cells, for HLA molecule such as HLA inhibiting NK cells activity, for molecules conferring resistance to solid tumor environment such conferring resistance to hypoxia as in PCT/EP2014/078876 or in Juillerat et al., 2017 http://www.nature.com/articles/srep39833.

Each set of 5 donors described in Table 1 is an object of the present invention.

Engineered cells provided in the set of pharmaceutical unit dose according to the present invention may be prepared according to WO 2015075195.

In particular embodiments, if a matched donor is not available, the following mismatches should be avoided those related to HLA DP, in particular to HLADP beta and more preferably those related to HLA-DPb1*0901 should be avoided.

Tissue/cell typing or crossmatching is performed prior to transplantation to assess donor-recipient compatibility for human leukocyte antigen (HLA) and ABO blood group. These tests include at least one of the followings:

The ABO blood group compatibility is tested first because incompatibility between the blood groups leads to rapid rejection.

In the lymphocytotoxicity assay, patient sera are tested for reactivity with donor lymphocytes. A positive crossmatch may be a contraindication to transplantation because of the risk of hyper acute rejection. In that case cells to be grafted are engineered to selectively target those expressing an Antigen recognized by the Antisera of the patient, Panel-reactive antibody (PRA) screens the serum of a patient for lymphocytic antibodies against a random cell panel. Patients with prior transfusions, transplants, or pregnancies may have a high degree of sensitization and are less likely to have a negative crossmatch with a donor. A reduced risk of sensitization at the time of second transplant has been observed when using more potent immunosuppression with rabbit anti-thymocyte globulin, tacrolimus, and mycophenolate mofetil/sodium for non-sensitized primary kidney or kidney/pancreas transplant patients, Mixed lymphocyte reaction (MLR) can be used to assess the degree of major histocompatibility complex (MHC) class I and class II compatibility. However, it is not a rapid test and can be used only in cases involving living related donors. It is an alternative to the known methods.

Located in the major histocompatibility complex (MHC) on the short arm of chromosome 6, the HLA genes define histocompatibility and determine tolerance of the graft. Although there are over 35 HLA class I and II genes and over 684 alleles, HLA-A, HLA-B (class I), and HLA-DRB1 (class II) genes are used primarily in determining the histocompatibility of donors and recipients for stem cell transplantation. A 6-of-6 match refers to matching these three genes, each of which have two alleles. When none of the 6 alleles match, it is termed a mismatch and the various degrees of mismatch are termed one-antigen mismatch, two-antigen mismatch, etc. When only 3 of 6 alleles mismatch, the term is haploidentical. Graft rejection and graft-versus-host disease (GVHD) are the major immune-mediated complications associated with HLA disparity. The greater the HLA disparity, the higher these risks. Only 25-50% of patients have an HLA-identical sibling, therefore large donor registries have recently been successful in identifying phenotypically matched unrelated donors. In the United States, the National Marrow Donor Program has typed nearly 4 million volunteer donors and uses 118 donor centers and over 57 transplant centers to add 40,000 potential new donors each month.

In one embodiment transplanted cells do not express the following non-HLA antigens including receptors expressed by the vascular endothelium such as the G protein coupled receptors (GPCRs), Major Histocompatibility Complex Class I Chain-related Gene A (MICA) and antigens expressed on the surface of stressed endothelial cells such as myosin, vimentin, collagen V, and Kal tubulin.

Of these antigens, commercially distributed reagents are only available for detection of the non-HLA specific antibodies to ATR, ETR, and MICA.

Further, proficiency testing programs are also available for these assays making their implementation in testing for clinical transplantation applicable.

The pharmaceutical unit doses comprise primary "allogeneic" (non alloreactive cells) cells, optionally redirected to target pathological cells or tissues and used as a sequential treatment in one individual P inducing no or reduce anamnestic response as compared to patient grafted successively with allogenic cells or tissue from one donor.

Specifically, the invention relies on the determination of a selection of particular combinations of HLA antigens expressing cells that are engineered in order to reduce drastically the risk of anamnestic response and graft-versus-host disease. The object of the present invention may be particularly useful in patients requiring successive treatments with engineered immune cells such as fast growing cancers, solid and/or relapsed/refractory tumors, successive cancers and provides a safer and more efficient treatment by immunotherapy in individuals already grafted.

Specifically, the invention relies on the determination of particular sequential combinations of said HLA antigens based in their frequencies in the human population. Matched combination of said HLA antigens is preferred. If not found in the available HLA databases, a mismatched combination is used.

For the subsequent sequential dose injection(s), the mismatch process is applied starting by HLA A, HLA B and HLA DR antigens from lowest to higher frequencies. This method allows to the keep a maximal potential for future grafts on patients by minimizing the alleles against which the patient will get immunized (giving a perilous anamnestic response).

Another aspect, the present invention discloses a kit including at least 2 up to 5 compositions comprising different allogeneic cells for their sequentially use as a treatment in a patient with reduced risk of anamnestic response and graft-versus-host disease. Said compositions are selected from homozygous donors with respect to their HLA A, HLA B and HLA DR alleles, and share no said alleles in common.

According to one aspect, this can be achieved by inactivating at least one HLA allele in order to achieve a full mismatch. Gene inactivation can be also envisioned on other genes such as those involved in the allogeneicity, immune checkpoints, suicide genes . . . .

According to another aspect, such allogeneic immune cells can be engineered to endow a chimeric antigen receptor, which targets specifically a tumor-specific antigen.

This method and kits thereof may be particularly useful in patients requiring several doses injections such as in solid and/or relapsed/refractory tumors.

Chimeric Antigen Receptor (CAR)

A CAR according to the present invention can be a single chain CAR or a multichain CAR.

In general, the CAR according to the present invention comprises
- a) at least a hinge linkable to a binding domain and/or an scfv, or a hinge already linked to a binding domain and/or an scfv,
- b) a transmembrane domain,
- c) an intracellular domain, comprising at least a signal transducing domain.

The CAR according to the present invention comprises
- a) at least a hinge linkable to a binding domain, linked to
- b) a transmembrane domain, liked to
- c) an intracellular domain, comprising at least a signal transducing domain.

In particular embodiments, a unit dose from the set or kit is provided and combined with a binding domain or an scfv specific for an antigen expressed by cancer cells P is suffering from. The binding domain or scfv specific for an antigen expressed by cancer cells P links to the CAR by its hinge, making engineered cells specific for the antigen expressed by cancer cells P is suffering from.

Accordingly, the present invention provides a set or kit of n pharmaceutical unit doses comprising engineered cells and a binding domain or a scfv specific for any of the cancer antigen described above and pharmaceutically acceptable vehicle, said binding domain or a scfv may be specific for any of the cancer antigen described above, and comprising a means for linking to the CAR's hinge expressed by engineered cells.

The CAR according to the present invention comprises: a hinge, preferably a hinge selected from a group consisting of IgG1 hinge, CD8a hinge, FcγRIIIa hinge and EpoR-D2 hinge, derived from the extracellular domain of a transmembrane receptor of the tumor necrosis factor (TNF) superfamily death receptor such as a hinge derived from the extracellular domain of CD95 and may have at least 80% sequence identity with the hinge of human CD95.

The CAR according to the present invention may comprise at least one transmembrane domain, preferably selected from the group consisting of CD95 (Fas) transmembrane domain, DR4 transmembrane domain, DR5 transmembrane domain, TNFR1 transmembrane domain, DR3 transmembrane domain, CD8 alpha transmembrane domain, 4-1BB transmembrane domain, DAP10 transmembrane domain and CD28 transmembrane domain.

The CAR according to the present invention may comprise at least one transmembrane domain, selected from the group consisting of the transmembrane domains of the FcεRI α, β and γ chains.

Optionally, the CAR according to the present invention comprises an ectodomain or extracellular binding domain specific for a target antigen expressed on a pathological cell or tissue. Said CAR allows engineered cells to target pathological cells or tissues and eventually affects their functioning. Upon binding of the binding domain specific for a target antigen to said specific target antigen, a signal is generated in the CAR expressing cells leading to various cellular effects.

A signal transducing domain or "cytoplasmic signaling domain" (or endodomain) of a CAR according to the present invention is responsible for intracellular signaling following the binding of extracellular ligand binding domain to the target resulting in the activation or inhibition of the immune cell and immune response. In other words, the signal transducing domain is responsible for the activation or inactivation of at least one of the normal effector functions of the immune cell in which the CAR is expressed. For example, the effector function of a T cell can be a cytolytic activity or helper activity including the secretion of cytokines. Thus, the term "cytoplasmic signaling domain" refers to the portion of a protein which transduces the effector signal function signal and directs the cell to perform a specialized function.

The cytoplasmic signaling domain, is preferably from a human protein involved in signal transduction pathway(s), it may have the effect of reducing the cellular immune activity, such as signaling domains of human immunoinhibitory receptors CTLA-4 and PD-1 (Federov et al., Sci Transl Med. 2013 Dec. 11; 5 (215): 215ra172). Preferred examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the CAR can comprise the CD3zeta signaling domain which has amino acid sequence with at least 70%, preferably at least 80%, more preferably at least 90%, 95% 97% or 99% or 100% sequence identity with amino acid sequence of the human CD3zeta.

In particular embodiment the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83. A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In a preferred embodiment, the signal transduction domain of the CAR of the present invention comprises a part of co-stimulatory signal molecule selected from the group consisting of fragment of human 4-1BB (GenBank: AAA53133.) and/or human CD28 (NP_006130.1).

The engineered cells of the present invention may express a CAR according to the present invention comprising at least a hinge linkable to a binding domain or at least a hinge linkable to an scfv, a transmembrane domain, an intracellular domain.

The engineered cells of the present invention may express a CAR according to the present invention comprising at least a hinge linkable to a binding domain or at least a hinge linkable to an scfv, a transmembrane domain, and an intracellular domain.

According to the present invention, cellular effects induced in CAR-expressing cells upon binding to a specific antigen and signaling can be for example degranulation, resistance to a drug, sensitivity to a drug, cytokine release, lyse of target cells or tissue, maturation of CAR-expressing cells, death of CAR-expressing cells.

The CAR according to the invention comprises (optionally) an extracellular ligand-binding domain or is linkable to a binding domain specific for an antigen selected from the group consisting of CD19 molecule (CD19); membrane spanning 4-domains A1 (MS4A1 also known as CD20); CD22 molecule (CD22); CD24 molecule (CD24); CD248 molecule (CD248); CD276 molecule (CD276 or B7H3); CD33 molecule (CD33); CD38 molecule (CD38); CD44v6; CD70 molecule (CD70); CD72; CD79a; CD79b; interleukin 3 receptor subunit alpha (IL3RA also known as CD123); TNF receptor superfamily member 8 (TNFRSF8 also known as CD30); KIT proto-oncogene receptor tyrosine kinase (CD117); V-set pre-B cell surrogate light chain 1 (VPREB1 or CD179a); adhesion G protein-coupled receptor E5 (ADGRE5 or CD97); TNF receptor superfamily member 17 (TNFRSF17 also known as BCMA); SLAM family member 7 (SLAMF7 also known as CS1); L1 cell adhesion molecule (L1CAM); C-type lectin domain family 12 member A (CLEC12A also known as CLL-1); tumor-specific variant of the epidermal growth factor receptor (EGFRvIII); thyroid stimulating hormone receptor (TSHR); Fms related tyrosine kinase 3 (FLT3); ganglioside GD3 (GD3); Tn antigen (Tn Ag); lymphocyte antigen 6 family member G6D (LY6G6D); Delta like canonical Notch ligand 3 (DLL3); Interleukin-13 receptor subunit alpha-2 (IL-13RA2); Interleukin 11 receptor subunit alpha (IL11RA); mesothelin (MSLN); Receptor tyrosine kinase like orphan receptor 1 (ROR1); Prostate stem cell antigen (PSCA); erb-b2 receptor tyrosine kinase 2 (ERBB2 or Her2/neu); Protease Serine 21 (PRSS21); Kinase insert domain receptor (KDR also known as VEGFR2); Lewis y antigen (LewisY); Solute carrier family 39 member 6 (SLC39A6); Fibroblast activation protein alpha (FAP); Hsp70 family chaperone (HSP70); Platelet-derived growth factor receptor beta (PDGFR-beta); Cholinergic receptor nicotinic alpha 2 subunit (CHRNA2); Stage-Specific Embryonic Antigen-4 (SSEA-4); Mucin 1, cell surface associated (MUC1); mucin 16, cell surface associated (MUC16); claudin 18 (CLDN18); claudin 6 (CLDN6); Epidermal Growth Factor Receptor (EGFR); Preferentially expressed antigen in melanoma (PRAME); Neural Cell Adhesion Molecule (NCAM); ADAM metallopeptidase domain 10 (ADAM10); Folate receptor 1 (FOLR1); Folate receptor beta (FOLR2); Carbonic Anhydrase IX (CA9); Proteasome subunit beta 9 (PSMB9 or LMP2); Ephrin receptor A2 (EphA2); Tetraspanin 10 (TSPAN10); Fucosyl GM1 (Fuc-GM1); sialyl Lewis adhesion molecule (sLe); TGS5; high molecular weight-melanoma-associated antigen (HMW-MAA); o-acetyl-GD2 ganglioside (OAcGD2); tumor endothelial marker 7-related (TEM7R); G protein-coupled receptor class C group 5, member D (GPRC5D); chromosome X open reading frame 61 (CXORF61); ALK receptor tyrosine kinase (ALK); Polysialic acid; Placenta-specific 1 (PLAC1); hexasaccharide portion of globoH glycoceramide (GloboH); NY-BR-1 antigen; uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 family member K (LY6K); olfactory receptor family 51 subfamily E member 2 (OR51E2); TCR Gamma Alternate Reading Frame Protein (TARP); Wilms tumor protein (WT1); ETV6-AML1 fusion protein due to 12; 21 chromosomal translocation (ETV6-AML1); sperm autoantigenic protein 17 (SPA17); X Antigen Family, Member 1E (XAGE1E); TEK receptor tyrosine kinase (Tie2); melanoma cancer testis antigen-1 (MAD-CT-1); melanoma cancer testis antigen-2 (MAD-CT-2); Fos-related antigen 1; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Cytochrome P450 1B 1 (CYP1B 1); CCCTC-Binding Factor (Zinc Finger Protein)-Like (BORIS); Squamous Cell Carcinoma Antigen Recognized By T Cells 3 (SART3); Paired box protein Pax-5 (PAX5); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1); PCTA-l/Galectin 8, CD171, TAG72, CEA, EPCAM, PSCA, PRSS21, PDGFR-beta, Prostase, PAP, ELF2M, Ephrin B2, IGF-I receptor, CAIX, gp100, bcr-abl, tyrosinase, GM3, NY-ESO-1, LAGE-la, MAGE-A1, legumain, HPV E6, E7, MAGE A1, prostein, survivin and telomerase, PCTA-l/Galectin 8, MelanA/MART1, Ras mutant, TRP-2, RAGE-1, RU1, RU2, intestinal carboxyl esterase and Heat shock protein 70.

The CAR of the invention may be a TCR, in particular any TCR specific for NY-ESO-1, LAGE-la, MAGE-A1, legumain, HPV E6, E7, MAGE A1, prostein, survivin and telomerase, PCTA-l/Galectin 8, MelanA/MARTI, Ras mutant, TRP-2, RAGE-1, RU1, RU2.

The CAR of the invention may be specific for a solid tumor antigen.

In some embodiments, the CAR according to the invention is a single chain CAR.

In some embodiments, the CAR according to the invention is a multi-chain CAR.

In some embodiments, the engineered cells of the invention express at least one CAR at the cell surface and may express two, three of for CAR, in addition to engineered MHC class I molecules.

In some embodiments, the CAR according to the invention may be a CAR wherein the at least one ectodomain and the at least one endodomain of said CAR are not born on the same polypeptide chain, but on at least two different polypeptide chains each containing a transmembrane domain, said at least two different polypeptide chains interact to form a dimeric or a multimeric CAR.

In some embodiments, the CAR according to the invention may be a CAR wherein said at least two different polypeptide chains comprise a portion of a FcERI alpha chain, FcERI beta chain and/or FcERI gamma chain.

In some embodiments, the CAR according to the invention may be a CAR wherein the polypeptide chain comprising the ectodomain comprises the transmembrane domain from the alpha chain of FcERI.

In some embodiments, the CAR according to the invention may be a CAR wherein the polypeptide chain comprising the endodomain comprising a death domain comprises the transmembrane domain from the gamma or beta chain of FcERI.

In some embodiments, the set or kit of n pharmaceutical unit doses according to the invention may comprise engineered cells comprising at least one polynucleotide comprising a nucleic acid sequence encoding a CAR, preferably inserted into the TCRA gene.

In some embodiments, the set of n pharmaceutical unit doses according to the invention wherein engineered cells comprise at least one polynucleotide operably linked to an active promoter preferably a TCRA promoter.

In some embodiments, the active promoter means a promoter that is active in cells used for immunotherapy.

In some embodiments, the cells according to the present invention may be immune cells, primary immune cells, immune cells derived from an inflammatory T-lymphocyte, cytotoxic T-lymphocyte, regulatory T-lymphocyte or helper T-lymphocyte.

In some embodiments, the cells according to the present invention, wherein the gene(s) encoding beta 2-microglobulin (B2M) and/or class II major histocompatibility complex transactivator (CIITA) has (have) been inactivated.

Other genes may be disrupted encoding HLA class II (HLA-II) molecules or proteins HLA class II-related gene is selected from the group consisting of regulatory factor X-associated ankyrin-containing protein (RFXANK), regulatory factor 5 (RFX5), regulatory factor X-associated protein (RFXAP), class II transactivator (CIITA), HLA-DPA (a chain), HLA-DPB (P chain), HLA-DQA, HLA-DQB, HLA-DRA, HLA-DRB, HLA-DMA, HLA-DMB, HLA-DOA and HLA-DOB as disclosed in WO2013 158292.

The dose of engineered cells of the invention in a kit comprises an exogenous gene encoding a CAR inserted into the TRAC locus as disclosed in WO2016120216A1 (incorporated herein by reference in its entirety for eliminating CAR expressing cells using a monoclonal antibody, preferably rituximab and/or QBEND-10 In embodiments, engineered cells of each dose in a kit of the invention comprises gene(s) encoding beta 2-microglobulin (B2M) and/or class II major histocompatibility complex (eg transactivator (CIITA)) and at least one gene conferring resistance to lymphodepletion which are inactivated. Gene conferring resistance to lymphodepletion may be anyone of the genes selected from a gene encoding dCK, CD52, CS1, CD38, CD70).

A provided:

In some embodiments, the cells according to the present invention, wherein at least one gene encoding a component of the T-cell receptor (TCR) has been inactivated In some embodiments, the cells according to the present invention, wherein said cell has been modified to confer resistant to at least one immune suppressive drug, chemotherapy drug, or anti-cancer drug.

According to one aspect, the present invention relates a method for preparing a set of successive injection doses for use of performing a sequential (N=graft number) treatment in a patient of allogeneic peripheral blood cells coming from different donors aiming at reducing risk of anamnestic response and graft-versus-host disease comprising the step of:

(a) randomly sampling several groups of 5 donors comprised in a bank of donors;
(b) comparing the genotypes of the 5 donors within said groups with respect to their HLA-A, HLA-B and HLA-DR alleles;
(c) selecting the groups of five donors which present no HLA-A, HLA-B and HLA-DR allele in common;
(d) selecting in the groups obtained from step (c) those displaying at least 50% match of HLA-A, HLA-B and HLA-DR alleles with the genotype of at least 80% (fmin), preferably more than 90% and even more preferentially more than 95% of the ethnic population of said patient;
(e) Engineering the allogeneic peripheral blood cells from each of the donors selected from step (d) to reduce or impair expression of the TCR in said peripheral blood cells;
(f) Optionally, expanding the engineered peripheral blood cells from the blood sample; Conditioning the engineered peripheral blood cells from the different donors separately.

According to one aspect, the present invention relates a method for preparing a set of successive injection doses for use of performing a sequential (N=graft number) treatment in a patient of allogeneic peripheral blood cells coming from different donors aiming at reducing risk of anamnestic response and graft-versus-host disease comprising the step of:

(a) randomly sampling several groups of 5 donors comprised in a bank of donors;
(b) comparing the genotypes of the 5 donors within said groups with respect to their HLA-A, HLA-B, HLA-C and HLA-DR alleles;
(c) selecting the groups of five donors which present no HLA-A, HLA-B, HLA-C and HLA-DR allele in common;
(d) selecting in the groups obtained from step (c) those displaying at least 50% match of HLA-A, HLA-B HLAC and HLA-DR alleles with the genotype of at least 80% (fmin), preferably more than 90% and even more preferentially more than 95% of the general population, (e) Engineering the allogeneic peripheral blood cells from each of the donors selected from step (d) to reduce or impair expression of the TCR at the cell surface in said peripheral blood cells;

(f) expanding the engineered peripheral blood cells from the blood sample;

(g) Conditioning the engineered peripheral blood cells from the different donors, separately.

According to another aspect, the present invention relates a method for preparing a set of successive injection doses for use of performing a sequential (N=graft number) treatment in a patient of allogeneic peripheral blood cells coming from different donors aiming at reducing risk of anamnestic response and graft-versus-host disease comprising the step of:

a) selecting donors displaying at least 50% match of HLA-A, HLA-B HLAC and HLA-DR alleles with the genotype of at least 80% (fmin), preferably more than 90% and even more preferentially more than 95% of the general population, in a bank of donors, b) comparing the genotypes with respect to their HLA-A, HLA-B, HLA-C and HLA-DR, HLA-DQ alleles of cells of the donors selected in (a), c) selecting a group of at least five donors which present no HLA-A, HLA-B, HLA-C and HLA-DR allele in common; or selecting a group of at least five donors which present no HLA-A, HLA-B, HLA-C and HLA-DR allele in common; between each other unless said allele match the HLA allele(s) of the patient intended to be treated by immunotherapy, d) engineering the peripheral blood cells from each of the donors selected from step (c) to reduce or impair expression of the TCR at the cell surface in said peripheral blood cells;

e) engineering the peripheral blood cells from each of the donors selected from step (c) or (d) for the expression of MHC class I and/or MHC Class I1 to be controllable at the cell surface in said peripheral blood cells;

e) Engineering the peripheral blood cells from each of the donors selected from step (c) or (d) or (e) so that they express an HLA inhibiting NK cells, preferably HLA-E, at the cell surface, said expression being controllable, f) expanding the engineered peripheral blood cells from the blood sample; g) Conditioning the engineered peripheral blood cells from the different donors, separately.

By "controllable expression" is meant an expression that may be inhibited or may be induced upon contact of engineered cells with a drug, such as a modified cytokine, an antibiotic.

In particular embodiments and part of the present invention are provided.

Definitions

By "allogeneic", it is meant that cells are transplanted into a genetically different recipient.

By "anamnestic response" is meant a bodily defense reaction that recognizes, within the present invention, transplanted immune cells and produces antibodies specific against that antigens By "graft-versus-host disease (GvHD)", it is meant, within the present invention, a common complication following an allogeneic transplant of immune cells which recognize the recipient (the host) as "foreign." The transplanted immune cells then attack the host's body cells.

According to a preferred embodiment, the peripheral blood cell (called also "graft") is a white primary blood cell (immune cell) and more preferably a T cell. Primary cells are cultured directly from a subject; they are to be differentiated from established cell lines which are not contemplated in the scope of the present invention. Hematopoietic cells correspond to lymphoid cells such as T-cells, B-cells, NK-cells and to myeloid cells such as monocytes, macrophages, neutrophils, basophils, eosinophils, erythrocytes, megakaryocytes/platelets and dendritic cells.

The "immunogenic antigen" considered within the present invention is dependent of the type of peripheral blood cell to be transplanted into the recipient.

According to a preferred embodiment, the immunogenic antigens are part of the HLA system.

According to a more preferred embodiment, the immunogenic antigens which are considered within the present invention are the combination of the HLA-A, HLA-B and HLA-DR genotypes. By "HLA-A, HLA-B and HLA-DR genotypes", it is meant two sets of haplotypes for these three particular HLA antigens. They may be homozygous, analogous alleles or heterozygous.

By "homozygote", it is applied to a particular gene.

There are thousands of different combinations of possible HLA tissue types. This can make it hard to find an exact match, especially when the method of the present invention is applied for genotype, i.e. HLA antigens inherited from both parents. Thus, within the present invention, the serotype (groups of alleles) is considered for HLA-A and HLA-B and the allele for the HLA-DR. In Prasad V K et al. (1999) it is reported that 83 HLA-A and 186 HLA-B alleles resolve into only 28 HLA-A and 59 HLA-B serotypes.

HLA-DR Alleles

For a definition see Prasad V K, Kernan N A, Heller G, O'Reilly R J, Yang S Y, (1999) "DNA typing for HLA-A and HLA-B identifies disparities between patients and unrelated donors matched by HLA-A and HLA-B serology and HLA-DRB1", Blood. 93(1):399-409.)

According to the present invention, the "population of reference" may be worldwide; subpopulations such as African, Caucasians, Asian, Hispanic and North American Natives, even limited to a single country. "By available panel of donors", it is meant a set of donors of several hundred or several thousand donors taken randomly in the population or a subset of the population.

Thus, said population is a subpopulation which is a composed of genetically similar and a reduced number of individuals at the world scale.

According to one embodiment, said patient (or "recipient") and said population of reference are Caucasian.

According to another embodiment, said patient (or "recipient") and said population of reference are African-Americans.

According to another embodiment, said patient (or "recipient") and said population of reference are Asian/Pacific Islanders.

According to another embodiment, said patient (or "recipient") and said population of reference are Hispanics.

According to another embodiment, said patient (or "recipient") and said population of reference are Native Americans.

In facts different populations correspond to groups of individuals that designated their origin according to the countrie they originated from. This segregation is consistent with criteria previously defined in Chew A, Han J H, et al. Haplotype variation and linkage disequilibrium in 313 human genes. Science. 2001; 293:489-493 or in Risch N, Burchard E, Ziv E, Tang H. Categorization of humans in biomedical research: genes, race and disease. Genome Biology. 2002; 3(7):comment 2007.1-comment2007.12.

According to the method of the present invention, for the first injection, it is preferred to choose matched HLA genotypes, or the closest possible. If this is not possible, the mismatched HLA genotypes should be selected for the graft.

HLA Matching

There are many HLA markers. Each HLA marker has a name. The names are letters or combinations of letters and numbers. In the present invention, at least 6 HLA markers, preferably at least 8 markers and even more preferably 10 markers, is the minimum requirements for "matching": two A markers, two B markers, two C markers, two DRB1 and two DQ markers, to match.

An adult donor must match at least 6 of these 8 HLA markers. Many transplant centers require at least a 7 of 8 match. Because cord blood cells are less mature than adult donor cells they have less strict matching criteria. A cord blood unit must match at least 4 of 6 markers at HLA-A, -B, and -DRB1. These guidelines are based on scientific studies of transplant results.

By "HLA matching" is meant the process by which the search of the best match between the donor's and recipient's HLA tissue types. Within the present invention, the best match is obtained when the HLA-A, HLA-B and the HLA-DR antigens are the same.

According to one preferred embodiment, the choice of a graft closely related to the receiving recipient is a single homozygote on 1 of HLA-A, HLA-B and HLA-DR genes.

"by homozygote": it is meant that the two haplotypes (one from each parent) are identical.

According to one preferred embodiment, the choice of a graft closely related to the receiving recipient is a double homozygote on 2 of HLA-A, HLA-B and HLA-DR genes.

According to one preferred embodiment, the choice of a graft closely related to the receiving recipient is a triple homozygote on HLA-A, HLA-B and HLA-DR genes.

"Mismatching" was defined, within the present invention, as the presence of donor HLA-A, HLA-B and the HLA-DR alleles not shared by the recipient.

By "immunogenic antigen alleles are the most identical to those genotyped in the patient", it is meant that a single mismatch may be tolerated, in condition that said mismatched HLA antigen is absolutely not used again in the next injection batches. Practically, if possible, the search for a donor usually starts with the patient's brothers and sisters (siblings), who have the same parents as the patient. The chance that any one sibling would be a perfect match (that is, that you both received the same set of HLA antigens from each of your parents) is 1 out of 4. If a sibling is not a good match, the search could then move on to relatives who are less likely to be a good match—parents, half siblings, and extended family, such as aunts, uncles, or cousins. (Spouses are no more likely to be good matches than other people who are not related.) If no relatives are found to be a close match, the transplant team will widen the search to the general public. It's possible to find a good match with a stranger. To help with this process, the team will use transplant registries. Registries serve as matchmakers between patients and volunteer donors. They can search for and access millions of possible donors and hundreds of thousands of cord blood units. Depending on a person's tissue typing, several other international registries also are available. Sometimes the best matches are found in people with a similar racial or ethnic background. A single match can require going through millions of records.

According to the second option for the first injection (less preferred), the HLA genotype of the donor is different of that of the recipient, in particular to the HLA-A, HLA-B and HLA-DR antigens.

According to one embodiment, if a full mismatch of HLA-A, HLA-B and HLA-DR genotypes is not possible to obtain, a partial mismatch may be tolerated, in condition that it is on the HLA-DR antigen.

HLA Databases

According to the present invention, in order to determine the best donor(s) for HLA matching/mismatching, it is suitable to process through HLA databases currently used in organ transplantation, since these enable to have access to millions of international records, and therefore optimize successfully matched thousands of donors and recipients.

Such HLA databases may be the largest registry in the United States is "Be the Match" (formerly called the National Marrow Donor Program), or the IMGT/HLA Database which provides a specialist database for sequences of the human major histocompatibility complex (HLA) and includes the official sequences for the WHO Nomenclature Committee For Factors of the HLA System.

According to another embodiment, said method is performed, wherein the step (b) (i) of HLA mismatch is made from a very low frequency of population.

Rare alleles (i.e. a frequency of less than 0.001) are preferred, however as those may not be found due to their rarity, it is possible to use common alleles (gene frequencies greater than 0.001). This step of choosing a graft bearing immunogenic antigens from a very low frequency in the population is realized by the compilation of available data from common allele frequencies databases.

HLA Genotyping

As part of the method of the present invention, having already determined the population of reference of potential donors, the first step consists to genotype the recipient (or "patient") before having the graft been transplanted into him.

For this purpose, the genotyping method to be used within the present invention is preferably any one which is a current international standard HLA genotyping technique such as Sanger sequencing technique-based PCR sequencing method (SBT) (Bentley. G., Higuchi, R., Hoglund, B., Goodridge, D., Sayer, D., Trachtenberg, E. A., and Erlich H. A. (2009) "High-resolution, high-throughput HLA genotyping by next-generation sequencing", Tissue Antigens. 74(5): 393-403). Instead, other well-established in HLA typing laboratories techniques can be used such as group-specific PCR or allele separation by group-specific sequencing primers (Danzer M., Niklas N., Stabentheiner S., Hofer K., Pröll, J., Stückler C., Raml E., Polin H. and Gabriel C. (2013) "Rapid, scalable and highly automated HLA genotyping using next-generation sequencing: a transition from research to diagnostics", BMC Genomics, 14:221). As stated in US20090035776, HLA genotyping by polymerase chain reaction (PCR) techniques has become an alternative to serological methods that is widely used in clinical practise. The most commonly used PCR-based typing methods are PCR with sequence-specific primers (PCR-SSP) and PCR with sequence-specific oligonucleotides (PCR-SSO). In the PCR-SSP method, the gene sequence is determined by the amplification of the hypervariable region of the target HLA antigen in order to determine the type of HLA antigen (e.g. cf. M. Bunce et al., "Phototyping: comprehensive DNA typing for HLA-A, B, C, DRB1, DRB3, DRB4, DRB5 & DQB1 by PCR with 144 primer mixes utilizing sequence-specific primers (PCR-SSP)", Tissue Antigens 1995, vol. 46, pp. 355-67). In the PCR-SSO method, a membrane is prepared (whereon the DNA amplified by the HLA gene specific primers is immobilised) and the specific oligonucleotide probes for the respective type of HLA are hybridised for typing (e.g. cf. R. K. Saiki et al., "Analysis of enzymatically amplified beta-globin and HLA-DQ alpha DNA with allele-specific oligonucleotide probes", Nature 1986, vol. 324, pp. 163-6). The HLA-B genotyping kits currently available in the market are based on these two methods, PCR-SSP and PCR-SSO.

HLA Serotyping of the Recipient

According to one embodiment, a step of detection of preformed circulating anti-HLA antibodies is performed before the first dose administration.

According to another embodiment, said detection is performed on the preformed circulating anti-HLA-A, anti-HLA-B and anti-HLA-DR antibodies.

Patients who have become sensitized to allogeneic HLA antigens through pregnancies, blood transfusions, failed transplants, or other means represent a challenge when requiring a transplant or platelet transfusion. Preformed anti-HLA antibodies are associated with hyperacute rejection of transplants. Anti-HLA antibodies in patient's serum may react with cells from a few or many individuals. Sensitization is reported as the percent Panel Reactive Antibody (PRA), which is the percentage of potential donors' cells tested that were killed by the patient's serum. The PRA also gives an estimate of the likelihood of finding a suitable donor. These antibodies can be identified and characterized using several approaches which vary in sensitivity and accuracy, as presented thereafter, all of them being contemplated within the present invention. The complement-Dependent Lymphocytotoxicity (CDC) may be used to detect cross-reaction (crossmatch) between the donor's immune cells and the existing patient's anti-HLA antibodies in the presence of the complement. Also, Luminex may be used before and after transplantation to monitor patients for presence or absence of anti-HLA class I and class II antibodies or to monitor the appearance or disappearance of antibodies over time. Positive sera are subsequently tested by luminex class I and class II identification assays to determine the HLA specificity of the antibodies. Flow cytometry represents another technique to assess the specificity of anti-HLA antibodies that are not normally detected by less sensitive methods such as cytotoxicity. Single HLA antigen beads are used to determine specific HLA antibodies in high PRA containing sera.

Engineering Immune Cells

The present invention encompasses the method of preparing immune cells for immunotherapy comprising introducing ex-vivo into said immune cells the polynucleotides or vectors encoding one specific endonuclease and/or a chimeric antigen receptor described thereafter.

In a preferred embodiment, said polynucleotides are included in lentiviral vectors in view of being stably expressed in the immune cells.

By inactivating a gene it is intended that the gene of interest is not expressed in a functional protein form. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated endjoining (Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event—i.e a mutagenesis event consecutive to an NHEJ event—has occurred can be identified and/or selected by well-known method in the art.

According to one embodiment, the step of inactivation is performed by homologous recombination mediated gene targeting. Endonucleolytic breaks are known to stimulate the rate of homologous recombination. Thus, in another embodiment, the genetic modification step of the method further comprises a step of introduction into cells an exogeneous nucleic acid comprising at least a sequence homologous to a portion of the target nucleic acid sequence, such that homologous recombination occurs between the target nucleic acid sequence and the exogeneous nucleic acid. In particular embodiments, said exogenous nucleic acid comprises first and second portions which are homologous to region 5' and 3' of the target nucleic acid sequence, respectively. Said exogenous nucleic acid in these embodiments also comprises a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogenous nucleic acid. Preferably, homologous sequences of at least 50 bp, preferably more than 100 bp and more preferably more than 200 bp are used within said donor matrix. Therefore, the exogenous nucleic acid is preferably from 200 bp to 6000 bp, more preferably from 1000 bp to 2000 bp. Indeed, shared nucleic acid homologies are located in regions flanking upstream and downstream the site of the break and the nucleic acid sequence to be introduced should be located between the two arms.

In a preferred embodiment said method of further engineering the immune cells involves introducing into said immune cells such, as T cells, polynucleotides, in particular mRNAs, encoding specific rare-cutting endonuclease to selectively inactivate the genes, as those mentioned below, by DNA cleavage. In a more preferred embodiment said rare-cutting endonucleases are TALE-nucleases or Cas9 endonuclease. TAL-nucleases have so far proven higher specificity and cleavage efficiency over the other types of rare-cutting endonucleases, making them the endonucleases of choice for producing of the engineered immune cells on a large scale with a constant turn-over.

According to a preferred embodiment, the gene inactivation is preferably performed by using a TAL-nuclease, meganuclease, zing-finger nuclease (ZFN), or RNA/DNA guided endonuclease, such as Cas9 or Argonaute.

According to a more preferred embodiment, the inactivation of said allele coding for the immunogenic antigen, preferably HLA-A, HLA-B and/or HLA-DR allele(s), is performed by using TALE-nucleases. This can be accomplished at a precise genomic location targeted by a specific TALE-nuclease, wherein said specific TALE-nuclease catalyzes a cleavage and wherein said exogenous nucleic acid successively comprising at least a region of homology and a sequence to inactivate one targeted gene selected from the group previously cited. Several genes can be, successively or at the same time, inactivated by using several TALE-nucleases respectively and specifically targeting one defined gene and several specific. By TALE-nuclease is intended a fusion protein consisting of a DNA-binding domain derived from a Transcription Activator Like Effector (TALE) and one nuclease catalytic domain to cleave a nucleic acid target sequence. (Boch, Scholze et al. 2009; Moscou and Bogdanove 2009; Christian, Cermak et al. 2010; Cermak, Doyle et al. 2011; Geissler, Scholze et al. 2011; Huang, Xiao et al. 2011; Li, Huang et al. 2011; Mahfouz, Li et al. 2011; Miller, Tan et al. 2011; Morbitzer, Romer et al. 2011; Mussolino, Morbitzer et al. 2011; Sander, Cade et al. 2011; Tesson, Usal et al. 2011; Weber, Gruetzner et al. 2011; Zhang, Cong et al. 2011; Deng, Yan et al. 2012; Li, Piatek et al. 2012; Mahfouz, Li et al. 2012; Mak, Bradley et al. 2012).

Inactivation of Immunogenic Antigen Allele

In one aspect, the present invention provides further a method by which it may be useful to inactivate at least one immunogenic antigen allele during the mismatch process—i.e. in step (c) (ii) applied to the first batch, or in step (d) applied to the subsequent batch(es) to be injected to the recipient.

According to a preferred embodiment, the immunogenic antigen allele(s) to be inactivated is (are) the HLA-A, HLA-B and/or HLA-DR allele(s).

According to another preferred embodiment, the inactivation of said allele coding for the immunogenic antigen, preferably HLA-A, HLA-B and/or HLA-DR allele(s) is performed by RNA-guided endonuclease such as Cas9 or DNA-guided endonuclease, such as Argonaute based techniques as described in WO2014189628.

According to further embodiments, said method further comprises the step of genetically modifying said cell to make them more suitable for allogeneic transplantation.

According to a first aspect, the immune cell can be made allogeneic, for instance, by inactivating at least one gene expressing one or more component of T-cell receptor (TCR) as described in WO 2013/176915, which can be combined with the inactivation of a gene encoding or regulating HLA or β2m protein expression. Accordingly the risk of graft versus host syndrome and graft rejection is significantly reduced.

According to another aspect, the immune cells can be further genetically engineered to improve their resistance to immunosuppressive drugs or chemotherapy treatments, which are used as standard care for treating positive malignant cells. For instance, CD52 and glucocorticoid receptors (GR), which are drug targets of Campath (alemtuzumab) and glucocorticoids treatments, can be inactivated to make the cells resistant to these treatments and give them a competitive advantage over patient's own T-cells. Expression of CD3 gene can also be suppressed or reduced to confer resistance to Teplizumab, which is another immune suppressive drug. Expression of HPRT can also be suppressed or reduced according to the invention to confer resistance to 6-thioguanine, a cytostatic agent commonly used in chemotherapy especially for the treatment of acute lymphoblastic leukemia.

According to further aspect of the invention, the immune cells can be further manipulated to make them more active or limit exhaustion, by inactivating genes encoding proteins that act as "immune checkpoints" that act as regulators of T-cells activation, such as PDCD1 or CTLA-4. Examples of genes, which expression could be reduced or suppressed are indicated in Table 1 of the application WO2014/184744.

Cells Endowing a Chimeric Antigen Receptor (CAR)

According to an important aspect of the invention, white blood cells to be engrafted into the recipient are genetically engineered to make them expressed a chimeric receptor antigen (CAR).

These artificial (engineered) T cell receptors are under investigation as a therapy for cancer, using a technique called adoptive cell transfer. T cells are removed from a patient and modified by grafting the specificity of a monoclonal antibody, so that they express receptors specific to the particular form of cancer. The immune cell (i.e. T cells), which can then recognize and kill the cancer cells, are reintroduced into the patient.

CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The invention encompasses first generation CARs wherein signaling domains for are derived from the cytoplasmic region of the CD3zeta or the Fc receptor gamma chains. The invention covers also second and third generations, which allow prolonged expansion and anti-tumor activity in vivo. For these CARs, signaling domains from co-stimulatory molecules, as well as transmembrane and hinge domains have been added to form CARs.

According to one embodiment, said CAR is a single-chain CAR.

They may be designed according to single-chain as well defined in the prior art, such as in U.S. Pat. No. 7,446,190, WO2008/121420, U.S. Pat. No. 8,252,592, US20140024809, WO2012/079000, WO2014153270, WO2012/099973, WO2014/011988, WO2014/011987, WO2013/067492, WO2013/070468, WO2013/040557, WO2013/126712, WO2013/126729, WO 2013/126726, WO2013/126733, U.S. Pat. No. 8,399,645, US20130266551, US20140023674, WO2014039523, U.S. Pat. Nos. 7,514,537, 8,324,353, WO2010/025177, U.S. Pat. No. 7,446,179, WO2010/025177, WO2012/031744, WO2012/136231A1, WO2012/050374A2, WO2013074916, WO/2009/091826A3, WO2013/176915 or WO/2013/059593. According to another embodiment, said CAR is a multichain CAR. Examples of multi-chain architectures of CAR are more particularly disclosed in WO2014039523.

According to another embodiment, said CAR comprises at least a CD3 zeta signaling domain and a 4-1BB co-stimulatory domain.

According to another embodiment, said CAR is specific to a cell surface antigen chosen amongst C38, CD123 or CS1.

According to another embodiment, said CAR is specific to a cancer cell surface antigen expressed or over expressed on a solid tumor of on a metastatic cell. Said cancer cell surface antigen may be chosen amongst CEA for Colorectal carcinoma, Breast cancer or liver metastases, EGFRvIII for Glioma-Glioblastoma, EGFR for treating Glioma-NSCL cancer, EphA2 or IL13-Rα2 for Glioma, EpCAM for carcinomas, FAP for Mesotelioma, FR-a for Ovarian carcinoma, O-acetyl-GD2 for Neuroblastoma, GPC3 for the treatment of Lung squamous cell carcinoma or Hepatocellular carcinoma, Mesothelin for the treatment of cancer such as Lung cancer, Pleural mesothelioma, Pancreatic carcinoma, Breast cancer, Lung cancer, or Metastatic cancer such as Metastatic colon cancer, Metastatic breast cancer, Metastatic lung cancer, MUC 1 for carcinoma, MUC16 for Ovarian carcinoma, PSMA for prostate cancer, ROR1 for the treatment of Breast lung carcinoma.

In preferred embodiments said engineered cells comprises a CAR specific for HtrA1 (Altobelli E, Angeletti P M, Morroni M, Profeta V F. HtrA1 as a promising tissue marker in cancer: a meta-analysis. *BMC Cancer.* 2018; 18:143. doi:10.1186/s12885-018-4041-2).

In a more preferred embodiments said engineered cells comprises a CAR specific for HtrA1 and for a cancer marker selected from the
group of cancer markers consisting of: CD123; CD19; CD22; CD30; CD79b, CD70; CD171; CS-1 (also referred to as CD2 subset 1, CRACC, SLAMF7, CD319, and 19A24); DLL3; TSPAN10; PRAME; C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(I-4)bDGlcp (I-l)Cer); TNF receptor family member B cell maturation (BCMA); Tn antigen ((Tn Ag) or (GalNAca-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-IIRa); prostate stem cell antigen (PSCA); Protease Serine 21 (Testisin or PRSS21); vascular endothelial growth factor receptor 2 (VEGFR2); Lewis (Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1 (MUC1); Mucin 16 (MUC16); Mucin 17 (MUC17); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAFX); Proteasome (Prosome, Macropain) Subunit, Beta Type, 9 (LMP2); glycoprotein 100 (gpIOO); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(I-4)bDGlcp(I-l)Cer); transglutaminase 5 (TGS5); high molecular weight-melanoma-associated antigen (HMWMAA); o-acetyl-GD2 (OAcGD2); Folate receptor beta; tumor endothelial marker 1 (TEM1/CD248); tumor endothelial marker 7-related (TEM7R); claudin 6 (CLDN6); claudin 18 (CLDN18), including splice variant 2 (claudin18.2); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCRI); adrenoceptor beta 3(ADRB3); pannexin 3 (PANX3); G protein-coupled receptor 20 (GPR20); lymphocyte antigen 6complex, locus K 9 (LY6K); Lymphocyte antigen 6 complex locus protein G6d (LY6G6D); Olfactory receptor 51 E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-la); Melanoma associated antigen 1 (MAGE-A1); ETS translocation-variant gene 6, located on chromosome 12p (ETV6-AML); sperm protein 17 (SPA17); X Antigen Family, Member 1A (XAGE1); angiopoietin binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); NAcetyl glucosaminyl-transferase V (NA17); paired box protein Pax-3 (PAX3); Androgen receptor; Cyclin BI; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70 (HSP70); heat shock protein 70-2 mutated (mut hsp70-2); CD79a; CD79b; CD72; Leukocyte-associated immunoglobulin-like receptor 1 (LAIR1); Fc35 fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In preferred embodiments said engineered cells comprises a CAR specific for HtrA1 and a CAR specific for at least one of the target antigen selected from the group consisting of: CD123, ROR1, BCMA, PSMA, CD33, CD38, CD22, CD79a or b, CS1, CLL-1, HSP70, EGFRVIII, FLT3, WT1, CD30, CD70, MUC1, MUC16, MUC17, PRAME, TSPAN10, Claudin18.2, DLL3, LY6G6D and o-acetyl-GD2 (OAcGD2).

In more more preferred embodiments said engineered cells comprises a CAR specific for HtrA1 and a CAR specific for a target antigen selected from the group consisting of: CD123, CD38, CD22, CS1, CLL-1, HSP70, CD30, MUC1 and o-acetyl-GD2 (OAcGD2).

According to another embodiment, said CAR is directed against solid tumor antigen.

The different methods described above involve introducing CAR into a cell. As non-limiting example, said CAR can be introduced as transgenes encoded by one plasmid vector. Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Therapeutic Applications

Cells that can be used with the disclosed methods and kits are described in the previous section. Said treatment can be used to treat patients diagnosed with cancer, viral infection, autoimmune disorders or Graft versus Host Disease (GvHD) as described in WO2015142675 (combo) or in WO2016201047 Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the immune cells endowed with an antigen-specific CAR include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Treatment

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably 105 to 106 cells/kg body weight including all integer values of cell numbers within those ranges. The cells or population of cells can be administered in one or more doses. In another embodiment, said effective amount of cells are administered as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

According to the present invention, the number of successive doses to be injected into the recipient is higher or equal to 2.

In a preferred embodiment, this number is comprised between 2 and 5. Said number is dependent of the type of tumor to be treated: a solid tumor may require more injections, as well as the case of relapsed or refractory cancers.

In another preferred embodiment, said successive administrations are performed every 45 days;

in another even preferred embodiment said successive administrations are performed every 14 days.

According to one aspect, the method of the invention is implemanted whereby the successive injections doses are injected into a lymphodepleted recipient. This optional step of lymphodepletion is performed before said administration. Said lymphodepletion as routinely performed in immunotherapy consists in the administration of one or more drugs in combination, such as an alkylating agent (for instance, cyclophosphamide . . . ), antimetabolites such as cyclophosphamide, methotrexate, or purine analogues (for instance fluarabine), pyrimidine analogues (for instance fluorouracil) or protein synthesis inhibitors. Cytotoxic drugs such as azathioprine or cytotoxic antibiotics such as dactinomycin, anthracyclines, mitomycin C or bleomycin, mithramycin may also be used. Preferably the lymphodepleting regimen is fludarabine and cyclophosphamide.

More preferably, the lymphodepleting regimen is fludarabine 30 mg/m2/day IV and cyclophosphamide 750 mg/m2/day IV.

Even more preferably, the lymphodepleting regimen is fludarabine 30 mg/m2/day IV for 4 days, and cyclophosphamide 750 mg/m2/day IV for 3 days.

Even more more preferably, the lymphodepleting regimen is fludarabine 30 mg/m2/day IV for 4 days over 15 to 30 minutes from Day −5 to Day −2, and cyclophosphamide 750 mg/m2/day IV over 1 hour for 3 days from Day −4 to Day −2.

Subsequently, the dose-escalation phase consisted of injecting four doses of UCART ranging from 1.25×105 cells/kg to 5.05×106 cells/kg.

One of most preferred embodiments, comprises administrating fludarabine 30 mg/m2/day IV for 4 days over 15 to 30 minutes from Day −5 to Day −2, and cyclophosphamide 750 mg/m2/day IV over 1 hour for 3 days from Day −4 to Day −2 and subsequently injecting two doses of UCART ranging from 1.25×104 cells/kg to 5.05×107 cells/kg.

One of most preferred embodiments, comprises administrating fludarabine 30 mg/m2/day IV for 4 days over 15 to 30 minutes from Day −5 to Day −2, and cyclophosphamide 750 mg/m2/day IV over 1 hour for 3 days from Day −4 to Day −2 and subsequently injecting two doses of UCART ranging from 1.25×105 cells/kg to 5.05×106 cells/kg.

One of most preferred embodiments, comprises administrating fludarabine 30 mg/m2/day IV for 4 days over 15 to 30 minutes from Day −5 to Day −2, and cyclophosphamide 750 mg/m2/day IV over 1 hour for 3 days from Day −4 to Day −2 and subsequently injecting two doses of UCART123 ranging from 1.25×105 cells/kg to 5.05×106 cells/kg.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Kits of the Present Invention

Also provided a kit of successive doses obtainable according to the method of preparation of said doses such as described above.

In another aspect, the invention provides a kit comprising at least 2, preferably at least 3, more preferably at least 4, and even more preferably at least 5 compositions comprising different allogeneic peripheral blood cells (graft) to be sequentially injected into a patient with reduced risk of anamnestic response and graft-versus-host disease, wherein said allogeneic peripheral blood cells are respectively selected from donors being homozygous with respect to their HLA-A, HLA-B, HLA-DR alleles and said donors share no HLA-A, HLA-B, HLA-DR allele in common.

In still another aspect, the invention provides a kit of allogeneic human peripheral blood cells compositions comprising:
  (a) at least a first peripheral blood cells composition comprising a graft closely matching the immunogenic antigens of a patient (matched composition),
  (b) at least a subsequent peripheral blood cells composition(s) comprising a graft which does not match the immunogenic antigens of said patient (mismatched composition).

In still another aspect, the invention provides a kit of allogeneic human peripheral blood cells compositions comprising:
  (a) at least a first peripheral blood cells composition(s) comprising a graft which does not match the immunogenic antigens of a patient (first mismatched composition);
  (b) a subsequent peripheral blood cells composition(s) comprising a graft which does not match the immunogenic antigens of a patient (second mismatched composition) and which does not match the first mismatched composition.

In a preferred embodiment, said peripheral blood cells are T cell.

In a preferred embodiment, said peripheral blood cells, preferably T cells, are genetically engineered to inactivate at least one immunogenic antigen to increase the HLA mismatch.

In a preferred embodiment, said peripheral blood cells, preferably T cells, are endowed with a chimeric receptor antigen (CAR), such as presented previously.

In a preferred embodiment, said CAR is directed against a solid tumor antigen.

In a preferred embodiment, said T cells are genetically engineered to inactivate the TCR receptor.

In a preferred embodiment, the step of inactivation of is performed by the use of specific rare-cutting endonuclease. In a more preferred embodiment, said endonuclease is a TALE-nuclease or a CRISPR/Cas nuclease.

In another preferred embodiment, the step of inactivation is performed by homologous recombination mediated gene targeting.

In a preferred embodiment, the graft closely related to the receiving recipient is a single homozygote on one of HLA-A, HLA-B and HLA-DR alleles.

In a more preferred embodiment, the graft closely related to the receiving recipient is a double homozygote on 2 of HLA-A, HLA-B and HLA-DR alleles.

In an even more preferred embodiment, the graft closely related to the receiving recipient is a triple homozygote on HLA-A, HLA-B and HLA-DR alleles.

In a preferred embodiment, said successive administrations are performed every 45 days In a preferred embodiment, a step of lymphodepletion is performed before said administration. Said lymphodepletion is performed by the administration of at least one immunosuppressive drug (alone or in combination) such as presented above.

In a preferred embodiment said number of grafts is comprised between 2 and 5.

In a preferred embodiment, said kit is used in immunotherapy.

In a more preferred embodiment, said kit is used in the treatment of tumor.

In an even more preferred embodiment, said kit is used in the treatment of solid tumor and/or refractory or relapsed cancer.

In a further aspect, the present invention relates to a method for treating a patient in need thereof by sequentially injecting said compositions comprising allogeneic peripheral blood cells (graft) included in a kit such as presented above.

In a preferred embodiment, at least 2 and up to five of said compositions are successively injected to the patient.

In a preferred embodiment, the interval between two injections are at least 45 days.

In a preferred embodiment, the patient's serum is assayed for antibodies directed to the immunogenic polypeptides encoded by the HLA-A, HLA-B, HLA-DR alleles belonging to the haplotype of the next of said composition to be injected.

Polynucleotides, Vectors:

The present invention also relates to polynucleotides, vectors encoding the above described CAR according to the invention.

The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

The different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptide into the secretory pathway of a host cell, a secretory signal sequence (also known as a leader sequence, prepro sequence or pre sequence) is provided in polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830).

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Activation and Expansion of Immune Cells

Whether prior to or after genetic modification of the immune cells such as T cells, even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). T cells that have been exposed to varied stimulation times may exhibit different characteristics Said cells can be expanded by co-culturing with tissue or cells. Said cells can also be expanded in vivo, for example in the subject's blood after administrating said cell into the subject.

Other Definitions

Adaptive immune response or adaptive immunity is the response of antigen-specific lymphocytes to antigen, including the development of immunological memory.

Adjuvant: An Adjuvant is any substance that enhances the immune response to an antigen with which it is mixed.

Affinity: The strength of the binding of one molecule to another at a single site, Anamnestic response: Anamnestic response is the rapid reappearance of antibody in the blood following introduction of an antigen to which the subject had previously developed a primary immune response.

Antibody: An antibody is a protein that binds specifically to a particular substance—its antigen. Each antibody molecule has a unique structure that enables it to bind specifically to its corresponding antigen, but all antibodies have the same overall structure and are known collectively as immunoglobulins or Igs. Antibodies are produced by plasma cells in response to infection or immunization, and bind to and neutralize pathogens or prepare them for uptake and destruction by phagocytes.

Antibody, Constant region: The part of the molecule that is relatively constant in amino acid sequence.

Antibody, variable region: The antigen binding sites of a molecule and the most variable part of the molecule.

Antigen: An antigen is any molecule that can bind specifically to an antibody. Their name arises from their ability to generate antibodies. However, some antigens do not, by themselves, elicit antibody production; those antigens that can induce antibody production are called immunogens.

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc), fused to the intracellular signaling domain of the T cell antigen receptor complex zeta chain (scFvFc:ζ) and have the ability, when expressed in T cells, to redirect antigen recognition based on the monoclonal antibody's specificity. CAR may sometimes comprise multiple transmembrane polypeptides (multi-chain CARs) as described in WO2014039523.

One example of CAR used in the present invention is a CAR directing against 5T4 antigen and can comprise as non-limiting example the amino acid sequences: SEQ ID NO: 19 to 42.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Perrin, Buckle et al. 1993; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005), a Cas9 endonuclease from CRISPR system (Gasiunas, Barrangou et al. 2012; Jinek, Chylinski et al. 2012; Cong, Ran et al. 2013; Mali, Yang et al. 2013) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

By a "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In a particular embodiment, the TALE domain can be fused to a meganuclease like for instance I-CreI and I-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al. 2011). Custom-made TAL-nucleases are commercially available under the trade name TALEN™ (Cellectis, 8 rue de la Croix Jarry, 75013 Paris, France).

The rare-cutting endonuclease according to the present invention can also be a Cas9 endonuclease. Recently, a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the proto-spacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010).

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adeno-associated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, fourty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83. Preferred co-stimulatory domains include costimulatory domain for the TCR such 4-1BB and/or costimulatory domains from MHC molecules (which binding activates cells).

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

The following criteria are considered for each patient for clinical trial
  Age
  Gender
  Blood type
  Body size
  The number of times a female donor has been pregnant
  Autoimmune disease history
  Measurement of the Anamnestic Response;

The immune response in Patients that benefited from cell therapy is usually less important that the immune response observed in tissue grafted individuals. In the present study, any arms of the humoral and/or T cell response can be measured, preferably the alloantibody response.

In human the alloantibody response can be measured for example as described in

Hickey M J, Valenzuela N M, Reed E F. Alloantibody Generation and Effector Function Following Sensitization to Human Leukocyte Antigen. Frontiers in Immunology. 2016; 7:30. doi:10.3389/fimmu.2016.00030 and in cited reference 34:

34. Scornik J C, Meier-Kriescje H U. Blood transfusions in organ transplant patients: mechanisms of sensitization and implications for prevention. *Am J Transplant* (2011) 11(9):1785-91. doi:10.1111/j.1600-6143.2011.03705/x In addition, IL-4, IFN-gamma and IL-17 release by immune cells can be measured using any classical method for human cytokine detection.

Antibody production, in particular both IgG1 and IgG2 increased is measured using any known method.

In human the CTL response against known antigen can be detected using circulating cells just after injection of the first sample, (or second, third, fourth and fifth sample), and measuring the expression of TCR using specific tetramers by flow cytometry.

Data Base Used

The data used was that from the National Marrow Donor Program, alias "Be the Match" program freely available from https://bioinformatics.bethematchclinica.org/HLA-Resources/Haplotype-Frequencies/A-B-DRB1-224-Haplotype-Frequencies (Maiers, M., Gragert, L., Klitz, W. High resolution HLA alleles and haplotypes in the US population. Human Immunology (2007) 68, 779-788). These data are from 2007 and comprise the statistics of haplotypes frequencies for MHC class I A and B gene+MHC class II DRB1 genes which seem to be the most important genes for histocompatibility. More precisely, these data indicate the frequency of each haplotype within 4 US sub-populations (American Census Bureau): Caucasian (European American), Hispanic, African, American and Asian/Pacific Islander. Precision on the alleles is on the first two digits for genes A and B, and the first four digits for gene DRB1.

The number of people involved in these frequency measures is quite high, from 200,000 to 300,000 for hispanic, african and asian/pacific populations to more than 1 million for the white caucasian population.

Some descriptive data on frequencies (not part of the present invention) To get an idea on the frequencies, in FIG. 1 is plotted the frequencies of haplotypes sorted by decreasing frequency in the caucasian sub-population (y axis in log scale). The highest frequency is about 6%, and then it decreases steeply for other haplotypes. For the caucasian populations, there are 12723 haplotypes found, corresponding to 21 alleles for A, 40 alleles for B and 166 alleles for DRB1 (thus, 9% of possible haplotypes really observed).

Example of Determination of the set of donor genotypes which maximize the percentage of patients that can be treated-based on a total HLA bank Methodology Used The rationale to find the best set of donor genotypes was based on the following parameters:
  the alleles present in these genotypes be disjoint (no common allele between two donors);
  the donor number is set in advance, fixed here to 5 donors;
  the frequency of the genotypes from these donors is not lower than a given threshold "fmin" (to make feasible find such donors);
  with these donors, the percentage of patients that can be treated with at most "m" mismatches be the highest possible;
  finally, the 5 donors found for a given solution were ordered systematically from the lowest frequency to the highest frequency (this is to preserve the maximum potential of the patient to have a graft without side effects).

The following paragraph is not part of the invention, it explains the rational for the hypothesis of work.

Notes: we could not handle the problem where we start with a library of donors from which 5 donors are extracted for each patient, adapting these 5 donors to each patient, and the problem is to optimize this library of donors. This problem was intractable algorithmically. The library of donors could not be constrained to disjoint donors, because it is very difficult to find for instance 15 disjoint donors with a relatively high frequency (as there are only 21 alleles for gene A). On the other hand, not having this constraint made the search of disjoint donor subsets very heavy and much worse, most of the libraries gave no solution at all of disjoint donor subsets. The result was that optimization of the library did not work at all remaining at 0 unless parameters m and fmin were more permissive.

The invention discloses therefore a method for which
  it was made the hypothesis that the frequency of a genotype is the product of the frequencies of both its haplotypes.
  in fact, it was not interested to work on the precise genotypes themselves, but rather by the allele content. Indeed, For instance, in case of a donor with the following genotype A1-B1-D1/A2-B2-D2 (haplotypes separated by a '/'), and another one which is A1-B2-D1/A2-B1-D2, they are strictly equivalent for the problem presented here. Thus, it was decided to sum their frequencies and treat them as one unique "genotype".

Starting with the N=12723 haplotypes from the Caucasian population, it can be computed the N(N+1)=80,943,726 genotypes. Since the interest was only in alleles content, this set was reduced to unique allele contents and there are 49,803,456 unique "genotypes" (allele combinations).

Then a number of different values was tried for fmin (minimum frequency of a donor genotype) and m (maximum total number of mismatches allowed between a patient and the 5 donors), trying to get the highest value of fmin, and the lowest value of m. With a fmin=1e−4, there are only 524 possible unique "genotypes" and it was not possible to find disjoint set of donors giving a solution even with large m values. With a fmin=5e−5, there are 1415 possible unique "genotypes", and it was possible to find disjoint set of donors. The latter value for fmin was retained in the following.

A number of runs was performed for different values of m to find the lowest value for which a good percentage of coverage of the patients (donors) was obtained. As each run uses an algorithm that uses random variables (genetic algorithm), each run can give solutions of variable quality. A set of 4 runs was done for various well-chosen values of m. For a defined (m) value, results were recorded for the maximum percentage of patient coverage was recorded aiming for the best solution (1=100%). The results are presented in the following Table 2.

TABLE 2

Patient coverage (1 = 100%) of 4 runs performed for (m) number of mismatches ranging from 12 to 15.

| m | results obtained |
|---|---|
| 12 | 0, 0, 0, 0, 0 |
| 13 | 0, 0, 0, 0, 0 |
| 14 | 0, 0, 0, 0.93, 0.03 |
| 15 | 0, 0.94, 0.99, 0, 0.99 |

Example of determination of the set of donor genotypes which maximize the percentage of patients that can be treated—on a set of donors drawn randomly Here, it was hypothesized that the process of determination of the best 5 donors was performed, not in a high number of donors, but in a restricted population of, for instance, 100 donors drawn randomly. As the result depend both on the sample of 100 candidate donors drawn, and also on the optimization run, it was made several runs to have a statistical view of the results. After some trials, the focus was done on two values of m, 20 and 22.

The results are show in the Table 3 below (note: runs for m=20 and m=22 are completely independent) run coverage for m=20 coverage for m=22

TABLE 3

Frequency of coverage (1 = 100%) for each group of 5 donors and for individual run (total of 30 runs) for 2 values of mismatch (m = 20 and m = 22)

| run | coverage for m = 20 | coverage for m = 22 |
|---|---|---|
| 1 | 0.32 | 0.99 |
| 2 | 0.47 | 0.87 |
| 3 | 0.29 | 0.90 |
| 4 | 0 | 0.56 |
| 5 | 0 | 0.59 |
| 6 | 0.52 | 0.54 |
| 7 | 0.54 | 0.96 |
| 8 | 0 | 0.97 |
| 9 | 0.23 | 0.81 |
| 10 | 0.23 | 0.67 |
| 11 | 0.12 | 0.54 |
| 12 | 0.07 | 0.25 |
| 13 | 0.04 | 0.72 |
| 14 | 0.005 | 0.98 |
| 15 | 0.16 | 0.46 |
| 16 | 0.43 | 0.98 |
| 17 | 0.18 | 0.62 |
| 18 | 0 | 0.48 |
| 19 | 0 | 0.90 |
| 20 | 0 | 0.87 |
| 21 | 0.25 | 0.87 |
| 22 | 0.39 | 0.90 |
| 23 | 0 | 0.05 |
| 24 | 0 | 0.46 |
| 25 | 0 | 0.64 |
| 26 | 0 | 0.85 |
| 27 | 0.006 | 0.61 |
| 28 | 0 | 0.69 |
| 29 | 0.12 | 0.75 |
| 30 | 0 | 0.64 |

The distribution of these values are represented below: Thus, with m=20, we often fail to cover all the patients, while with m=22, there is generally (except in one case out of 30 where we failed) a good to very good coverage.

Example of determination of the set of donor haplotypes with the highest frequency The problem here is to determine a set of N haplotypes (N fixed) that are disjoint and which minimum frequency is the highest possible, since it is desirable to maximize the chance to find these donors. It was considered here to select homozygous donors and thus which should enable to find haplotypes that are as frequent as possible.

The best solution is not necessarily the first solution of intersection-free most frequent haplotypes obtained by a greedy algorithm. The algorithm was a branch and bound exploration: sort haplotypes by decreasing frequencies, then iteratively examine all choices by including or not the next haplotype, inclusion being examined only for those haplotypes that are disjoint with the previous ones. A list of haplotypes lists is thus progressively built and the procedure stops when it contains a list of N disjoint) haplotypes which lowest frequency is higher than the next haplotype to examine. The solution is the haplotype list which has the lowest frequency at the highest value.

In the following Table 4 is represented the best set of haplotypes.

TABLE 4 best set of haplotypes

| haplotype (A-B-DRB1) | frequency |
|---|---|
| 1-8-0301 | 0.062183 |
| 29-43-0701 | 0.015507 |
| 2-62-0401 | 0.01241 |
| 3-35-0101 | 0.011204 |
| 24-7-1501 | 0.0071 |

Example of determination of the set of donor haplotypes with highest potential for future grafts on patients
General Methodology Used When repeated injections of allogenic T-cells will be done, all MHC alleles from these T-cells should never be re-used, either in subsequent T-cells injections or for grafts. Thus, it is of interest to minimize the alleles against which the patient will get immunized. We hypothesized that a patient will receive 5 injections of T-cells from different haplotypes, and then should receive a graft (say kidney) that should be compatible with his MHC except for perhaps one allele, and that should not contain any MHC from the T-cells injections. The question was to find out how should be chosen the 5 T-cells universal donors (donors used for all patients) to maximize the frequency of graft donors for an average patient.

In order to render computation reasonable, it was considered that donors and patients have both only one haplotype (homozygous). We then searched for the list of 5 donor haplotypes that maximize the frequency of graft donors, compatible except on perhaps one allele, on an average patient (weighted frequency). An additional constraint was that the frequency of T-cell donor haplotype should be 0.1% or higher (we need to be able to find the donors). For the caucasian population, it was found the optimum haplotype list to be the following, with a score (frequency) of 0.011468.

It happens that computations can be expressed with matrices patients x donors, with each cell representing the compatibility of a given donor haplotype for a given donor haplotype. As there are about 12,000 haplotypes, the matrices have about 100 million cells but that can be still reasonably handled. The principle is then to represent the successive T-cells injections by a boolean matrix (1 if donor is usable, 0 if not) and score the matrix to estimate the frequency of compatible donors which amounts to a vector operation. We systematically investigated the best list of haplotypes that gives the highest possible score at each step.
Results The results are shown in the following Table 5.

TABLE 5 example of sets of 5 donors (homozygous) with a maximized graft potential using HLAA-B and DRB1 haplotype (A-B-DRB1)

| 29-58-0807 |
| 68-75-0413 |
| 32-42-0302 |
| 2-70-1322 |
| 69-35-1305 |

Figure 3:
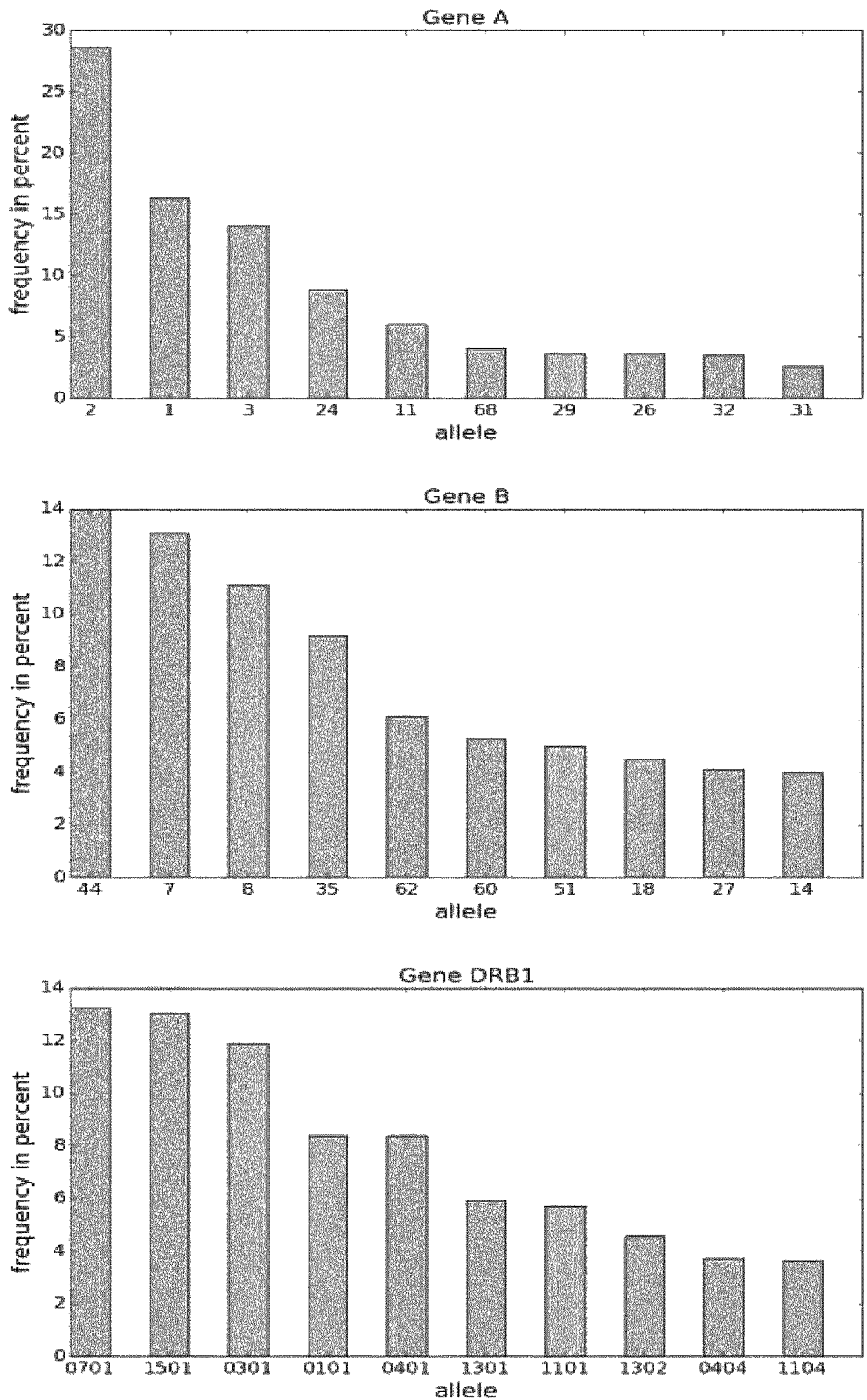
FIG. 3: Frequency (in percent) for HLA A (gene A), HLA B(gene B) and HLA DRB1 (gene DRB1) for specific alleles in the bank
Figure 4:
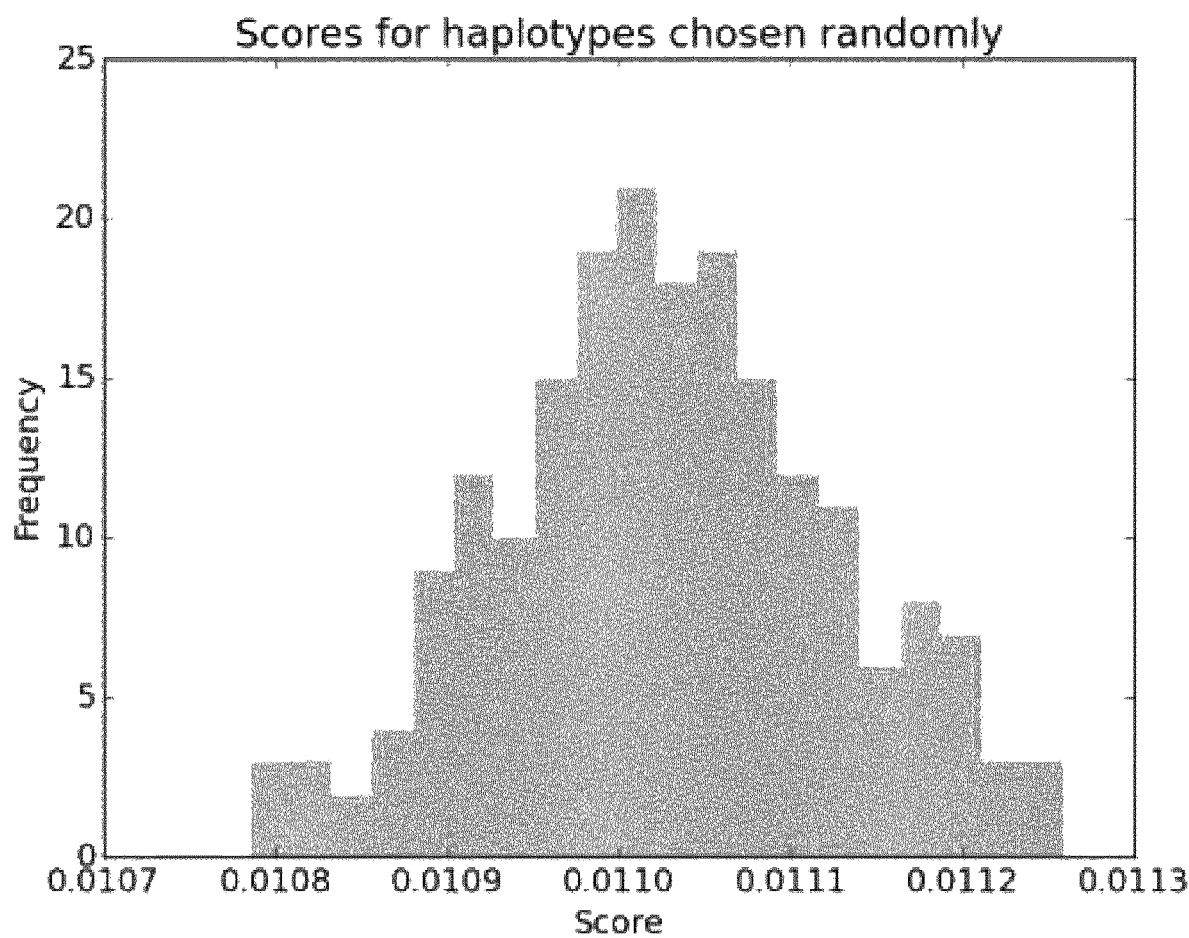
FIG. 4: Scores for haplotype chosen randomly

The next step is to evaluate this solution is compared to randomly determined solutions ("how much we have optimized"). For that, it was taken randomly chosen lists of 5 non-overlapping haplotypes having a frequency of 0.1% or greater, and computed the equivalent frequency for graft donors for an average patient. In FIG. 3 is represented the distribution of scores. It can be seen that the optimized score is higher than all the values we obtained from random donors, but the difference is rather small (and in fact, the difference from donor set to donor set is already small: the distribution has a quite small variance). Note: by taking the most frequent (but rare) haplotypes, a score much lower would be probably obtained. A try was performed by taking the donor set from example 1 and a score of 0.010934 was obtained.

TABLE 6

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d 6.LisOva |
|---|---|---|---|---|---|---|
| Il3 | interleukin 21 | 16.4 | 12.8 | 208.9 | 18.4 | 13.6 |
| Il2 | interleukin 3 | 97.0 | 16.0 | 1554.4 | 17.7 | 18.1 |
| Ccl4 | isopentenyl-diphosphate delta isomerase 2 | 2.1 | 16.8 | 35.6 | 17.6 | 19.7 |
| Il21 | granzyme C | 9.2 | 17.4 | 160.5 | 20.4 | 24.9 |
| Gp49a | chemokine (C-C motif) receptor 8 | 5.9 | 18.5 | 108.4 | 31.5 | 20.9 |
| Cxcl10 | interleukin 2 | 58.4 | 21.1 | 1229.6 | 32.7 | 17.9 |
| Nr4a3 | interleukin 1 receptor, type 1 | 2.6 | 21.2 | 54.6 | 35.5 | 21.7 |
| Lilrb4 | tumor necrosis factor (ligand) superfamily, member 4 | 4.1 | 21.8 | 88.8 | 29.3 | 20.0 |
| Cd200 | neuronal calcium sensor 1 | 4.5 | 24.1 | 109.6 | 46.3 | 23.2 |
| Cdkn1a | CDK5 and Abl enzyme substrate 1 | 3.1 | 26.2 | 80.9 | 49.1 | 32.8 |
| Gzmc | transmembrane and tetratricopeptide repeat containing 2 | 2.0 | 26.8 | 53.9 | 26.2 | 29.4 |
| Nr4a2 | LON peptidase N-terminal domain and ring finger 1 | 3.2 | 28.4 | 90.4 | 50.4 | 28.3 |
| Cish | glycoprotein 49 A | 15.0 | 31.6 | 472.4 | 30.6 | 212.5 |
| Nr4a1 | polo-like kinase 2 | 3.6 | 31.7 | 114.3 | 39.0 | 32.5 |
| Tnf | lipase, endothelial | 2.1 | 32.4 | 66.7 | 35.9 | 33.3 |
| Ccr8 | cyclin-dependent kinase inhibitor 1A (P21) | 9.7 | 34.6 | 335.4 | 54.4 | 71.0 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d 6.LisOva |
|---|---|---|---|---|---|---|
| Lad1 | grainyhead-like 1 (*Drosophila*) | 2.1 | 35.1 | 73.4 | 52.0 | 44.1 |
| Slamf1 | cellular retinoic acid binding protein II | 5.3 | 35.4 | 187.2 | 43.3 | 36.3 |
| Crabp2 | adenylate kinase 4 | 2.2 | 35.9 | 80.4 | 58.5 | 39.8 |
| Furin | microtubule-associated protein 1B | 2.1 | 36.2 | 77.7 | 36.4 | 38.4 |
| Gadd45g | acyl-CoA synthetase long-chain family member 6 | 2.0 | 37.2 | 76.0 | 45.2 | 41.3 |
| Bcl2l1 | zinc finger E-box binding homeobox 2 | 2.1 | 38.6 | 80.7 | 44.9 | 455.4 |
| Ncs1 | CD200 antigen | 9.8 | 41.2 | 404.3 | 70.4 | 36.8 |
| Ciart | carboxypeptidase D | 3.1 | 41.6 | 127.7 | 71.4 | 71.6 |
| Ahr | thioredoxin reductase 3 | 3.6 | 43.4 | 157.8 | 61.7 | 28.8 |
| Spry1 | myosin IE | 2.3 | 43.6 | 100.2 | 61.3 | 77.0 |
| Tnfsf4 | RNA binding protein with multiple splicing 2 | 2.1 | 43.6 | 91.5 | 49.8 | 36.5 |
| Myo10 | mitogen-activated protein kinase kinase 3, opposite strand | 2.9 | 44.8 | 127.9 | 66.4 | 43.1 |
| Dusp5 | PERP, TP53 apoptosis effector | 2.8 | 44.9 | 127.2 | 78.4 | 72.4 |
| Myc | myosin X | 4.1 | 45.5 | 184.9 | 81.6 | 57.5 |
| Psrc1 | immediate early response 3 | 2.7 | 45.6 | 121.6 | 63.9 | 66.2 |
| St6galnac4 | folliculin interacting protein 2 | 2.6 | 47.5 | 124.2 | 87.4 | 96.6 |
| Nfkbid | leukocyte immunoglobulin-like receptor, subfamily B, member 4 | 9.9 | 48.9 | 483.3 | 64.5 | 179.1 |
| Bst2 | circadian associated repressor of transcription | 4.5 | 50.6 | 225.5 | 100.3 | 33.8 |
| Txnrd3 | RAR-related orphan receptor gamma | 2.1 | 51.7 | 106.7 | 47.5 | 52.8 |
| Plk2 | proline/serine-rich coiled-coil 1 | 3.9 | 52.9 | 205.9 | 92.3 | 79.6 |
| Gfi1 | cysteine rich protein 2 | 2.4 | 54.2 | 127.7 | 90.3 | 182.9 |
| Pim1 | cAMP responsive element modulator | 2.0 | 55.7 | 112.6 | 54.4 | 57.3 |
| Pvt1 | chemokine (C-C motif) ligand 4 | 20.2 | 55.8 | 1125.8 | 103.1 | 89.0 |
| Nfkbib | nuclear receptor subfamily 4, group A, member 2 | 7.8 | 58.5 | 457.6 | 78.7 | 72.0 |
| Gnl2 | transglutaminase 2, C polypeptide | 2.3 | 58.7 | 132.1 | 69.8 | 64.7 |
| Cd69 | synapse defective 1, Rho GTPase, homolog 2 (*C. elegans*) | 2.1 | 62.5 | 132.7 | 111.3 | 31.0 |
| Dgat2 | sprouty homolog 1 (*Drosophila*) | 4.2 | 63.8 | 268.5 | 76.8 | 61.4 |
| Atf3 | activating transcription factor 3 | 3.2 | 65.8 | 210.3 | 88.3 | 75.8 |
| Tnfrsf21 | pogo transposable element with KRAB domain | 2.9 | 68.6 | 196.9 | 91.1 | 293.2 |
| Lonrf1 | tumor necrosis factor receptor superfamily, member 21 | 3.2 | 70.6 | 224.5 | 126.5 | 72.9 |
| Cables1 | cytokine inducible Shy-containing protein | 7.5 | 74.3 | 558.7 | 82.5 | 133.9 |
| Cpd | lymphotoxin A | 2.6 | 74.6 | 197.2 | 93.4 | 58.6 |
| Qtrtd1 | FBJ osteosarcoma oncogene | 3.0 | 74.9 | 224.1 | 89.0 | 61.1 |
| Polr3d | signaling lymphocytic activation molecule family member 1 | 5.4 | 75.6 | 412.0 | 108.4 | 190.4 |
| Kcnq5 | syndecan 3 | 2.4 | 76.0 | 180.0 | 77.2 | 85.3 |
| Fos | mitochondrial ribosomal protein L47 | 2.1 | 77.2 | 161.7 | 152.0 | 72.3 |
| Slc19a2 | ladinin | 5.5 | 77.3 | 423.2 | 152.5 | 70.4 |
| Hif1a | E2F transcription factor 5 | 2.5 | 77.7 | 198.0 | 92.0 | 65.2 |
| Il15ra | ISG15 ubiquitin-like modifier | 2.8 | 77.9 | 221.0 | 88.9 | 45.1 |
| Nfkb1 | aryl-hydrocarbon receptor | 4.2 | 78.7 | 333.2 | 145.7 | 91.4 |
| Phlda3 | diacylglycerol O-acyltransferase 2 | 3.2 | 81.0 | 259.2 | 150.0 | 84.4 |
| Mtrr | FBJ osteosarcoma oncogene B | 2.0 | 81.3 | 163.7 | 139.3 | 98.5 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d 6.LisOva |
|---|---|---|---|---|---|---|
| Pogk | pleckstrin homology-like domain, family A, member 3 | 2.9 | 84.8 | 244.5 | 126.9 | 83.8 |
| Map2k3os | potassium voltage-gated channel, subfamily Q, member 5 | 3.0 | 86.3 | 261.0 | 118.1 | 63.4 |
| Egr2 | tumor necrosis factor receptor superfamily, member 10b | 2.5 | 88.6 | 219.0 | 106.1 | 51.0 |
| Isg15 | Mir17 host gene 1 (non-protein coding) | 2.1 | 90.4 | 190.1 | 120.0 | 51.2 |
| Perp | glucose-fructose oxidoreductase domain containing 1 | 2.2 | 92.9 | 208.5 | 168.7 | 237.4 |
| Ipo4 | plexin A1 | 2.1 | 94.8 | 200.7 | 118.0 | 90.3 |
| Mphosph10 | heat shock factor 2 | 2.4 | 96.8 | 233.2 | 191.0 | 104.8 |
| Plk3 | carbohydrate sulfotransferase 11 | 2.4 | 96.8 | 235.1 | 180.8 | 385.7 |
| Ifitm3 | growth arrest and DNA-damage-inducible 45 gamma | 4.8 | 104.6 | 504.8 | 109.3 | 95.0 |
| Polr1b | solute carrier family 5 (sodium-dependent vitamin transporter), member 6 | 2.1 | 107.0 | 227.3 | 192.8 | 75.8 |
| Usp18 | interferon induced transmembrane protein 3 | 2.8 | 109.2 | 302.6 | 43.9 | 106.4 |
| Top1mt | DENN/MADD domain containing 5A | 2.6 | 109.5 | 279.9 | 102.0 | 517.4 |
| Dkc1 | plasminogen activator, urokinase receptor | 2.1 | 112.4 | 234.8 | 55.7 | 57.3 |
| Polr1c | solute carrier family 19 (thiamine transporter), member 2 | 3.0 | 115.4 | 343.1 | 221.7 | 138.4 |
| Cdk6 | ubiquitin domain containing 2 | 2.2 | 117.4 | 255.7 | 198.9 | 122.2 |
| Ier3 | nuclear receptor subfamily 4, group A, member 3 | 11.8 | 118.0 | 1394.1 | 114.2 | 69.6 |
| Lta | zinc finger protein 52 | 2.5 | 118.8 | 295.6 | 160.9 | 167.4 |
| Ptprs | SH3 domain containing ring finger 1 | 2.4 | 119.3 | 280.9 | 116.5 | 156.5 |
| Fnip2 | dihydrouridine synthase 2 | 2.1 | 122.7 | 260.3 | 237.7 | 202.8 |
| Asna1 | cyclin-dependent kinase 5, regulatory subunit 1 (p35) | 2.1 | 122.7 | 259.3 | 168.4 | 124.0 |
| Mybbp1a | processing of precursor 7, ribonuclease P family, (S. cerevisiae) | 2.1 | 125.9 | 264.9 | 235.7 | 150.6 |
| Il1r1 | growth factor independent 1 | 3.5 | 126.8 | 437.7 | 212.0 | 156.6 |
| Dennd5a | interleukin 15 receptor, alpha chain | 2.9 | 130.9 | 380.1 | 144.3 | 167.8 |
| E2f5 | BCL2-like 1 | 4.7 | 133.7 | 627.4 | 257.4 | 231.2 |
| Rcl1 | protein tyrosine phosphatase, receptor type, S | 2.6 | 136.6 | 358.8 | 157.5 | 125.0 |
| Fosl2 | plasmacytoma variant translocation 1 | 3.4 | 136.7 | 465.5 | 179.8 | 140.7 |
| Atad3a | fos-like antigen 2 | 2.5 | 137.0 | 347.5 | 107.2 | 177.8 |
| Bax | BCL2-associated X protein | 2.5 | 138.0 | 347.3 | 260.1 | 150.2 |
| Phf6 | solute carrier family 4, sodium bicarbonate cotransporter, member 7 | 2.3 | 140.3 | 328.2 | 258.7 | 397.5 |
| Zfp52 | tumor necrosis factor receptor superfamily, member 4 | 2.2 | 141.7 | 311.1 | 161.7 | 111.6 |
| Crtam | chemokine (C-X-C motif) ligand 10 | 12.7 | 141.7 | 1798.3 | 242.1 | 59.4 |
| Nop14 | polo-like kinase 3 | 2.8 | 144.8 | 406.3 | 200.1 | 119.9 |
| Rel | CD3E antigen, epsilon polypeptide associated protein | 2.2 | 158.7 | 350.2 | 260.9 | 111.4 |
| Gramd1b | tumor necrosis factor (ligand) superfamily, member 11 | 2.1 | 162.4 | 342.1 | 242.1 | 169.7 |
| Ifi27l2a | polymerase (RNA) III (DNA directed) polypeptide D | 3.0 | 166.3 | 503.7 | 296.1 | 121.6 |
| Tnfrsf10b | early growth response 2 | 2.8 | 173.5 | 494.0 | 136.3 | 68.2 |
| Rpl7l1 | DnaJ (Hsp40) homolog, subfamily C, member 2 | 2.1 | 173.6 | 369.4 | 346.2 | 254.3 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d 6.LisOva |
|---|---|---|---|---|---|---|
| Eif1a | DNA topoisomerase 1, mitochondrial | 2.7 | 182.2 | 498.2 | 338.6 | 114.4 |
| Nfkb2 | tripartite motif-containing 30D | 2.3 | 182.6 | 423.4 | 65.8 | 90.6 |
| Heatr1 | DnaJ (Hsp40) homolog, subfamily C, member 21 | 2.0 | 190.1 | 389.4 | 285.5 | 228.2 |
| Utp20 | SAM domain, SH3 domain and nuclear localization signals, 1 | 2.2 | 191.5 | 422.1 | 222.8 | 304.1 |
| Chst11 | solute carrier family 5 (inositol transporters), member 3 | 2.1 | 191.6 | 400.2 | 210.0 | 123.4 |
| Ddx21 | mitochondrial ribosomal protein L15 | 2.1 | 191.6 | 396.3 | 329.8 | 137.7 |
| Hsf2 | dual specificity phosphatase 5 | 4.0 | 203.5 | 818.1 | 307.5 | 560.7 |
| Bccip | apoptosis enhancing nuclease | 2.3 | 211.1 | 478.5 | 288.2 | 137.9 |
| Tagap | ets variant 6 | 2.3 | 218.3 | 508.1 | 220.5 | 297.3 |
| Sdc3 | DIM1 dimethyladenosine transferase 1-like (*S. cerevisiae*) | 2.2 | 218.4 | 486.0 | 356.0 | 129.7 |
| Sytl3 | 2'-5' oligoadenylate synthetase-like 1 | 2.1 | 229.0 | 473.3 | 130.7 | 124.3 |
| Gtpbp4 | UTP18, small subunit (SSU) processome component, homolog (yeast) | 2.1 | 232.0 | 494.3 | 384.9 | 189.5 |
| Crip2 | BRCA2 and CDKN1A interacting protein | 2.4 | 234.6 | 563.3 | 437.5 | 269.8 |
| Sh3rf1 | synaptotagmin-like 3 | 2.4 | 242.4 | 572.9 | 316.7 | 700.7 |
| Nsfl1c | 5-methyltetrahydrofolate-homocysteine methyltransferase reductase | 2.9 | 245.7 | 706.5 | 334.6 | 150.6 |
| Gtf2f1 | URB2 ribosome biogenesis 2 homolog (*S. cerevisiae*) | 2.0 | 245.7 | 500.2 | 489.8 | 184.6 |
| Slc4a7 | ubiquitin-conjugating enzyme E2C binding protein | 2.1 | 251.2 | 530.5 | 288.2 | 85.2 |
| Etv6 | lysine (K)-specific demethylase 2B | 2.2 | 251.8 | 547.1 | 332.7 | 262.1 |
| Trim30d | queuine tRNA-ribosyltransferase domain containing 1 | 3.0 | 260.3 | 788.7 | 358.0 | 75.5 |
| Ddx27 | ubiquitin specific peptidase 31 | 2.0 | 265.2 | 533.2 | 277.1 | 176.2 |
| Pwp2 | eukaryotic translation initiation factor 2-alpha kinase 2 | 2.0 | 267.7 | 540.5 | 260.8 | 244.8 |
| Chchd2 | ATPase family, AAA domain containing 3A | 2.5 | 268.8 | 679.7 | 523.1 | 147.1 |
| Myo1e | adhesion molecule, interacts with CXADR antigen 1 | 2.3 | 269.5 | 610.9 | 272.9 | 182.8 |
| Eif5b | SUMO/sentrin specific peptidase 3 | 2.0 | 272.5 | 548.7 | 544.5 | 298.4 |
| Stat5a | ESF1, nucleolar pre-rRNA processing protein, homolog (*S. cerevisiae*) | 2.2 | 276.3 | 610.4 | 482.2 | 266.5 |
| Cops6 | deoxynucleotidyltransferase, terminal, interacting protein 2 | 2.1 | 282.9 | 600.4 | 359.9 | 326.1 |
| D19Bwg1357e | TGFB-induced factor homeobox 1 | 2.1 | 300.5 | 618.9 | 217.5 | 210.6 |
| Aatf | eukaryotic translation initiation factor 1A | 2.5 | 300.8 | 738.7 | 597.7 | 262.8 |
| Aen | interferon-stimulated protein | 2.1 | 305.7 | 651.2 | 144.3 | 138.4 |
| Amica1 | pleiomorphic adenoma gene-like 2 | 2.1 | 311.5 | 651.9 | 376.2 | 405.9 |
| Wdr43 | PWP2 periodic tryptophan protein homolog (yeast) | 2.3 | 321.8 | 743.3 | 586.5 | 189.3 |
| Cct4 | furin (paired basic amino acid cleaving enzyme) | 5.2 | 329.7 | 1728.3 | 271.7 | 421.5 |
| Nifk | tumor necrosis factor | 6.6 | 330.7 | 2188.4 | 489.9 | 213.3 |
| Tgm2 | apoptosis antagonizing transcription factor | 2.3 | 331.4 | 754.8 | 523.1 | 221.5 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d 6.LisOva |
|---|---|---|---|---|---|---|
| Ero1l | interferon, alpha-inducible protein 27 like 2A | 2.5 | 334.0 | 828.1 | 296.0 | 221.4 |
| Gfod1 | ST6 (alpha-N-acetyl-neuraminyl-2,3-beta-galactosyl-1,3)-N-acetylgalactosaminide alpha-2,6-sialyltransferase 4 | 3.9 | 338.4 | 1311.3 | 636.0 | 298.2 |
| Ak4 | methyltransferase like 1 | 2.2 | 339.4 | 744.7 | 662.8 | 94.5 |
| Sdad1 | notchless homolog 1 (*Drosophila*) | 2.0 | 339.4 | 690.3 | 610.3 | 158.1 |
| Dimt1 | mitochondrial ribosomal protein L3 | 2.1 | 340.0 | 725.5 | 651.4 | 359.8 |
| Esf1 | UBX domain protein 2A | 2.1 | 343.8 | 732.9 | 532.1 | 428.5 |
| Cd3eap | guanine nucleotide binding protein-like 2 (nucleolar) | 3.2 | 347.6 | 1124.7 | 647.4 | 227.5 |
| Samsn1 | programmed cell death 11 | 2.0 | 353.9 | 711.8 | 435.9 | 287.4 |
| Tnfrsf4 | cyclin-dependent kinase 8 | 2.0 | 364.0 | 731.1 | 702.5 | 346.2 |
| Mettl1 | eukaryotic translation initiation factor 5B | 2.3 | 365.1 | 838.2 | 544.5 | 355.5 |
| Cd274 | RNA terminal phosphate cyclase-like 1 | 2.5 | 373.3 | 948.8 | 746.4 | 155.8 |
| Ubtd2 | NSFL1 (p97) cofactor (p47) | 2.3 | 374.1 | 876.1 | 725.9 | 369.7 |
| Icos | nuclear factor of kappa light polypeptide gene enhancer in B cells inhibitor, delta | 3.9 | 378.5 | 1465.1 | 389.9 | 224.0 |
| Kdm2b | M-phase phosphoprotein 10 (U3 small nucleolar ribonucleoprotein) | 2.8 | 379.8 | 1069.3 | 738.4 | 290.8 |
| Larp4 | GRAM domain containing 1B | 2.5 | 382.7 | 949.6 | 363.4 | 659.2 |
| Eif3d | ERO1-like (*S. cerevisiae*) | 2.2 | 387.7 | 872.3 | 773.0 | 520.9 |
| Tnfaip3 | nuclear receptor subfamily 4, group A, member 1 | 6.8 | 387.8 | 2639.0 | 343.7 | 220.7 |
| Map1b | surfeit gene 2 | 2.1 | 399.8 | 852.2 | 696.3 | 204.0 |
| Cdv3 | N(alpha)-acetyltransferase 25, NatB auxiliary subunit | 2.1 | 405.7 | 847.3 | 669.5 | 194.1 |
| Plac8 | yrdC domain containing (*E. coli*) | 2.0 | 406.7 | 830.8 | 635.3 | 267.0 |
| Mrpl3 | La ribonucleoprotein domain family, member 4 | 2.2 | 408.8 | 887.9 | 586.6 | 358.3 |
| Surf2 | SDA1 domain containing 1 | 2.2 | 419.8 | 939.9 | 631.4 | 284.7 |
| Ubxn2a | importin 4 | 2.8 | 420.3 | 1183.6 | 777.8 | 173.5 |
| Utp18 | inducible T cell co-stimulator | 2.2 | 423.9 | 920.9 | 818.8 | 796.9 |
| Isg20 | solute carrier family 7 (cationic amino acid transporter, y+ system), member 1 | 2.1 | 439.4 | 934.4 | 842.6 | 344.6 |
| Dnajc2 | arsA arsenite transporter, ATP-binding, homolog 1 (bacterial) | 2.6 | 446.6 | 1165.0 | 717.9 | 963.9 |
| Jak2 | polymerase (RNA) 1 polypeptide C | 2.7 | 447.8 | 1208.4 | 854.0 | 295.9 |
| Slc7a1 | spermatogenesis associated 5 | 2.0 | 450.8 | 920.2 | 516.0 | 361.6 |
| Syde2 | ubiquitin specific peptidase 18 | 2.7 | 451.8 | 1240.5 | 296.0 | 250.7 |
| Slc5a6 | placenta-specific 8 | 2.1 | 452.4 | 967.3 | 888.6 | 590.8 |
| Dnttip2 | general transcription factor IIF, polypeptide 1 | 2.3 | 454.8 | 1063.9 | 890.0 | 680.8 |
| Idi2 | nuclear factor of kappa light polypeptide gene enhancer in B cells inhibitor, beta | 3.4 | 456.4 | 1535.5 | 679.1 | 502.7 |
| Dus2 | PHD finger protein 6 | 2.5 | 462.0 | 1159.5 | 775.8 | 510.4 |
| Pitrm1 | RRN3 RNA polymerase 1 transcription factor homolog (yeast) | 2.1 | 462.2 | 948.4 | 913.2 | 388.9 |
| Plxna1 | cytotoxic and regulatory T cell molecule | 2.5 | 473.7 | 1177.8 | 586.8 | 431.8 |
| Cdk5r1 | COP9 (constitutive photomorphogenic) homolog, subunit 6 (*Arabidopsis thaliana*) | 2.3 | 483.6 | 1101.9 | 947.8 | 560.3 |
| Ube2cbp | asparagine-linked glycosylation 3 (alpha-1,3-mannosyltransferase) | 2.1 | 485.9 | 1006.3 | 758.7 | 339.4 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d 6.LisOva |
|---|---|---|---|---|---|---|
| Tnfsf11 | tryptophanyl-tRNA synthetase | 2.0 | 486.1 | 987.1 | 897.1 | 504.7 |
| Pop7 | hypoxia up-regulated 1 | 2.0 | 494.3 | 996.6 | 802.4 | 690.3 |
| Psme3 | family with sequence similarity 60, member A | 2.0 | 500.8 | 1002.1 | 834.7 | 417.6 |
| Mir17hg | bone marrow stromal cell antigen 2 | 3.8 | 502.5 | 1922.9 | 925.5 | 246.0 |
| Tsr1 | nuclear factor of kappa light polypeptide gene enhancer in B cells 2, p49/p100 | 2.4 | 503.2 | 1231.8 | 494.0 | 341.8 |
| Rbpms2 | UTP20, small subunit (SSU) processome component, homolog (yeast) | 2.4 | 510.5 | 1240.2 | 696.4 | 245.8 |
| Mrpl47 | CD274 antigen | 2.2 | 516.6 | 1128.7 | 246.9 | 220.2 |
| Rab8b | proviral integration site 1 | 3.4 | 518.4 | 1766.4 | 676.9 | 970.0 |
| Plagl2 | signal transducer and activator of transcription 5A | 2.3 | 530.0 | 1210.4 | 496.6 | 507.8 |
| Grhl1 | CD69 antigen | 3.2 | 535.7 | 1725.8 | 289.5 | 153.9 |
| Zeb2 | pitrilysin metallopetidase 1 | 2.1 | 544.9 | 1153.8 | 968.4 | 349.3 |
| sept-02 | cyclin-dependent kinase 6 | 2.7 | 550.3 | 1476.5 | 1064.0 | 642.1 |
| Slc5a3 | DEAD (Asp-Glu-Ala-Asp) box polypeptide 27 | 2.3 | 556.2 | 1286.9 | 987.2 | 480.4 |
| Naa25 | polymerase (RNA) I polypeptide B | 2.8 | 556.2 | 1536.0 | 1070.4 | 201.3 |
| Plaur | tumor necrosis factor, alpha-induced protein 3 | 2.2 | 560.6 | 1212.2 | 255.5 | 446.0 |
| Metap1 | nodal modulator 1 | 2.1 | 563.0 | 1161.0 | 988.9 | 439.8 |
| Alg3 | NOP14 nucleolar protein | 2.5 | 570.9 | 1418.9 | 925.3 | 398.0 |
| Mrpl15 | ribosomal protein L7-like 1 | 2.5 | 586.7 | 1448.7 | 1030.2 | 687.2 |
| Oasl1 | methionyl aminopeptidase 1 | 2.1 | 597.5 | 1244.1 | 1139.3 | 433.4 |
| Rorc | hypoxia inducible factor 1, alpha subunit | 3.0 | 624.2 | 1854.6 | 809.4 | 838.4 |
| Nomo1 | Janus kinase 2 | 2.1 | 624.5 | 1328.7 | 390.6 | 917.8 |
| Tgif1 | nuclear factor of kappa light polypeptide gene enhancer in B cells 1, p105 | 2.9 | 661.5 | 1913.3 | 713.9 | 720.5 |
| Lipg | reticuloendotheliosis oncogene | 2.5 | 678.9 | 1686.4 | 409.8 | 580.5 |
| Rrn3 | septin 2 | 2.1 | 687.3 | 1436.0 | 1354.1 | 1181.3 |
| Dnajc21 | nucleolar protein interacting with the FHA domain of MKI67 | 2.3 | 733.4 | 1658.2 | 1280.0 | 407.2 |
| Yrdc | elongation factor Tu GTP binding domain containing 2 | 2.0 | 739.3 | 1483.5 | 1439.0 | 904.3 |
| Acsl6 | myelocytomatosis oncogene | 4.0 | 761.0 | 3022.8 | 1064.0 | 211.5 |
| Spata5 | dyskeratosis congenita 1, dyskerin | 2.7 | 778.2 | 2112.0 | 1549.5 | 484.2 |
| Urb2 | carnitine deficiency-associated gene expressed in ventricle 3 | 2.1 | 801.6 | 1718.2 | 1274.7 | 1010.3 |
| Nle1 | GTP binding protein 4 | 2.4 | 824.2 | 1942.6 | 1578.7 | 567.3 |
| Wars | HEAT repeat containing 1 | 2.4 | 830.3 | 2020.6 | 1235.5 | 495.4 |
| Crem | proteaseome (prosome, macropain) activator subunit 3 (PA28 gamma, Ki) | 2.1 | 838.4 | 1763.5 | 1471.1 | 936.1 |
| Larp1 | La ribonucleoprotein domain family, member 1 | 2.0 | 861.7 | 1742.1 | 1250.9 | 854.3 |
| Eif2ak2 | DNA segment, Chr 19, Brigham & Women's Genetics 1357 expressed | 2.3 | 868.6 | 1978.4 | 1218.0 | 653.4 |
| Hyou1 | eukaryotic translation initiation factor 3, subunit D | 2.2 | 909.1 | 1971.6 | 1641.9 | 920.6 |
| Senp3 | TSR1 20S rRNA accumulation | 2.1 | 913.9 | 1915.9 | 1474.6 | 477.2 |
| Tmtc2 | MYB binding protein (P160) 1a | 2.6 | 1140.0 | 2962.9 | 2200.7 | 459.8 |
| Fosb | T cell activation Rho GTPase activating protein | 2.4 | 1176.7 | 2794.4 | 489.3 | 704.2 |
| Pdcd11 | RAB8B, member RAS oncogene family | 2.1 | 1189.5 | 2492.2 | 1671.3 | 2512.5 |
| Usp31 | DEAD (Asp-Glu-Ala-Asp) box polypeptide 21 | 2.4 | 1210.2 | 2928.0 | 2221.1 | 1098.2 |
| Cdk8 | chaperonin containing Tcp1, subunit 4 (delta) | 2.3 | 1321.4 | 2989.7 | 2462.5 | 1294.8 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d 6.LisOva |
| --- | --- | --- | --- | --- | --- | --- |
| Eftud2 | coiled-coil-helix-coiled-coil-helix domain containing 2 | 2.3 | 1374.2 | 3171.2 | 2636.9 | 1008.9 |
| Fam60a | WD repeat domain 43 | 2.3 | 1727.6 | 3912.6 | 2927.5 | 1014.9 |

Methodology

Definitions

All definitions and standards are those known by the skilled person of the art and as published for example in http://hla.alleles.org/definitions/index.html, with special reference and emphasis to:

Nunes E, Heslop H, Fernandez-Vina M, Taves C, Wagenknecht D R, Eisenbrey A B, Fischer G, Poulton K, Wacker K, Hurley C K, Noreen H, Sacchi N. *Human Immunology.* 2011 72:1214-6 *Blood.* 2011 118:e180-3 and Hollenbach J A, Mack S J, Gourraud P A, Single R M, Maiers M, Middleton D, Thomson G, Marsh S G E, Varney M D. for the Immunogenomics Data Analysis Working Group Tissue Antigens. 201178:333-44.

The present invention can include any new allele, the method being the same in principle. To aid in migration of data to a new nomenclature here is provided conversion tables, and conversion tool as described by the Immunogenetics Data Analysis Working Group. This allows to enter an HLA allele name and provides with both the current and new versions of the allele name using conversion tools for handling large data sets.

Thus, Allele Name Translation applications are available for download or use over the internet.

Two examples of conversion tools are described here: "The Allele Name Translation Tool (ANTT) which is a downloadable application that translates the allele names in entire datasets, and can be customized to translate allele names between any pair of naming conventions (including user-defined naming conventions) and the "Update NomenCLature (UNCL)" which is a web-based implementation of an R-script that translates the allele names in entire datasets. UNCL can be used by anyone with an internet connection and a modern web-browser.

These tools are both described in the following paper: Mack S J, Hollenbach J A. Allele Name Translation Tool and Update NomenCLature: Software tools for the automated translation of HLA allele names between successive nomenclatures. Tissue Antigens 2010: 75:457-461

Data Used.

The objective of the present study is to provide a set of at least 5 known donors in any "population" which immune cells will be engineered to treat a single individual by immunotherapy with a reduced risk of anamnestic response.

Here is provided the number of donors necessary to constitute the object of the present invention and a method for producing the same, using data obtained from a large sample of the population.

The data available from any program of cell donor can be used for example those of the National Marrow Donor Program (NMDP) also called "Be the Match" program can be used, from the Japan cord blood bank network (JCBBN), Chinese Stem Cell Donor Database Management Center (with 1,149,189 data in the China Marrow Donor Program (CMDP) in Aug. 31, 2010), ABMDR in Australia, in searchable databases, such as Bone Marrow Donors Worldwide (BMDW), the Netcord Foundation, the National Marrow Donor Program (NMDP) and other national registries, Eurocord, the Center for International Blood and Marrow Transplant Research (CIBMTR), For statistics on haplotypes frequencies to be significant, the number of data must be at least 230.

Data set comprises the haplotypes for the A-B-DRB1 genes, and datasets which comprise 6 loci haplotypes with A-C-B-DRB3/4/5-DRB1-DQB1 genes (see Maiers et al, High-resolution HLA alleles and haplotypes in the United States population, Hum. Immunol., 2007, 68, 779-788 and also the newer publication Gragert et al, Six-locus high resolution HLA haplotype frequencies derived from mixed-resolution DNA typing for the entire US donor registry., Hum. Immunol., 2013, 74, 1313-1320.)

the first dataset A-B-DRB1 genes corresponds to 412,861 African Americans, 359,423 Asians/Pacific Islanders and 2,361,208 Whites (see https://bioinformatics.bethematchclinical.org/hla-resources/haplotype-frequencies/a-b-drb1-224-haplotype-frequencies/)

the other newer datasets which comprise the 6 loci correspond to 505,250 African Americans, 568,597 Asians/Pacific Islanders, 3,912,440 Caucasians and 712,764 Hispanics (see Gragert et al 2013 cited above)

These data sets consist mainly of the frequency of the different haplotypes measured in the different populations (that is, the joint frequency of the different alleles of the genes considered).

Studies using the first data set with A-B-DRB1

First, this dataset was determined using 4 "populations" or groups delineated on the basis of each individual perception of its belonging to an ethnic group as follows:

African Americans: AFA
Asians and Pacific Islanders: API
European Americans (Caucasian): CAU
Hispanics: HIS These categories are defined by the people themselves that are going to be tested for their HLA.

Allele Frequency

The dataset consists in the frequency of all combinations of alleles of the 3 genes found in the population sample, resulting in a haplotype frequency. From this, we computed the frequency of each allele in each population for the 3 genes. In each population and for each gene, the alleles are sorted by decreasing frequency and are described in Table 1. There were 21 alleles for gene A, 41 for gene B and 236 for gene DRB1.

Minimum Number of Donors

Results.

To solve the following question what is the minimum number n of donors to obtain a set of 5 anamnestic compatible donors that have to have a 95% chance (or 99% chance) to have no common allele of the genes considered (here, HLA-A, B and DRB1 (provided that the patient has never been treated/grafted previously with a donor that would have an allele present in these 5 new donors).

To solve this issue, the strategy used was to fix n to a given value of 5, to choose randomly 5 donors from a given population and determine if we could find a solution of 5 anamnestic compatible donors. This procedure was repeated several times with different random draws to estimate the frequency with which 5 anamnestic compatible donors were found. Then, we repeated the whole procedure on the different populations and with different values of n. More details can be found in the "Methods" paragraph.

The results are for the 4 populations. It shows that the sample size required in the AFA or HIS population to have a 95% confidence (or 99% confidence) of finding 5 anamnestic compatible donors is lower than in the API or CAU populations:

From the values used to generate the graph, we determined the minimum sample size required to have a 95% or 99% chance to be able to find 5 anamnestic compatible donors. The results are in this table.

We also assessed for the selected donors (from donor pool size of 50 and 1000 iterations) the frequencies of the haplotypes of the selected donors. The distribution of these frequencies is shown on the FIG. 2.
Methods.

For each population, and for different donor sample sizes n, n being between 20 and 75 with increment steps of 5, we investigated what is the probability to find 5 anamnestic compatible donors in a draw of n donors (anamnestic compatible here means no common alleles between any pairs of donors for the 3 genes). For that, we made a draw of n donors which have two independent haplotypes following the distribution probability of their population. Then, these n donors were tested to find if they contain a subset of 5 anamnestic compatible donors. To assess this, we did the following:
1. we computed for each pair of donors their compatibility (resulting in 1 if they have no common allele, 0 otherwise). This gave us a graph of compatibility between donors: each vertex represent a donor, and and edge between two donors is present if they are anamnestic compatible.
2. we then searched for cliques within this graph that contain at least 5 nodes, using a standard graph search library. If one such clique is found, this donor set is considered successful, that is, we can extract from it at least one set of 5 anamnestic compatible donors. Otherwise, it is a failure.

We iterated this process on 10,000 independent draws and counted the percentage of successes to estimate the probability with which we can isolate a group of 5 anamnestic compatible donors. Then, we repeated the computation three times to have 3 different percentages from which we can compute a mean and a standard deviation for our estimate. Finally, the whole procedure is repeated on the different populations and with different values of n.

Studies using the data set with A-C-B
This dataset contained 22 subpopulations, but these could be grouped into 4 populations as above:
African Americans: AFA
Asians and Pacific Islanders: API
European Americans (Caucasian): CAU
Hispanics: HIS
Allele Frequency Again, from the available haplotype table, we computed the frequency of each allele in each population for the 3 genes. There are 21 alleles for A gene, 14 alleles for gene C and 36 alleles for gene B. There are less alleles for gene B than in previous dataset, probably because new alleles were identified in the first dataset (all the alleles in the first dataset have high numbers above 60). The frequencies are given in the attached table.
Minimum Number of Donors
Results.

We solved the same problem as in the previous study with A-B-DRB1. we determined the minimum sample size required to have a 95% or 99% chance to be able to find 5 anamnestic compatible donors (anamnestic compatible in the sense above).
Studies Using the Data Set with A-C-B-DRB1

We then attempted to use the same strategy with all four genes A, C, B and DRB1, on the same 4 populations. While the number of starting haplotypes was not particularly high (20036 haplotypes), the number of donors required to find 5 donors without any common alleles increases significantly. As the number of combinations increases exponentially with the number of donors, so does the computation time. The current graph is the following (computation not finished to reach 99% chance): see FIG. 1.

From the values used to generate the graph, we determined the minimum sample size required to have a 95% or 99% chance to be able to find 5 anamnestic compatible donors (anamnestic compatible in the sense above). the minimum sample size is 230.
Cells Engineering
CAR Cells of each pharmaceutical unit dose comprise at least one chimeric receptor (CAR). The CAR of the present invention has an adapted architecture for targeting an antigen expressed at the cell surface of a pathological cell. Example of CARs according to the present invention are described in WO2015140268, WO2014039523, WO2016166268A1, WO2015136001, WO2014184741, WO2013176916, WO2013176915 WO2016201047, WO2015/092024 all incorporated herein by reference.
Gene Editing Cells of each pharmaceutical unit dose comprise at least one edited gene as described for example in WO2016064929.

The extracellular-ligand binding domain was made specific for a target antigen (e.g., cell surface antigen) selected from the group consisting of: CD123; CD19; CD22; CD30; CD79b, CD70; CD171; CS-1 (also referred to as CD2 subset 1, CRACC, SLAMF7, CD319, and 19A24); DLL3; TSPAN10; PRAME; C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(I-4)bDGlcp(I-I)Cer); TNF receptor family member B cell maturation (BCMA); Tn antigen ((Tn Ag) or (GalNAca-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-IIRa); prostate stem cell antigen (PSCA); Protease Serine 21 (Testisin or PRSS21); vascular endothelial growth factor receptor 2 (VEGFR2); Lewis (Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1 (MUC1); Mucin 16 (MUC16);

Mucin 17 (MUC17); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAFX); Proteasome(Prosome, Macropain) Subunit, Beta Type, 9 (LMP2); glycoprotein 100 (gplOO); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(I-4)bDGlcp(I-l)Cer); transglutaminase 5 (TGS5); high molecular weight-melanoma-associated antigen (HMWMAA); o-acetyl-GD2 (OAcGD2); Folate receptor beta; tumor endothelial marker 1 (TEM1/CD248); tumor endothelial marker 7-related (TEM7R); claudin 6 (CLDN6); claudin 18 (CLDN18), including splice variant 2 (claudin18.2); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCRI); adrenoceptor beta 3(ADRB3); pannexin 3 (PANX3); G protein-coupled receptor 20 (GPR20); lymphocyte antigen 6complex, locus K 9 (LY6K); Lymphocyte antigen 6 complex locus protein G6d (LY6G6D); Olfactory receptor 51 E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-la); Melanoma associated antigen 1 (MAGE-A1); ETS translocation-variant gene 6, located on chromosome 12p (ETV6-AML); sperm protein 17 (SPA17); X Antigen Family, Member 1A (XAGE1); angiopoietin binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); NAcetyl glucosaminyl-transferase V (NA17); paired box protein Pax-3 (PAX3); Androgen receptor; Cyclin BI; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70 (HSP70); heat shock protein 70-2 mutated (mut hsp70-2); CD79a; CD79b; CD72; Leukocyte-associated immunoglobulin-like receptor 1 (LAIR1); Fc35 fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In other experiments the extracellular-ligand binding domain is specific for at least one of the target antigen selected from the group consisting of: CD123, ROR1, BCMA, PSMA, CD33, CD38, CD22, CD79a or b, CS1, CLL-1, HSP70, EGFRVIII, FLT3, WT1, CD30, CD70, MUC1, MUC16, MUC17, PRAME, TSPAN10, Claudin18.2, DLL3, LY6G6D and o-acetyl-GD2 (OAcGD2).

According to certain embodiments, the extracellular-ligand binding domain is specific for a target antigen selected from the group consisting of: CD123, CD38, CD22, CS1, CLL-1, HSP70, CD30, MUC1 and o-acetyl-GD2 (OAcGD2).

According to certain embodiments, the extracellular ligand-binding domain is specific for CD123. Such extracellular ligand-binding domain may be a scFV derived from a monoclonal CD123 antibody, such as a scFV derived from a human or humanized monoclonal CD123 antibody.

Immune cells of the invention are further engineered to be resistant to drugs used either to deplete T cells in the patient or as part of the treatment that is in combination with Immune cells of the invention. Examples of gene editing to obtain drug resistant cells are described for example in PA 2016 70232, PA 2016 70233, PA 2017 70038 incorporated by reference herein in their entirety.

In a particular embodiment, said drug resistance can be conferred to the T-cell by the expression of a gene or a mutated gene, deletion or mutation of a gene or insertion of a gene or a mutated gene (as in PA 2016 70840 incorporated entirely by reference) of at least one gene (drug resistance gene). Said drug resistance gene refers to a nucleic acid sequence that encodes a protein or a level of protein conferring "resistance" to an agent, such as a chemotherapeutic agent (e.g. methotrexate). In other words, the expression of the drug resistance gene in a cell permits survival and proliferation of the cells in the presence of the agent to a greater extent than the proliferation of a corresponding cell without the drug resistance gene. A drug resistance gene of the invention can encode resistance to anti-metabolite, methotrexate, vinblastine, cisplatin, alkylating agents, Purine nucleotide analogs (PNA), proteasome inhibitors anthracyclines, cytotoxic antibiotics, anti-immunophilins, their analogs or derivatives, and the like.

Several drug resistance genes have been identified that can potentially be used to confer drug resistance to targeted cells (Takebe, Zhao et al. 2001; Sugimoto, Tsukahara et al. 2003; Zielske, Reese et al. 2003; Nivens, Felder et al. 2004; Bardenheuer, Lehmberg et al. 2005; Kushman, Kabler et al. 2007).

One example of drug resistance gene can also be a mutant or modified form of Dihydrofolate reductase (DHFR). DHFR is an enzyme involved in regulating the amount of tetrahydrofolate in the cell and is essential to DNA synthesis. Folate analogs such as methotrexate (MTX) inhibit DHFR and are thus used as anti-neoplastic agents in clinic. Different mutant forms of DHFR which have increased resistance to inhibition by anti-folates used in therapy have been described. In a particular embodiment, the drug resistance gene according to the present invention can be a nucleic acid sequence encoding a mutant form of human wild type DHFR (GenBank: AAH71996.1) which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 ((Schweitzer, Dicker et al. 1990); International application WO94/24277; U.S. Pat. No. 6,642,043). In a particular embodiment, said DHFR mutant form comprises two mutated amino acids at position L22 and F31. Correspondence of amino acid positions described herein is frequently expressed in terms of the positions of the amino acids of the form of wild-type DHFR polypeptide. In a particular embodiment, the serine residue at position 15 is preferably replaced with a tryptophan residue. In another particular embodiment, the leucine residue at position 22 is preferably replaced with an amino acid which will disrupt binding of the mutant DHFR to antifolates, preferably with uncharged amino acid residues such as phenylalanine or tyrosine. In another particular embodiment, the phenylalanine residue at positions 31 or 34 is preferably replaced with a small hydrophilic amino acid such as alanine, serine or glycine.

As used herein, "antifolate agent" or "folate analogs" refers to a molecule directed to interfere with the folate metabolic pathway at some level. Examples of antifolate agents include, e.g., methotrexate (MTX); aminopterin; trimetrexate (Neutrexin™); edatrexate; N10-propargyl-5,8-dideazafolic acid (CB3717); ZD1694 (Tumodex), 5,8-dideazaisofolic acid (IAHQ); 5,10-dideazatetrahydrofolic acid (DDATHF); 5-deazafolic acid; PT523 (N alpha-(4-amino-4-deoxypteroyl)-N delta-hemiphthaloyl-L-ornithine); 10-ethyl-10-deazaaminopterin (DDATHF, lomatrexol); piritrexim; 10-EDAM; ZD1694; GW1843; Pemetrexate and PDX (10-propargyl-10-deazaaminopterin).

Another example of drug resistance gene can also be a mutant or modified form of ionisine-5'-monophosphate dehydrogenase II (IMPDH2), a rate-limiting enzyme in the de novo synthesis of guanosine nucleotides. The mutant or modified form of IMPDH2 is an IMPDH inhibitor resistance gene. IMPDH inhibitors can be mycophenolic acid (MPA) or its prodrug mycophenolate mofetil (MMF). The mutant IMPDH2 can comprises at least one, preferably two mutations in the MAP binding site of the wild type human IMPDH2 (NP_000875.2) that lead to a significantly increased resistance to IMPDH inhibitor. The mutations are preferably at positions T333 and/or 5351 (Yam, Jensen et al. 2006; Sangiolo, Lesnikova et al. 2007; Jonnalagadda, Brown et al. 2013). In a particular embodiment, the threonine residue at position 333 is replaced with an isoleucine residue and the serine residue at position 351 is replaced with a tyrosine residue. Correspondence of amino acid positions described herein is frequently expressed in terms of the positions of the amino acids of the form of wild-type human IMPDH2.

Another drug resistance gene is the mutant form of calcineurin. Calcineurin (PP2B) is an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms). After engagement of the T-cell receptor, calcineurin dephosphorylates the transcription factor NFAT, allowing it to translocate to the nucleus and active key target gene such as IL2. FK506 in complex with FKBP12, or cyclosporine A (CsA) in complex with CyPA block NFAT access to calcineurin's active site, preventing its dephosphorylation and thereby inhibiting T-cell activation (Brewin, Mancao et al. 2009). The drug resistance gene of the present invention can be a nucleic acid sequence encoding a mutant form of calcineurin resistant to calcineurin inhibitor such as FK506 and/or CsA. In a particular embodiment, said mutant form can comprise at least one mutated amino acid of the wild type calcineurin heterodimer a at positions: V314, Y341, M347, T351, W352, L354, K360, preferably double mutations at positions T351 and L354 or V314 and Y341. In a particular embodiment, the valine residue at position 341 can be replaced with a lysine or an arginine residue, the tyrosine residue at position 341 can be replaced with a phenylalanine residue; the methionine at position 347 can be replaced with the glutamic acid, arginine or tryptophane residue; the threonine at position 351 can be replaced with the glutamic acid residue; the tryptophane residue at position 352 can be replaced with a cysteine, glutamic acid or alanine residue, the serine at position 353 can be replaced with the histidine or asparagine residue, the leucine at position 354 can be replaced with an alanine residue; the lysine at position 360 can be replaced with an alanine or phenylalanine residue of GenBank: ACX34092.1. Correspondence of amino acid positions described herein is frequently expressed in terms of the positions of the amino acids of the form of wild-type human calcineurin heterodimer a polypeptide set forth in GenBank: ACX34092.1.

In another particular embodiment, said mutant form can comprise at least one mutated amino acid of the wild type calcineurin heterodimer b at positions: V120, N123, L124 or K125, preferably double mutations at positions L124 and K125. In a particular embodiment, the valine at position 120 can be replaced with a serine, an aspartic acid, phenylalanine or leucine residue; the asparagine at position 123 can be replaced with a tryptophan, lysine, phenylalanine, arginine, histidine or serine; the leucine at position 124 can be replaced with a threonine residue; the lysine at position 125 can be replaced with an alanine, a glutamic acid, tryptophan, or two residues such as leucine-arginine or isoleucine-glutamic acid can be added after the lysine at position 125 in the amino acid sequence GenBank: ACX34095.1. Correspondence of amino acid positions described herein is frequently expressed in terms of the positions of the amino acids of the form of wild-type human calcineurin heterodimer b polypeptide set forth in GenBank: ACX34095.1.

Another drug resistance gene is 0(6)-methylguanine methyltransferase (MGMT) encoding human alkyl guanine transferase (hAGT). AGT is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze, Kurpad et al. 1999). In a particular embodiment, AGT mutant form can comprise a mutated amino acid of the wild type AGT position P140, in the amino acid sequence UniProtKB: P16455. In a preferred embodiment, said proline at position 140 is replaced with a lysine residue.

Another drug resistance gene can be multidrug resistance protein 1 (MDR1) gene. This gene encodes a membrane glycoprotein, known as P-glycoprotein (P-GP) involved in the transport of metabolic byproducts across the cell membrane. The P-Gp protein displays broad specificity towards several structurally unrelated chemotherapy agents. Thus, drug resistance can be conferred to cells by the expression of nucleic acid sequence that encodes MDR-1 (NP_000918).

Drug resistance gene can also be cytotoxic antibiotics, such as ble gene or mcrA gene. Ectopic expression of ble gene or mcrA in an immune cell gives a selective advantage when exposed to the chemotherapeutic agent, respectively the bleomycine or the mitomycin C. The most practical approach to gene therapy is the addition of a gene to engineer T-cell by using efficient gene delivery with vectors, preferably viral vector. Thus, in a particular embodiment, said drug resistance gene can be expressed in the cell by introducing a transgene preferably encoded by at least one vector into a cell.

The random insertion of genes into the genome may lead to the inappropriate expression of the inserted gene or the gene near the insertion site. Specific gene therapy using homologous recombination of exogenous nucleic acid comprising endogenous sequences to target genes to specific sites within the genome can allow engineering secure T-cells. As described above, the genetic modification step of the method can comprise a step of introduction into cells of an exogeneous nucleic acid comprising at least a sequence encoding the drug resistance gene and a portion of an endogenous gene such that homologous recombination occurs between the endogenous gene and the exogeneous nucleic acid. In a particular embodiment, said endogenous gene can be the wild type "drug resistance" gene, such that after homologous recombination, the wild type gene is replaced by the mutant form of the gene which confers resistance to the drug.

Endonucleolytic breaks are known to stimulate the rate of homologous recombination. Thus, in a particular embodiment, the method of the invention further comprises the step of expressing in the cell a rare-cutting endonuclease which is able to cleave a target sequence within an endogenous gene. Said endogenous gene can encode for examples DHFR, IMPDH2, calcineurin or AGT. Said rare-cutting endonuclease can be a TALE-nuclease, a Zinc finger nuclease, a CRISPR/Cas9 endonuclease, a MBBBD-nuclease or a meganuclease.

Inactivation of Drug Sensitizing Genes

In another particular embodiment, said drug resistance can be conferred to the T-cell by the inactivation of a drug sensitizing gene. For the first time, the inventor sought to inactivate potential drug sensitizing gene to engineer T-cell for immunotherapy.

By inactivating a gene it is intended that the gene of interest is not expressed in a functional protein form. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. In a particular embodiment, the step of inactivating at least one drug sensitizing gene comprises introducing into the cell a rare-cutting endonuclease able to disrupt at least one drug sensitizing gene. In a more particular embodiment, said cells are transformed with nucleic acid encoding a rare-cutting endonuclease capable of disrupting a drug sensitizing gene, and said rare-cutting endonuclease is expressed into said cells. Said rare-cutting endonuclease can be a meganuclease, a Zinc finger nuclease, CRISPR/Cas9 nuclease, A MBBBD-nuclease or a TALE-nuclease. In a preferred embodiment, said rare-cutting endonuclease is a TALE-nuclease.

In a preferred embodiment, drug sensitizing gene which can be inactivated to confer drug resistance to the T-cell is the human deoxycytidine kinase (dCK) gene. This enzyme is required for the phosphorylation of the deoxyribonucleosides deoxycytidine (dC), deoxyguanosine (dG) and deoxyadenosine (dA). Purine nucleotide analogs (PNAs) are metabolized by dCK into mono-, di- and tri-phosphate PNA. Their triphosphate forms and particularly clofarabine triphosphate compete with ATP for DNA synthesis, acts as proapoptotic agent and are potent inhibitors of ribonucleotide reductase (RNR) which is involved in trinucleotide production.

Preferably, the inactivation of dCK in T cells is mediated by TALE nuclease. To achieve this goal, several pairs of dCK TALE-nuclease have been designed, assembled at the polynucleotide level and validated by sequencing. Thus, dCK inactivation in T cells confers resistance to purine nucleoside analogs (PNAs) such as clofarabine and fludarabine.

In another preferred embodiment, the dCK inactivation in T cells is combined with an inactivation of TRAC genes rendering these double knock out (KO) T cells both resistant to drug such as clofarabine and allogeneic. This double features is particularly useful for a therapeutic goal, allowing "off-the-shelf" allogeneic cells for immunotherapy in conjunction with chemotherapy to treat patients with cancer. This double KO inactivation dCK/TRAC can be performed simultaneously or sequentially.

Figure 2:
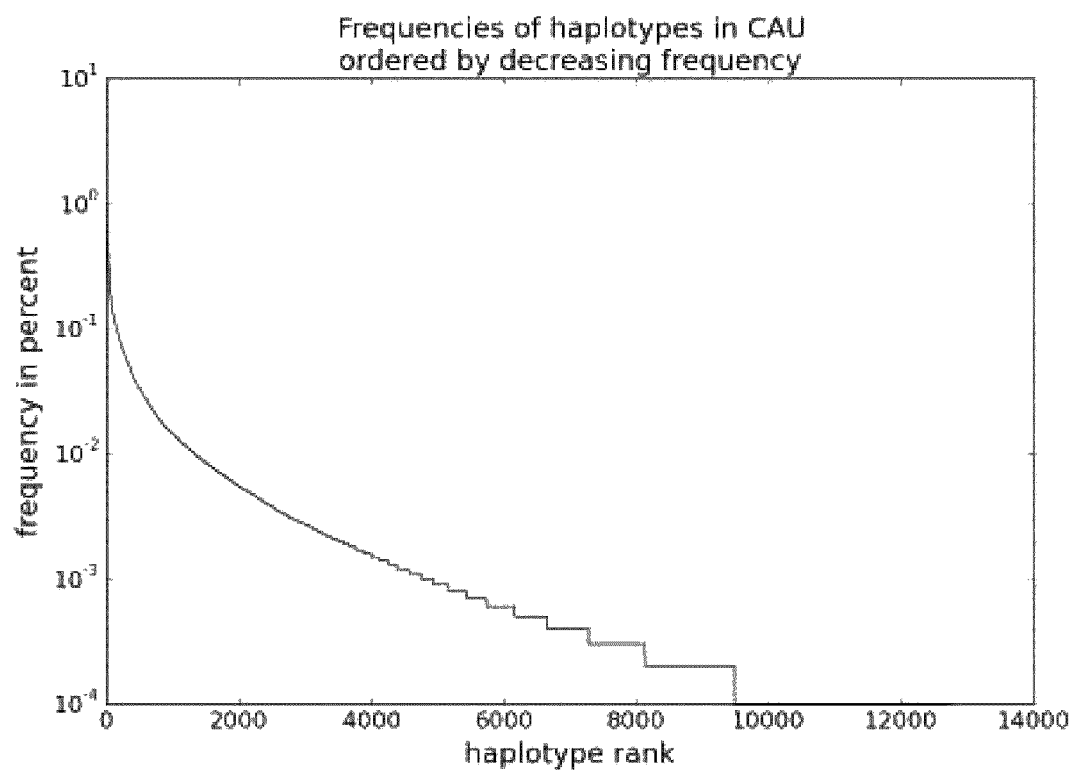
FIG. 2: Frequency of haplotypes in CAU ordered by decreasing frequency

Another example of enzyme which can be inactivated is human hypoxanthine-guanine phosphoribosyl transferase (HPRT) gene (Genbank: M26434.1). In particular HPRT can be inactivated in engineered T-cells to confer resistance to a cytostatic metabolite, the 6-thioguanine (6TG) which is converted by HPRT to cytotoxic thioguanine nucleotide and which is currently used to treat patients with cancer, in particular leukemias (Hacke, Treger et al. 2013). Guanines analogs are metabolized by HPRT transferase that catalyzes addition of phosphoribosyl moiety and enables the formation of TGMP (FIG. 2). Guanine analogues including 6 mercapthopurine (6MP) and 6 thioguanine (6TG) are usually used as lymphodepleting drugs to treat ALL. They are metabolized by HPRT (hypoxanthine phosphoribosyl transferase that catalyzes addition of phosphoribosyl moiety and enables formation TGMP. Their subsequent phosphorylations lead to the formation of their triphosphorylated forms that are eventually integrated into DNA. Once incorporated into DNA, thio GTP impairs fidelity of DNA replication via its thiolate group and generate random point mutations that are highly deleterious for cell integrity.

In another embodiment, the inactivation of the CD3 normally expressed at the surface of the T-cell can confer resistance to anti-CD3 antibodies such as teplizumab. CD19+/Luc+ Drug Resistant Daudi Cells for Testing the Cytotoxicity of by Drug Resistant Allogenic CAR T Cells.

The present invention encompasses also a method for manufacturing target cells which express both a surface receptor specific to the CAR T cells and a resistance gene. These target cells are particularly useful for testing the cytotoxicity of CAR T cells. These cells are readily resistant to clinically relevant dose of clofarabine and harbor luciferase activity. This combination of features enables tracking them in vivo in a mice model. More particularly, they can be used to assess the cytotoxicity properties drug resistant T cells in mice in the presence of clofarabine or other PNAs. Clofarabine resistant Daudi cells mimic the physiological state of acute lymphoblastic leukemia (ALL) patients relapsing form induction therapy, that harbor drug resistant B cell malignancies. Thus, these cells are of great interest to evaluate the reliability and cytotoxicity of drug resistant CAR T cells. Preferably, these target cells are CD19+ Luciferase+ Daudi cells. Isolated cell In particular, the present invention relates to isolated T-cells resistant to a drug which comprises at least one disrupted gene encoding a T-cell receptor component. In a particular embodiment, said T-cell expresses at least one drug resistance gene, preferably ble gene or mcrA gene or gene encoding a mutant DHFR, a mutant IMPDH2, a mutant AGT or a mutant calcineurin. In another particular embodiment, said T-cell comprises at least one disrupted drug sensitizing gene such as dCK or HPRT gene. In a more particular embodiment, said isolated T-cell comprises a disrupted HPRT gene and express a DHFR mutant; said isolated T-cell comprises a disrupted HPRT gene and express a IMPDH2 mutant; said isolated T-cell comprises a disrupted HPRT gene and express a calcineurin mutant; said isolated T-cell comprises a disrupted HPRT gene and express a AGT mutant.

Allogeneic T-Cell Resistant to a Drug

In particular, the present invention relates to an allogeneic T-cell resistant to a drug, specifically suitable for immunotherapy. The resistance of a drug can be acquired by inactivation of drug sensitizing genes or by expression of drug resistance genes such as previously described. Some examples of drugs which suit to the invention are the purine nucleoside analogues (PNAs) such as clofarabine or fludarabine, or other drugs such as 6-Mercaptopurine (6MP) and 6 thio-guanine (6TG).

A cell or cells according to the present invention refers to cell of hematopoietic origin functionally involved in the initiation and/or execution of innate and/or adaptative immune response. Cells according to the present invention are preferably a T-cell or a population of T cells obtained from a donor.

Said T cell according to the present invention can be derived from a stem cell. The stem cells can be adult stem cells, embryonic stem cells, more particularly non-human stem cells, cord blood stem cells, progenitor cells, bone marrow stem cells, totipotent stem cells or hematopoietic stem cells. Representative human stem cells are CD34+ cells. Said cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T-cell lines available and known to those skilled in the art, may be used. In another embodiment, said cell is preferably derived from a healthy donor. In another embodiment, said cell is part of a mixed population of cells which present different phenotypic characteristics.

Multiple Drug Resistance

In another particular embodiment, the inventors sought to develop an "off-the shelf" immunotherapy strategy, using allogeneic T-cells resistant to multiple drugs to mediate selection of engineered T-cells when the patient is treated with different drugs. The therapeutic efficiency can be significantly enhanced by genetically engineering multiple drug resistance allogeneic T-cells. Such a strategy can be particularly effective in treating tumors that respond to drug combinations that exhibit synergistic effects. Moreover multiple resistant engineered T-cells can expand and be selected using minimal dose of drug agents. Thus, the method according to the present invention can comprise modifying T-cell to confer multiple drug resistance to said T-cell. Said multiple drug resistance can be conferred by either expressing more than one drug resistance gene or by inactivating more than one drug sensitizing gene. In another particular embodiment, the multiple drug resistance can be conferred to said T-cell by expressing at least one drug resistance gene and inactivating at least one drug sensitizing gene. In particular, the multiple drug resistance can be conferred to said T-cell by expressing at least one drug resistance gene such as mutant form of DHFR, mutant form of IMPDH2, mutant form of calcineurin, mutant form of MGMT, the ble gene, and the mcrA gene and inactivating at least one drug sensitizing gene such as HPRT gene. In a preferred embodiment, multiple drug resistance can be conferred by inactivating HPRT gene and expressing a mutant form of DHFR; or by inactivating HPRT gene and expressing a mutant form of IMPDH2; or by inactivating HPRT gene and expressing a mutant form of calcineurin; by inactivating HPRT gene and expressing a mutant form of MGMT; by inactivating HPRT-gene and expressing the ble gene; by inactivating HPRT gene and expressing the mcrA gene.

Method of Engineering Drug Resistance Allogeneic T-Cells:

To improve cancer therapy and selective engraftment of allogeneic T-cells, drug resistance is conferred to said cells to protect them from the toxic side effects of chemotherapy agent. The drug resistance of T-cells also permits their enrichment in or ex vivo, as T-cells which express the drug resistance gene will survive and multiply relative to drug sensitive cells. In particular, the present invention relates to a method of engineering allogeneic and drug resistance T-cells resistant for immunotherapy comprising:

(a) Providing a T-cell;
(b) Selecting at least one drug;
(c) Modifying said T-cell by inactivating at least one gene encoding a T-cell receptor (TCR) component;
(d) Modifying T-cell to confer drug resistance to said T-cell;
(e) Expanding said engineered T-cell in the presence of said drug.

Samples comprising at least 5 doses of engineered immune cells of the invention may be engineered to be resistant to a drug.

Clinical Trials

Each embodiment directed to the following clinical trials is part of the present invention and may be claimed as such.

Liquid cancers (CLL, NHL, AML) patients data from four clinical studies Fludarabine, cyclophosphamide administered for 3-4 days were combined to a set or a kit of n pharmaceutical unit doses according to the present invention and used to treat patients with relapsed or refractory cancer (CLL) and low-grade non-Hodgkin's lymphoma (NHL).

Doses and timing used: Patients were treated fludarabine 25 mg/m2 i.v. for 3 days or 24 mg/m2 orally for 5 days, cyclophosphamide 250 mg/m2 i.v. for 3 days or 150 mg/m2 orally for 5 days inclusive. As another example: Treatment consisted in Fludarabine (F) 25 mg/m(2)/day on days 2-4, Cyclophosphamide © 250 mg/m(2)/day on days 2-4, Mitoxantrone (M) 6 mg/m(2) on day 2, and Ritiximab 375 mg/m(2) on day 1. For cycles 2-6, FCM started day 1 together with R 500 mg/m(2). Pegfilgrastim (recombinant human G-CSF) is administered with each cycle. Cycles are repeated every 4-6 weeks and each is followed by an administration of a unit dose of engineered cells. Cells ($6.25 \times 10^6$ cells/kg were allogenic TCR-negative (less than 3% TCR+) CD123 CAR positive and CD52 or dcK deficient administered 3-4 times.

CTL and antibody response were measured: No anamnestic response was measured in these patients despite a repeated exposure to the same Antigen carried by antigen born by engineered immune cells.

Previous reports disclosed the development of an immune response in patients infused with several doses of CART T (autologous setting) that was identified as an anti-CAR response (Hege et al., 2017).

The data here demonstrated that UCART as selected and engineered according to the present study can be administered several times in the same lymphodepleted patient P without inducing any adverse immune response. In fact, redosing allowed a better engraftment of allogenic T cells as compared to a single injection of cells (same final dose $2 \times 1.10^5$). This is likely at least in part due to the nature of the antigens born by cells, the amount of these antigens at the cell surface and the relative inefficiency of the host immune/system/response under lymphodepletion. Indeed, the cells used here were engineered (no detectable level of TCR and MHC-1 after TALEN inactivation of the TRAC gene and Beta 2 microglobulin gene) to minimize or even prevent any immunogenicity and selected (with respect to their HLA Class II) to reduce the immune response.

AML Patients Treated with UCART 123

UCART123 is a phase I, first-in-human, open-label, dose-finding study of UCART123 administered intravenously to patients with AML (see AML123 (UCART123 in Acute Myeloid Leukemia-ClinicalTrials.gov Identifier: NCT03190278 for details).

The study consists of two phases, a dose-escalation phase in relapsed or refractory AML patients and a dose-expansion phase in relapsed/refractory or newly diagnosed AML patients and, in poor-prognosis (Döhner et al., 2010; Röllig et al., 2011).

Doses

The dose of UCART123 used at the dose level where activity is observed was used in the dose-expansion phase.

Increase of dose levels: (DL) with one sample UCART DL1 was increased from $6.25 \times 10^4$ to $2.5 \times 10^5$ UCART123 cells per kg. DL2 & DL3 were respectively at $6.25 \times 10^5$ and $5.05 \times 10^6$.

Treatment interval could be then shortened from 42 days to 28 days then to 14 days.

A treatment is an injection of UCART.

Lymphodepleting Regimen:

Patients were treated with a lymphodepleting regimen with fludarabine 30 mg/m2/day IV for 4 days over 15 to 30 minutes from Day −5 to Day −2, and cyclophosphamide 750 mg/m2/day IV over 1 hour for 3 days from Day −4 to Day −2. Subsequently, the dose-escalation phase consisted of injecting four doses of UCART123 ranging from $1.25 \times 10^5$ cells/kg to $5.05 \times 10^6$ cells/kg.

The lymphodepleting regimen (doses, time between injection) could be modified depending on composition, dose upon safety, biological, and/or clinical activity observations, to maintain the lymphodepletion to a level allowing side effects (neurotoxicity), immunogenicity of the CAR and/or of the CART cells to be tamed to undetectable.

Dose Limiting Toxicity Definitions:

A dose limiting toxicity (DLT) is an adverse event (excluding anorexia and fatigue) or an abnormal laboratory value observed during the DLT observation period (for example 28 days from Day 0 or 42 days from Day 0 if the patient experiences bone marrow aplasia at Day 28), assessed as unrelated to leukemia, intercurrent illness, or concomitant medications, considered as related to UCART123 by the investigator and which meets specific pre-established criteria. Any other unacceptable toxicity encountered, which in the view of the investigator or the DSMB, qualifies as a DLT.

DLT Observation Period:

The DLT observation period is 28 days from Day 0 of the initial UCART123 administration, except for patients with aplastic bone marrow defined by cellularity<5% in the absence of residual AML for whom DLT observation period is extended to Day 42 to allow re-evaluation of the bone marrow.

Successive UCART123 Administration:

Several batches of UCART cells were prepared according to the present invention and were named UCART1, UCART 2, UCART3, UCART4, and UCART 5. The 5 samples of UCART cells selected in a bank of donors for having no common HLA alleles according to the method of the present invention corresponded to 5 different batches.

Once patients were enrolled, and their MHC known, samples with HLA I and II matching the HLA I and II of the patient were prepared.

Patients who did not experience any DLTs during their DLT observation period after UCART1 injection were considered for a second administration of UCART123 (UCART 1 DL2&DL3 or UCART2) upon investigator's recommendation and Sponsor's agreement, depending on whether (i) they were in complete remission but with MRD≥0.1% on flow cytometry, in partial remission or with stable disease after first UCART123 administration or (ii) they achieved a complete remission with MRD<0.1% on flow cytometry but subsequently relapsed.

Patients receiving a second UCART123 dose (UCART 2) would receive the same dose-level of UCART123 (UCART1) as for their first administration, after a new lymphodepletion if necessary (according to the same modalities as for the first administration). Of note, the safety and efficacy data were analyzed during the overall study duration but the determination of the MTD is based only on the results of DLT observation period following the initial UCART123 administration.

In the first studies, UCART1 and UCART2 were both allogenic cells from the same donor. Arms of the different studies ongoing corresponded to repeating an injection (redosing, injection of two different doses (different number of cells) and injection of two identical successive doses using the same sample UCART1, or two samples UCART1 and UCART 2.

HLA of the UCART:

High resolution DNA typing of HLA Class I and Class II alleles was performed for each donors of cells by HEMACARE, a blood bank from the state of California providing fresh or frozen mononuclear cells (MNCs) from healthy volunteer donors in compliance with the US and EP regulatory requirements, for GMP production of UCART cells.

HLA typing was performed by amplification of genomic DNA with sequence specific primers and/or by sequencing, based typing Analysis performed for HLA class I (-A, -B, -C) and HLA class II (-DR, -DQ and DP) loci.

Preexisting Immunity of Patients—Immunity Developed after One, or after Several Injection of Allogenic Engineered UCART Immune Cells It was unlikely that in patients who were never treated with immune cells (never exposed to allogenic cells, platelets or grafts, that is to say in naïve patients), a single injection of UCART induced an anamnestic response.

Indeed, to trigger an anamnestic response a patient must have had mounted an immune response against an antigen and then be reexposed to the same antigen.

Thus, measuring preexisting Ab against MHC in such naïve individual may be therefore optional but was performed as a control and for measuring background immunity.

The presence of anti-HLA antibodies was therefore evaluated in patients before any treatment, especially if the patient already benefited from a treatment with immune cells (platelets, T cells, bone marrow graft . . . ). Thus, serum (serial dilutions from 1:2 to 1:20 000) of each patient enrolled who previously benefited from a transfusion with immune cells or platelets was analyzed for the presence of anti-HLA antibodies.

As a control, sera of each patient enrolled who did not previously benefited from a transfusion with immune cells or platelets were analyzed.

Sera were analyzed for the presence of anti-HLA Ab, once before treatment and at different times after treatment and after each of the successive treatments to day 82 post UCART2.

Antibody screening and specificity were analyzed using a semi-quantitative solid-phase fluorescent bead assay, such as the Lab Screen Single Antigen Assay (One Lambda, Thermo Fisher).

In this flow cytometric method, microbeads coated with recombinant single antigen HLA molecules were employed.

Sera obtained from patients were incubated with the fluorescent beads. Any HLA antibodies present in the test serum binding to the antigens on the beads were labeled with Phycoerythrin (PE) conjugated goat anti-human IgG.

Flow cytometry was then used to simultaneously detect the fluorescent emission of PE and a dye signature from each bead. To assign HLA specificity, the reaction pattern of the test serum was compared to the list of dye signatures for each antigen. An approximation of the strength of antibody reactivity was derived from the mean fluorescence intensity (MFI). Values above the pre-defined MFI threshold were considered positive.

In vitro CTL

In order to evaluate the possibility that the patient has developed an immune response (CTL, Ab) against a HLA molecule, and/or UCART product, after the first injection of UCART, tests measuring the IFN gamma, CTL activity under allogenic context as compared to autologous context were developed.

These tests were adapted to test the hypothesis that if the HLA allele of UCART1 is not matching the HLA molecules of the patient, the patient will develop an immune response against UCART1, but no anamnestic response against UCART2 because UCART 2 has no common allele with UCART 1, several tests.

A T-cell-mediated immune response against UCART was measured by proliferation in response to UCART cells. In such an assay, patient derived lymphocytes obtained both prior to and following UCART therapy are co-cultured with UCART cells that have been activated with plate-bound antigen and irradiated before setting up the co-culture. After 5 days of co-culture cell proliferation was measured by incorporation of $^3$H-thymidine. As a control, proliferation in presence of UCART cells can be compared to proliferation in absence of UCART cells or to T-cells derived from the same donor as the UCART cells that do not express TCR or MHC class I/II (due to the inactivation of the TRAC, B2-microglobulin or CIITA genes).

Interferon Gamma (IFNγ) Activity

The possibility of a T cell mediated immune response against UCART was also evaluated using an MLR-ELISPOT assay. In this assay UCART cells are co-cultured with PBMCs derived from the patient that have been obtained both prior to and following UCART therapy.

The UCART cells utilized were activated with plate-bound antigen and irradiated. Following the co-culture, the patient's cells were incubated in a 96-well ELISPOT plate coated with purified anti-interferon-γ monoclonal antibody. The plate was then developed with streptavidin alkaline phosphatase and a colorimetric substrate. Visualized spots were then counted and indicative of interferon-γ positive cells.

Controls included patient PBMCs cultured alone, PBMCs co-cultured with T-cells derived from the same donor as UCART cells that do not express TCR or MHC class I/II (due to TALEN inactivation of the TRAC, B2-microglobulin or CIITA genes) or PBMCs co-cultured with stimulator cells.

PBMCs derived from the patient were also analyzed before treatment with UCART cells as well as at several timepoints following UCART administration (i.e. D28, D56, D84 and every three to six months afterwards). An increase in the number of IFNγ producing cells after UCART administration or in comparison to the control reaction containing T-cells that do not express TCR or MHC class I/II can be measured to evaluate the presence of allo-antigen specific T-cells in the patient.

This method was used for detecting an immune response in patients treated with successive doses of UCART (sample of 5 doses selected in the bank of donor available).

CTL Activity

CFSE Labeling:

Target Cells (UCART1 to 5) were resuspended at room temperature in PBS at 107 cells/ml. 2 µl l of a solution of 10 mM CFSE was added for each ml of PBMC and mixed by vortexing for 5 seconds. After 10 minutes of incubation at 37° C. protected from light, cells were washed one time from the original labeling using the same volume of fetal bovine serum. Cells were pelleted by centrifugation (5 minutes, 300 g) and washed a second time with fresh culture medium. After an additional centrifugation, cells were resuspended at 106 cells/ml in complete culture medium for functional assay.

In Vitro Alloreactivity:

To determine whether a given individual A (e.g. patient) has developed alloreactivity against cells from another individual B (e.g. donor for UCAR T cell production), T cells from each individual were used in an in vitro cytotoxicity assay. Cells used as target (from individual B) were CFSE-labelled where cells used as effector (from individual A) were left unlabeled. The two cell populations were then mixed and co-incubated in complete culture medium at different effector to target (E:T) ratios.

After 5 hours at 37° C., the cytotoxicity of A against B was estimated by labeling the cells with a fixable viability dye eFluor780 (eBioscience) and measuring by flow cytometry the viability of the CFSE-labeled population and comparing it to that of CFSE-labeled cells that had been incubated in parallel without the presence of effectors cells from A.

Cell Irradiations:

All target cell irradiations were performed at 20 RADs on CellRad instrument from Flaxitron, according to the manufacturer's recommendations.

Generation of donor-specific alloreactive cell population: positive control

To generate a donor-specific alloreactive T cell population, 106 PBMCs from individual A (effectors) were co-cultured with 106 CFSE labeled irradiated PBMCs from allogenic donor B (targets) for 7 days (priming reaction) in 1 ml complete culture medium. After the first week, 106 effector cells from the priming reaction were counted and re-challenged with 106 CFSE labeled irradiated PBMC targets from the same allogeneic donor B for 7 days (secondary challenge). After the second week, 106 effector cells from the secondary challenge were counted and re-challenged with 106 CFSE labeled irradiated PBMC targets from the same allogeneic donor for 7 days.

The serum and immune cells of one patient exhibiting anti-HLA antibodies as well as cells with which he was transfused were also used to set up the test for measuring CTL activity.

This test was also adapted and used to measure the CTL activity in patients treated with successive doses of UCART (UCART1, UCART2, UCART3, UCART4, UCART5).

REFERENCES

R Pei, J-H Lee, T Chen, S Rojo, and PI Terasaki. Flow cytometric detection of HLA antibodies using a spectrum of microbeads. Human Immunology 60, 1293-1302 (1999)

R Pei, G Wang, C Tarsitani, S Rojo, T Chen, S Takemura, A Liu, and J-H Lee. Simultaneous HLA Class I and Class II antibodies screening with flow cytometry. Human Immunology 59, 313-322 (1998)

P S Heeger, NS Greenspan, S Kuhlenschmidt, C Dejelo, D E Hricik, JA Schulak, and M Tary-Lehmann. Pretransplant frequency of donor-specific, IFN-gamma-producing lymphocytes is a manifestation of immunologic memory and correlates with the risk of posttransplant rejection episodes. J Immunol. 163:2267-75 (1999).

Hege K M, Bergsland E K, Fisher G A, et al. Safety, tumor trafficking and immunogenicity of chimeric antigen receptor (CAR)-T cells specific for TAG-72 in colorectal cancer. Journal for Immunotherapy of Cancer. 2017; 5:22. doi:10.1186/s40425-017-0222-9.

M Araki, M Hirayama, E Azuma, T Kumamoto, S Iwamoto, H Toyoda, M Ito, K Amano, and Y Komada. Prediction of reactivity to noninherited maternal antigen in MHC-mismatched, minor histocompatibility antigen-matched stem cell transplantation in a mouse model. J Immunol. 185:7739-45 (2010).

DW Lee, JN Kochenderfer, M Stetler-Stevenson, Y K Cui, C Delbrook, S A Feldman, TJ Fry, R Orentas, M Sabatino, NN Shah, SM Steinberg, D Stroncek, N Tschernia, C Yuan, H Zhang, L Zhang, S A Rosenberg, A S Wayne, CL Mackall. T cells expressing CD19 chimeric antigen receptors for acute lymphoblastic leukaemia in children and young adults: a phase 1 dose-escalation trial. Lancet. February 7:517-528 (2015).

Results

An example of results of High resolution DNA typing of HLA Class I and Class II alleles performed for each donors of cells is described here: HLA typing was performed by amplification of genomic DNA with sequence specific primers and/or by sequencing based typing Analysis performed for HLA class I (-A, -B, -C) and HLA class II (-DR, -DQ and -DP) loci.

| MNC number | 1 | 2 | 3 | | | | | |
|---|---|---|---|---|---|---|---|---|
| sex of the donor | m | m | m | | | | | |
| blood group | O+ | O+ | AB+ | | | | | |
| age | 26 | 20 | 24 | years old | | | | |
| HLA Typing Results | | | | | | | | |
| Patient no | A* | B* | C* | DRB1* | DRB3* | DRB4* | DRB5* | DQB1* |
| W313716038336 C165190 | 02: 06 | 15: 55 | 04: 07 | 10: 01 | 01: 01 | | | 03: 02 | m: male

HLA Typing was performed by amplification of genomic DNA with sequence specific primers and/or by DNA sequence based typing.

Donor identification and results were analyzed and confirmed by two independent individuals.

Antibody Titer

In sera obtained from patients who received successive injections of UCART123, no anti-UCART antibodies reacting with precedent treatments could be detected and the CTL activity against previous treatment remained below detection (more than 0.25 at E:T=1 without activation of E).

We concluded that no anamnestic response was detected.

Test to measure a CTL activity

Cytotoxicity of immune cells first stimulated 1, 2 or 3 times using their own irradiated cells (A:A) (autologous) or irradiated cells from another donor B (A:B) (allogenic) was measured. For that purpose, these "selected" effector cells (stimulated cells) were incubated at various effector to target ratios (5, 10, 15, 20, 25, 30) either with their own CFSE-labelled target cells (A:A+A) or with CFSE-labelled target cells from the donor to which they were exposed (A:B+B).

CFSE-labelled target cells were also incubated alone to determine the 100% of viable target cells.

After at least 24 hours to 5 days incubation, viable cells were analyzed by flow cytometry.

Figure 5:
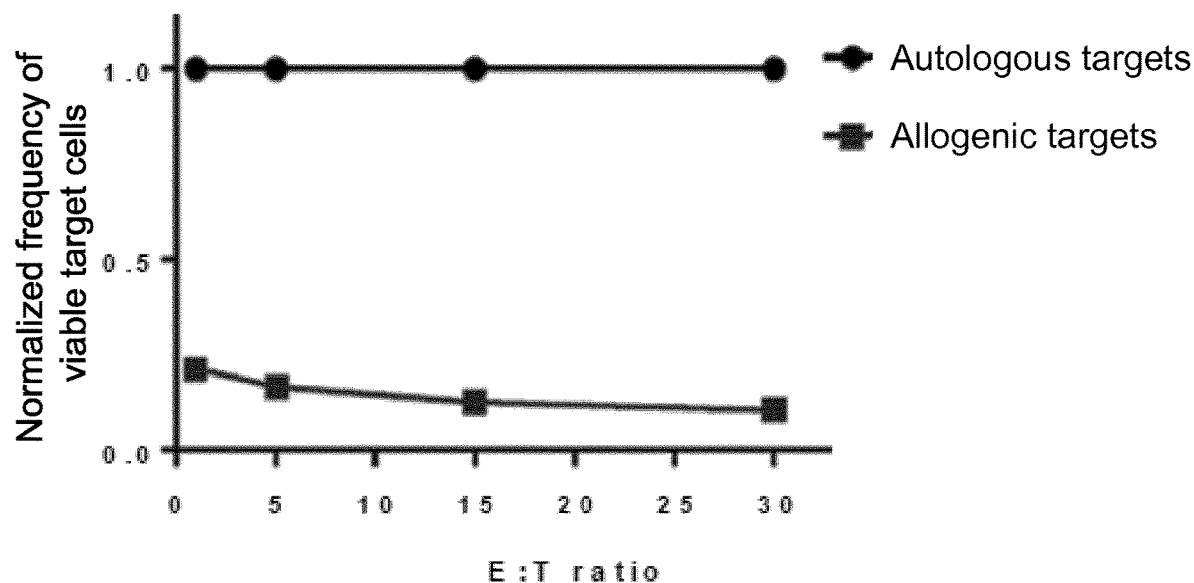
FIG. 5: In vitro assay to identify a CTL-mediated anamnestic response in patients

FIG. 5 shows the ratio of number of live target cells per well in the presence of effectors divided by the number of live target cells in the absence of effectors.

Figure 6:
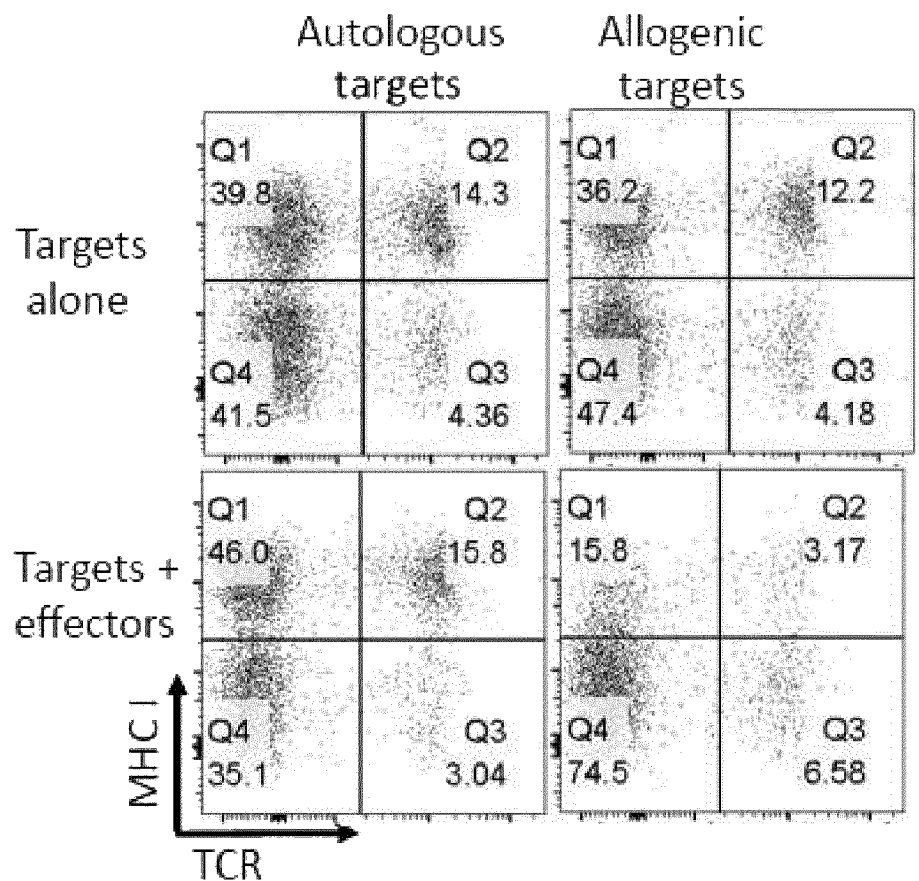
FIG. 6: Cytotoxic activity of allogenic cells is HLA I-dependent Table 1: Examples of set or kit according to the present invention Cells of table 1 express at least one CAR and at least one of their genes encoding a subunit of the TCR molecule is inactivated).

The results in FIG. 5 demonstrated that effector cells from donor A obtained by successive challenges with irradiated cells from donor B are specifically cytotoxic against cells from donor B and not against their own cells (autologous) Similar experiments were performed using target cells that been transfected with both TALEN targeting B2M and TRAC genes to obtain HLA Class I negative and TCR negative T cells. Before flow cytometry analysis, cells were also stained using HLA ABC-specific antibodies and TCRαβ-specific antibodies; FIG. 6 shows that HLA ABC-TCR positive cells are sensitive to alloreactive effector cells whereas B2M-TRAC KO cells that HLA ABC-TCR negative are resistant to cytotoxicity by alloreactive effector cells.

This confirms that the cytotoxicity observed in this test is mediated through allogenic TCR-MHC interactions between targets and effectors. Moreover, this test allowed to identify whether CTL can be generated and which HLA is involved.

These data provided a threshold for measuring the pre-existing or acquired CTL activity in individuals treated with various samples of UCART cells.

Thus, this test was used to identify a CTL activity in patients treated successively with UCART and to show/predict whether an individual may develop an anamnestic response when treated with successive doses of UCART from i) the himself (autologous), ii) different donors matching his HLA of the patient, iii) different donors mismatching his HLA but with no common allele (HLA-A, B, C and DR).

Anti-CAR T Immunity

The results obtained using the serum of a patient transfused with platelets suggested that a patient transfused with immune cells can develop an immunity (anti-HLA Ab) against the transfused cells that can be detected in our test.

The results obtained by measuring i) the CTL activity in cocultures of irradiated UCART with effector cells and ii) anti-HLA antibody in serum of patients infused with two doses of UCART1 or two UCART1 and then UCART2 suggested that an immunodepleted patient transfused with immune cells may not develop any immunity (anti-HLA Ab, CTL) neither against the first transfused cells nor against the second transfused cells.

Indeed, the results showed that in patients treated with allogenic UCART1, no immunity (anti-HLA Ab, CTL) against the UCART1 graft was detected in serum diluted at 1:2 and in circulating immune cells.

The observation that the level of UCART cells picked between day 10 and day 30, and then collapsed is consistent with the fact that in immunodepleted hosts, CART can proliferate and be engrafted at least temporarily. This was confirmed again in vivo by measuring a decrease in the amount of UCART1 in the blood at different times after injection (pick at d10-15 and then decrease to undetectable at d42, d56 and d84) and detection of a second pick upon injection of UCART2—at the same level or even higher—of UCART2 (with the same UCART and with HLA matching HLA of the patient) after injection.

Upon injection of UCART2 having no common HLA A B C and DR alleles with UCART1, The Ab level against UCART1 remained to background level in the serum and no detectable level of anti-HLA Ab of UCART1 were measured. In these patients no CTL activity against UCART1 nor CTL activity against UCART2 was detected. Finally, the CTL activity against each of the 5 irradiated UCART cell successive samples (selected according to the method developed by Cellectis) was measured using immune cells of a patient treated with two doses of UCART1 $5.05 \times 10^6$) collected before each injection of UCART cells and after, at day 14, or at day 45 after infusion. Cells collected were not activated or activated once using anti-CD3/CD28 Ab and then exposed to the irradiated UCARTs.

As expected the two patients treated with UCART1 and UCART 2 developed no detectable (at ratio 0.2:1 and 1:1 E:T) CTL activity against the administered UCART1.

When tested against irradiated UCART2, UCART 3, UCART 4 or UCART 5 (used as target), the CTL activity against UCART1 was not detectable at ratio E:T=1 and E:T=5).

Collectively, these data suggested that the samples of 5 UCART doses of allogenic cells of the invention may be administered successively to a patient without inducing a anamnestic response.

Altogether, these data indicated that in vitro it is possible to detect a CTL activity, to measure the CTL activity developed in a patient treated with UCART cells. When selected appropriately, and according to the present invention, cells further engineered can be used safely to treat pathologies requiring successive injections.

The present invention provides therefore:

A kit of at least five samples comprising engineered cells for immunotherapy wherein the MHC of the cells are or match those of the patient in combination with a lymphodepletion regimen for successive administrations A kit of at least five samples comprising engineered cells for immunotherapy in combination with a lymphodepletion regimen for successive administrations wherein the MHC of the cells have no common allele within each other A Method for preparing said samples for successive immunotherapy or An in vitro method for analyzing the cross CTL activity against doses of cells in a kit intended for successive immunotherapy comprising:

Providing doses of cells in a kit intended for successive immunotherapy wherein the MHC of the cells in a kit intended for successive immunotherapy are from a patient P or match those of the patient P or wherein the MHC of the cells in a kit intended for successive immunotherapy have no common allele within each other, unless they match those of P,
  analyzing immune cells isolated from P before any treatment and after (at least 3 months after the end of a treatment) a treatment with one dose CART cells, preferably UCART cells, for their cytolytic activity against the cells in the successive doses of cells in a kit intended for successive immunotherapy,
  repeating the analysis after each treatment and against each of the UCART used, optionally analyzing immune cells isolated from P before any treatment and after (at least 3 months after the end of a treatment) a treatment with one dose CART cells, preferably UCART cells, for their cytolytic activity against the cells in the successive doses of cells in a kit intended for successive immunotherapy, in the presence of antibodies in the serum of P before any treatment and after (at least 3 months after the end of a treatment) a treatment with one dose CART cells, preferably UCART cells (if the cytolytic activity (ratio living cells in E+T/living cells alone) is less than 0.5 preferably about 0.25 at E:T is 1:1 after 3 to 5 days incubation (in the test as those described in FIG. 5).

Annex 1
Nomenclature for Factors of the HLA System
June 2016
Compiled by Steven G. E. Marsh for the WHO Nomenclature Committee for Factors of the HLA System.
Published In:
  HLA (2016) 88:142-51
  Human Immunology (2016) 77:1309-17
  International Journal of Immunogenetics (2016) 43:320-9
  The following sequences have been submitted to the Nomenclature Committee since the May 2016 nomenclature update and, following agreed policy, have been assigned official allele designations (1). Full details of all sequences will be published in a forthcoming report.

Below are listed the newly assigned sequences (Table A1) and confirmations of previously reported sequences (Table A2). The accession number of each sequence is given and these can be used to retrieve the sequence files from the EMBL, GenBank or DDBJ data libraries. Although accession numbers have been assigned by the data-libraries and most sequences are already available, there is still the possibility that an author may not yet have allowed the sequence to be released; in such a case you will have to contact the submitting author directly. Additional information pertaining to new sequences is often included in the publications describing these alleles; a listing of recent publications that describe new HLA sequences is given in Table A3.

All new and confirmatory sequences should now be submitted directly to the WHO Nomenclature Committee for Factors of the HLA System via the IMGT/HLA Database using the sequence submission tool provided (2). The IMGT/HLA Database may be accessed via the world wide web at: http://www.ebi.ac.uk/ipd/imgt/hla/.

TABLE A1

New Sequences

| Sequence | Cell identification | Accession number | Submitting author |
|---|---|---|---|
| A*01: 09: 02 | HG00011561 | KU992456 | Histogenetics, Ossining, USA |
| A*01: 203 | HG00011553 | KU963012 | Histogenetics, Ossining, USA |
| A*01: 204 | HG00011555 | KU992458 | Histogenetics, Ossining, USA |
| A*01: 205 | HG00011556 | KU992465 | Histogenetics, Ossining, USA |
| A*01: 206 | HG00011557 | KU992460 | Histogenetics, Ossining, USA |
| A*01: 207 | M-566764 | LT559473 | Kristin Kipper, Martinsried, Germany |
| A*01: 208Q | M-505547 | LT559474 | Kristin Kipper, Martinsried, Germany |
| A*02: 30: 02 | HG00011568 | KU992455 | Histogenetics, Ossining, USA |
| A*02: 630 | HG00011562 | KU992475 | Histogenetics, Ossining, USA |
| A*02: 631 | HG00011563 | KU992469 | Histogenetics, Ossining, USA |
| A*02: 632 | HG00011565 | KU992461 | Histogenetics, Ossining, USA |
| A*02: 633 | HG00011566 | KU963013 | Histogenetics, Ossining, USA |
| A*02: 634 | HG00011567 | KU853071 | Histogenetics, Ossining, USA |
| A*03: 249 | HG00011558 | KU853074 | Histogenetics, Ossining, USA |
| A*11: 242 | HG00011533 | KU963008 | Histogenetics, Ossining, USA |
| A*11: 243 | HG00011534 | KU963011 | Histogenetics, Ossining, USA |
| A*11: 244 | HG00011538 | KU992473 | Histogenetics, Ossining, USA |
| A*11: 245 | HG00011539 | KU853072 | Histogenetics, Ossining, USA |
| A*23: 74 | HG00011548 | KU963005 | Histogenetics, Ossining, USA |
| A*24: 343 | HG00011543 | KU992454 | Histogenetics, Ossining, USA |
| A*24: 344 | HG00011544 | KU992476 | Histogenetics, Ossining, USA |
| A*24: 345 | HG00011545 | KU963007 | Histogenetics, Ossining, USA |
| A*24: 346 | HG00011547 | KU963014 | Histogenetics, Ossining, USA |
| A*24: 347 | HG00011549 | KU992464 | Histogenetics, Ossining, USA |
| A*24: 348 | HG00011550 | KU992471 | Histogenetics, Ossining, USA |
| A*26: 123 | HG00011532 | KU992466 | Histogenetics, Ossining, USA |
| A*26: 124 | HG00011537 | KU992447 | Histogenetics, Ossining, USA |
| A*29: 89 | HG00011527 | KU992452 | Histogenetics, Ossining, USA |
| A*29: 90 | HG00011529 | KU992451 | Histogenetics, Ossining, USA |
| A*31: 111 | AN00002, AN00005 | LT575566, LT575567 | Steven GE Marsh, London, United Kingdom |
| A*32: 85 | HG00011559 | KU992450 | Histogenetics, Ossining, USA |

TABLE A1-continued

| New Sequences | | | |
|---|---|---|---|
| Sequence | Cell identification | Accession number | Submitting author |
| A*32: 86 | HG00011560 | KU992453 | Histogenetics, Ossining, USA |
| A*33: 112 | HG00011525 | KU992470 | Histogenetics, Ossining, USA |
| A*33: 113 | HG00011526 | KU963009 | Histogenetics, Ossining, USA |
| A*33: 114 | HG00011530 | KU963003 | Histogenetics, Ossining, USA |
| A*66: 25 | HG00011535 | KU992468 | Histogenetics, Ossining, USA |
| A*66: 26Q | HG00011536 | KU992477 | Histogenetics, Ossining, USA |
| A*68: 147 | HG00011531 | KU963006 | Histogenetics, Ossining, USA |
| A*68: 148Q | HG00011540 | KU992449 | Histogenetics, Ossining, USA |
| B*07: 273 | HG00011605 | KU963023 | Histogenetics, Ossining, USA |
| B*07: 274 | HG00011607 | KU963030 | Histogenetics, Ossining, USA |
| B*07: 275 | HG00011610 | KU963020 | Histogenetics, Ossining, USA |
| B*08: 164 | HG00011581 | KU853068 | Histogenetics, Ossining, USA |
| B*08: 165 | 15005164, 16001439 | KX343895 | Olaida Valdez, LAquila, Italy |
| B*13: 93 | HG00011580 | KU992480 | Histogenetics, Ossining, USA |
| B*14: 02: 14 | AN00027 | LT575573 | Steven GE Marsh, London, United Kingdom |
| 8*15: 242: 02 | AN00052 | LT575520 | Steven GE Marsh, London, United Kingdom |
| B*15: 394 | HG00011592 | KU992498 | Histogenetics, Ossining, USA |
| B*15: 395 | HG00011593 | KU992490 | Histogenetics, Ossining, USA |
| B*15: 396 | HG00011594 | KU963019 | Histogenetics, Ossining, USA |
| B*15: 397 | HG00011600 | KU992478 | Histogenetics, Ossining, USA |
| B*15: 398 | 49003 | KT804925 | Weijian Yu, DaLian, China |
| B*18: 125 | HG00011424 | KU668755 | Histogenetics, Ossining, USA |
| B*18: 126 | M-613166 | LT559478 | Kristin Kipper, Martinsried, Germany |
| B*18: 127 | HG00011579 | KU963021 | Histogenetics, Ossining, USA |
| B*27: 05: 32 | RMC30387, RMC31828, RMC31833 | LN830753 | Maria Loginova, Kirov, Russia |
| B*27: 153 | HG00011576 | KU963036 | Histogenetics, Ossining, USA |
| B*27: 154 | HG00011577 | KU992494 | Histogenetics, Ossining, USA |
| B*35: 317 | HG00011574 | KU963024 | Histogenetics, Ossining, USA |
| B*35: 318 | HG00011591 | KU853066 | Histogenetics, Ossining, USA |
| B*35: 319 | HG00011597 | KU992483 | Histogenetics, Ossining, USA |
| B*35: 320 | HG00011599 | KU992495 | Histogenetics, Ossining, USA |
| B*35: 321 | HG00011611 | KU963034 | Histogenetics, Ossining, USA |
| B*35: 322 | M-613627 | LT559479 | Kristin Kipper, Martinsried, Germany |
| B*37: 59 | HG00011578 | KU963018 | Histogenetics, Ossining, USA |
| B*38: 01: 12 | HG00011603 | KU992499 | Histogenetics, Ossining, USA |
| B*38: 62 | HG00011608 | KU992493 | Histogenetics, Ossining, USA |
| B*38: 63 | HG00011609 | KU963022 | Histogenetics, Ossining, USA |

TABLE A1-continued

| New Sequences | | | |
|---|---|---|---|
| Sequence | Cell identification | Accession number | Submitting author |
| B*40: 336 | HG00011572 | KU992497 | Histogenetics, Ossining, USA |
| B*40: 337N | HG00011575 | KU947984 | Histogenetics, Ossining, USA |
| B*40: 338N | P10544 | KX354735 | Faming Zhu, Hangzhou, China |
| B*42: 23 | HG00011604 | KU992482 | Histogenetics, Ossining, USA |
| B*44: 03: 36 | HG00011586 | KU963017 | Histogenetics, Ossining, USA |
| B*44: 247 | HG00011585 | KU963025 | Histogenetics, Ossining, USA |
| B*44: 248 | HG00011588 | KU992479 | Histogenetics, Ossining, USA |
| B*44: 249 | HG00011602 | KU992486 | Histogenetics, Ossining, USA |
| B*44: 69: 02 | HG00011587 | KU992487 | Histogenetics, Ossining, USA |
| B*45: 19 | AN00042 | LT575512 | Steven GE Marsh, London, United Kingdom |
| B*46: 01: 22 | 409043 | LT223709 | Edward KL Yang, Hualien, Taiwan |
| B*46: 68 | H160267 | KX346176 | Faming Zhu, Hangzhou, China |
| B*50: 01: 08 | 203927910 | KX423690 | Ivan Bernardo, Logrono, Spain |
| B*50: 46 | HG00011569, HG00011570 | KU963032, KU963033 | Histogenetics, Ossining, USA |
| B*50: 47 | HG00011573 | KU963031 | Histogenetics, Ossining, USA |
| B*51: 207 | HG00011601 | KU992489 | Histogenetics, Ossining, USA |
| B*51: 208 | AN00062 | LT575625 | Steven GE Marsh, London, United Kingdom |
| B*52: 25: 02 | HG00011589, HG00011590 | KU853067, KU963035 | Histogenetics, Ossining, USA |
| B*53: 43 | HG00011598 | KU963016 | Histogenetics, Ossining, USA |
| B*58: 01: 20 | C15-327 | KU258149 | Eun-Jeong Choi, Seoul, Korea |
| B*58: 81 | M-302235 | LT559480 | Kristin Kipper, Martinsried, Germany |
| C*01: 02: 40 | DKMS-LSL-C-593 | LN912860 | DKMS Life Sciences Lab, Dresden, Germany |
| C*01: 122 | HG00011612 | KU992508 | Histogenetics, Ossining, USA |
| C*01: 123 | HG00011614 | KU963048 | Histogenetics, Ossining, USA |
| C*01: 124 | HG00011615 | KU963037 | Histogenetics, Ossining, USA |
| C*01: 32: 02 | D25028 | KU312098 | Eun-Jeong Choi, Seoul, Korea |
| C*02: 10: 02 | DKMS-LSL-C-652 | LN912919 | DKMS Life Sciences Lab, Dresden, Germany |
| C*02: 119 | HG00011635 | KUB53062 | Histogenetics, Ossining, USA |
| C*02: 120 | DKMS-LSL-C-591 | LN912858 | DKMS Life Sciences Lab, Dresden, Germany |
| C*03: 02: 15 | DKMS-LSL-C-655 | LN912922 | DKMS Life Sciences Lab, Dresden, Germany |
| C*03: 03: 01: 02 | DKMS-LSL-C-635 | LN912902 | DKMS Life Sciences Lab, Dresden, Germany |
| C*03: 03: 32 | DKMS-LSL-C-664 | LN912931 | DKMS Life Sciences Lab, Dresden, Germany |
| C*03: 04: 50 | DKMS-LSL-C-572 | LN912839 | DKMS Life Sciences Lab, Dresden, Germany |

TABLE A1-continued

| New Sequences | | | |
|---|---|---|---|
| Sequence | Cell identification | Accession number | Submitting author |
| C*03: 04: 51 | DKMS-LSL-C-609 | LN912876 | DKMS Life Sciences Lab, Dresden, Germany |
| C*03: 322 | HG00011638 | KU963039 | Histogenetics, Ossining, USA |
| C*03: 323N | HG00011641 | KU947987 | Histogenetics, Ossining, USA |
| C*03: 324 | DKMS-LSL-C-653 | LN912920 | DKMS Life Sciences Lab, Dresden, Germany |
| C*04: 01: 75 | DKMS-LSL-C-603 | LN912870 | DKMS Life Sciences Lab, Dresden, Germany |
| C*04: 240 | HG00011642 | KU992510 | Histogenetics, Ossining, USA |
| C*04: 241 | HG00011644 | KU853063 | Histogenetics, Ossining, USA |
| C*04: 242 | HG00011645 | KU853058 | Histogenetics, Ossining, USA |
| C*04: 243 | DKMS-LSL-C-594 | LN912861 | DKMS Life Sciences Lab, Dresden, Germany |
| C*04: 244 | DKMS-LSL-C-577 | LN912844 | DKMS Life Sciences Lab, Dresden, Germany |
| C*05: 103: 02 | HG00011625 | KU2963041 | Histogenetics, Ossining, USA |
| C*05: 134 | DKMS-LSL-C-576 | LN912843 | DKMS Life Sciences Lab, Dresden, Germany |
| C*05: 135 | DKMS-LSL-C-638 | LN912905 | DKMS Life Sciences Lab, Dresden, Germany |
| C*05: 58: 03 | DKMS-LSL-C-595 | LN912862 | DKMS Life Sciences Lab, Dresden, Germany |
| C*06: 155: 01: 02 | DKMS-LSL-C-665 | LN912932 | DKMS Life Sciences Lab, Dresden, Germany |
| C*06: 181 | HG00011617 | KU963043 | Histogenetics, Ossining, USA |
| C*06: 182 | DKMS-LSL-C-580 | LN912847 | DKMS Life Sciences Lab, Dresden, Germany |
| C*06: 183 | DKMS-LSL-C-561, DKMS-LSL-C-673 | LN912828, LN912940 | DKMS Life Sciences Lab, Dresden, Germany |
| C*06: 184 | DKMS-LSL-C-570 | LN912837 | DKMS Life Sciences Lab, Dresden, Germany |
| C*06: 185 | DKMS-LSL-C-632 | LN912899 | DKMS Life Sciences Lab, Dresden, Germany |
| C*06: 186 | DKMS-LSL-C-662 | LN912929 | DKMS Life Sciences Lab, Dresden, Germany |
| C*06: 187 | DKMS-LSL-C-663 | LN912930 | DKMS Life Sciences Lab, Dresden, Germany |
| C*07: 01: 54 | DKMS-LSL-C-584 | LN912851 | DKMS Life Sciences Lab, Dresden, Germany |
| C*07: 01: 55 | DKMS-LSL-C-574 | LN912S41 | DKMS Life Sciences Lab, Dresden, Germany |
| C*07: 01: 56 | DKMS-LSL-C-615 | LN912882 | DKMS Life Sciences Lab, Dresden, Germany |
| C*07: 02: 74 | DKMS-LSL-C-614 | LN912881 | DKMS Life Sciences Lab, Dresden, Germany |
| C*07: 02: 75 | DKMS-LSL-C-616 | LN912883 | DKMS Life Sciences Lab, Dresden, Germany |

TABLE A1-continued

| New Sequences | | | |
|---|---|---|---|
| Sequence | Cell identification | Accession number | Submitting author |
| C*07: 02: 76 | DKMS-LSL-C-625, DKMS-LSL-C-660 | LN912892, LN912927 | DKMS Life Sciences Lab, Dresden, Germany |
| C*07: 04: 01: 02 | DKMS-LSL-C-642 | LN912909 | DKMS Life Sciences Lab, Dresden, Germany |
| C*07: 204: 02 | HG00011621 | KU992516 | Histogenetics, Ossining, USA |
| C*07: 246: 02 | HG00011647 | KU853056 | Histogenetics, Ossining, USA |
| C*07: 330: 02 | DKMS-LSL-C-592 | LN912859 | DKMS Life Sciences Lab, Dresden, Germany |
| C*07: 368: 02 | HG00011648 | KU853060 | Histogenetics, Ossining, USA |
| C*07: 454: 02 | HG00011619 | KU992511 | Histogenetics, Ossining, USA |
| C*07: 515 | HG00011620 | KU992517 | Histogenetics, Ossining, USA |
| C*07: 516 | HG00011622 | KU963040 | Histogenetics, Ossining, USA |
| C*07: 517 | DKMS-LSL-C-513 | LN912780 | DKMS Life Sciences Lab, Dresden, Germany |
| C*07: 518 | DKMS-LSL-C-585 | LN912852 | DKMS Life Sciences Lab, Dresden, Germany |
| C*07: 519 | DKMS-LSL-C-568 | LN912835 | DKMS Life Sciences Lab, Dresden, Germany |
| C*07: 520 | DKMS-LSL-C-583 | LN912850 | DKMS Life Sciences Lab, Dresden, Germany |
| C*07: 521 | DKMS-LSL-C-600 | LN912867 | DKMS Life Sciences Lab, Dresden, Germany |
| C*07: 522 | DKMS-LSL-C-587 | LN912854 | DKMS Life Sciences Lab, Dresden, Germany |
| C*07: 523 | DKMS-LSL-C-675 | LN912942 | DKMS Life Sciences Lab, Dresden, Germany |
| C*07: 524 | DKMS-LSL-C-668 | LN912935 | DKMS Life Sciences Lab, Dresden, Germany |
| C*07: 525 | DKMS-LSL-C-671 | LN912938 | DKMS Life Sciences Lab, Dresden, Germany |
| C*07: 526 | DKMS-LSL-C-639 | LN912906 | DKMS Life Sciences Lab, Dresden, Germany |
| C*07: 527 | DKMS-LSL-C-612 | LN912879 | DKMS Life Sciences Lab, Dresden, Germany |
| C*07: 528 | DKMS-LSL-C-657 | LN912924 | DKMS Life Sciences Lab, Dresden, Germany |
| C*07: 529 | DKMS-LSL-C-649 | LN912916 | DKMS Life Sciences Lab, Dresden, Germany |
| C*07: 530 | 5781500349 | KX426316 | Faming Zhu, Hangzhou, China |
| C*08: 02: 13 | DKMS-LSL-C-516 | LN912783 | DKMS Life Sciences Lab, Dresden, Germany |
| C*08: 02: 14 | DKMS-LSL-C-677 | LN912944 | DKMS Life Sciences Lab, Dresden, Germany |
| C*08: 03: 04 | DKMS-LSL-C-651 | LN912918 | DKMS Life Sciences Lab, Dresden, Germany |
| C*08: 133 | HG00011613 | KU992507 | Histogenetics, Ossining, USA |
| C*08: 134 | HG00011624 | KU992515 | Histogenetics, Ossining, USA |

TABLE A1-continued

New Sequences

| Sequence | Cell identification | Accession number | Submitting author |
|---|---|---|---|
| C*08: 135 | HG00011626 | KU992503 | Histogenetics, Ossining, USA |
| C*08: 136 | HG00011627 | KU992506 | Histogenetics, Ossining, USA |
| C*12: 03: 38 | AN00012 | LT575571 | Steven GE Marsh, London, United Kingdom |
| C*12: 181 | DKMS-LSL-C-521 | LN912788 | DKMS Life Sciences Lab, Dresden, Germany |
| C*12: 182 | HG00011630 | KU992514 | Histogenetics, Ossining, USA |
| C*12: 183 | HG00011632 | KU992509 | Histogenetics, Ossining, USA |
| C*12: 184 | DKMS-LSL-C-573 | LN912840 | DKMS Life Sciences Lab, Dresden, Germany |
| C*12: 185 | DKMS-LSL-C-559 | LN912826 | DKMS Life Sciences Lab, Dresden, Germany |
| C*12: 186 | DKMS-LSL-C-679 | LN912946 | DKMS Life Sciences Lab, Dresden, Germany |
| C*14: 74 | DKMS-LSL-C-571 | LN912838 | DKMS Life Sciences Lab, Dresden, Germany |
| C*15: 05: 12 | DKMS-LSL-C-604 | LN912871 | DKMS Life Sciences Lab, Dresden, Germany |
| C*15: 129 | DKMS-LSL-C-658 | LN912925 | DKMS Life Sciences Lab, Dresden, Germany |
| C*15: 44: 02 | DKMS-LSL-C-91 | LN912948 | DKMS Life Sciences Lab, Dresden, Germany |
| C*16: 01: 22 | DKMS-LSL-C-607 | LN912874 | DKMS Life Sciences Lab, Dresden, Germany |
| C*16: 98 | HG00011628 | KU853057 | Histogenetics, Ossining, USA |
| DRB1*03: 132 | M-577538 | LT559475 | Kristin Kipper, Martinsried, Germany |
| DRB1*04: 01: 01: 02 | BM14 | LT220246 | Steven GE Marsh, London, United Kingdom |
| DRB1*04: 213 | HG00011662, HG00011663 | KU963064, KU963065 | Histogenetics, Ossining, USA |
| DRB1*04: 214N | HG00011670 | KU947992 | Histogenetics, Ossining, USA |
| DRB1*07: 70 | HG00011668 | KU992521 | Histogenetics, Ossining, USA |
| DRB1*11: 201 | HG00011669 | KU963070 | Histogenetics, Ossining, USA |
| DRB1*11: 202 | NT01378 | KX239876 | Carolyn K Hurley, Washington DC, USA |
| DRB1*13: 219 | HG00011672 | KU963069 | Histogenetics, Ossining, USA |
| DRB1*13: 220 | HG00011673 | KU963062 | Histogenetics, Ossining, USA |
| DRB1*14: 178 | HG00011674 | KU853055 | Histogenetics, Ossining, USA |
| DRB1*16: 41N | HG00011664, HG00011665 | KU947991, KU947994 | Histogenetics, Ossining, USA |
| DRB3*01: 25 | HG00011676 | KU992577 | Histogenetics, Ossining, USA |
| DRB3*01: 26N | HG00011677 | KU947995 | Histogenetics, Ossining, USA |
| DRB3*01: 27 | HG00011678 | KU992566 | Histogenetics, Ossining, USA |
| DRB3*01: 28 | HG00011679 | KU992580 | Histogenetics, Ossining, USA |
| DRB3*01: 29 | HG00011681 | KU992539 | Histogenetics, Ossining, USA |
| DRB3*01: 30 | HG00011683, HG00011684, HG00011685 | KU992591, KU992595, KU992598 | Histogenetics, Ossining, USA |

TABLE A1-continued

| New Sequences | | | |
|---|---|---|---|
| Sequence | Cell identification | Accession number | Submitting author |
| DRB3*01: 31 | HG00011686, HG00011687, HG00011688 | KU992537, KU992538, KU992602 | Histogenetics, Ossining, USA |
| DRB3*01: 32 | HG00011694 | KU992583 | Histogenetics, Ossining, USA |
| DRB3*01: 33 | HG00011695 | KU992542 | Histogenetics, Ossining, USA |
| DRB3*01: 34 | HG00011696, HG00011697, HG00011698 | KU963081, KU992544, KU992556 | Histogenetics, Ossining, USA |
| DRB3*01: 35 | HG00011699 | KU992540 | Histogenetics, Ossining, USA |
| DRB3*01: 36 | HG00011700 | KU963085 | Histogenetics, Ossining, USA |
| DRB3*01: 37 | HG00011702 | KU992587 | Histogenetics, Ossining, USA |
| DRB3*01: 38 | HG00011703 | KU963075 | Histogenetics, Ossining, USA |
| DRB3*01: 39 | HG00011709 | KU963080 | Histogenetics, Ossining, USA |
| DRB3*02: 22: 02 | HG00011722, HG00011723, HG00011724 | KU992524, KU992564, KU992574 | Histogenetics, Ossining, USA |
| DRB3*02: 31: 02 | HG00011719, HG00011720 | KU992530, KU992536 | Histogenetics, Ossining, USA |
| DRB3*02: 42 | HG00011701 | KU992569 | Histogenetics, Ossining, USA |
| DRB3*02: 43 | HG00011712 | KU992584 | Histogenetics, Ossining, USA |
| DRB3*02: 44 | HG00011713 | KU992532 | Histogenetics, Ossining, USA |
| DRB3*02: 45 | HG00011718 | KU963086 | Histogenetics, Ossining, USA |
| DRB3*02: 46 | HG00011721 | KU992522 | Histogenetics, Ossining, USA |
| DRB3*02: 47 | HG00011725 | KU992541 | Histogenetics, Ossining, USA |
| DRB3*02: 48 | HG00011727 | KU992560 | Histogenetics, Ossining, USA |
| DRB3*02: 49 | HG00011731 | KU992586 | Histogenetics, Ossining, USA |
| DRB3*02: 50 | HG00011733 | KU992526 | Histogenetics, Ossining, USA |
| DRB3*02: 51 | HG00011734, HG00011735 | KU992529, KU992553 | Histogenetics, Ossining, USA |
| DRB3*02: 52 | HG00011740 | KU992589 | Histogenetics, Ossining, USA |
| DRB3*02: 53 | HG00011745 | KU992582 | Histogenetics, Ossining, USA |
| DRB3*02: 54 | HG00011748 | KU992545 | Histogenetics, Ossining, USA |
| DRB3*03: 01: 05 | HG00011743 | KU963078 | Histogenetics, Ossining, USA |
| DRB3*03: 08 | HG00011704, HG00011705 | KU963073, KU963083 | Histogenetics, Ossining, USA |
| DRB3*03: 09 | HG00011711 | KU963077 | Histogenetics, Ossining, USA |
| DRB3*03: 10 | HG00011741 | KU963087 | Histogenetics, Ossining, USA |
| DRB3*03: 11 | HG00011742 | KU992552 | Histogenetics, Ossining, USA |
| DRB4*01: 01: 02 | HG00011755 | KU992610 | Histogenetics, Ossining, USA |
| DRB4*01: 26 | HG00011751 | KU963130 | Histogenetics, Ossining, USA |
| DRB4*01: 27 | HG00011752 | KU963127 | Histogenetics, Ossining, USA |
| DRB4*01: 28 | HG00011753 | KU992607 | Histogenetics, Ossining, USA |
| DRB4*01: 29 | HG00011754 | KU963116 | Histogenetics, Ossining, USA |
| DRB4*01: 30 | HG00011756 | KU963124 | Histogenetics, Ossining, USA |
| DRB4*01: 31 | HG00011757 | KU992613 | Histogenetics, Ossining, USA |

TABLE A1-continued

New Sequences

| Sequence | Cell identification | Accession number | Submitting author |
|---|---|---|---|
| DRB4*01: 32 | HG00011758 | KU992618 | Histogenetics, Ossining, USA |
| DRB4*01: 33 | HG00011759 | KU992603 | Histogenetics, Ossining, USA |
| DRB4*01: 34 | HG00011761 | KU992609 | Histogenetics, Ossining, USA |
| DRB4*01: 35 | HG00011762 | KU963118 | Histogenetics, Ossining, USA |
| DRB4*01: 36 | HG00011764, HG00011765, HG00011766, HG00011767 | KU992611, KU992612, KU963128, KU963129 | Histogenetics, Ossining, USA |
| DQB1*02: 73 | HG00011653 | KU963058 | Histogenetics, Ossining, USA |
| DQB1*02: 74 | HG00011654 | KU853052 | Histogenetics, Ossining, USA |
| DQB1*03: 230 | HG00011656 | KU992520 | Histogenetics, Ossining, USA |
| DQB1*04: 35 | HG00011659 | KU963060 | Histogenetics, Ossining, USA |
| DQB1*04: 36N | HG00011660 | KU947989 | Histogenetics, Ossining, USA |
| DQB1*05: 120 | HG00011649 | KU963052 | Histogenetics, Ossining, USA |
| DQB1*05: 121 | HG00011651 | KU963053 | Histogenetics, Ossining, USA |
| DQB1*05: 122 | HG00011652 | KU992518 | Histogenetics, Ossining, USA |
| DQB1*05: 123 | HG00011658 | KU963055 | Histogenetics, Ossining, USA |
| DQB1*06: 207 | HG00011655 | KU963051 | Histogenetics, Ossining, USA |
| DQB1*06: 208 | HG00011661 | KU963056 | Histogenetics, Ossining, USA |
| DQB1*06: 209 | 5791500157 | KX346175 | Faming Zhu, Hangzhou, China |
| DQB1*06: 53: 02 | HG00011650 | KU963050 | Histogenetics, Ossining, USA |
| DPB1*571: 01 | AN00060 | LT575580 | Steven GE Marsh, London, United Kingdom |
| DPB1*572: 01 | M-609652 | LT559476 | Kristin Kipper, Martinsried, Germany |

TABLE A2

Confirmatory Sequences

| Sequence | Cell identification | Accession number | Submitting author |
|---|---|---|---|
| A*01:01:65 | AN00044 | LT575515 | Steven GE Marsh, London, United Kingdom |
| A*01:01:75 | HG00011871 | KT162060 | Histogenetics, Ossining, USA |
| A*01:197 | HG00011870 | KU853070 | Histogenetics, Ossining, USA |
| A*01:199 | HG00012039 | KX425939 | Histogenetics, Ossining, USA |
| A*02:01:01:05 | DKMS-LSL-A-681 | LN912949 | DKMS Life Sciences Lab, Dresden, Germany |
| A*02:01:05 | AN00059 | LT575579 | Steven GE Marsh, London, United Kingdom |
| A*02:01:120 | DKMS-LSL-A-922 | LN999610 | DKMS Life Sciences Lab, Dresden, Germany |
| A*02:01:21 | NT01399 | KX373268 | Carolyn K Hurley, Washington DC, USA |
| A*02:02:01:01 | DKMS-LSL-A-903 | LN999592 | DKMS Life Sciences Lab, Dresden, Germany |

TABLE A2-continued

| Confirmatory Sequences | | | |
|---|---|---|---|
| Sequence | Cell identification | Accession number | Submitting author |
| A*02:06:01:02 | DKMS-LSL-A-749, DKMS-LSL-A-856, DKMS-LSL-A-858, DKMS-LSL-A-908, DKMS-LSL-A-902 | LN994650, LN994757, LN994759, LN999596, LN999590 | DKMS Life Sciences Lab, Dresden, Germany |
| A*02:08 | DKMS-LSL-A-807 | LN994709 | DKMS Life Sciences Lab, Dresden, Germany |
| A*02:09 | AN00028, AN00029 | LT57560S, LT575505 | Steven GE Marsh, London, United Kingdom |
| A*02:17:02 | AN00017 | LT575642 | Steven GE Marsh, London, United Kingdom |
| A*02:20:02 | AN00020 | LT575501 | Steven GE Marsh, London, United Kingdom |
| A*02:24:01 | AN00045, AN00046 | LT575516, LT575633 | Steven GE Marsh, London, United Kingdom |
| A*02:30:01 | DKMS-LSL-A-843 | LN994744 | DKMS Life Sciences Lab, Dresden, Germany |
| A*02:580 | HG00011875, HG00011876, HG00011877, HG00011878 | KU668727, KU668712, KX060761, KX173345 | Histogenetics, Ossining, USA |
| A*02:581 | HG00011874 | KU853069 | Histogenetics, Ossining, USA |
| A*02:587 | HG00011564 | KU992472 | Histogenetics, Ossining, USA |
| A*02:64:01 | AN00115 | LT575616 | Steven GE Marsh, London, United Kingdom |
| A*02:66 | AN00040 | LT575510 | Steven GE Marsh, London, United Kingdom |
| A*03:01:01:05 | DKMS-LSL-A-768, DKMS-LSL-A-905 | LN994669, LN999594 | DKMS Life Sciences Lab, Dresden, Germany |
| A*03:01:55 | HG00011872, HG00011873 | KU725851, KU748645 | Histogenetics, Ossining, USA |
| A*24:02:01:04 | DKMS-LSL-A-888 | LN999576 | DKMS Life Sciences Lab, Dresden, Germany |
| A*24:02:13 | AN00048, AN00049, AN00047 | LT575517, LT575632, LT575623 | Steven GE Marsh, London, United Kingdom |
| A*24:322 | HG00011869 | KU992467 | Histogenetics, Ossining, USA |
| A*24:36N | DKMS-LSL-A-794, DKMS-LSL-A-849 | LN994695, LN994750 | DKMS Life Sciences Lab, Dresden, Germany |
| A*24:56 | DKMS-LSL-A-773 | LN994674 | DKMS Life Sciences Lab, Dresden, Germany |
| A*24:56 | NT01401 | KX373267 | Carolyn K Hurley, Washington DC, USA |
| A*25:01:01 | DKMS-LSL-A-758, DKMS-LSL-A-785, DKMS-LSL-A-831, DKMS-LSL-A-813, DKMS-LSL-A-921 | LN994660, LN994686, LN994731, LN994714, LN999608 | DKMS Life Sciences Lab, Dresden, Germany |
| A*26:01:01:02 | IME 302-15 | KR831282 | Manuela Testi, Rome, Italy |
| A*26:01:01:02 | DKMS-LSL-A-909 | LN999598 | DKMS Life Sciences Lab, Dresden, Germany |
| A*26:08 | NT01387 | KX343008 | Carolyn K Hurley, Washington DC, USA |
| A*26:116 | HG00011867 | KU725850 | Histogenetics, Ossining, USA |
| A*26:14 | AN00077 | LT575584 | Steven GE Marsh, London, United Kingdom |

TABLE A2-continued

| Confirmatory Sequences | | | |
|---|---|---|---|
| Sequence | Cell identification | Accession number | Submitting author |
| A*29:87 | 210708 | LT593864 | Maria Peixoto, Porto, Portugal |
| A*30:02:01:01 | DKMS-LSL-A-718, DKMS-LSL-A-795, DKMS-LSL-A-801 | LN994620, LN994697, LN994702 | DKMS Life Sciences Lab, Dresden, Germany |
| A*30:03 | AN00127 | LT575555 | Steven GE Marsh, London, United Kingdom |
| A*31:105 | HG00011866 | KU668706 | Steven GE Marsh, London, United Kingdom |
| A*33:03:01 | DKMS-LSL-A-717 | LN994618 | DKMS Life Sciences Lab, Dresden, Germany |
| A*33:05 | AN00019, AN00018 | LT575643, LT575615 | Steven GE Marsh, London, United Kingdom |
| A*34:05 | NT01389 | KX343009 | Carolyn K Hurley, Washington DC, USA |
| A*66:02 | NT01390 | KX343010 | Carolyn K Hurley, Washington DC, USA |
| A*66:17 | DKMS-LSL-A-244 | LN880520 | DKMS Life Sciences Lab, Dresden, Germany |
| A*68:01:02:02 | DKMS-LSL-A-752, DKMS-LSL-A-868 | LN9946N, LN999657 | DKMS Life Sciences Lab, Dresden, Germany |
| A*68:01:02:03 | DKMS-LSL-A-858 | LN994758 | DKMS Life Sciences Lab, Dresden, Germany |
| A*68:02:01-03 | DKMS-LSL-A-727 | LN994628 | DKMS Life Sciences Lab, Dresden, Germany |
| A*68:117 | HG00011542 | KU992448 | Histogenetics, Ossining, USA |
| A*68:136 | HG00011868 | KU748647 | Histogenetics, Ossining, USA |
| B*07:02:45 | AN00008 | LT575651 | Steven GE Marsh, London, United Kingdom |
| B*07:07 | AN00056 | LT575577 | Steven GE Marsh, London, United Kingdom |
| B*07:262 | HG00011887 | KU992491 | Histogenetics, Ossining, USA |
| B*14:03 | AN00121 | LT575618 | Steven GE Marsh, London, United Kingdom |
| B*15:01:01:01 | DoGr | LT575607 | Steven GE Marsh, London, United Kingdom |
| B*15:01:01:04 | DKMS-LSL-B-685, DKMS-LSL-B-684 | LN912953, LN912952 | DKMS Life Sciences Lab, Dresden, Germany |
| B*15:03:01:02 | DKMS-LSL-B-693 | LN912961 | DKMS Life Sciences Lab, Dresden, Germany |
| B*15:09 | AN00150 | LT575621 | Steven GE Marsh, London, United Kingdom |
| B*15:09 | NT01391 | KX343011 | Carolyn K Hurley, Washington DC, USA |
| B*15:15 | NT01392 | KX343012 | Carolyn K Hurley, Washington DC, USA |
| B*15:24:01 | AN00122 | LT575551 | Steven GE Marsh, London, United Kingdom |
| B*15:35 | NT01393 | KX373269 | Carolyn K Hurley, Washington DC, USA |
| B*15:378 | HG00011882 | KU668736 | Histogenetics, Ossining, USA |
| B*15:380N | AN00006, AN00007 | LT575568, LT575569 | Steven GE Marsh, London, United Kingdom |

TABLE A2-continued

| Confirmatory Sequences | | | |
|---|---|---|---|
| Sequence | Cell identification | Accession number | Submitting author |
| B*15:54 | AN00030 | LT575507 | Steven GE Marsh, London, United Kingdom |
| B*15:64:02 | AN00053 | LT575521 | Steven GE Marsh, London, United Kingdom |
| B*18:01:01:01 | VEN | LN877363 | Steven GE Marsh, London, United Kingdom |
| B*18:04 | AN00016 | LT575500 | Steven GE Marsh, London, United Kingdom |
| B*18:14 | AN00069 | LT575581 | Steven GE Marsh, London, United Kingdom |
| B*27:05:18 | HG00011879 | KU992485 | Histogenetics, Ossining, USA |
| B*35:03:01 | 1UP | LT575660 | Steven GE Marsh, London, United Kingdom |
| B*35:55 | AN00071 | LT575530 | Steven GE Marsh, London, United Kingdom |
| B*38:09 | AN00055 | LT575522 | Steven GE Marsh, London, United Kingdom |
| B*39:08 | NT01394 | KX373270 | Carolyn K Hurley, Washington DC, USA |
| B*40:04 | EC | LT575647 | Steven GE Marsh, London, United Kingdom |
| B*40:05 | NT01388 | KX343013 | Carolyn K Hurley, Washington DC, USA |
| B*44:226 | HG00011880 | KU725857 | Histogenetics, Ossining, USA |
| B*51:08:01 | NT01395 | KX373271 | Carolyn K Hurley, Washington DC, USA |
| B*51:13:01 | AN00051 | LT575519 | Steven GE Marsh, London, United Kingdom |
| B*51:193 | AN00014 | LT575572 | Steven GE Marsh, London, United Kingdom |
| B*52:58 | HG00011881 | KU668751 | Histogenetics, Ossining, USA |
| B*55:01:01 | VEN | LN877364 | Steven GE Marsh, London, United Kingdom |
| B*57:78 | HG00011884 | KU668745 | Histogenetics, Ossining, USA |
| B*57:81 | HG00011883 | KX173355 | Histogenetics, Ossining, USA |
| B*58:02:01 | NT01396 | KX373272 | Carolyn K Hurley, Washington DC, USA |
| B*58:74 | HG00011885, HG00011886 | KU963029, KX017407 | Histogenetics, Ossining, USA |
| B*78:02:02 | AN00070 | LT575529 | Steven GE Marsh, London, United Kingdom |
| C*01:59 | DKMS-LSL-C-546 | LN912813 | DKMS Life Sciences Lab, Dresden, Germany |
| C*01:93 | DKMS-LSL-C-967 | LN999655 | DKMS Life Sciences Lab, Dresden, Germany |
| C*03:07 | AN00039 | LT575509 | Steven GE Marsh, London, United Kingdom |
| C*03:211:01 | AN00004 | LT575496 | Steven GE Marsh, London, United Kingdom |
| C*03:251 | DKMS-LSL-C-530 | LN912797 | DKMS Life Sciences Lab, Dresden, Germany |

TABLE A2-continued

Confirmatory Sequences

| Sequence | Cell identification | Accession number | Submitting author |
|---|---|---|---|
| C*03:311 | DKMS-LSL-C-637 | LN912904 | DKMS Life Sciences Lab, Dresden, Germany |
| C*03:318N | DKMS-LSL-C-959 | LN999647 | DKMS Life Sciences Lab, Dresden, Germany |
| C*03:51 | DKMS-LSL-C-958 | LN999646 | DKMS Life Sciences Lab, Dresden, Germany |
| C*04:01:70 | HG00011643 | KU963038 | Histogenetics, Ossining, USA |
| C*04:187 | DKMS-LSL-C-965 | LN999653 | DKMS Life Sciences Lab, Dresden, Germany |
| C*04:201 | DKMS-LSL-C-678 | LN912945 | DKMS Life Sciences Lab, Dresden, Germany |
| C*04:206 | DKMS-LSL-C-631 | LN912898 | DKMS Life Sciences Lab, Dresden, Germany |
| C*04:219 | DKMS-LSL-C-630 | LN912897 | DKMS Life Sciences Lab, Dresden, Germany |
| C*04:223 | HG00011898 | KU668785 | Histogenetics, Ossining, USA |
| C*05:118 | DKMS-LSL-C-676 | LN912943 | DKMS Life Sciences Lab, Dresden, Germany |
| C*05:119 | DKMS-LSL-C-605 | LN912872 | DKMS Life Sciences Lab, Dresden, Germany |
| C*05:26 | DKMS-LSL-C-547 | LN912814 | DKMS Life Sciences Lab, Dresden, Germany |
| C*05:98 | DKMS-LSL-C-525 | LN912792 | DKMS Life Sciences Lab, Dresden, Germany |
| C*06:04:01 | DKMS-LSL-C-562 | LN912830 | DKMS Life Sciences Lab, Dresden, Germany |
| C*06:124 | DKMS-LSL-C-608 | LN912875 | DKMS Life Sciences Lab, Dresden, Germany |
| C*06:132:01 | DKMS-LSL-C-565 | LN912832 | DKMS Life Sciences Lab, Dresden, Germany |
| C*06:136 | DKMS-LSL-C-619 | LN912886 | DKMS Life Sciences Lab, Dresden, Germany |
| C*06:138 | DKMS-LSL-C-536 | LN912803 | DKMS Life Sciences Lab, Dresden, Germany |
| C*06:142 | DKMS-LSL-C-654 | LN912921 | DKMS Life Sciences Lab, Dresden, Germany |
| C*06:148 | DKMS-LSL-C-669 | LN912936 | DKMS Life Sciences Lab, Dresden, Germany |
| C*07:01:09 | AN00064 | LT575524 | Steven GE Marsh, London, United Kingdom |
| C*07:02:01:03 | 31667 | LT221891 | Maria Peixoto, Porto, Portugal |
| C*07:02:01:07 | DKMS-LSL-C-613 | LN912880 | DKMS Life Sciences Lab, Dresden, Germany |
| C*07:02:30 | DKMS-LSL-C-527 | LN912794 | DKMS Life Sciences Lab, Dresden, Germany |
| C*07:276 | DKMS-LSL-C-531 | LN912798 | DKMS Life Sciences Lab, Dresden, Germany |
| C*07:322 | DKMS-LSL-C-566 | LN912833 | DKMS Life Sciences Lab, Dresden, Germany |

TABLE A2-continued

| Confirmatory Sequences | | | |
|---|---|---|---|
| Sequence | Cell identification | Accession number | Submitting author |
| C*07:326 | DKMS-LSL-C-528 | LN912795 | DKMS Life Sciences Lab, Dresden, Germany |
| C*07:342 | DKMS-LSL-C-618 | LN912885 | DKMS Life Sciences Lab, Dresden, Germany |
| C*07:343 | AN00058 | LT575578 | Steven GE Marsh, London, United Kingdom |
| C*07:360 | DKMS-LSL-C-945 | LN999633 | DKMS Life Sciences Lab, Dresden, Germany |
| C*07:396 | DKMS-LSL-C-602 | LN912869 | DKMS Life Sciences Lab, Dresden, Germany |
| C*07:425 | DKMS-LSL-C-656 | LN912923 | DKMS Life Sciences Lab, Dresden, Germany |
| C*07:429 | DKMS-LSL-C-548 | LN912815 | DKMS Life Sciences Lab, Dresden, Germany |
| C*07:439 | HG00011890 | KU725859 | Histogenetics, Ossining, USA |
| C*07:450 | HG00011888 | KX173381 | Histogenetics, Ossining, USA |
| C*07:451N | HG00011889 | KU947986 | Histogenetics, Ossining, USA |
| C*07:456 | DKMS-LSL-C-674 | LN912941 | DKMS Life Sciences Lab, Dresden, Germany |
| C*07:457 | HG00011891 | KU748659 | Histogenetics, Ossining, USA |
| C*07:462 | DKMS-LSL-C-507 | LN880522 | DKMS Life Sciences Lab, Dresden, Germany |
| C*07:476N | HG00011893 | KU947985 | Histogenetics, Ossining, USA |
| C*07:485 | HG00011892 | KU668789 | Histogenetics, Ossining, USA |
| C*07:485 | DKMS-LSL-C-601 | LN912868 | DKMS Life Sciences Lab, Dresden, Germany |
| C*08:22 | ISK | LT575565 | Steven GE Marsh, London, United Kingdom |
| C*08:92 | DKMS-LSL-C-606 | LN912873 | DKMS Life Sciences Lab, Dresden, Germany |
| C*12:02:12 | DKMS-LSL-C-954 | LN999642 | DKMS Life Sciences Lab, Dresden, Germany |
| C*12:03:01:04 | DKMS-LSL-C-586DKMS-LSL-C-955 | LN912853 | DKMS Life Sciences Lab, Dresden, Germany |
| C*12:143 | DKMS-LSL-C-616 | LN912884 | DKMS Life Sciences Lab, Dresden, Germany |
| C*12:149 | DKMS-LSL-C-553 | LN912820 | DKMS Life Sciences Lab, Dresden, Germany |
| C*12:153 | DKMS-LSL-C-508 | LN912775 | DKMS Life Sciences Lab, Dresden, Germany |
| C*12:153 | HG00011896 | KU360753 | Histogenetics, Ossining, USA |
| C*12:156 | HG00012128 | KX289900 | Histogenetics, Ossining, USA |
| C*12:162 | HG00011894, HG00011895 | KU992504, KU668771 | Histogenetics, Ossining, USA |
| C*12:163 | DKMS-LSL-C-599 | LN912866 | DKMS Life Sciences Lab, Dresden, Germany |
| C*15:04:01 | NT01397 | KX373273 | Carolyn K Hurley, Washington DC, USA |
| C*15:06:01 | NT01398 | KX373274 | Carolyn K Hurley, Washington DC, USA |

TABLE A2-continued

| Confirmatory Sequences | | | |
|---|---|---|---|
| Sequence | Cell identification | Accession number | Submitting author |
| C*15:108 | HG00011897 | KX060772 | Histogenetics, Ossining, USA |
| C*15:123 | HG00012135 | KX173383 | Histogenetics, Ossining, USA |
| C*16:01:20 | HG00012121 | KX173372 | Histogenetics, Ossining, USA |
| C*16:73 | DKMS-LSL-C-526 | LN912793 | DKMS Life Sciences Lab, Dresden, Germany |
| C*17:01:01:05 | DKMS-LSL-C-633DKMS-LSL-C-643 | LN912901LN912911 | DKMS Life Sciences Lab, Dresden, Germany |
| | HG00011914 | KU668807 | Histogenetics, Ossining, USA |
| DRB1*01:07 | NT01385 | KX255493 | Carolyn K Hurley, Washington DC, USA |
| DRB1*03:14 | NT01384 | KX255494 | Carolyn K Hurley, Washington DC, USA |
| DRB1*04:01:01:01 | BOLETH | LT220230 | Steven GE Marsh, London, United Kingdom |
| DRB1*04:212N | HG00011913 | KU947993 | Histogenetics, Ossining, USA |
| DRB1*04:43 | NT01377 | KX239877 | Carolyn K Hurley, Washington DC, USA |
| DRB1*07:61 | HG00011911 | KU963068 | Histogenetics, Ossining, USA |
| DRB1*07:65 | HG00011912 | KX173402 | Histogenetics, Ossining, USA |
| DRB1*11:196 | HG00011675 | KU963067 | Histogenetics, Ossining, USA |
| DRB1*11:24 | NT01383 | KX255495 | Carolyn K Hurley, Washington DC, USA |
| DRB1*11:84:01 | NT01367 | KX239885 | Carolyn K Hurley, Washington DC, USA |
| DRB1*13:104 | NT01381 | KX255497 | Carolyn K Hurley, Washington DC, USA |
| DRB1*13:23:01 | NT01382 | KX255496 | Carolyn K Hurley, Washington DC, USA |
| DRB1*14:47 | NT01386 | KX255492 | Carolyn K Hurley, Washington DC, USA |
| DRB1*15:02:14 | HG00011910 | KX173394 | Histogenetics, Ossining, USA |
| DRB1*15:136 | HG00011855 | KX017425 | Histogenetics, Ossining, USA |
| DRB1*16:02:06 | HG00011909 | KU963061 | Histogenetics, Ossining, USA |
| DRB1*16:12 | NT01380 | KX255498 | Carolyn K Hurley, Washington DC, USA |
| DRB1*16:35 | HG00011908 | KU963066 | Histogenetics, Ossining, USA |
| DRB3*02:02:06 | HG00011937, HG00011938, HG00011939, HG00011940, HG00011941, HG00011942, HG00011943, HG00011944, HG00011945, HG00011946, HG00011947, HG00011948, HG00011949, HG00011950, HG00011951, HG00011952, HG00011953, HG00011954 | KU992534, KU992535, KU992547, KU992554, KU992557, KU214482, KU992562, KU963088, KU992528, KU963090, KU992570, KU992571, KU992573, KU992576, KU992585, KU360769, KU668814, KU668818 | Histogenetics, Ossining, USA |
| DRB3*02:32 | HG00011958, HG00011959, HG00011960, HG00011961, HG00011962 | KU992567, KU992531, KU992578, KU992523, KU992596 | Histogenetics, Ossining, USA |
| DRB3*02:33 | HG00011956 | KU963091 | Histogenetics, Ossining, USA |

TABLE A2-continued

Confirmatory Sequences

| Sequence | Cell identification | Accession number | Submitting author |
|---|---|---|---|
| DRB3*02:34 | HG00011955 | KX060781 | Histogenetics, Ossining, USA |
| DRB3*02:35 | HG00011957 | KU963089 | Histogenetics, Ossining, USA |
| DRB3*02:36 | HG00011736, HG00011737, HG00011738, HG00011739 | KU992549, KU992559, KU992563, KU992588 | Histogenetics, Ossining, USA |
| DRB3*02:37 | HG00011732 | KU992593 | Histogenetics, Ossining, USA |
| DRB3*02:39 | HG00011717 | KU992550 | Histogenetics, Ossining, USA |
| DRB3*03:04 | HG00011970, HG00011971 | KU214483, KU992581 | Histogenetics, Ossining, USA |
| DRB3*03:05 | HG00011963, HG00011964 | KU963092, KU668819 | Histogenetics, Ossining, USA |
| DRB3*03:06 | HG00011965, HG00011966, HG00011967, HG00011968, HG00011969 | KU992590, KU992592, KU992597, KU992599, KU992600 | Histogenetics, Ossining, USA |
| DRB4*01:07:02 | HG00011763 | KU992615 | Histogenetics, Ossining, USA |
| DRB4*01:11 | HG00011972 | KU992614 | Histogenetics, Ossining, USA |
| DRB4*01:13 | HG00011973 | KX173404 | Histogenetics, Ossining, USA |
| DRB4*01:14 | HG00011974, HG00011975, HG00011976, HG00011977, HG00011978, HG00011979, HG00011980, HG00011981, HG00011982, HG00011983 | KU963125, KU963126, KU668825, KU360773, KU668826, KU668827, KU668828, KU66S829, KU992616, KU360772 | Histogenetics, Ossining, USA |
| DRB4*01:17 | HG00011984, HG00011985, HG00011986, HG00011987, HG00011988, HG00011989, HG00011990, HG00011991, HG00011992, HG00011993, HG00011994, HG00011995, HG00011996 | KU992617, KX173405, KX173406, KU992605, KU992608, KU963122, KU963123, KU963114, KU963115, KU963117, KU668822, KU853053, KU668824 | Histogenetics, Ossining, USA |
| DRB5*01:17 | HG00012005 | KU963141 | Histogenetics, Ossining, USA |
| DRB5*01:18 | HG00011997, HG00011998, HG00011999, HG00012000, HG00012001, HG00012002, HG00012003, HG00012004 | KU668833, KU668832, KU668831, KU963152, KU963148, KU963150, KU963151, KU963139 | Histogenetics, Ossining, USA |
| DRB5*01:20 | HG00011787, HG00011788 | KU963137, KU963147 | Histogenetics, Ossining, USA |
| DRB5*01:21 | HG00011780 | KU 963134 | Histogenetics, Ossining, USA |
| DRB5*02:07 | HG00012006 | KU963144 | Histogenetics, Ossining, USA |
| DQB1*02:530 | DKMS-LSL-DQB1-1068, DKMS-LSL-DQB1-1065, DKMS-LSL-DQB1-1082, DKMS-LSL-DQB1-1006 | LN999756, LN999753, LN999770, LN999669 | DKMS Life Sciences Lab, Dresden, Germany |
| DQB1*03:05:01 | DKMS-LSL-DQB1-1062 | LN999749 | DKMS Life Sciences Lab, Dresden, Germany |

TABLE A2-continued

Confirmatory Sequences

| Sequence | Cell identification | Accession number | Submitting author |
|---|---|---|---|
| DQB1*03:132 | BY01299 | KX267770 | Carolyn K Hurley, Washington DC, USA |
| DQB1*03:199 | HG00011848 | KX017424 | Histogenetics, Ossining, USA |
| DQB1*03:19:01 | AN00024, AN00025, AN00023, AN00022, AN00021, AN-53 | LT575502, LT575506, LT575575, LT575576, LT575527, LT575564 | Steven GE Marsh, London, United Kingdom |
| DQB1*03:201 | HG00011901 | KU725862 | Histogenetics, Ossining, USA |
| DQB1*03:207 | HG00011900 | KX017420 | Histogenetics, Ossining, USA |
| DQB1*03:25:01 | AN00015 | LT575499 | Steven GE Marsh, London, United Kingdom |
| DQB1*04:33 | HG00011906, HG00011907 | KU748662, KU963057 | Steven GE Marsh, London, United Kingdom |
| DQB1*05:01:01:03 | DKMS-LSL-DQB1-998, DKMS-LSL-DQB1-977, DKMS-LSL-DQB1-1007 | LN999701, LN999678, LN999670 | DKMS Life Sciences Lab, Dresden, Germany |
| DQB1*05:112 | AN00010 | LT575641 | Steven GE Marsh, London, United Kingdom |
| DQB1*06:122 | HG00011905 | KM216200 | Histogenetics, Ossining, USA |
| DQB1*06:184 | HG00011904 | KU963054 | Histogenetics, Ossining, USA |
| DQB1*06:191 | HG00011902, HG00011903 | KU709837, KU668794 | Histogenetics, Ossining, USA |
| DQB1*06:194 | HG00011899 | KU992519 | Histogenetics, Ossining, USA |
| DQB1*06:202 | HG00012157 | KU360758 | Histogenetics, Ossining, USA |
| DQB1*06:37 | was1 | GQ422610 | Thomas Binder, Hamburg, Germany |
| DPB1*01:01:02 | AN00063 | LT575523 | Steven GE Marsh, London, United Kingdom |
| DPB1*02:01:04 | AN00066 | LT575526 | Steven GE Marsh, London, United Kingdom |
| DPB1*02:01:18 | HG00011923 | KU963156 | Histogenetics, Ossining, USA |
| DPB1*04:01:32 | HG00011916, HG00011917 | KT803924, KU963165 | Histogenetics, Ossining, USA |
| DPB1*104:01 | DKMS-LSL-DPB1-767 | LN994667 | DKMS Life Sciences Lab, Dresden, Germany |
| DPB1*155:01:02 | HG00011927 | KX173419 | Histogenetics, Ossining, USA |
| DPB1*445:01 | HG00011929, HG00011930, HG00011931, HG00011932 | KX017443, KX173416, KU668843, KU963164 | Histogenetics, Ossining, USA |
| DPB1*458:01 | HG00011936 | KX173411 | Histogenetics, Ossining, USA |
| DPB1*470:01 | HG00011928 | KU963172 | Histogenetics, Ossining, USA |
| DPB1*475:01 | HG00011921 | KU963160 | Histogenetics, Ossining, USA |
| DPB1*482:01 | HG00011934 | KX017442 | Histogenetics, Ossining, USA |
| DPB1*484:01 | HG00011920 | KX017439 | Histogenetics, Ossining, USA |
| DPB1*488:01 | HG00011922 | KX173407 | Histogenetics, Ossining, USA |
| DPB1*495:01 | HG00011918, HG00011919 | KX017445, KU963163 | Histogenetics, Ossining, USA |
| DPB1*501:01 | HG00011926 | KU668844 | Histogenetics, Ossining, USA |
| DPB1*505:01 | HG00011933 | KU709843 | Histogenetics, Ossining, USA |
| DPB1*511:01 | HG00011915 | KU992621 | Histogenetics, Ossining, USA |
| DPB1*526:01 | HG00011925 | KU853047 | Histogenetics, Ossining, USA |

TABLE A2-continued

Confirmatory Sequences

| Sequence | Cell identification | Accession number | Submitting author |
|---|---|---|---|
| DPB1*531:01 | HG00011935 | KU668846 | Histogenetics, Ossining, USA |
| DPB1*539:01 | HG00011924 | KU668847 | Histogenetics, Ossining, USA |

TABLE A3

Recently Published Sequences

| Sequence | References |
|---|---|
| B*14:53 | (3) |
| B*35:279 | (4) |
| B*40:01:40 | (5) |
| B*40:186:02 | (6) |
| MICA*012:05 | (7) |

REFERENCES

1. Marsh S G E, Albert E D, Bodmer W F, et al. Nomenclature for factors of the HLA system, 2010. *Tissue Antigens* 2010 75: 291-455.
2. Robinson J, Halliwell J A, Hayhurst J D, Flicek P, Parham P, Marsh S G E. The IPD and IMGT/HLA database: allele variant databases. Nucleic Acids Res 2015: 43: D423-31.
3. Street J, Davies E, Darke C. A novel HLA-B*14 allele-B*14:53—genetics and serology. *Int J Immunogenet* 2016 43: 236-9.
4. Mrazek F, Onderkova J, Konigova N, et al. A novel HLA-B allele, HLA-B*35:279, identified by sequencing-based typing in a Czech patient. *Int J Immunogenet* 2016 43: 246-8.
5. Pei Y F, Huang H N, Li H C, Shen W D. A novel HLA-B*40 allele, B*40:01:40, identified in a Chinese individual. *Int J immunogenet* 2016 43: 249-50.
6. Wang W Y, Zhang W, Cai J H, Zhu F M, Tian W. Characterization of a novel HLA-B*40 allele, HLA-B*40:186:02, by cloning and sequencing. *Int J immunogenet* 2016 43: 240-1.
7. Wang W Y, Tian W, Wang F, Zhu F M, Li L X. Characterization of a novel MICA allele, MICA*012:05, by cloning and sequencing. *Int J Immunogenet* 2016 43: 244-5.

The invention claimed is:

1. A method for immunotherapy for treating cancer in a human comprising:
   a) genotyping and/or phenotyping the HLA molecules and/or HLA alleles of a patient;
   b) administering to the patient a dose of a first set of engineered allogeneic T cells from a single donor having at least one difference from the patient in the following ten HLA markers: two A markers, two B markers, two C markers, two DRB1 markers and two DQ,
   wherein said first set of engineered allogeneic T cells has been modified to contain at least one chimeric antigen receptor (CAR) or one transgenic T-cell receptor (TCR) and to inactivate at least one component of the endogenous TCR gene; and
   c) at least 30 days after the administration of the dose of the first set, administering to the patient a dose of a second set of engineered allogeneic T cells from a different single donor, wherein said second set of engineered T cells has no common HLA-A, HLA-B, HLA-C and HLA-DR alleles with those of the first set of engineered T cells other than those fully matching the patient,
   wherein said second set of engineered T cells has been modified to contain at least one chimeric antigen receptor (CAR) or one transgenic T-cell receptor (TCR) and to inactivate at least one component of the endogenous TCR gene.

2. The method of claim 1, further comprising administering, at least 30 days after the administration of the dose of the second set, a dose of a third set of engineered allogeneic T cells from a different single donor, wherein said third set of engineered T cells has no common HLA-A, HLA-B, HLA-C and HLA-DR alleles with those of the first or second set of engineered T cells other than those fully matching the patient,
   wherein said third set of engineered T cells has been modified to contain at least one chimeric antigen receptor (CAR) or one transgenic T-cell receptor (TCR) and to inactivate at least one component of the endogenous TCR gene.

3. The method of claim 2, further comprising administering, at least 30 days after the administration of the dose of the third set, a dose of a fourth set of engineered allogeneic T cells from a different single donor, wherein said fourth set of engineered T cells has no common HLA-A, HLA-B, HLA-C and HLA-DR alleles with those of the first, second, or third set of engineered T cells other than those fully matching the patient,
   wherein said fourth set of engineered T cells has been modified to contain at least one chimeric antigen receptor (CAR) or one transgenic T-cell receptor (TCR) and to inactivate at least one component of the endogenous TCR gene.

4. The method of claim 3, further comprising administering, at least 30 days after the administration of the dose of the fourth set, a dose of a fifth set of engineered allogeneic T cells from a different single donor, wherein said fifth set of engineered T cells with no common HLA-A, HLA-B, HLA-C and HLA-DR alleles with those of the first, second, third, or fourth set of engineered T cells other than those fully matching the patient,
   wherein said fifth set of engineered T cells has been modified to contain at least one chimeric antigen receptor (CAR) or one transgenic T-cell receptor (TCR) and to inactivate at least one component of the endogenous TCR gene.

5. The method of claim 1, wherein the first set of engineered allogeneic T cells matches at least six of the following eight HLA markers of the patient: two A markers, two B markers, two C markers, two DRB1 markers.

6. The method of claim 1, wherein the first set of engineered allogeneic T cells matches at least eight of the following ten HLA markers of the patient: two A markers, two B markers, two C markers, two DRB1 markers and two DQ.

7. The method of claim 1, wherein the first set of engineered allogeneic T cells matches nine of the following ten HLA markers of the patient: two A markers, two B markers, two C markers, two DRB1 markers and two DQ.

8. The method of claim 1, wherein the second set of engineered allogeneic T cells is administered 30-60 days after the first set of engineered allogeneic T cells.

9. The method of claim 2, wherein the third set of engineered allogeneic T cells is administered 30-60 days after the second set of engineered allogeneic T cells.

10. The method of claim 3, wherein the fourth set of engineered allogeneic T cells is administered 30-60 days after the third set of engineered allogeneic T cells.

11. The method of claim 4, wherein the fifth set of engineered allogeneic T cells is administered 30-60 days after the fourth set of engineered allogeneic T cells.

12. The method of claim 1, wherein the first set of engineered allogeneic T cells is administered in a dose ranging from $1.25 \times 10^5$ cells/kg of the patient to $5.05 \times 10^6$ cells/kg of the patient.

13. The method of claim 1, wherein the patient is treated with an immunosuppressive drug for 2 to 5 days prior to administration of the first set of engineered allogeneic T cells.

14. The method of claim 13, wherein the immunosuppressive drug is fludarabine and/or cyclophosphamide.

15. The method of claim 1, wherein the said first set of engineered T cells has been modified to contain at least one chimeric antigen receptor (CAR).

16. The method of claim 15, wherein the first set of engineered T cells and the second set of engineered T cells have been modified to contain at least one chimeric antigen receptor (CAR).

17. The method of claim 16, wherein the CAR of the first set of engineered T cells and the CAR of the second set of engineered T cells are directed against the same antigen.

18. The method of claim 17, wherein the antigen is CD123, CD19, or CD22 for treating leukemia.

19. The method of claim 16, wherein the CAR of the first set of engineered T cells and the CAR of the second set of engineered T cells are directed against different antigens.

20. The method of claim 19, wherein the antigens are selected from CD123, CD19, and CD22 for treating leukemia.

* * * * *